(12) United States Patent
Kato et al.

(10) Patent No.: US 7,989,446 B2
(45) Date of Patent: *Aug. 2, 2011

(54) 4-AMINO 5-CYANOPYRIMIDINE DERIVATIVES

(75) Inventors: Masaya Kato, Kokubunji (JP); Norifumi Sato, Himeji (JP); Minoru Okada, Ako (JP); Tetsuyuki Uno, Soja (JP); Nobuaki Ito, Tokushima (JP); Yasuhiro Takeji, Ako (JP); Hisashi Shinohara, Himeji (JP); Masahiro Fuwa, Ikoma (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/923,451

(22) Filed: Sep. 22, 2010

(65) Prior Publication Data

US 2011/0009620 A1 Jan. 13, 2011

Related U.S. Application Data

(63) Continuation of application No. 11/579,067, filed as application No. PCT/JP2005/008568 on Apr. 28, 2005.

(30) Foreign Application Priority Data

Apr. 30, 2004 (JP) ................... 2004-135999

(51) Int. Cl.
*C07D 401/12* (2006.01)
*C07D 401/14* (2006.01)
*A61K 31/506* (2006.01)

(52) U.S. Cl. ........... 514/217.06; 514/218; 514/277.8; 514/252.11; 514/252.14; 514/255.05; 514/274; 540/575; 540/601; 544/60; 544/122; 544/295; 544/296; 544/317

(58) Field of Classification Search .......... 544/60, 544/122, 295, 296, 317; 540/575, 601; 514/217.06, 514/218, 227.8, 235.8, 252.11, 252.14, 255.05, 514/274
See application file for complete search history.

(56) References Cited

U.S. PATENT DOCUMENTS

| | | | |
|---|---|---|---|
| 4,956,345 A | 9/1990 | Miyasaka |
| 4,968,697 A | 11/1990 | Hutchison |
| 5,270,304 A | 12/1993 | Kogi |
| 5,593,975 A | 1/1997 | Cristalli |
| 5,877,180 A | 3/1999 | Linden |
| 6,180,615 B1 | 1/2001 | Zablocki |
| 6,214,807 B1 | 4/2001 | Zablocki |
| 6,232,297 B1 | 5/2001 | Linden |
| 6,326,359 B1 | 12/2001 | Monaghan |
| 6,387,899 B1 | 5/2002 | Berg |
| 6,403,567 B1 | 6/2002 | Zablocki |
| 6,426,337 B1 | 7/2002 | Cox |
| 6,440,948 B1 | 8/2002 | Zablocki |
| 6,448,235 B1 | 9/2002 | Linden |
| 6,448,236 B1 | 9/2002 | Monaghan |
| 6,495,528 B1 | 12/2002 | Allen |
| 6,514,949 B1 | 2/2003 | Linden |
| 6,528,494 B2 | 3/2003 | Cox |
| 6,531,457 B2 | 3/2003 | Linden |
| 6,534,486 B1 | 3/2003 | Allen |
| 6,610,665 B1 | 8/2003 | Bays |
| 6,642,210 B1 | 11/2003 | Zablocki |
| 6,762,170 B1 | 7/2004 | Chan |
| 6,770,634 B1 | 8/2004 | Zablocki |
| 6,855,818 B2 | 2/2005 | Zablocki |
| 6,900,309 B1 | 5/2005 | Mantell |
| 7,045,631 B2 | 5/2006 | Rosentreter |
| 7,078,417 B2 | 7/2006 | Rosentreter |
| 7,109,180 B2 | 9/2006 | Zablocki |
| 7,109,218 B2 | 9/2006 | Rosentreter |

(Continued)

FOREIGN PATENT DOCUMENTS

JP 2003055395 2/2003

(Continued)

OTHER PUBLICATIONS

Craig E. Crosson, "Adenosine Receptor Activation Modulates Intraocular Pressure in Rabbits[1]," Journal of Pharmacology and Experimental Therapeutics, vol. 273, No. 1, (1995), pp. 320-326.

(Continued)

*Primary Examiner* — Deepak Rao
(74) *Attorney, Agent, or Firm* — Finnegan, Henderson, Farabow, Garrett & Dunner, L.L.P.

(57) ABSTRACT

The present invention provides 4-amino-5-cyanopyrimidine derivatives of the formula: wherein $R_1$, $R_2$ and $R_3$ are defined herein, or pharmaceutically acceptable salts thereof, having a safe and potent adenosine A2a receptor agonistic activity; and also provides an adenosine A2a receptor agonist, an intraocular pressure reducing agent, or a medicine for treating glaucoma, etc., which comprises the compound as an active ingredient.

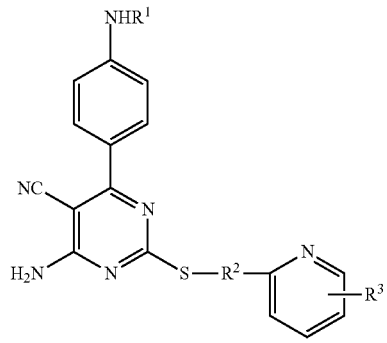

(1)

5 Claims, No Drawings

U.S. PATENT DOCUMENTS

| | | |
|---|---|---|
| 7,129,255 B2 | 10/2006 | Rosentreter |
| 7,135,486 B1 | 11/2006 | Rosentreter |
| 7,144,872 B2 | 12/2006 | Zablocki |
| 2004/0162427 A1 | 8/2004 | Rosentreter |
| 2005/0261502 A1 | 11/2005 | Rosentreter |
| 2006/0154969 A1 | 7/2006 | Rosentreter |

FOREIGN PATENT DOCUMENTS

| | | |
|---|---|---|
| JP | 2003206230 | 7/2003 |
| WO | WO 99/67263 | 12/1999 |
| WO | WO 99/67264 | 12/1999 |

OTHER PUBLICATIONS

Satomi Onoue et al, "α-Helical structure in the C-terminus of vasoactive intestinal peptide: functional and structural consequences," European Journal of Pharmacology 485 (2004) pp. 307-316.

Baraldi et al., Pyrazolo-triazolo-pyrimidine derivatives as adenosine receptor antagonists: a possible template for adenosine receptor subtypes?, Current Pharmaceutical Design, vol. 8, No. 26 pp. 2299-23332, 2002.

Feoktislov et al., Adenosine A2B receptors, Pharmacological Reviews, vol. 49, No. 4, pp. 381-402, 1997.

4-AMINO 5-CYANOPYRIMIDINE DERIVATIVES

RELATED APPLICATIONS

This is a continuation of application Ser. No. 11/579,067, filed Nov. 16, 2007, which is a §371 of International Application No. PCT/JP2005/008568 filed Apr. 28, 2005, which claims priority of Japanese Application No. 2004-135999 filed Apr. 30, 2004, the contents of all of which are incorporated herein by reference.

TECHNICAL FIELD

The present invention relates to a useful medicine as an agonist of adenosine A2a receptor comprising a 4-amino-5-cyanopyrimidine derivative or a pharmaceutically acceptable salt thereof, and a pharmaceutical formulation including these compounds.

BACKGROUND ART

Adenosine is a substance that may exhibit various physiological actions when it binds to a receptor on a cell surface. The adenosine receptor on the cell surface belongs to G-protein-coupled receptor family, and it is classified into A1, A2a, A2b and A3. Among them, the adenosine A1 and adenosine A3 receptors are coupled with Gi-protein and the activation thereof results in lowering of the intracellular c-AMP level. In addition, adenosine A2a and adenosine A2b receptors are coupled with Gs-protein and the activation thereof results in heightening of the intracellular c-AMP level. These 4 kinds of adenosine receptor subtypes each have been cloned.

A variety of studies about agonists and antagonists which may work on each of the above adenosine receptor subtypes have been already reported. It has been disclosed that these agonists and antagonists could be used as medicaments for treating cardiovascular disorder, ischemic reperfusion injury, inflammation, Parkinson's disease, schizophrenia and so on. In particular, a lot of adenosine derivatives have been reported as an active compound of an adenosine A2a receptor agonist (see WO 01/027131 A1, WO 00/077018 A1, WO 00/078776 A1, WO 00/078777 A1, WO 00/078778 A1, WO 00/078779 A1, WO 00/072799 A1, WO 00/023457 A1, WO 99/67266 A1, WO 99/67265 A1, WO 99/67264 A1, WO 99/67263 A1, WO 99/41267 A1, WO 99/38877 A1, WO 98/28319 A1, U.S. Pat. No. 5,877,180, WO 00/044763 A1, WO 93/22328 A1, JP-B-1-33477, JP-B-2774169, U.S. Pat. No. 4,968,697, JP-A-63-201196, JP-A-2003-055395 and JP-A-2002-173427).

In addition, compounds which are structurally different from the above adenosine derivatives and have not any adenine structure have been also reported as an active compound of an adenosine A1 or A2 receptor agonist. The examples of the compounds include dicyanopyridine derivatives (see WO 00/125210 A1, WO 02/070484 A1, WO 02/070485 A1, WO 02/070520 A1, WO 02/079195 A1, WO 02/079196 A1, WO 03/008384 A1 and WO 03/053441 A1). However, cyanopyrimidine derivatives having an action which can activate an adenosine A2a receptor have been not known.

On the other hand, glaucoma is an intractable ophthalmopathy which most species of mammals including primates may suffer. The observed symptoms are blurred vision and ophthalmic pain or loss of vision, and field of vision may be affected through the disorder of optic nerve, in some case, leading to blindness. The glaucoma can be classified into two types: ocular hypertensive glaucoma which is characterized in an increase of intraocular pressure (a facilitation of intraocular pressure) and normal tension glaucoma without any facilitation of intraocular pressure. The facilitation of intraocular pressure in glaucoma may be induced by the loss of the balance between a flow rate of aqueous humor which is secreted from ciliary epithelium into posterior chamber and an outflow rate of aqueous humor which is excreted from anterior chamber mainly via Schlemm's canal. This loss of the balance is considered to be induced from the enhanced flow resistance of aqueous humor due to mainly blocking the outflow pathway of aqueous humor. The glaucoma is an important disease whose patients have been increasing year by year in each advanced country with the advance of aging of society, and so the social requirement regarding the development of the treatment medicament is supposed to increase more and more.

At present, in treating glaucoma, the control of the intraocular pressure which is related with the most critical factor is the most important problem, and the medicaments used in the treatment thereof include β blockers such as carteolol and timolol, prostaglandin derivatives such as latanoprost and isopropyl unoprostone, carbonic anhydrase inhibitors such as dorzolamide. These medicaments may modulate the formation or outflow of aqueous humor to lower an intraocular pressure.

The adenosine A2a receptor agonists have been reported not only to exhibit the potent antihypertensive action and to be useful as above-mentioned drugs such as an antihypertensive drug, a medicament for treating/preventing cardiac or cerebral ischemic disease and antiarteriosclerotic drug, but also to exhibit an ocular hypotensive action (see J. Pharmcol. Exp. Ther. 320-326, 273 (1995) and Eur. J. Pharmacol. 307-316, 486 (2004)).

In addition, with respect to adenosine derivatives having the intraocular pressure lowering action it has already progressed partly the research and development thereof (see JP-A-2003-055395 and JP-A-2002-173427).

However, these adenosine derivatives might be feared to accompany with some side effect for central nerve and cardiovascular system when these compounds are used as a medicament for treating glaucoma.

As mentioned above, the adenosine derivatives having the adenine structure are expected to exhibit the effect as an adenosine A2a receptor agonist, especially as a medicament for treating glaucoma and the like due to the intraocular pressure lowering action thereof, but the intraocular pressure lowering action is not enough, furthermore these compounds have a critical demerit to accompany with the side effect for central nerve and cardiovascular system, for example, the potent antihypertensive action generated from the potential adenosine A2a receptor agonistic activity arising from an adenine structure thereof. Therefore, in the related field, it is required to develop a compound that can exhibit the desired reduction of intraocular pressure as an adenosine A2a receptor agonist, especially a medicament for treating glaucoma and the like, and used more safely instead of the above compounds.

DISCLOSURE OF INVENTION

Problem to be Solved by the Invention

An object of the present invention is to provide a compound having a safe and potent adenosine A2a receptor agonistic activity, and provide an adenosine A2a receptor agonist, an intraocular pressure reducing agent, a medicine for treating glaucoma, etc. including the compound as an active ingredient.

Means to Solve the Problem

The present inventors have extensively studied to reach for the above object, and have succeeded in preparing some kinds of 4-amino-5-cyanopyrimidine derivatives and also found that the compounds exhibited a potent adenosine A2a receptor agonistic action. The present invention has been completed by the additional studies based on these findings.

The present invention provides the compounds as set forth in the following 1-13 and the pharmaceutical compositions thereof.

1. A 4-amino-5-cyanopyrimidine derivative of the formula (1):

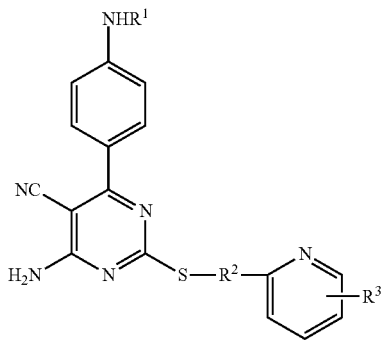

(1)

or a pharmaceutically acceptable salt thereof,
wherein $R^1$ is a hydrogen atom, a lower alkylcarbonyl group, a lower alkenylcarbonyl group, a phenylcarbonyl group or a lower alkoxycarbonyl group;

$R^2$ is a lower alkylene group;

$R^3$ is any one of (1) a hydrogen atom, (2) a lower alkyl group or any one of the following groups (3)-(12):

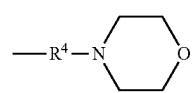

Group (3)

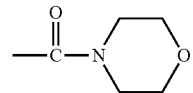

Group (4)

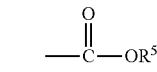

Group (5)

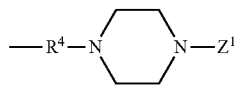

Group (6)

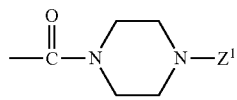

Group (7)

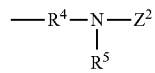

Group (8)

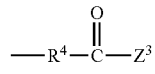

Group (9)

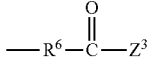

Group (10)

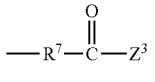

Group (11)

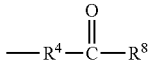

Group (12)

wherein
$R^4$ is a lower alkylene group, $R^5$ is a hydrogen atom or a lower alkyl group, $R^6$ is a lower alkenylene group, $R^7$ is a lower alkynylene group, and $R^8$ is a lower alkyl group;

$Z^1$, $Z^2$, and $Z^3$ are selected from (a1)-(a38), (b1)-(b8), and (c1)-(c22) respectively as defined below:

$Z^1$: (a1) a lower alkyl group, (a2) an aryl-lower alkyl group, (a3) an aminoaryl-lower alkyl group, (a4) an aryl-lower alkenyl group, (a5) a heteroaryl-lower alkyl group, (a6) a heteroaryl-lower alkenyl group, (a7) a heteroarylaryl-lower alkyl group, (a8) a hydroxy-lower alkyl group, (a9) an aryloxy-lower alkyl group, (a10) an amino-lower alkyl group, (a11) an aminocarbonyl-lower alkyl group, (a12) a lower alkylcarbonyl group, (a13) a lower alkoxy-lower alkylcarbonyl group, (a14) an amino-lower alkylcarbonyl group, (a15) an arylcarbonyl group, (a16) an aryl-lower alkylcarbonyl group, (a17) an aryl-lower alkenylcarbonyl group, (a18) an aryloxy-lower alkylcarbonyl group, (a19) an heteroarylcarbonyl group, (a20) a heteroaryl-lower alkylcarbonyl group, (a21) a heteroaryl-lower alkenylcarbonyl group, (a22) a heteroaryloxy-lower alkylcarbonyl group, (a23) a heteroarylsulfanyl-lower alkylcarbonyl group, (a24) a heteroarylarylcarbonyl group, (a25) an arylsulfanyl-lower alkylcarbonyl group, (a26) an arylcarbonyl-lower alkylcarbonyl group, (a27) an arylamino-lower alkylcarbonyl group, (a28) a lower alkoxycarbonyl group, (a29) a lower alkylsulfonyl group, (a30) an arylsulfonyl group, (a31) a heteroarylsulfonyl group, (a32) a hydrogen atom, (a33) a lower alkyl group having a saturated heterocycle, (a34) a carbonyl-lower alkyl group having a saturated heterocycle, (a35) an aryl-lower alkyl group having a saturated heterocycle, (a36) a carbonyl group having a saturated heterocycle, (a37) a lower alkylcarbonyl group having a saturated heterocycle, or (a38) an arylcarbonyl group having a saturated heterocycle;

the amino moiety included as a part of the groups in the above (a3), (a10), (a11), and (a14) may be optionally substituted with 1 or 2 substituents selected from the group consisting of a lower alkyl group, a carbonyl group, and a lower alkylcarbonyl group;

the aryl moiety included as a part of the groups in the above (a2), (a15), (a16), (a17), (a18), (a30), and (a35) may be optionally substituted with 1 to 3 substituents selected from the group consisting of a halogen, a hydroxy group, a lower alkyl group, a lower alkoxy group, a halogeno-lower alkoxy group, an aryl group, an aryloxy group, a methylenedioxy group, a dihalogenomethylenedioxy group, a carboxyl group, a lower alkoxycarbonyl group, a lower alkylcarbonyloxy group, a nitro group, a lower alkylamino group, a lower alkylcarbonylamino group, and an aminosulfonyl group;

the heteroaryl moiety included as a part of the groups in the above (a5), (a19)-(a24), and (a31) may be optionally substituted with 1 to 3 substituents selected from the group consisting of a halogen, a hydroxy group, a lower alkyl group, a hydroxy-lower alkyl group, a halogeno-lower alkyl group, an aryl group, a halogenoaryl group, a lower alkylsulfanyl group, an aminocarbonyl group, and a carboxyl group; and the saturated heterocycle moiety included as a part of the groups in the above (a33)-(a38) may be 5- to 7-membered saturated nitrogen-containing heterocyclic group or said heterocyclic group fused with 1 to 2 benzene rings, optionally having a lower alkyl group or a lower alkylcarbonyl group on the nitrogen atom of the ring system, or optionally having 1 or 2 oxo groups on the carbon atoms of the ring system;

$Z^2$: (b1) a hydrogen atom, (b2) a lower alkoxycarbonyl group, (b3) an amino-lower alkylcarbonyl group, (b4) a lower alkenylcarbonyl group, (b5) a lower alkylcarbonyl group having a saturated heterocycle, (b6) a piperidino-lower alkylcarbonyl group having a saturated heterocycle, (b7) a carbonyl group having a saturated heterocycle, or (b8) a lower alkylsulfonyl group;

the amino group included as a part of the group in the above (b3) may be optionally substituted with 1 or 2 lower alkyl groups; and the saturated heterocycle moiety included as a part of the groups in the above (b5)-(b7) may be 5- to 7-membered saturated nitrogen-containing heterocyclic group, optionally having a lower alkyl group on the nitrogen atom of the ring system;

$Z^3$ (c1) a hydroxy group, (c2) a lower alkoxy group, (c3) an amino group, (c4) an amino-lower alkylamino group, (c5) a piperazino group, (c6) an amino-lower alkylpiperazino group, (c7) an aminocarbonyl-lower alkylpiperazino group, (c8) a 1,4-diazepan-1-yl group, (c9) an amino-lower alkyl-1,4-diazepan-1-yl group, (c10) a piperidino group, (c11) an aminopiperidino group, (c12) an amino-lower alkylaminopiperidino group, (c13) an amino-lower alkylpiperidino group, (c14) a pyrrolidino group, (c15) an amino group having a saturated heterocycle, (c16) a lower alkylamino group having a saturated heterocycle, (c17) a piperazino group having a saturated heterocycle, (c18) a lower alkylpiperazino group having a saturated heterocycle, (c19) a carbonyl-lower alkylpiperazino group having a saturated heterocycle, (c20) a lower alkyl-1,4-diazepan-1-yl group having a saturated heterocycle, (c21) a piperidino group having a saturated heterocycle, or (c22) a lower alkylmorpholino group having a saturated heterocycle;

the amino group of the above (c3) and the amino moiety included as a part of the groups in the above (c4), (c6), (c7), (c9), (c11), (c12), (c13), (c15) and (c16) may be optionally substituted with 1 or 2 substituents selected from the group consisting of a lower alkyl group, a hydroxy-lower alkyl group, an aryl group, a heteroaryl group, an aryl-lower alkyl group, an alkoxyaryl-lower alkyl group, a heteroaryl-lower alkyl group and a lower alkoxycarbonyl group;

the amino moiety included as a part of the groups in the above (c11) may be optionally substituted with an aryl-lower alkylcarbonyl group;

the piperazino group of the above (c5) and 1,4-diazepan-1-yl group of the above (c8) may be substituted with any one of the substituents selected from the group consisting of a lower alkyl group, a hydroxy-lower alkyl group, a lower alkoxy-lower alkyl group, an aryl group, a lower alkylaryl group, a hydroxyaryl group, a cyanoaryl group, a halogenoaryl group, an aryl-lower alkyl group, a lower alkoxyaryl-lower alkyl group, a halogenoaryloxy-lower alkyl group, a heteroaryl group, a lower alkylheteroaryl group, a halogeno-lower alkylheteroaryl group, a cyanoheteroaryl group, a heteroaryl-lower alkyl group, a lower alkoxycarbonyl group and a lower alkylcarbonyl group on 4-position of the ring system; further the saturated heterocycle moiety included as a part of the groups in the above (c15)-(c22) may be 5- to 7-membered saturated nitrogen-containing heterocyclic group or said heterocyclic group fused with 1 to 2 benzene rings, optionally having any one of the substituents selected from the group consisting of a lower alkyl group, an aryl group, a cyanoaryl group, a lower alkylcarbonyl group, a halogeno-lower alkylaryl group and an aryl-lower alkyl group on the nitrogen atom of the ring system; and furthermore the piperazino group of the above (c5), the piperidino group of the above (c10) and the saturated heterocycle moiety included as a part of the groups in the above (c15)-(c22) may be substituted with any one of the substituents selected from the group consisting of a hydroxy group, an oxo group, a lower alkyl group, a hydroxy-lower alkyl group, an aryl group, an aryl-lower alkyl group, an aminocarbonyl group and a lower alkylamino group on the carbon atom of the ring system.

2. The 4-amino-5-cyanopyrimidine derivative according to the above 1 or a pharmaceutically acceptable salt thereof wherein $R^2$ is a methylene group, $R^3$ is a hydrogen atom or a lower alkyl group.

3. The 4-amino-5-cyanopyrimidine derivative according to the above 1 or a pharmaceutically acceptable salt thereof wherein $R^1$ is a lower alkylcarbonyl group, $R^2$ is a methylene group, and $R^3$ is the group (3) or the group (6).

4. The 4-amino-5-cyanopyrimidine derivative according to the above 3 or a pharmaceutically acceptable salt thereof wherein $R^4$ is a lower alkylene group, and $Z^1$ is any one of the substituents selected from the group consisting of (a2), (a14), (a15), (a28), (a32), and (a37).

5. The 4-amino-5-cyanopyrimidine derivative according to the above 1 or a pharmaceutically acceptable salt thereof wherein $R^1$ is a lower alkylcarbonyl group, $R^2$ is a methylene group, and $R^3$ is the group (4), the group (5) or the group (7) wherein $Z^1$ is a lower alkoxycarbonyl group or a hydrogen atom.

6. The 4-amino-5-cyanopyrimidine derivative according to the above 1 or a pharmaceutically acceptable salt thereof wherein $R^1$ is a lower alkylcarbonyl group, $R^2$ is a methylene group, and $R^3$ is the group (8).

7. The 4-amino-5-cyanopyrimidine derivative according to the above 1 or a pharmaceutically acceptable salt thereof wherein $R^1$ is a hydrogen atom or a lower alkylcarbonyl group, $R^2$ is a methylene group, and $R^3$ is the group (9), the group (10), or the group (11).

8. The 4-amino-5-cyanopyrimidine derivative according to the above 1 or a pharmaceutically acceptable salt thereof wherein $R^1$ is a hydrogen atom or a lower alkylcarbonyl group, $R^2$ is a methylene group, and $R^3$ is the group (9), the group (10), or the group (11), wherein $Z^3$ is (c1), (c2), (c4), (c5), (c6), (c7), (c8), (c10), (c11), (c15), (c16), (c18), (c21), or (c22).

9. The 4-amino-5-cyanopyrimidine derivative according to the above 1 or a pharmaceutically acceptable salt thereof wherein $R^1$ is an acetyl group, $R^2$ is a methylene group, and $R^3$ is the group (9) wherein $Z^3$ is (c4), (c5), (c6), (c10), (c11), (c16), (c18), (c21), or (c22).

10. The 4-amino-5-cyanopyrimidine derivative according to the above 1-9 or a pharmaceutically acceptable salt thereof, wherein the compound is selected from the group consisting of the following 1)-19):
1) N-{4-[6-amino-5-cyano-2-(pyridin-2-ylmethylsulfanyl)-pyrimidin-4-yl]phenyl}acetamide,
2) N-{4-[6-amino-5-cyano-2-(6-methylpyridin-2-ylmethylsulfanyl)pyrimidin-4-yl]phenyl}acetamide,
3) N-{4-[6-amino-5-cyano-2-(6-{4-[2-(4-methylpiperazin-1-yl)acetyl]piperazin-1-ylmethyl}pyridin-2-ylmethylsulfanyl)-pyrimidin-4-yl]phenyl}acetamide,
4) N-[4-(6-amino-5-cyano-2-{6-[3-(4-methylpiperazin-1-yl)-3-oxopropyl]pyridin-2-ylmethylsulfanyl}pyrimidin-4-yl)phenyl]acetamide,
5) 3-{6-[4-(4-acetylaminophenyl)-6-amino-5-cyano-pyrimidin-2-ylsulfanylmethyl]pyridin-2-yl}-N-(2-dimethylaminoethyl)propionamide,
6) 3-{6-[4-(4-acetylaminophenyl)-6-amino-5-cyano-pyrimidin-2-ylsulfanylmethyl]pyridin-2-yl}-N-(2-dimethylaminoethyl)-N-methylpropionamide,
7) 3-{6-[4-(4-acetylaminophenyl)-6-amino-5-cyano-pyrimidin-2-ylsulfanylmethyl]pyridin-2-yl}-N-(2-dimethylaminopropyl)-N-methylpropionamide,
8) 3-{6-[4-(4-acetylaminophenyl)-6-amino-5-cyano-pyrimidin-2-ylsulfanylmethyl]pyridin-2-yl}-N-(2-methyl-piperidin-1-ylethyl)propionamide,
9) 3-{6-[4-(4-acetylaminophenyl)-6-amino-5-cyano-pyrimidin-2-ylsulfanylmethyl]pyridin-2-yl}-N-(2-diethyl-aminoethyl)propionamide,
10) 3-{6-[4-(4-acetylaminophenyl)-6-amino-5-cyano-pyrimidin-2-ylsulfanylmethyl]pyridin-2-yl}-N-methyl-N-(1-methylpiperidin-4-yl)propionamide,
11) N-(4-{6-amino-2-[6-(3-[1,4']bipiperidinyl-1'-yl-3-oxopropyl)pyridin-2-ylmethylsulfanyl]-5-cyanopyrimidin-4-yl}-phenyl)acetamide,
12) N-[4-(6-amino-5-cyano-2-{6-[3-oxo-3-(2-piperidin-1-ylmethylmorpholin-4-yl)propyl]pyridin-2-ylmethylsulfanyl}-pyrimidin-4-yl)phenyl]acetamide,
13) N-{4-[6-amino-5-cyano-2-(6-{3-[2-(4-ethylpiperazin-1-ylmethyl)morpholin-4-yl]-3-oxopropyl}pyridin-2-ylmethyl-sulfanyl)pyrimidin-4-yl]phenyl}acetamide,
14) N-{4-[6-amino-5-cyano-2-(6-{3-[4-(2-diethylaminoethyl)piperazin-1-yl]-3-oxopropyl}pyridin-2-ylmethylsulfanyl)pyrimidin-4-yl]phenyl}acetamide,
15) N-{4-[6-amino-5-cyano-2-(6-{3-[4-(2-diisopropyl-aminoethyl)piperazin-1-yl]-3-oxopropyl}pyridin-2-ylmethylsulfanyl)pyrimidin-4-yl]phenyl}acetamide,
16) N-{4-[6-amino-5-cyano-2-(6-{3-oxo-3-[4-(2-pyrrolidin-1-ylethyl)piperazin-1-yl]propyl}pyridin-2-yl-methylsulfanyl)pyrimidin-4-yl]phenyl}acetamide,
17) N-{4-[6-amino-5-cyano-2-(6-{3-[4-(2-morpholin-4-ylethyl)piperazin-1-yl]-3-oxopropyl}pyridin-2-ylmethylsulfanyl)pyrimidin-4-yl]phenyl}acetamide,
18) N-{4-[6-amino-5-cyano-2-(6-{3-[4-(2-diethylaminoethyl)piperazin-1-yl]-3-oxopropyl}pyridin-2-ylmethylsulfanyl)pyrimidin-4-yl]phenyl}acetamide, and
19) N-[4-(6-amino-5-cyano-2-{6-[3-(4-methyl-[1,4]-diazepan-1-yl)-3-oxopropyl]pyridin-2-ylmethylsulfanyl}-pyrimidin-4-yl)phenyl]acetamide.

11. An adenosine A2a receptor agonist comprising any one of the 4-amino-5-cyanopyrimidine derivatives as set forth in the above 1-10 or a pharmaceutically acceptable salt thereof as an active ingredient.

12. An intraocular pressure reducing agent comprising any one of the 4-amino-5-cyanopyrimidine derivatives as set forth in the above 1-10 or a pharmaceutically acceptable salt thereof as an active ingredient.

13. A medicine for the treatment of ocular hypertension or glaucoma comprising any one of the 4-amino-5-cyanopyrimidine derivatives as set forth in the above 1-10 or a pharmaceutically acceptable salt thereof as an active ingredient.

The 4-amino-5-cyanopyrimidine derivative of the present invention has the following structural property. That is, it has a pyrimidine structure, and a phenyl ring having a specific substituent is substituted on the 6-position of the pyrimidine ring, and a pyridine ring is substituted on the 2-position of the pyrimidine ring via a sulfanylalkylene chain, or further the pyridine ring has a specific substituent. Based on this structural property, the compounds of the invention have an effect to activate the adenosine A2a receptor, that is, a remarkable pharmacological property of the adenosine A2a receptor agonistic action. Hitherto, the compounds having such original structural property were unknown, and it was unpredicted that the compounds may exert any pharmacological effect from the prior art.

Compounds of the Invention

The term "lower alkyl group" as employed herein means a straight or branched chain alkyl group, containing 1 to 6 carbons, i.e., $C_{1-6}$ straight or branched chain alkyl group.

The terms "lower alkoxy group" and "lower alkylene group" also mean a straight or branched chain alkoxy group and alkylene group respectively, containing 1 to 6 carbons.

The terms "lower alkenyl group", "lower alkenylene group", and "lower alkynylene group" mean a straight or branched chain alkenyl group, alkenylene group, and alkynylene group respectively, containing 2 to 6 carbons, i.e., $C_{2-6}$ straight or branched chain alkenyl, alkenylene, and alkynylene groups respectively.

The term "aryl group" means a monovalent group comprising mono-cyclic or multi-cyclic aromatic hydrocarbon, including for example, phenyl group and naphthyl group.

The term "heteroaryl group" means a monovalent group comprising a 5 to 6-membered aromatic heteromonocyclic group having one or more, especially 1 to 3 of same or different heteroatoms selected from the group consisting of nitrogen, oxygen, and sulfur, or an aromatic heterocyclic group composed of said heteromonocyclic group fused with an aryl group, such as furyl, thienyl, thiazolyl, imidazolyl, pyrazolyl, benzofuryl, indolyl, benzothiazolyl, pyridyl, pyrazinyl group and the like.

The term "saturated heterocycle" means a 5 to 7-membered saturated heterocycle, having one or more, especially 1-3 of same or different heteroatoms selected from the group consisting of nitrogen, oxygen, and sulfur. The saturated heterocycle is contained as a monovalent saturated heterocycle group in any substituent, for example, pyrrolidinyl, pyrrolidino, piperidyl, piperidino, piperazinyl, piperazino, 1,4-diazepan-1-yl, tetrahydrofuryl, 1,3-dioxolanyl, tetrahydrothienyl, morpholinyl, morpholino, tetrahydroimidazolyl group and the like are exemplified. For example, in the case of a lower alkyl group having a saturated heterocycle, the lower alkyl group means a lower alkyl group substituted with the saturated heterocycle group mentioned above. In the lower alkyl group substituted with the saturated heterocycle, the binding is not limited, that is, it may be bound to a lower alkyl group on the nitrogen atom which is a hetero atom included in the heterocycle or on the carbon atom thereof. In addition, the above-mentioned 5- to 7-membered saturated heterocyclic group may be fused with additional 1 or 2 benzene rings. Such fused ring groups include for example, dihydroindolyl, dihydroisoindolyl, tetrahydroquinolyl, tetrahydroquinolino, benzomorpholinyl, benzomorpholino group, and the like.

Hereinafter, each group included in the compounds of the invention shown as the above-mentioned general formula (1)

is individually illustrated. The definitions of each group mentioned below are adapted to not only the compounds shown as the formula (1), but also the other compounds herein.

The examples of the lower alkylcarbonyl group shown as $R^1$ include acetyl, propanoyl, butanoyl, butylcarbonyl, pentylcarbonyl, hexylcarbonyl, isopropylcarbonyl groups and the like, preferably acetyl and propanoyl groups.

The examples of the lower alkenylcarbonyl group shown as $R^1$ include acryloyl, methacryloyl, crotonoyl, isocrotonoyl groups and the like, preferably acryloyl group.

The examples of the lower alkoxycarbonyl group shown as $R^1$ include methoxycarbonyl, ethoxycarbonyl, t-butoxycarbonyl, n-butoxycarbonyl groups and the like, preferably methoxycarbonyl group.

The examples of the lower alkylene group shown as $R^2$ include methylene, ethylene, trimethylene, tetramethylene, pentamethylene and hexamethylene as well as structural isomers thereof such as 1-methylethylene. Among them, methylene group is preferred.

The examples of the lower alkyl group shown as $R^3$ include methyl, ethyl, propyl, butyl, pentyl and hexyl groups as well as structural isomers thereof such as isopropyl. Among them, methyl group is preferred.

The examples of the lower alkylene group shown as $R^4$ include methylene, ethylene, trimethylene, tetramethylene, heptamethylene and hexamethylene as well as structural isomers thereof such as 1-methylethylene. The lower alkylene group shown as $R^4$ is preferably methylene group or ethylene group when $R^3$ is group (3); the lower alkylene group shown as $R^4$ is preferably methylene group when $R^3$ group is group (6) or group (8); the lower alkylene group shown as $R^4$ is preferably ethylene group or tetramethylene group when $R^3$ group is group (9).

The examples of the lower alkyl group shown as $R^5$ include methyl, ethyl, propyl, butyl, pentyl and hexyl groups as well as structural isomers thereof such as isopropyl group. Among them, methyl group is preferred.

The examples of the lower alkenylene group shown as $R^6$ include a straight chain lower alkenylene group such as ethenylene, propenylene, butenylene, pentenylene, hexenylene, and butane dienylene, and structural isomers thereof such as 2-methylpropenylene group. Among them, ethenylene group is preferred.

The examples of the lower alkynylene group shown as $R^7$ include a straight chain lower alkynylene group such as ethynylene, propynylene, butynylene, pentynylene, hexynylene and butanediynylene, and structural isomers thereof such as 3-methylbutynylene group. Among them, butynylene group is preferred.

The examples of the lower alkyl group shown as $R^8$ include methyl, ethyl, propyl, butyl, pentyl and hexyl as well as structural isomers thereof such as isopropyl. Among them, ethyl group is preferred.

The examples of the lower alkyl group (a1) shown as $Z^1$ include a straight chain lower alkyl group such as methyl, ethyl, propyl, butyl, pentyl and hexyl as well as structural isomers thereof such as isopropyl. Among them, $C_{1-4}$ alkyl group is preferred.

The aryl-lower alkyl group (a2) shown as $Z^1$ means a lower alkyl group substituted with an aryl group. The examples include benzyl, phenethyl, phenylpropyl, naphthylmethyl groups and the like. Among them, benzyl group or phenethyl group is preferred.

The aminoaryl-lower alkyl group (a3) shown as $Z^1$ means an aryl-lower alkyl group having an amino group on its aryl moiety. For example, aminobenzyl, aminophenethyl, aminophenylpropyl, aminonaphthylmethyl groups and the like are exemplified. Among them, aminobenzyl group or aminophenethyl group is preferred.

The aryl-lower alkenyl group (a4) shown as $Z^1$ means a lower alkenyl group substituted with an aryl group. For example, phenylethenyl, phenylpropenyl, phenylbutenyl groups and the like are exemplified. Among them, phenylpropenyl group is preferred.

The heteroaryl-lower alkyl group (a5) shown as $Z^1$ means a lower alkyl group substituted with a heteroaryl group. For example, furylmethyl, pyrazolylethyl, imidazolylpropyl, pyridylmethyl groups and the like are exemplified. Among them, furylmethyl group or pyridylmethyl group is preferred.

The heteroaryl-lower alkenyl group (a6) shown as $Z^1$ means a lower alkenyl group substituted with a heteroaryl group. For example, pyridylethenyl, pyridylpropenyl, furylpropenyl groups and the like are exemplified. Among them, pyridylpropenyl group or furylpropenyl group is preferred.

The heteroarylaryl-lower alkyl group (a7) shown as $Z^1$ means an aryl-lower alkyl group having a heteroaryl group on its aryl group. For example, furylphenylmethyl, thienylphenylethyl, pyridylphenylpropyl, triazolylphenylmethyl, imidazolylphenylmethyl groups and the like are exemplified. Among them, triazolylphenylmethyl group or imidazolylphenylmethyl group is preferred.

The examples of the hydroxy-lower alkyl group (a8) shown as $Z^1$ include hydroxymethyl, 1-hydroxyethyl, 2-hydroxyethyl, 1-hydroxypropyl, 2-hydroxypropyl, 3-hydroxypropyl, 4-hydroxybutyl groups and the like, preferably 3-hydroxypropyl group and 4-hydroxybutyl group.

The examples of the aryloxy-lower alkyl group (a9) shown as $Z^1$ include phenoxymethyl, 1-phenoxyethyl, 2-phenoxyethyl, 1-phenoxypropyl, 2-phenoxypropyl, 3-phenoxypropyl groups and the like, preferably 3-phenoxypropyl group.

The examples of the amino-lower alkyl group (a10) shown as $Z^1$ include aminomethyl, 1-aminoethyl, 2-aminoethyl, 1-aminopropyl, 2-aminopropyl, 3-aminopropyl groups and the like, preferably 2-aminoethyl and 3-aminopropyl groups.

The examples of the aminocarbonyl-lower alkyl group (a11) shown as $Z^1$ include aminocarbonylmethyl, 1-aminocarbonylethyl, 2-aminocarbonylethyl, 1-aminocarbonylpropyl, 2-aminocarbonylpropyl, 3-aminocarbonylpropyl groups and the like, preferably aminocarbonylmethyl group.

The lower alkylcarbonyl group (a12) shown as $Z^1$ includes acetyl, propanoyl, propylcarbonyl, butylcarbonyl, pentylcarbonyl, hexylcarbonyl, isopropylcarbonyl groups and the like, preferably acetyl and propanoyl group.

The examples of the lower alkoxy-lower alkylcarbonyl group (a13) shown as $Z^1$ include methoxymethylcarbonyl, methoxyethylcarbonyl, ethoxyethylcarbonyl groups and the like, preferably methoxymethylcarbonyl group.

The examples of the amino-lower alkylcarbonyl group ((a14) and (b3)) shown as $Z^1$ and $Z^2$ include amino-methylcarbonyl, aminoethylcarbonyl, aminopropylcarbonyl, aminobutylcarbonyl groups and the like, preferably aminomethylcarbonyl group and aminoethylcarbonyl group.

The examples of the arylcarbonyl group (a15) shown as $Z^1$ include benzoyl, naphthylcarbonyl groups and the like, preferably benzoyl group.

The examples of the aryl-lower alkylcarbonyl group (a16) shown as $Z^1$ include benzylcarbonyl, naphthylmethylcarbonyl, phenethylcarbonyl, phenylpropylcarbonyl, phenylbutylcarbonyl groups and the like, preferably benzylcarbonyl group and phenethylcarbonyl group.

The examples of the aryl-lower alkenylcarbonyl group (a17) shown as $Z^1$ include phenylethenylcarbonyl, phenylpropenylcarbonyl, phenylbutenylcarbonyl groups and the like, preferably phenylethenylcarbonyl group.

The examples of the aryloxy-lower alkylcarbonyl group (a18) shown as $Z^1$ include phenoxymethylcarbonyl, phenoxy-ethylcarbonyl, phenoxypropylcarbonyl, phenoxybutylcarbonyl groups and the like, preferably phenoxymethylcarbonyl group and phenoxyethylcarbonyl group.

The examples of the heteroarylcarbonyl group (a19) shown as $Z^1$ include furylcarbonyl, thienylcarbonyl, imidazolyl-carbonyl, thiazolylcarbonyl, pyridylcarbonyl, quinolyl-carbonyl groups and the like, preferably pyridylcarbonyl group, furylcarbonyl group and thienylcarbonyl group.

The examples of the heteroaryl-lower alkylcarbonyl group (a20) shown as $Z^1$ include furylmethylcarbonyl, furylethylcarbonyl, thienylmethylcarbonyl, pyridylmethyl-carbonyl, pyridylethylcarbonyl, pyridylpropylcarbonyl groups and the like, preferably thienylmethylcarbonyl group and pyridylmethylcarbonyl group.

The examples of the heteroaryl-lower alkenylcarbonyl group (a21) shown as $Z^1$ include pyridylacryloyl, imidazolyl-acryloyl groups and the like, preferably pyridylacryloyl group.

The examples of the heteroaryloxy-lower alkylcarbonyl group (a22) shown as $Z^1$ include pyridyloxymethylcarbonyl, quinolyloxyethylcarbonyl, tetrahydroquinolinonyloxymethylcarbonyl, tetrahydroquinolinonyloxypropylcarbonyl groups and the like, preferably tetrahydroquinolinonyloxymethylcarbonyl group and tetrahydroquinolinonyloxypropylcarbonyl group.

The examples of the heteroarylsulfanyl-lower alkylcarbonyl group (a23) shown as $Z^1$ include furylsulfanylmethylcarbonyl, pyridylsulfanylethylcarbonyl, quinolyl-sulfanylpropylcarbonyl groups and the like, preferably pyridylsulfanylmethylcarbonyl.

The examples of the heteroarylarylcarbonyl group (a24) shown as $Z^1$ include pyrrolylphenylcarbonyl, pyrazolylphenylcarbonyl, imidazolylphenylcarbonyl, triazolylphenylcarbonyl, thienylphenylcarbonyl, furylphenylcarbonyl, pyridylphenylcarbonyl groups and the like, preferably pyrrolylphenylcarbonyl, pyrazolylphenylcarbonyl and imidazolylphenylcarbonyl, triazolylphenylcarbonyl groups.

The examples of the arylsulfanyl-lower alkylcarbonyl group (a25) shown as $Z^1$ include phenylsulfanylmethylcarbonyl, phenylsulfanylethylcarbonyl, phenylsulfanylpropylcarbonyl groups and the like, preferably phenylsulfanylmethylcarbonyl group.

The examples of arylcarbonyl-lower alkylcarbonyl group (a26) shown as $Z^1$ include benzoylmethylcarbonyl, benzoylethylcarbonyl, benzoylpropylcarbonyl groups and the like, preferably benzoylethylcarbonyl group.

The examples of the arylamino-lower alkylcarbonyl group (a27) shown as $Z^1$ include phenylaminomethylcarbonyl, phenylaminoethylcarbonyl, phenylaminopropylcarbonyl groups and the like, preferably phenylaminomethylcarbonyl group.

The examples of the lower alkoxycarbonyl group ((a28) and (b2)) shown as $Z^1$ and $Z^2$ include methoxycarbonyl, ethoxycarbonyl, propoxycarbonyl, butoxycarbonyl, pentyloxy-carbonyl, hexyloxycarbonyl, isopropoxycarbonyl groups and the like. Among them, methoxycarbonyl group and t-butoxycarbonyl group are preferred.

The examples of the lower alkylsulfonyl group ((a29) and (b8)) shown as $Z^1$ and $Z^2$ include methylsulfonyl, ethylsulfonyl, propylsulfonyl, butylsulfonyl groups and the like. Among them, the preferred lower alkylsulfonyl group (a29) shown as $Z^1$ is methylsulfonyl or ethylsulfonyl group; and the preferred lower alkylsulfonyl group (b8) shown as $Z^2$ is ethylsulfonyl or propylsulfonyl group.

The examples of the arylsulfonyl group (a30) shown as $Z^1$ include phenylsulfonyl, toluenesulfonyl, naphthalenesulfonyl group and the like, preferably phenylsulfonyl group.

The examples of the heteroarylsulfonyl group (a31) shown as $Z^1$ include furylsulfonyl, thienylsulfonyl, pyridylsulfonyl, imidazolylsulfonyl groups and the like, preferably imidazolylsulfonyl group.

The lower alkyl group having a saturated heterocycle (a33) shown as $Z^1$ means a lower alkyl group substituted with a saturated heterocyclic group. For example, pyrrolidino-ethyl, piperidinoethyl, piperidylethyl, morpholinoethyl, morpholinylmethyl groups and the like are exemplified, preferably piperidinoethyl group and morpholinoethyl group.

The carbonyl-lower alkyl group having a saturated heterocycle (a34) shown as $Z^1$ means a carbonyl-lower alkyl group substituted with a saturated heterocyclic group. For example, pyrrolidinocarbonylethyl, piperidinocarbonylethyl, piperidylcarbonylethyl, morpholinocarbonylethyl, morpholinyl-carbonylmethyl groups and the like are exemplified, preferably piperidinocarbonylmethyl group.

The aryl-lower alkyl group having a saturated heterocycle (a35) shown as $Z^1$ means an aryl-lower alkyl group having a saturated heterocyclic group on the aryl ring. For example, pyrrolidinophenylethyl, piperidinophenylmethyl, piperidylphenylethyl, morpholinophenylethyl, morpholinylphenylmethyl, piperazinophenylmethyl groups and the like are exemplified, preferably piperazinophenylmethyl group.

The examples of the carbonyl group having a saturated heterocycle ((a36) and (b7)) shown as $Z^1$ and $Z^2$ include pyrrolidinocarbonyl, piperidinocarbonyl, piperidylcarbonyl, morpholinocarbonyl, morpholinylcarbonyl, piperazinocarbonyl, piperazinylcarbonyl, thiazolylcarbonyl, pyrrolylcarbonyl groups and the like, preferably piperazinocarbonyl, thiazolylcarbonyl and pyrrolylcarbonyl groups.

The examples of the lower alkylcarbonyl group having a saturated heterocycle ((a37) and (b5)) shown as $Z^1$ and $Z^2$ include pyrrolidinoethylcarbonyl, piperidinomethylcarbonyl, piperidinoethylcarbonyl, piperidylmethylcarbonyl, morpholino-ethylcarbonyl, morpholinylmethylcarbonyl, piperazinomethyl-carbonyl, piperazinylpropylcarbonyl, thiazolylmethylcarbonyl groups and the like, preferably piperazinomethylcarbonyl, piperidinomethylcarbonyl and piperidinoethylcarbonyl groups.

The examples of the arylcarbonyl group having a saturated heterocycle (a38) shown as $Z^1$ include pyrrolidinophenylcarbonyl, piperidinophenylcarbonyl, piperidylphenylcarbonyl, morpholinophenylcarbonyl, morpholinylphenylcarbonyl, thiomorpholinophenylcarbonyl, piperazinophenylcarbonyl groups and the like, preferably pyrrolidinophenylcarbonyl, morpholinylphenylcarbonyl and thiomorpholinophenylcarbonyl groups.

The examples of the optional substituent included in each group as a part of the group shown as above $Z^1$ are mentioned as follows:

The examples of the lower alkyl group include methyl, ethyl, propyl, butyl, pentyl, hexyl, isopropyl, isobutyl groups and the like. Among them, methyl, ethyl and isopropyl groups are preferred.

The examples of the lower alkylcarbonyl group include acetyl, propanoyl, butanoyl, butylcarbonyl, pentylcarbonyl groups and the like, preferably acetyl group.

The examples of the halogen include fluorine, chlorine, bromine, and iodine atoms, preferably fluorine and chlorine atoms.

The examples of the lower alkoxy group include methoxy, ethoxy, propoxy, butoxy, pentyloxy, hexyloxy, isopropoxy and the like. Among them, $C_{1-4}$ alkoxy group is preferred.

The examples of the halogeno-lower alkoxy group include chloromethoxy, dichloromethoxy, trichloromethoxy, trifluoro-methoxy, 2,2,2-trifluoroethoxy groups and the like, preferably trifluoromethoxy group.

The examples of the aryl group include phenyl, naphthyl groups and the like, preferably phenyl group.

The examples of the aryloxy group include phenoxy, naphthoxy groups and the like, preferably phenoxy group.

The examples of the dihalogenomethylenedioxy group include difluoromethylenedioxy, dichloromethylenedioxy groups and the like, preferably difluoromethylenedioxy group.

The examples of the lower alkoxycarbonyl group include methoxycarbonyl, ethoxycarbonyl, t-butoxycarbonyl groups and the like, preferably methoxycarbonyl group.

The examples of the lower alkylcarbonyloxy group include acetoxy, propylcarbonyloxy groups and the like, preferably acetoxy group.

The examples of the lower alkylamino group include mono- or di(lower alkyl)amino group such as methylamino, dimethylamino, diethylamino, diisopropylamino groups and the like, preferably dimethylamino group.

The examples of the lower alkylcarbonylamino group include acetylamino, propionylamino groups and the like, preferably acetylamino group.

The examples of the hydroxy-lower alkyl group include lower alkyl group having one hydroxyl group such as hydroxymethyl, 1-hydroxyethyl, 2-hydroxyethyl, 1-hydroxy-propyl, 2-hydroxypropyl, 3-hydroxypropyl, 2-hydroxy-2-methylethyl groups and the like, preferably hydroxymethyl or 2-hydroxyethyl group.

The examples of the halogeno-lower alkyl group include lower alkyl group having 1 to 5 halogen atoms such as chloroethyl, dichloromethyl, trifluoromethyl, pentafluoro-ethyl groups and the like, preferably trifluoromethyl group.

The examples of the halogenoaryl group include chlorophenyl, dichlorophenyl, fluorophenyl, difluorophenyl, pentafluorophenyl, bromophenyl, iodophenyl, chloronaphthyl groups and the like, preferably chlorophenyl group.

The examples of the lower alkylsulfanyl group include methylsulfanyl, ethylsulfanyl, propylsulfanyl groups and the like, preferably methylsulfanyl group.

The examples of the amino group substituted with 1 or 2 lower alkyl groups, which is included as a part of the aminoaryl-lower alkyl group (a3), the amino-lower alkyl group (a10), the aminocarbonyl-lower alkyl group (a11) or the amino-lower alkylcarbonyl group (a14), include dimethylaminophenylethyl, dimethylaminoethyl, diethylaminoethyl, diisopropylaminoethyl, dimethylaminocarbonylmethyl, diethyl-aminomethylcarbonyl, diethylaminoethylcarbonyl group and the like. In addition, the examples of said amino group substituted with one carbonyl group include N-formylaminomethylcarbonyl group, and the examples of said amino group substituted with one lower alkylcarbonyl groups include acetylaminomethylcarbonyl group.

The examples of the aryl group substituted with halogen atom(s) where the aryl group is included as a part of the aryl-lower alkyl group (a2), the arylcarbonyl group (a15), the aryl-lower alkylcarbonyl group (a16), the aryl-lower alkenyl-carbonyl group (a17), the aryloxy-lower alkylcarbonyl group (a18), the arylsulfonyl group (a30) and the aryl-lower alkyl group having a saturated heterocycle (a35), include chlorophenylcarbonyl, dichloro(aminosulfonyl)phenylcarbonyl, chlorophenylmethylcarbonyl and fluoro(4-methylpiperazino)-phenylmethyl groups. The examples of the aryl group substituted with hydroxy group(s) include hydroxyphenylmethyl group. The examples of the aryl group substituted with lower alkyl group(s) include methylphenylcarbonyl, methylphenyl-methylcarbonyl, methylphenoxymethylcarbonyl and methyl-phenylsulfonyl groups. The examples of the aryl group substituted with lower alkoxy group(s) include methoxyphenylmethyl, trimethoxyphenylmethyl, butoxyphenylmethyl, ethoxyphenylmethyl, methoxyphenylcarbonyl, methoxy-phenylmethylcarbonyl, methoxyphenoxymethylcarbonyl and methoxyphenylsulfonyl groups. The examples of the aryl group substituted with halogeno-lower alkoxy group(s) include trifluoromethoxyphenylmethylcarbonyl group. The examples of the aryl group substituted another aryl group(s) include biphenyl group. The examples of the aryl group substituted with aryloxy group(s) include phenoxyphenylmethyl and phenoxyphenylcarbonyl group. The examples of the aryl group substituted with methylenedioxy group(s) include methylenedioxyphenylmethyl and methylenedioxyphenylcarbonyl groups. The examples of the aryl group substituted with dihalogenomethylenedioxy group(s) include difluoromethylene-dioxyphenylmethyl group. The examples of the aryl group substituted with carboxyl group(s) include hydroxycarbonylphenylmethyl group. The examples of the aryl group substituted with lower alkoxycarbonyl group(s) include methoxycarbonylphenylmethyl and methoxycarbonylphenylcarbonyl groups. The examples of the aryl group substituted with lower alkylcarbonyloxy group(s) include methylcarbonyloxyphenylmethyl and methylcarbonyloxyphenylcarbonyl groups. The examples of the aryl group substituted with nitro group(s) include nitrophenylcarbonyl group. The examples of the aryl group substituted with lower alkylamino group(s) include dimethylaminophenylcarbonyl and dimethylaminophenylethenylcarbonyl groups. The examples of the aryl group substituted with lower alkylcarbonylamino group(s) include acetylaminophenylcarbonyl group. The examples of the aryl group substituted with aminosulfonyl group(s) include dichloro(aminosulfonyl)phenylcarbonyl group.

The examples of the heteroaryl group substituted with halogen atom(s) where the heteroaryl group is included as a part of the heteroaryl-lower alkyl group (a5), the heteroarylcarbonyl group (a19), the heteroaryl-lower alkyl-carbonyl group (a20), the heteroaryl-lower alkenylcarbonyl group (a21), the heteroaryloxy-lower alkenylcarbonyl group (a22), the heteroarylsulfanyl-lower alkylcarbonyl group (a23), the heteroarylarylcarbonyl group (a24) and the heteroarylsulfonyl group (a31), include chlorothienylmethyl, dichloroimidazolylmethyl and chloro(hydroxy)pyridylcarbonyl groups. The examples of the heteroaryl group substituted with hydroxy group(S) include hydroxypyridylcarbonyl and chloro(hydroxy)pyridylcarbonyl groups. The examples of the heteroaryl group substituted with lower alkyl group(s) include methylthiazolylmethyl, n-hexyltetrazolylmethyl, methylisoxazolylmethyl and methylimidazolylmethyl groups. The examples of the heteroaryl group substituted with hydroxy-lower alkyl group(s) include hydroxymethyl-pyridylmethyl group. The examples of the heteroaryl group substituted with halogeno-lower alkyl group(s) include trifluoromethylbenzofuranylmethyl group. The examples of the heteroaryl group substituted with aryl group(s) include phenylthiazolylmethyl and phenylimidazolylmethyl groups. The examples of the heteroaryl group substituted with halogenoaryl group(s) include chlorophenylpyrrolylmethyl group. The examples of the heteroaryl group substituted with lower alkylsulfanyl group(s) include methylsulfanyl-pyridylcarbonyl group. The examples of the heteroaryl group substituted with aminocarbonyl group(s) include aminocarbonylpyrazolylcarbonyl group. The examples of the heteroaryl group substituted with carboxyl group(s) include hydroxycarbonylfurylmethyl and hydroxycarbonylthienylmethyl groups.

The saturated heterocycle moiety included as a part of the groups described in (a33)-(a38) may have a specific substituent on the nitrogen atom or the carbon atom thereof (lower alkyl group or lower alkoxycarbonyl group as a substituent on the nitrogen atom and oxo group as a substituent on the carbon atom). The examples of preferable groups among the above ones are as follows.

The examples of the lower alkyl group having a saturated heterocycle (a33) which further has a lower alkyl group on the nitrogen atom of the heterocycle are

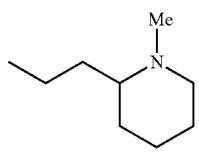

and the like, wherein Me means methyl, the same hereinafter.

The examples of the aryl-lower alkyl group having a saturated heterocycle (a35) which further has one lower alkyl group on the nitrogen atom of the heterocycle are

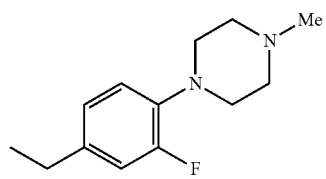

and the like.

The examples of the carbonyl group having a saturated heterocycle (a36) which further has a lower alkylcarbonyl group on the nitrogen atom of the heterocycle are

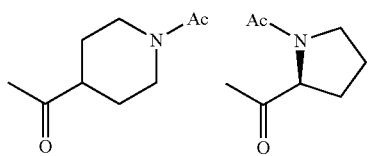

and the like, wherein Ac means acetyl, the same hereinafter.

The examples of the carbonyl group having a saturated heterocycle (a36) which further has one oxo group on the carbon atom of the heterocycle are

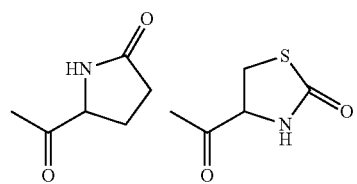

and the like.

The examples of the lower alkylcarbonyl group having a saturated heterocycle (a37) which further has one lower alkyl group on the nitrogen atom of the heterocycle are

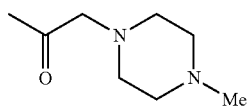

and the like.

The examples of the lower alkylcarbonyl group having a saturated heterocycle (a37) which further has two oxo groups on the carbon atoms of the heterocycle are

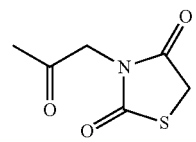

and the like.

The examples of the arylcarbonyl group having a saturated heterocycle (a38) which further has one oxo group on the carbon atom of the heterocycle are

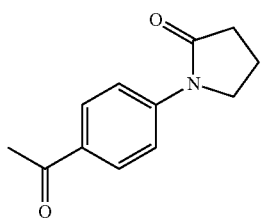

and the like.

Among each group of (b1)-(b7) shown as $Z^2$, (b2), (b3), (b5) and (b7) are mentioned above.

The examples of the lower alkenylcarbonyl group (b4) shown as $Z^2$ include acryloyl, methacryloyl, crotonoyl, isocrotonoyl groups and the like, preferably acryloyl group.

The examples of piperidino-lower alkylcarbonyl group having a saturated heterocycle (b6) shown as $Z^2$ include pyrrolidinopiperidinomethylcarbonyl, pyrrolidinylpiperidinoethylcarbonyl, piperidinopiperidinomethylcarbonyl, piperidyl-piperidinoethylcarbonyl, morpholinopiperidinoethylcarbonyl, piperazinopiperidinopropylcarbonyl groups and the like, preferably

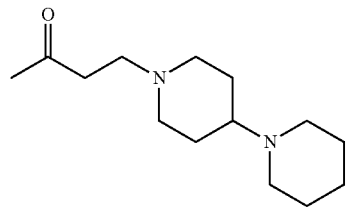

and the like.

The examples of the lower alkyl group which is optionally substituted on the amino moiety included as a part of the group of (b3) shown as $Z^2$ include methyl, ethyl, propyl, butyl, pentyl or hexyl, and structural isomers thereof such as isopropyl. Among them, methyl, ethyl and isopropyl groups are preferred. In addition, the examples of the lower alkyl group which is optionally substituted on the nitrogen atom of the saturated heterocyclic group included in each group of (b5)-(b7) are also the same as above. The preferable examples of the amino group having said lower alkyl group and the group having a saturated heterocycle which has said lower alkyl group on the nitrogen atom are dimethylaminomethylcarbonyl and 4-methylpiperazinocarbonyl group, respectively.

The examples of the lower alkoxy group (c2) shown as $Z^3$ include methoxy, ethoxy, t-butoxy, n-butoxy groups and the like, preferably ethoxy and t-butoxy groups.

The examples of the amino-lower alkylamino group (c4) shown as $Z^3$ include aminomethylamino, aminoethylamino, aminopropylamino, aminobutylamino groups and the like, preferably aminoethylamino and aminopropylamino groups.

The examples of the amino-lower alkylpiperazino group (c6) shown as $Z^3$ include aminomethylpiperazino, aminoethyl-piperazino, aminopropylpiperazino, aminobutylpiperazino groups and the like, preferably aminoethylpiperazino and aminopropylpiperazino groups.

The examples of the aminocarbonyl-lower alkylpiperazino group (c7) shown as $Z^3$ include aminocarbonylmethylpiperazino, aminocarbonylethylpiperazino, aminocarbonylpropylpiperazino, aminocarbonylbutylpiperazino groups and the like, preferably aminocarbonylmethylpiperazino group.

The examples of the amino-lower alkyl-1,4-diazepan-1-yl group (c9) shown as $Z^3$ include aminomethyl-1,4-diazepan-1-yl, aminoethyl-1,4-diazepan-1-yl, aminopropyl-1,4-diazepan-1-yl, aminobutyl-1,4-diazepan-1-yl groups and the like, preferably aminopropyl-1,4-diazepan-1-yl group.

The examples of the amino-lower alkylaminopiperidino group (c12) shown as $Z^3$ include aminomethylaminopiperidino, aminoethylaminopiperidino, aminopropylaminopiperidino, amino-butylaminopiperidino groups and the like, preferably aminoethylaminopiperidino group.

The examples of the amino-lower alkylpiperidino group (c13) shown as $Z^3$ include aminomethylpiperidino, aminoethylpiperidino, aminopropylpiperidino, aminobutylpiperidino groups and the like, preferably aminoethylpiperidino group.

The examples of the amino group having a saturated heterocycle (c15) shown as $Z^3$ include piperidinoamino, piperidylamino, piperazinoamino, piperazinylamino, pyrrolidinylamino, morpholinylamino groups and the like, preferably piperidinoamino and piperazinoamino groups.

The examples of the lower alkylamino group having a saturated heterocycle (c16) shown as $Z^3$ include piperidinoethylamino, piperidylmethylamino, pyrrolidinoethylamino, morpholinopropylamino, piperazinopropylamino groups and the like, preferably piperidinoethylamino group.

The examples of the piperazino group having a saturated heterocycle (c17) shown as $Z^3$ include piperidylpiperazino, morpholinylpiperazino groups and the like, preferably piperidylpiperazino group.

The lower alkylpiperazino group having a saturated heterocycle (c18) shown as $Z^3$ means a lower alkylpiperazino group substituted with a saturated heterocyclic group on the lower alkyl group thereof. The examples include pyrrolidinoethylpiperazino, morpholinoethylpiperazino, piperidinoethylpiperazino, piperidylethylpiperazino, piperidylmethylpiperazino, 1,3-dioxolanylmethylpiperazino, tetrahydrofurylmethylpiperazino groups and the like, preferably pyrrolidinoethylpiperazino, morpholinoethyl-piperazino, piperidinoethylpiperazino, piperidylmethyl-piperazino groups.

The examples of the carbonyl-lower alkylpiperazino group having a saturated heterocycle (c19) shown as $Z^3$ include pyrrolidinocarbonylmethylpiperazino, piperidinocarbonylethyl-piperazino groups and the like, preferably pyrrolidinocarbonylmethylpiperazino group.

The examples of the lower alkyl-1,4-diazepan-1-yl group having a saturated heterocycle (c20) shown as $Z^3$ include morpholinopropyl-1,4-diazepan-1-yl, piperidinoethyl-1,4-diazepan-1-yl groups and the like, preferably morpholinopropyl-1,4-diazepan-1-yl group.

The examples of the piperidino group having a saturated heterocycle (c21) shown as $Z^3$ include piperidinopiperidino, piperazinopiperidino, morpholinopiperidino, morpholinylpiperidino groups and the like, preferably piperidinopiperidino and piperazinopiperidino groups.

The examples of the lower alkylmorpholino group having a saturated heterocycle (c22) shown as $Z^3$ include piperidinomethylmorpholino, piperazinomethylmorpholino, 1,4-diazepan-1-ylmethylmorpholino groups and the like, preferably piperidinomethylmorpholino and piperazinomethylmorpholino groups.

The preferable examples of the amino group (c3) and the amino groups included as a part of the amino-lower alkylamino group (c4), the amino-lower alkylpiperazino group (c6), the aminocarbonyl-lower alkylpiperazino group (c7), the amino-lower alkyl-1,4-diazepan-1-yl group (c9), the aminopiperidino group (c11), the amino-lower alkylaminopiperidino group (c12), the amino-lower alkylpiperidino group (c13), the amino group having a saturated heterocycle (c15) and the lower alkylamino group having a saturated heterocycle (c16), which are substituted with 1-2 substituents selected from the group consisting of lower alkyl group, hydroxy-lower alkyl group, aryl group, heteroaryl group, aryl-lower alkyl group, alkoxyaryl-lower alkyl group, heteroaryl-lower alkyl group, lower alkylcarbonyl group and lower alkoxycarbonyl group, are shown below.

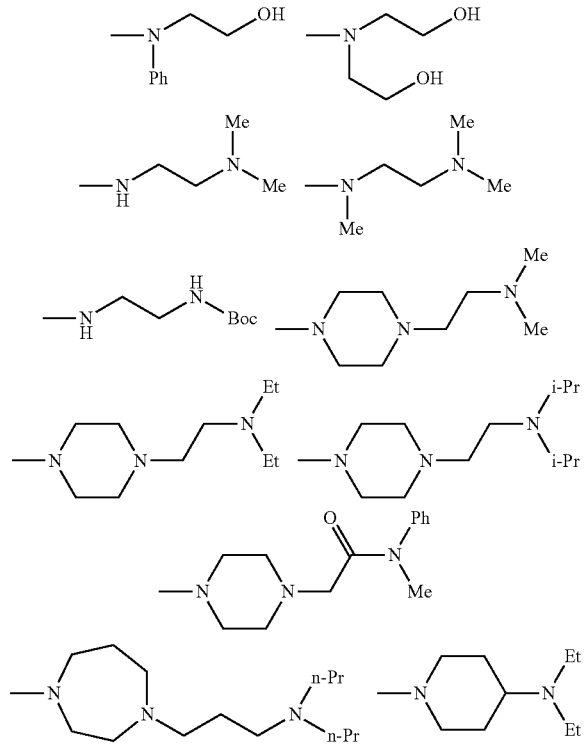

-continued

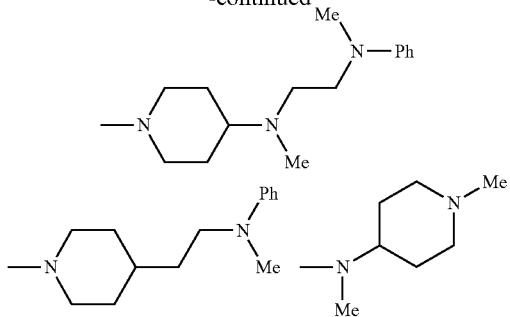

In the exemplified groups as shown above, Ph means phenyl group, Boc means t-butoxycarbonyl group, i-Pr means isopropyl group, n-Pr means n-propyl group, and Et means ethyl group (the same hereinafter).

The preferable examples of the amino group included as a part of the aminopiperidino group (c11) which is substituted with aryl-lower alkylcarbonyl group are shown below.

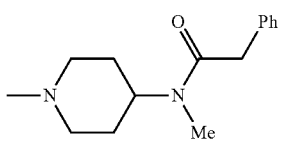

The preferable examples of the piperazino group (c5) and the 1,4-diazepan-1-yl group (c8), which have any one of the substituents selected from the group consisting of lower alkyl group, hydroxy-lower alkyl group, lower alkoxy-lower alkyl group, aryl group, lower alkylaryl group, hydroxylaryl group, cyanoaryl group, halogenoaryl group, aryl-lower alkyl group, lower alkoxyaryl-lower alkyl group, halogenoaryloxy-lower alkyl group, heteroaryl group, lower alkylheteroaryl group, halogeno-lower alkylheteroaryl group, cyanoheteroaryl group, heteroaryl-lower alkyl group, lower alkoxycarbonyl group and lower alkylcarbonyl group on 4-position of the rings, are shown below.

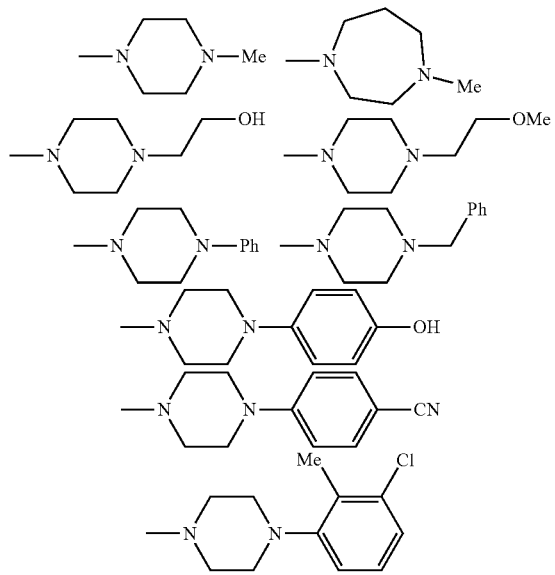

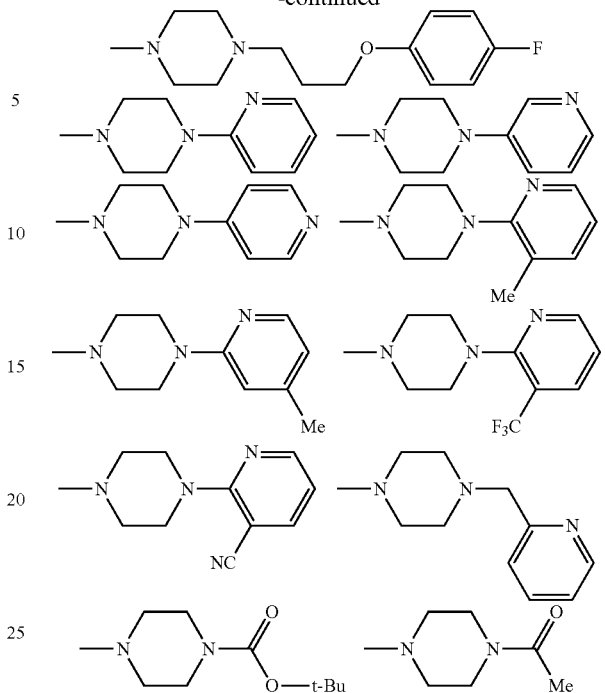

In the exemplified groups as shown above, OMe means methoxy group, and O-t-Bu means tert-butoxy group (the same hereinafter).

The preferable examples of the saturated heterocycle included as a part of the groups in (c15)-(c22), which has any one of substituents selected from the group consisting of lower alkyl group, aryl group, cyanoaryl group, lower alkylcarbonyl group, halogeno-lower alkylaryl group and aryl-lower alkyl group on the nitrogen atom in the ring, are shown below.

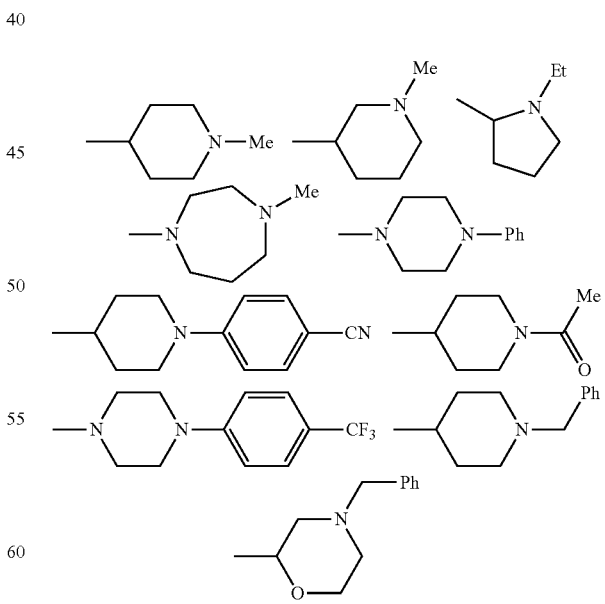

The preferable examples of piperazino group (c5), piperidino group (c10) and the saturated heterocycle included as a part of the groups in (c15)-(c22), which have any one of substituents selected from the group consisting of hydroxy group, oxo group, lower alkyl group, hydroxy-lower alkyl group, aryl group, aryl-lower alkyl group, aminocarbonyl group and lower alkylamino group on the carbon atom of the ring, are shown below.

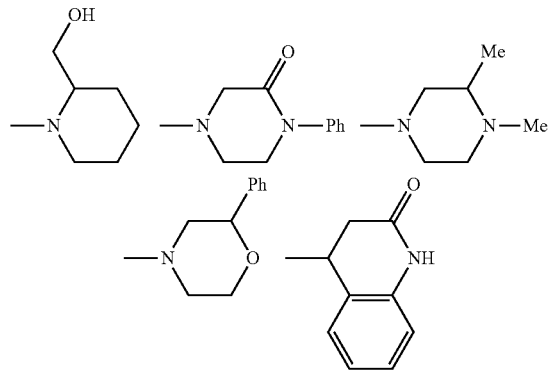

The preferable examples of the group having substituent(s) selected from the group consisting of lower alkyl group, aryl group, cyanoaryl group, lower alkylcarbonyl group, halogeno-lower alkylaryl group and aryl-lower alkyl group on the nitrogen atom of the saturated heterocycle included as a part of the groups in (c15)-(c22), and the preferable examples of the groups having substituents selected from the group consisting of hydroxy group, oxo group, lower alkyl group, hydroxy-lower alkyl group, aryl group, aryl-lower alkyl group, aminocarbonyl group and lower alkylamino group on the carbon atom of the saturated heterocycle are shown below.

The examples of the amino group having a saturated heterocycle (c15) which has a substituent on the heterocycle include

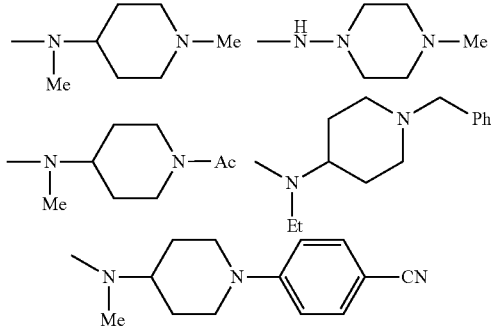

and the like.

The examples of the lower alkylamino group having a saturated heterocycle (c16) which has a substituent on the heterocycle include

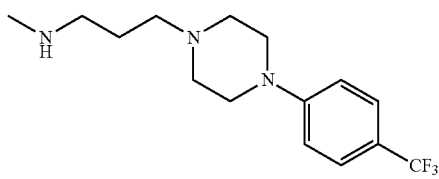

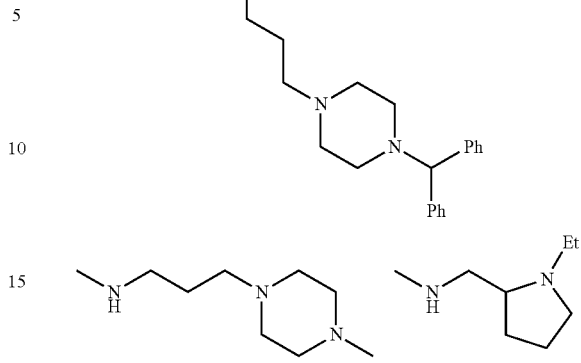

and the like.

The examples of the piperazino group having a saturated heterocycle (c17) which has a substituent on the heterocycle include

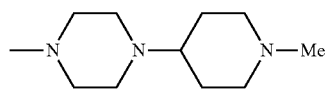

and the like.

The examples of the lower alkylpiperazino group having a saturated heterocycle (c18) which has a substituent on the heterocycle include

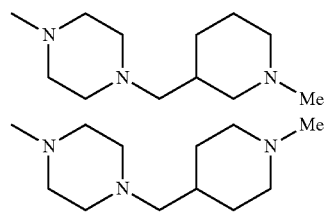

and the like.

The examples of the piperidino group having a saturated heterocycle (c21) which has substituents on the heterocycle include

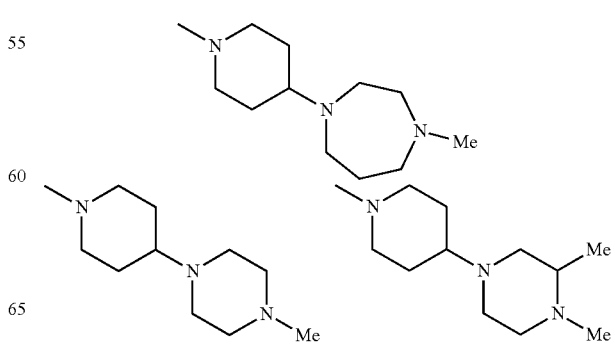

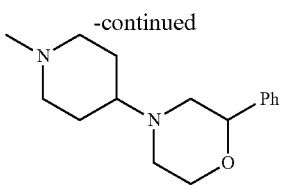

and the like.

The examples of the lower alkylmorpholino group having a saturated heterocycle (c22) include

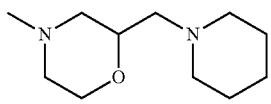

and the like, and the examples further having a substituent on the nitrogen atom of the heterocycle include

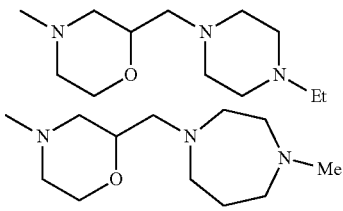

and the like.

The preferred compounds of the invention shown as the above-mentioned general formula (1) may include the compound wherein $R^2$ is a methylene group, and $R^3$ is a hydrogen atom or a lower alkyl group.

The second preferred compounds may include the compound wherein $R^1$ is a lower alkylcarbonyl group, $R^2$ is a methylene group, and $R^3$ is the group (3) or the group (6). Among such compounds, more preferred compounds may include the compound wherein $R^4$ is a lower alkylene group and $Z^1$ is any one group selected from (a2), (a14), (a15), (a28), (a32) and (a37).

The third preferred compounds may include the compound wherein $R^1$ is a lower alkylcarbonyl group, $R^2$ is a methylene group, and $R^3$ is the group (4), the group (5) or the group (7) provided that $Z^1$ is a lower alkoxycarbonyl group or a hydrogen atom.

The forth preferred compounds may include the compound wherein $R^1$ is a lower alkylcarbonyl group, $R^2$ is a methylene group, and $R^3$ is the group (8).

The fifth preferred compounds may include the compound wherein $R^1$ is a hydrogen atom or a lower alkylcarbonyl group, $R^2$ is a methylene group, and $R^3$ is the group (9), the group (10) or the group (11).

The sixth preferred compounds may include the compound wherein $R^1$ is a hydrogen atom or a lower alkylcarbonyl group, $R^2$ is a methylene group, and $R^3$ is the group (9), the group (10) or the group (11) provided that $Z^3$ is (c1), (c2), (c4), (c5), (c6), (c7), (c8), (c10), (c11), (c15), (c16), (c18), (c21) or (c22).

The seventh preferred compounds may include the compound wherein $R^1$ is an acetyl group, $R^2$ is a methylene group, and $R^3$ is the group (9) provided that $Z^3$ is (c4), (c5), (c6), (c10), (c11), (c16), (c18), (c21) or (c22).

The examples of the preferable compounds of the invention include the following compounds shown in 1)-19):

1) N-{4-[6-amino-5-cyano-2-(pyridin-2-ylmethylsulfanyl)-pyrimidin-4-yl]phenyl}acetamide,
2) N-{4-[6-amino-5-cyano-2-(6-methylpyridin-2-ylmethylsulfanyl)pyrimidin-4-yl]phenyl}acetamide,
3) N-{4-[6-amino-5-cyano-2-(6-{4-[2-(4-methylpiperazin-1-yl)-acetyl]piperazin-1-ylmethyl}pyridin-2-ylmethylsulfanyl)-pyrimidin-4-yl]phenyl}acetamide,
4) N-[4-(6-amino-5-cyano-2-{6-[3-(4-methylpiperazin-1-yl)-3-oxopropyl]pyridin-2-ylmethylsulfanyl}pyrimidin-4-yl)phenyl]-acetamide,
5) 3-{6-[4-(4-acetylaminophenyl)-6-amino-5-cyanopyrimidin-2-ylsulfanylmethyl]pyridin-2-yl}-N-(2-dimethylaminoethyl)-propionamide,
6) 3-{6-[4-(4-acetylaminophenyl)-6-amino-5-cyanopyrimidin-2-ylsulfanylmethyl]pyridin-2-yl}-N-(2-dimethylaminoethyl)-N-methylpropionamide,
7) 3-{6-[4-(4-acetylaminophenyl)-6-amino-5-cyanopyrimidin-2-ylsulfanylmethyl]pyridin-2-yl}-N-(2-dimethylaminopropyl)-N-methylpropionamide,
8) 3-{6-[4-(4-acetylaminophenyl)-6-amino-5-cyanopyrimidin-2-ylsulfanylmethyl]pyridin-2-yl}-N-(2-methylpiperidin-1-ylethyl)propionamide,
9) 3-{6-[4-(4-acetylaminophenyl)-6-amino-5-cyanopyrimidin-2-ylsulfanylmethyl]pyridin-2-yl}-N-(2-diethylaminoethyl)-propionamide,
10) 3-{6-[4-(4-acetylaminophenyl)-6-amino-5-cyanopyrimidin-2-ylsulfanylmethyl]pyridin-2-yl}-N-methyl-N-(1-methylpiperidin-4-yl)propionamide,
11) N-(4-{6-amino-2-[6-(3-[1,4']bipiperidinyl-1'-yl-3-oxopropyl)pyridin-2-ylmethylsulfanyl]-5-cyanopyrimidin-4-yl}phenyl)acetamide,
12) N-[4-(6-amino-5-cyano-2-{6-[3-oxo-3-(2-piperidin-1-ylmethylmorpholin-4-yl)propyl]pyridin-2-ylmethylsulfanyl}-pyrimidin-4-yl)phenyl]acetamide,
13) N-{4-[6-amino-5-cyano-2-(6-{3-[2-(4-ethylpiperazin-1-ylmethyl)morpholin-4-yl]-3-oxopropyl}pyridin-2-ylmethyl-sulfanyl)pyrimidin-4-yl]phenyl}acetamide,
14) N-{4-[6-amino-5-cyano-2-(6-{3-[4-(2-diethylaminoethyl)-piperazin-1-yl]-3-oxopropyl}pyridin-2-ylmethylsulfanyl)-pyrimidin-4-yl]phenyl}acetamide,
15) N-{4-[6-amino-5-cyano-2-(6-{3-[4-(2-diisopropylamino-ethyl)piperazin-1-yl]-3-oxopropyl}pyridin-2-yl-methyl-sulfanyl)pyrimidin-4-yl]phenyl}acetamide,
16) N-{4-[6-amino-5-cyano-2-(6-{3-oxo-3-[4-(2-pyrrolidin-1-ylethyl)piperazin-1-yl]propyl}pyridin-2-ylmethyl-sulfanyl)-pyrimidin-4-yl]phenyl}acetamide,
17) N-{4-[6-amino-5-cyano-2-(6-{3-[4-(2-morpholin-4-yl-ethyl)-piperazin-1-yl]-3-oxopropyl}pyridin-2-ylmethyl-sulfanyl)-pyrimidin-4-yl]phenyl}acetamide,
18) N-{4-[6-amino-5-cyano-2-(6-{3-[4-(2-diethylaminoethyl)-piperazin-1-yl]-3-oxopropyl}pyridin-2-ylmethylsulfanyl)-pyrimidin-4-yl]phenyl}acetamide, and
19) N-{4-(6-amino-5-cyano-2-{6-[3-(4-methyl-[1,4]diazepan-1-yl)-3-oxopropyl]pyridin-2-ylmethylsulfanyl}pyrimidin-4-yl)-phenyl]acetamide.

Some compounds of the invention may have their geometrical isomers or tautomeric forms due to a substituent, a double bond, an amide bond, etc. The present invention comprises all of the separated isomers thereof and the mixture thereof.

In addition, some compounds of the invention may have some asymmetric carbon atoms, hence may have some optical isomers due to the asymmetric carbon atoms. The present invention comprises all of the mixture of the optical isomers and the isolated isomers.

Further, the present invention comprises a radioisotope-labeled compound of the above-mentioned compounds of the invention.

In addition, the compounds of the invention include pharmacologically acceptable prodrugs thereof. The "pharmacologically acceptable prodrug" refers to a compound having a group (protective group) which may be transformed to the group of the compounds of the invention by solvolysis or physiological action and the like. The groups which may be included in prodrugs are known (see, e.g., Prog. Med., 5, 2157-2161, 1985; and "Pharmaceutical Research and Development" Vol 7, p 163-196, 1990 by Hirokawa Publishing Company). Such groups can be transformed to functional groups such as —NH$_2$, —OH, and —COOH by above solvolysis and so on. For example, the compounds of the invention having ethyl ester form such as the compound of Example 43 may be transformed to the compound of the invention having carboxylic acid form, that is, the compound of Example 45 with in vivo esterase.

Furthermore, the compound of the invention may be formed to a salt with acid or base according to the type of the substituent. The present invention includes such salt, especially salt with a pharmaceutically acceptable acid and base. The acid addition salts include, for example, salts with inorganic acid such as hydrochloric acid, hydrobromic acid, hydroiodic acid, sulfuric acid, nitric acid, and phosphoric acid; salts with organic acid such as formic acid, acetic acid, propionic acid, oxalic acid, malonic acid, succinic acid, fumaric acid, maleic acid, lactic acid, malic acid, citric acid, tartaric acid, carbonic acid, picric acid, methanesulfonic acid, ethanesulfonic acid, and glutamic acid. In addition, the examples of the base to form a salt include inorganic base such as sodium, potassium, magnesium, calcium and aluminum; organic base such as methylamine, ethylamine, meglumine and ethanolamine; and basic amino acid such as lysine, arginine and ornithine. The salts with a base also include ammonium salt. Such salts can be prepared by conventional procedures.

Additionally, the present invention also includes the hydrate, solvate and polymorph of the compound of the invention and the pharmaceutically acceptable salt thereof.

Preparation of the Compounds of the Invention

Hereinafter, the preparation of the compounds of the invention including the pharmaceutically acceptable salts thereof (hereinafter, referred to as "the compound(s) of the invention" unless otherwise indicated) is described in detail.

The compounds of the invention may be prepared according to various known methods, using appropriate starting compounds, corresponding to the basic structure thereof or the type of substituents. Then, depending on the type of functional group in the desired compound, it may be effective at the manufacturing technique that the functional group in the starting compound (or the intermediate compound) is substituted by an appropriate protective group which is a group easily transformable to the functional group. Such functional groups include —NH$_2$, —OH, —COOH and the like. The protective groups are exemplified by the textbook by Greene and Wuts, "Protective Groups in Organic Synthesis" 3rd edition, 1999 by John Wiley & Sons Inc. The substitution reaction of the protective group may be determined, depending on the type of protective group and according to the reaction condition described in the above textbook. In addition, by conventional processes, e.g. the methods described in the above textbook, the protective group introduced by the above substitution reaction can be cleaved from the compound after the desired compound is obtained by a suitable reaction.

The compounds of the invention can be prepared according to the method described in the following Scheme 1.

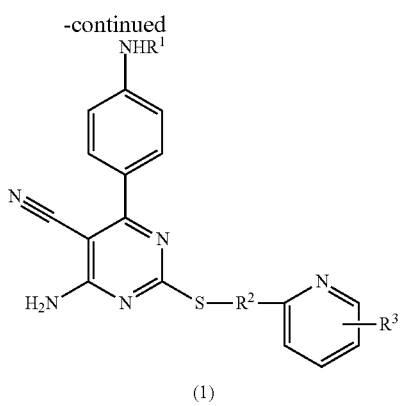

wherein $R^1$, $R^2$, and $R^3$ are as defined above, provided that $R^1$ is not a hydrogen atom. X is a halogen atom, an alkylsulfonyloxy group or an arylsulfonyloxy group.

The compounds (1) of the invention can be prepared from the aldehyde compound (the compound (2a)) via the dicyanoethylene compound (the compound (2b)) and 2-mercaptopyrimidine compound (the compound (2c)) or 2-mercaptodihydropyrimidine compound (the compound (2d)).

The compound (2a) used herein as the starting material is a known compound.

In addition, the compound (2d) includes an isomer which has a double bond differently positioned in the ring.

Each of the reactions shown in Scheme 1 may be carried out according to the methods described in each reference. In detail, the following method may make it possible.

First of all, the compound (2a) and the malononitrile compound (11) can be reacted according to the method of the reference (see, for example, W. S. Emerson, T. M. Patrick, J. Org. Chem., 790, 14, 1949). That is, the compound (2a) can be reacted with an equimolecular to an excess molecular amount of malononitrile (11) without solvent or in an inert solvent such as water, dimethylformamide (DMF), dimethyl sulfoxide (DMSO), diethyl ether, tetrahydrofuran (THF), dioxane, acetone, methyl ethyl ketone (MEK), methanol, ethanol, methylene chloride, dichloroethane, and chloroform to give the compound (2b). Preferably, the above reaction is carried out in an inert solvent, especially ethanol. Although the above reaction may be carried out without any catalyst, preferably a catalytic to an equimolar amount of catalyst to one mole of the compound (2a), may be used. The examples of the catalyst include an organic base such as piperidine or salt thereof, an amino acid such as glycine, and an ammonium salt such as ammonium acetate. The especially preferable base among them is piperidine. The temperature condition of the above reaction may be room temperature to enhanced temperature even if any solvent and catalyst are used or not. Especially, the room temperature is preferred.

Then the compound (2b) from the above reaction may be transformed to the compound (2c) or the compound (2d) or the mixture thereof by reaction with the thiourea (12). This reaction may be carried out according to the method of the reference (see, for example, Daboun, H. A.; El-Reedy, A. M.; Z. Naturforsch., 1983, 38 (12), 1686). To mention above in detail, the reaction can be carried out with an equimolecular to an excess molecular amount of the thiourea (12) to one mole of the compound (2b), without solvent or in an inert solvent such as water, DMF, DMSO, diethyl ether, THF, dioxane, acetone, MEK, methanol, ethanol, acetonitrile, methylene chloride, dichloroethane, and chloroform. In the reaction medium, some base such as potassium carbonate, sodium hydroxide, sodium acetate, sodium methoxide, sodium ethoxide, and triethylamine may be optionally added. Preferably, the above reaction may be carried out in ethanol in the presence of sodium ethoxide. The reaction temperature condition of the above reaction may be room temperature to enhanced temperature, preferably reflux temperature of the solvent.

Then, according to the method of Scheme 1, the compound (2c) or the compound (2d) or the mixture thereof which is obtained from the above reaction can be reacted with the compound (13) (i.e. the substituted pyridyl-lower alkyl compound having a leaving group such as halogen, arylsulfonyloxy group, alkylsulfonyloxy group) to provide the compounds of the invention (1) or the dihydro compound (2e) or the mixture thereof. This reaction may be carried out using an equimolecular to an excess molecular amount of compound (13) to one mole of compound (2c) or the compound (2d) or the mixture thereof. The reaction may be carried out without solvent or in an inert solvent such as DMF, DMSO, diethyl ether, THF, dioxane, acetone, MEK, methanol, ethanol, acetonitrile, methylene chloride, dichloroethane, and chloroform. In the reaction medium, some base such as potassium carbonate, sodium bicarbonate, sodium hydroxide, sodium acetate, sodium methoxide, sodium ethoxide, triethylamine may be further added when necessary. Among above conditions, especially the reaction using DMF as the reaction solvent and in the presence of sodium bicarbonate as the base is preferred. The reaction may be carried out at room temperature to enhanced temperature, preferably at room temperature.

The compound (13) which is used in the above reaction includes a novel compound through the type of $R^2$ group and $R^3$ group thereof. Such novel compounds will be mentioned below.

Furthermore, the dihydro compound (2e) of the invention obtained from the above reaction can be led to the compound (1) of the invention by an oxidation reaction. This reaction may be carried out without solvent or in an inert solvent such as water, DMF, DMSO, diethyl ether, THF, dioxane, acetone, MEK, methanol, ethanol, acetonitrile, ethyl acetate methylene chloride, dichloroethane, and chloroform, using a catalytic amount to an excess molecular amount of oxidizing agent to one mole of the dihydro compound (2e), such as DDQ (2,3-dichloro-5,6-dicyano-p-benzoquinone) and NBS (N-bromosuccinimide). In this way, the compounds of the invention (1) can be prepared. Among the above conditions, especially the reaction using ethanol as the reaction solvent and in the presence of NBS, or using dioxane as the reaction solvent and in the presence of DDQ is preferred. The temperature condition of the above reaction may be room temperature to enhanced temperature, preferably reflux temperature of the solvent.

The compounds of the invention may be also prepared according to the method of the following Scheme 2.

Scheme 2

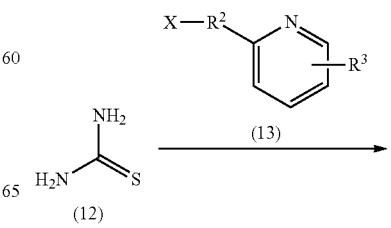

-continued

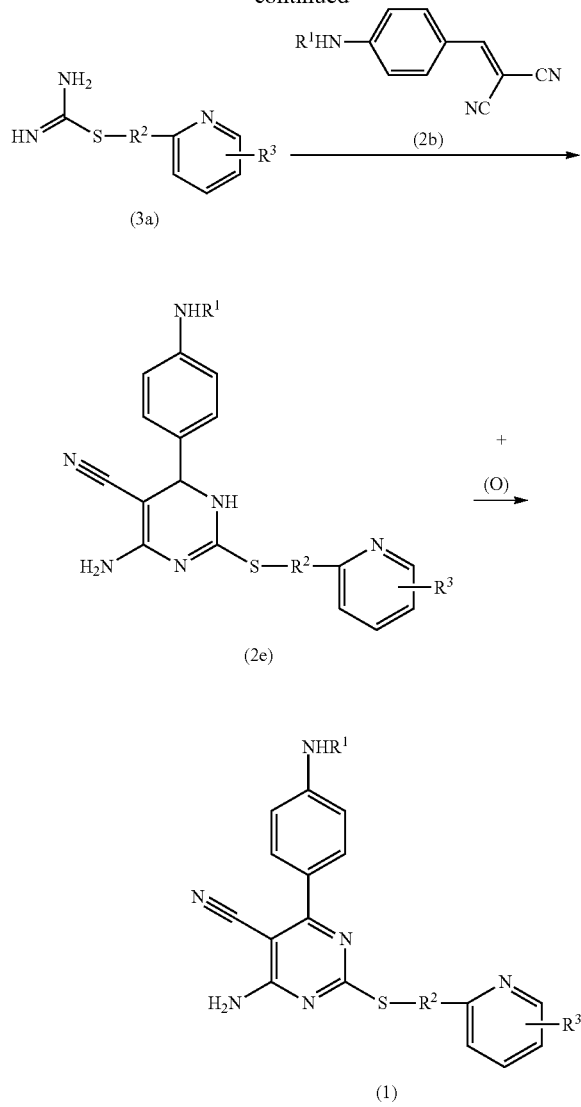

wherein $R^1$, $R^2$, $R^3$ and X are defined the same as above Scheme 1, provided that $R^1$ is not hydrogen atom.

According to the method of Scheme 2, the compound (1 of the invention can be prepared by the reaction between the compound (3a) which is prepared by the reaction between the thiourea (12) and the compound (13), and the compound (2b), via compound (2e). Accordingly, the compound (1) of the invention may be obtained as the mixture with the compound (2e) via the compound (2e) (the dihydropyrimidine compound) by the above reaction.

The compound (13) used herein as the starting compound includes both of a known compound and a novel compound as mentioned in above Scheme 1. Such novel compounds will be mentioned below.

In addition, the compound (2b) may be prepared by the reaction between the compound (2a) and the compound (11) shown in above scheme 1.

The compound (2e) includes the isomer which has a double bond differently positioned in the ring.

In the method shown in Scheme 2, first of all, an equimolecular to an excess molecular amount of the compound (13) to one mole of the thiourea (12) is reacted without solvent or in an inert solvent such as water, DMF, DMSO, diethyl ether, THF, dioxane, acetone, MEK, methanol, ethanol, acetonitrile, methylene chloride, dichloroethane, and chloroform. This reaction can be carried out according to the synthetic method of S-alkyl isothioureas described in the reference such as Urquhart, G. G.; Gates, J. W. Jr; Connor, R.; Org. Synth., 1941, 21, 36. In the reaction medium, some base such as potassium carbonate, sodium hydroxide, sodium acetate, sodium methoxide, sodium ethoxide, and triethylamine or some mineral acid such as hydrochloric acid and sulfuric acid, or some organic acid such as acetic acid may be optionally added. Preferably, the reaction solvent is ethanol. The reaction may be carried out at room temperature to enhanced temperature, preferably at enhanced temperature (especially, about 60° C.). In this way, the compound (3a) can be obtained as a free form or a salt form.

Then, to the obtained compound (3a) (it may be as a free form or a salt form), an equimolecular to an excess molecular amount of the compound (2b) is added without solvent or in an inert solvent such as DMF, DMSO, diethyl ether, THF, dioxane, acetone, MEK, methanol, ethanol, acetonitrile, methylene chloride, dichloroethane, and chloroform, and optionally added an equimolecular to an excess molecular amount of some base such as potassium carbonate, sodium bicarbonate, sodium hydroxide, sodium acetate, sodium methoxide, sodium ethoxide, triethylamine, and diisopropylethylamine to the reaction medium to proceed to the reaction. This reaction may be carried out according to the method of the reference (El-Sharabsy, S. A.; Abdel Gawad, S. M.; Hussain, S. M.; J. Prakt. Chem., 1989, 331 (2), 207). In this reaction, ethanol can be exemplified as a preferable solvent. In addition, it is also preferable to added sodium bicarbonate in the reaction medium. The reaction may be carried out at room temperature to enhanced temperature, preferably reflux temperature of the solvent. In this way, the compound (1) of the invention or the dihydro compound (2e) or the mixture thereof can be given.

The dihydro compound (2e) of the invention obtained above may be transformed to the compounds (1) of the invention by the oxidation reaction shown in above Scheme 1.

In the preparation of Scheme 2, the compound (3a) is prepared from the thiourea (12), and said compound is isolated and then this compound is reacted with the compound (2b). However, without isolating the compound (3a), the reaction wherein the compound (2b) is added to the reaction medium under the same condition can be also led to the compound (1) of the invention or the dihydro compound (2e) thereof or the mixture thereof.

The compound of the invention may be also prepared according to the method of the following Scheme 3.

Scheme 3

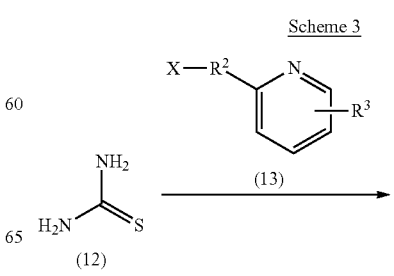

-continued

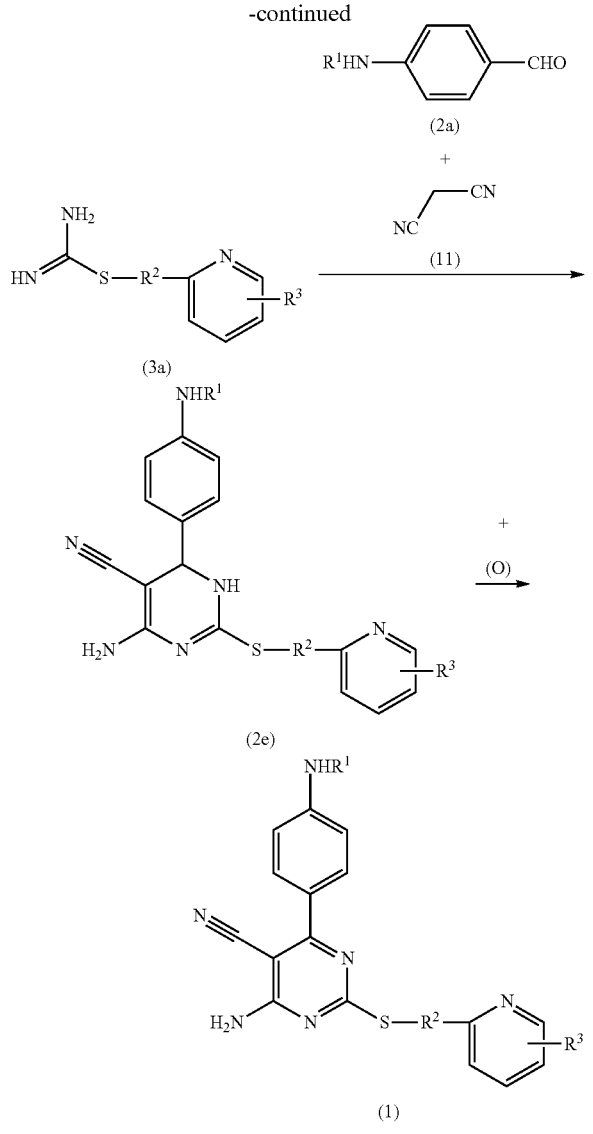

wherein $R^1$, $R^2$, $R^3$ and X are defined the same as above Scheme 1, provided that $R^1$ is not hydrogen atom.

According to the method of Scheme 3, with or without isolating the compound (3a) obtained by the reaction between the thiourea (12) and the compound (13), the compound (1) of the invention or the dihydro compound (2e) thereof or the mixture thereof can be obtained by reacting the compound (3a) simultaneously with the compound (2a) and malononitrile (11).

The preparing reaction of the compound (3a) is shown in above Scheme 2. The reaction of the compound (3a) with the compound (2a) and malononitrile (11) may be carried out as follows: the compound (3a) (it may be as a free form or a salt form) is reacted with an equimolecular to an excess molecular amount of compound (2a) and an equimolecular to an excess molecular amount of malononitrile (11) under the same reaction condition as above Scheme 2 to give the compound (1) of the invention or the dihydro compound (2e) thereof or the mixture thereof.

The dihydro compound (2e) of the invention obtained above may be transformed to the compound (1) of the invention by the oxidation reaction according to above Scheme 1.

Additionally, the compounds of the invention can be prepared according to known methods from the compounds obtained by above the various methods as the starting compound, as mentioned below.

Preparation of Starting Compound

The compound (13) which is used as the starting material in above Scheme 1-Scheme 3 includes a novel compound through the type of $R^2$ group and $R^3$ group thereof. For example, these compounds can be prepared according to the methods of the following Scheme 4-Scheme 9.

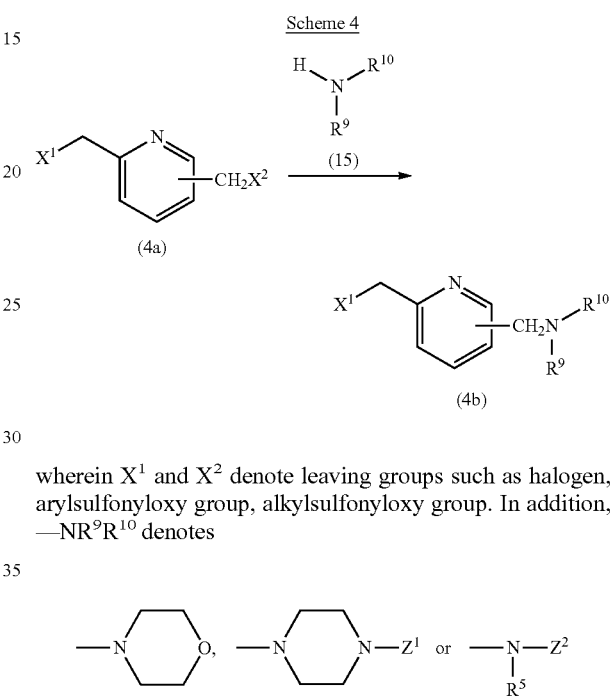

wherein $X^1$ and $X^2$ denote leaving groups such as halogen, arylsulfonyloxy group, alkylsulfonyloxy group. In addition, —$NR^9R^{10}$ denotes $$-N\diagdown O, \quad -N\diagdown N-Z^1 \quad or \quad -N-Z^2$$
$$\qquad\qquad\qquad\qquad\qquad\qquad\qquad\qquad\quad\; |$$
$$\qquad\qquad\qquad\qquad\qquad\qquad\qquad\qquad\; R^5$$

(in each group, $Z^1$, $Z^2$ and $R^5$ are defined the same as above the general formula (1)).

According to the method of Scheme 4, the starting material (compound (4b)) of the invention, wherein $R^2$ is methylene group, $R^3$ is the group (3), the group (6) or the group (8), can be prepared by the reaction between the known compound (4a) and the compound (15).

In the reaction, the compound (15) is generally used in an equimolecular to an excess molecular amount to one mole of the compound (4a). The reaction may be carried out without solvent or in an inert solvent such as DMF, DMSO, diethyl ether, THF, dioxane, acetone, MEK, methanol, ethanol, acetonitrile, methylene chloride, dichloroethane, and chloroform. Optionally, the reaction medium may include an equimolecular to an excess molecular amount of a base to one mole of the compound (4a), such as potassium carbonate, sodium bicarbonate, sodium hydroxide, sodium acetate, sodium methoxide, sodium ethoxide, triethylamine and diisopropylethylamine. In this way, the compound (4b) can be obtained. This reaction using ethanol as the solvent and using an excess molecular amount of the compound (15) to one mole of the compound (4a) and in the absence of a base is preferred. The reaction temperature may be room temperature to enhanced temperature, preferably room temperature.

Scheme 5

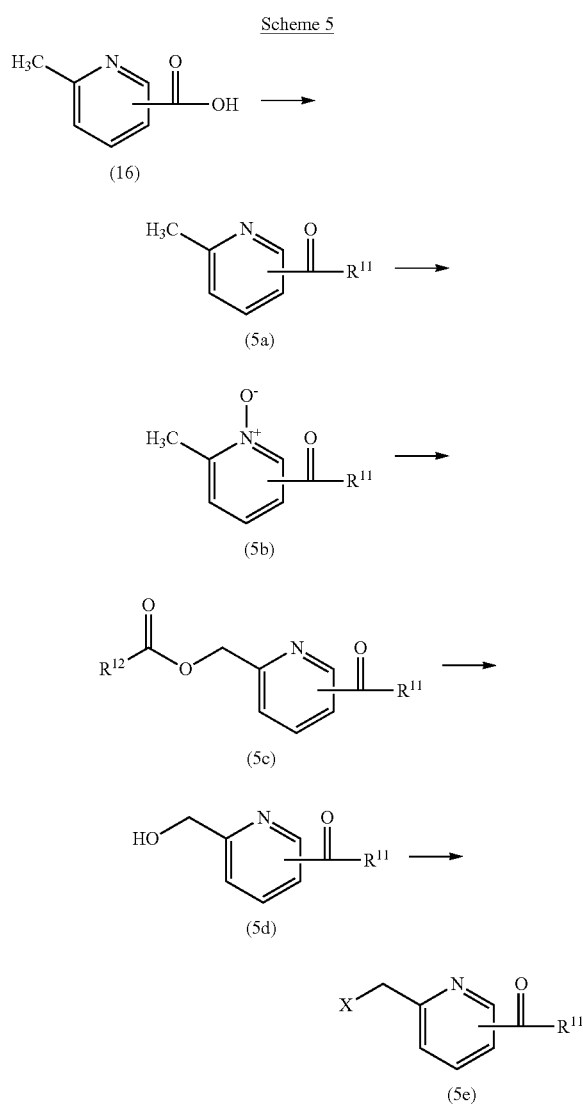

wherein $R^{11}$ denotes

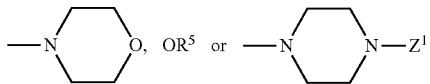

(in each group, $R^5$ and $Z^1$ are defined the same as the general formula (1)), $R^{12}$ denotes a lower alkyl group, an aryl group or a halogeno-lower alkyl group, and X is define the same as above Scheme 1.

According to Scheme 5, the starting material (the compound (5e)) of the invention, wherein $R^2$ is a methylene group, $R^3$ is the group (4), the group (5) or the group (7), can be prepared. Each the reaction shown in this method may be carried out as follows. That is, the compound (5a) which is obtained according to a conventional method from 6-methyl-2-picolinic acid (16) (or 6-methyl-3-picolinic acid, 6-methyl-4-picolinic acid, 6-methyl-5-picolinic acid) can be reacted with an equimolecular to an excess molecular amount of oxidizing agent such as m-chloroperbenzoic acid (m-CPBA) and hydrogen peroxide in an inert solvent such as diethyl ether, THF, dioxane, acetonitrile, methylene chloride, dichloroethane and chloroform to give the compound (5b). The reaction temperature may be ice temperature to reflux temperature of the solvent. Especially, this reaction using an excess amount of oxidizing agent such as m-CPBA in chloroform at room temperature is preferred.

Next, to the obtained compound (5b), an equimolecular to an excess molecular amount of organic acid anhydride such as acetic anhydride may be added without solvent or in an inert solvent such as DMF, DMSO, diethyl ether, THF, dioxane, acetone, MEK, methanol, ethanol, acetonitrile, methylene chloride, dichloroethane and chloroform and the mixture may be reacted at room temperature or with heat to give the compound (5c).

Furthermore, the obtained compound (5c) is hydrolyzed in an inert solvent such as water, diethyl ether, THF, dioxane, acetone, MEK, methanol, ethanol, acetonitrile, methylene chloride, dichloroethane and chloroform in the presence of an equimolecular to an excess molecular amount of base such as sodium hydroxide, potassium hydroxide, potassium carbonate, sodium bicarbonate, sodium acetate, sodium methoxide and sodium ethoxide at room temperature or with heat to give the compound (5d). Especially, this reaction in methanol with an excess amount of potassium hydroxide with heating to reflux is preferred. Besides, the compound (5d) obtained by this reaction can be also obtained directly in one step from the compound (5b). In this reaction, the compound (5b) can be reacted with an equimolecular to an excess molecular amount of trifluoroacetic anhydride in an inert solvent such as diethyl ether, THF, dioxane, acetone, MEK, acetonitrile, methylene chloride, dichloroethane and chloroform, or without solvent, and then hydrolyzed with water, methanol, ethanol and the like. Preferably, this reaction is carried out with an excess amount of trifluoroacetic anhydride without solvent, and then methanol is added thereto and the mixture is stirred.

In conclusion, the reaction from the compound (5d) to the compound (5e) can be carried out by the following three methods.

Method 1): The compound (5d) is reacted with an equimolecular to an excess molecular amount of halogenation agent such as thionyl chloride, thionyl bromide and oxalyl chloride without solvent or in an inert solvent such as diethyl ether, THF, dioxane, acetone, MEK, acetonitrile, methylene chloride, dichloroethane and chloroform.

Method 2): The compound (5d) is reacted with an equimolecular to an excess molecular amount of alkylsulfonyl chloride such as methanesulfonyl chloride without solvent or in inert solvent such as diethyl ether, THF, dioxane, acetone, MEK, acetonitrile, methylene chloride, dichloroethane and chloroform in the presence of an equimolecular to an excess molecular amount of base such as potassium carbonate, sodium bicarbonate, sodium hydroxide, sodium acetate, sodium methoxide, sodium ethoxide, triethylamine and diisopropylethylamine.

Method 3): The compound (5d) is reacted with an equimolecular to an excess molecular amount of halogenoalkyl such as carbon tetrachloride, chloroform and carbon tetrabromide in the presence of an equimolecular to an excess molecular amount of phosphine ligand such as triphenylphosphine and tri(n-butyl)phosphine in an inert solvent such as diethyl ether, THF, dioxane, acetone, MEK, acetonitrile, methylene chloride, dichloroethane and chloroform.

Scheme 6

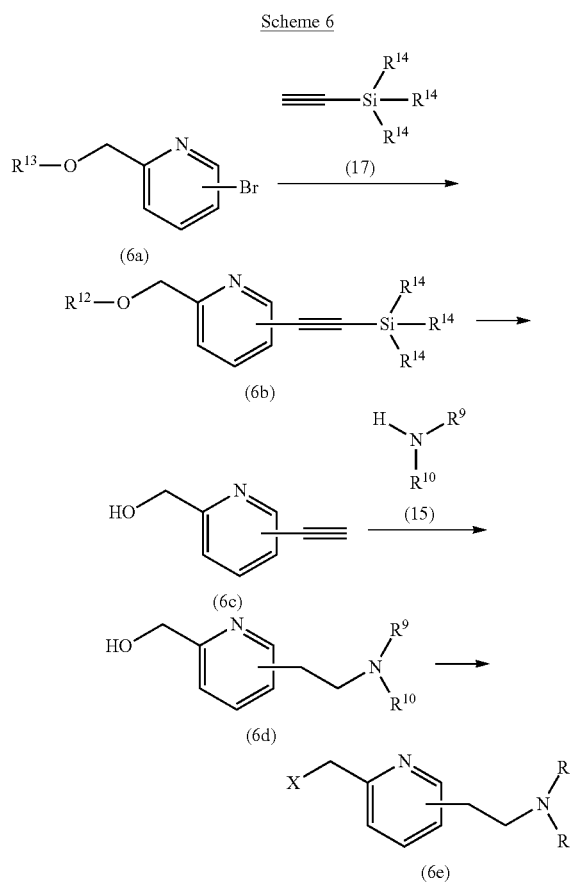

wherein R[13] denotes a hydrogen atom or a protective group, R[14] denotes a lower alkyl group. X is defined the same as above Scheme 1. R[9] and R[10] are defined the same as above Scheme 4.

The protective group mentioned above, which is shown as R[13], includes a conventional protective group for an alcoholic hydroxy group such as acetyl group, methoxymethyl group and tetrahydropyranyl group.

According to Scheme 6, the compound (6e) which is the starting material of the invention wherein R[4] is an ethylene group, R[3] is any one of the group (3), the group (6) and the group (8), can be prepared. Each the reaction shown in this method may be carried out as follows. That is, firstly the compound (6a) with or without a protective group on the hydroxy group is coupled with an equimolecular to an excess molecular amount of trialkyl silylacetylene (17) in a base such as triethylamine in the presence of a catalytic amount of organic metal catalyst such as bis(triphenylphosphine)-palladium (II) chloride, and an activator such as copper(I) iodide. This reaction can lead to the compound (6b).

Then, the compound (6b) may be desilylated in an inert solvent such as DMF, DMSO, diethyl ether, THF, dioxane, acetone, MEK, methanol, ethanol, acetonitrile, methylene chloride, dichloroethane and chloroform in the presence of an equimolecular to an excess molecular amount of base such as potassium carbonate and sodium hydroxide to give the compound (6c). In some case, the protective group cannot be cleaved due to the difference of the protective group R[12]. In this case, the protective group may be cleaved according to any conventional method.

Furthermore, to the obtained compound (6c), an equimolecular to an excess molecular amount of the compound (15) is added without solvent or in an inert solvent such as DMF, DMSO, diethyl ether, THF, dioxane, acetone, MEK, methanol, ethanol, acetonitrile, methylene chloride, dichloroethane and chloroform, and the mixture can be reacted at ice temperature to reflux temperature of the solvent, optionally in the presence of an equimolecular to an excess molecular amount of base such as potassium carbonate, sodium bicarbonate, sodium hydroxide, sodium acetate, sodium methoxide, sodium ethoxide, triethylamine and diisopropylethylamine to give the compound (6d). It is preferable to heat to reflux with an excess molecular amount of compound (15) in ethanol.

Finally, the compound (6d) can be reacted by the same synthetic method of the compound (5e) as above Scheme 5 to give the desired compound (6e).

Scheme 7

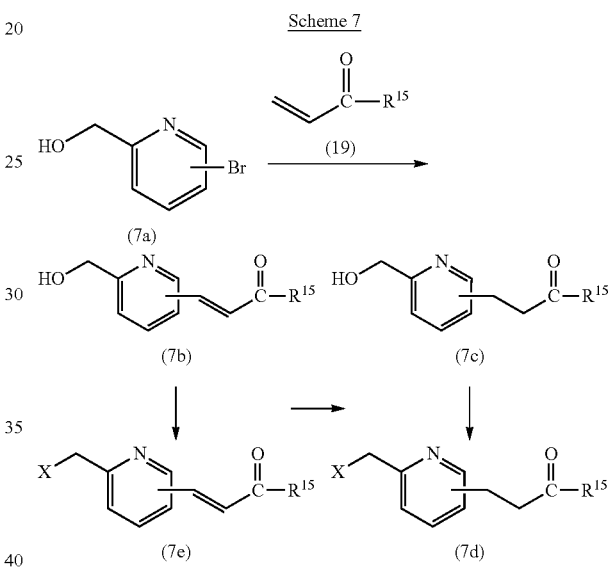

wherein R[15] denotes a lower alkoxy group. X is defined the same as above Scheme 1.

According to the method of Scheme 7, the starting material (the compound (7d)) of the invention wherein R[2] is a methylene group, R[3] is the group (9), and Z[3] is (c2) lower alkoxy group; and the starting material (the compound (7e)) of the invention wherein R[2] is a methylene group, R[3] is the group (10), and Z[3] is (c2) lower alkoxy group can be synthesized.

In this method, to mention below in detail, firstly the compound (7a) is reacted with an equimolecular to an excess molecular amount of the lower alkyl acrylate (19) to give the compound (7b). This reaction may be carried out according to the following two methods.

That is, the compound (7a) is reacted with the compound (19) without solvent or in an inert solvent such as DMF, DMSO, diethyl ether, THF, dioxane, acetone, MEK, methanol, ethanol, acetonitrile, methylene chloride, dichloroethane and chloroform, optionally under an inert gas such as argon and nitrogen, in the presence of an equimolecular to an excess molecular amount of base such as triethylamine and diisopropylethylamine, in the presence of a catalytic amount to an equimolecular amount of organic metal catalyst such as palladium(II) acetate and bis(triphenylphosphine) palladium chloride, and in the presence of an equimolecular to an excess molecular amount of phosphine ligand such as triphenylphosphine and tri(o-tolyl)phosphine, and at room temperature or with heat (Heck reaction) (Method 1).

The compound (7a) is reacted with the compound (19) without solvent or in an inert solvent such as DMF, DMSO, diethyl ether, THF, dioxane, acetone, MEK, methanol, ethanol, acetonitrile, methylene chloride, dichloroethane and chloroform, optionally under an inert gas such as argon and nitrogen, in the presence of an equimolecular to an excess molecular amount of base such as potassium carbonate, sodium bicarbonate, sodium hydroxide, sodium acetate, sodium methoxide, sodium ethoxide, triethylamine and diisopropylethylamine, in the presence of an equimolecular to an excess molecular amount of phase-transfer catalyst such as tetra(n-butyl)ammonium chloride and tetramethyl ammonium chloride, in the presence of a catalytic amount to an equimolecular amount of organic metal catalyst such as palladium(II) acetate and bis(triphenylphosphine)palladium chloride, and optionally in the presence of an additional dehydrator such as Molecular Sieves, and at room temperature or with heat (Heck reaction, Jeffery condition) (Method 2).

Among them, Method 2, especially the reaction under argon atmosphere in DMF in the presence of an equimolecular amount of tetra(n-butyl)ammonium chloride, an excess molecular amount of sodium bicarbonate, an excess molecular amount of Molecular Sieves (for example, "3A 1/16", see Showa Kagaku Chemical Database) and a catalytic amount of palladium(II) acetate at 80° C. is preferable.

Then, the obtained compound (7b) can be reacted with atmospheric or pressured hydrogen gas in an inert solvent such as DMF, DMSO, diethyl ether, THF, dioxane, methanol, ethanol, acetonitrile and methylene chloride at room temperature or with heat, in the presence of a catalytic amount of catalyst for hydrogenation such as platinum dioxide and palladium-carbon to give the compound (7c). Among these reactions, especially the reaction with vigorously stirring with atmospheric or pressured hydrogen gas (1-3 kgf/cm²) in methanol or ethanol at room temperature in the presence of a catalytic amount of platinum dioxide is preferable.

The compound (7c) obtained above can be transformed to the desired compound (7d) by the same method that the compound (5e) is obtained from the compound (5d) in above Scheme 5.

In addition, the above compound (7b) can be reacted by the same method that the compound (5e) is obtained from the compound (5d) in above Scheme 5 to give the compound (7e).

The starting material of the compound of the invention wherein R² is a lower alkylene group, and R³ is the group (9), the group (10) or the group (12) can be synthesized when an appropriate starting material is used in the method of Scheme 7.

Scheme 8

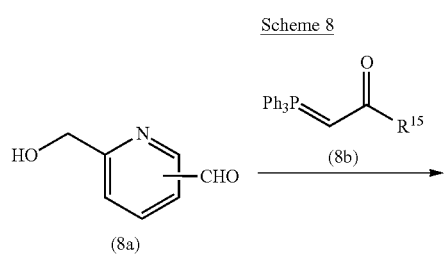

wherein R¹⁵ is defined the same as above Scheme 7. Ph denotes phenyl group.

As shown in above Scheme 8, the compound (7b) shown in above Scheme 7 can be also prepared using the known compound (8a) as the starting material according to Wittig reaction (A. Maercher, O R, 14, 270 (1965) B. E. Maryanoff et al., CRV, 89, 863 (1989)) or Wittig-Horner reaction (the reaction using a phosphonic acid ester instead of a phosphonium salt in Wittig reaction).

In the case of Wittig reaction, the desired compound (7b) can be obtained when the compound (8a) is reacted with an equimolecular to an excess molecular amount of the compound (8b) without solvent or in an inert solvent such as DMF, diethyl ether, THF, dioxane, methanol, ethanol, acetonitrile, methylene chloride, dichloroethane and chloroform, optionally under an inert atmosphere such as argon and nitrogen, at ice temperature, at room temperature or with heat. Especially, the reaction of an excess molecular amount of the compound (8b) in DMF is preferable. Wittig-Horner reaction can be carried out as the same way, using the corresponding phosphonate ester of the compound (8b) instead of the compound (8b), and an appropriate base such as sodium methoxide.

The starting material of the compounds of the invention wherein R² is a lower alkylene group, and R³ is the group (9), the group (10) or the group (12) can be synthesized when an appropriate starting material is used in the method of Scheme 8.

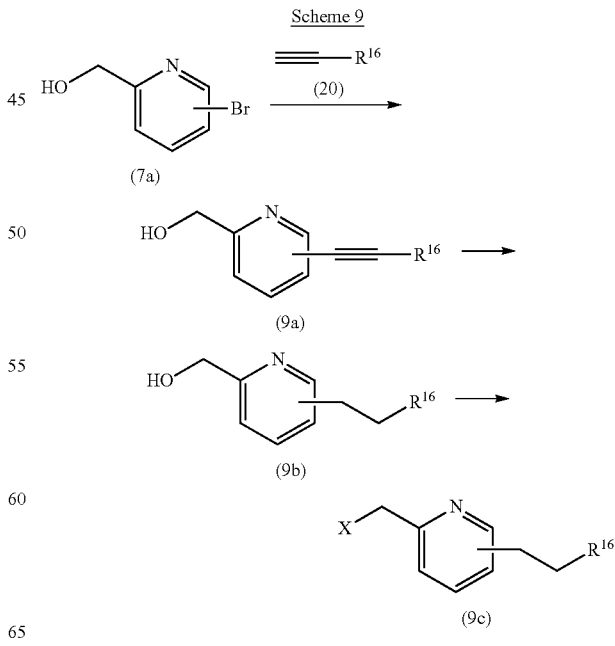

Wherein $R^{16}$ is a hydrogen atom, or

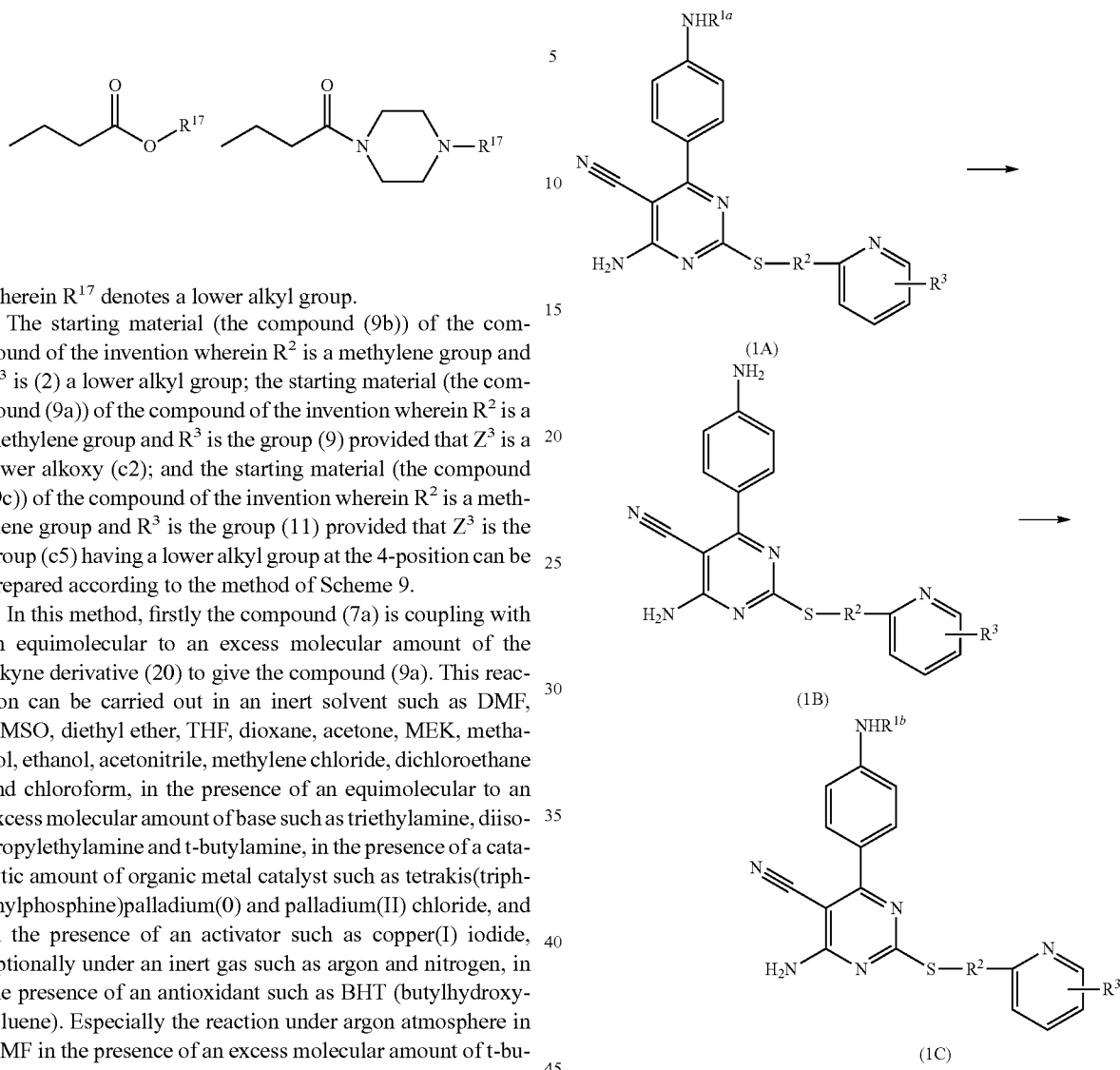

Scheme 10 wherein $R^{17}$ denotes a lower alkyl group.

The starting material (the compound (9b)) of the compound of the invention wherein $R^2$ is a methylene group and $R^3$ is (2) a lower alkyl group; the starting material (the compound (9a)) of the compound of the invention wherein $R^2$ is a methylene group and $R^3$ is the group (9) provided that $Z^3$ is a lower alkoxy (c2); and the starting material (the compound (9c)) of the compound of the invention wherein $R^2$ is a methylene group and $R^3$ is the group (11) provided that $Z^3$ is the group (c5) having a lower alkyl group at the 4-position can be prepared according to the method of Scheme 9.

In this method, firstly the compound (7a) is coupling with an equimolecular to an excess molecular amount of the alkyne derivative (20) to give the compound (9a). This reaction can be carried out in an inert solvent such as DMF, DMSO, diethyl ether, THF, dioxane, acetone, MEK, methanol, ethanol, acetonitrile, methylene chloride, dichloroethane and chloroform, in the presence of an equimolecular to an excess molecular amount of base such as triethylamine, diisopropylethylamine and t-butylamine, in the presence of a catalytic amount of organic metal catalyst such as tetrakis(triphenylphosphine)palladium(0) and palladium(II) chloride, and in the presence of an activator such as copper(I) iodide, optionally under an inert gas such as argon and nitrogen, in the presence of an antioxidant such as BHT (butylhydroxytoluene). Especially the reaction under argon atmosphere in DMF in the presence of an excess molecular amount of t-butylamine, a catalytic amount of tetrakis(triphenylphosphine)palladium(0), copper(I) iodide and BHT at 80° C. is preferable.

Then, the obtained compound (9a) can be reacted by the same method that the compound (7b) is transformed to the compound (7c) as shown in above Scheme 7 to give the compound (9b).

Furthermore, the compound (9b) is reacted by the same method that the compound (5d) is converted to the compound (5e) as shown in above Scheme 5 to give the desired compound (9c).

Some compounds of the invention may be also prepared according to various known synthetic methods from the other compounds of the invention obtained by above-mentioned methods as a starting material, using the properties based on the basic structure and the type of the substituent. Hereinafter, the preparing methods of the compounds of the invention that the present compound of the invention can be transformed to the other compound of the invention will be illustrated with showing the schemes.

wherein $R^2$ and $R^3$ are defined the same as above the general formula (1). $R^{1a}$ denotes a lower alkylcarbonyl group. $R^{1b}$ denotes a lower alkylcarbonyl group, a lower alkenyl-carbonyl group or a phenylcarbonyl group.

As shown in Scheme 10, the compound of the invention (the compound 1B) wherein $R^1$ is a hydrogen atom in the general formula (1) can be obtained, when the compound (1A) of the invention wherein $R^1$ is a alkylcarbonyl group such as acetyl group is reacted with an equimolecular to n excess molecular amount of base such as potassium carbonate, sodium bicarbonate, sodium acetate, sodium hydroxide, potassium hydroxide, sodium methoxide and sodium ethoxide, or acid such as hydrochloric acid, sulfuric acid, acetic acid and citric acid in an inert solvent such as water, DMF, DMSO, diethyl ether, THF, dioxane, acetone, MEK, methanol, ethanol, acetonitrile, methylene chloride, dichloroethane and chloroform, and hydrolyzed. The hydrolytic reaction can be carried out at room temperature to enhanced temperature. In particular, preferably the hydrolytic reaction is carried out by stirring in a mixture of ethanol and water with aqueous hydrochloric acid at 80° C.

The compound (1C) of the invention wherein $R^1$ is a lower alkylcarbonyl group, a lower alkenylcarbonyl group and a phenylcarbonyl group can be synthesized, when the compound (1B) of the invention wherein $R^1$ is a hydrogen atom is reacted with an equimolecular to an excess molecular amount of an acylation agent such as acid chloride and active ester, in an inert solvent such as DMSO, diethyl ether, THF, dioxane, acetone, MEK, acetonitrile, methylene chloride, dichloroethane and chloroform, in the presence of an equimolecular to an excess molecular amount of base such as potassium carbonate, sodium bicarbonate, sodium acetate, sodium hydroxide, potassium hydroxide, triethylamine and diisopropylethylamine, at ice temperature, at room temperature or at enhanced temperature.

In particular, preferably this reaction is carried out by reacting with an excess molecular amount of acid chloride in the presence of an excess molecular amount of triethylamine in acetonitrile at room temperature.

Scheme 11

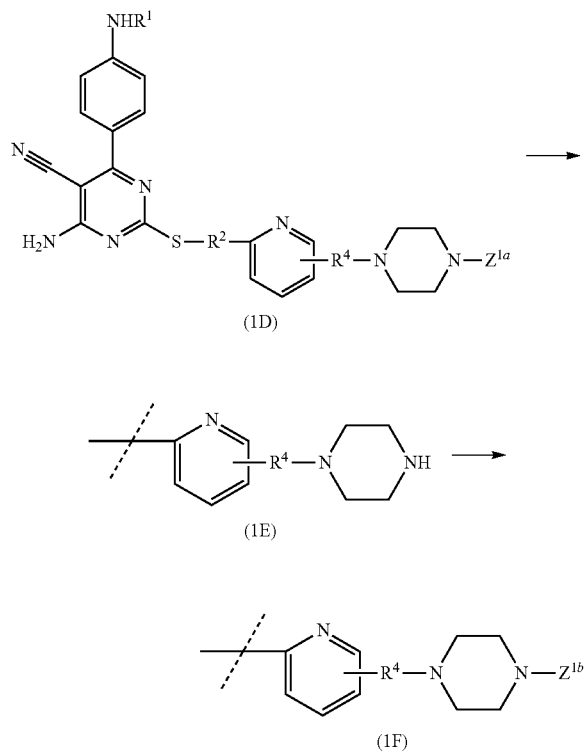

wherein $R^1$, $R^2$ and $R^4$ are defined the same as the above general formula (1). $Z^{1a}$ denotes (a12) a lower alkylcarbonyl group or (a28) a lower alkoxycarbonyl group. And $Z^{1b}$ is defined the same as the $Z^1$ group of the general formula (1) except a hydrogen atom, that is, it denotes any one of the groups selected from (a1)-(a31) and (a33)-(a38) of the general formula (1).

As shown in Scheme 11, the compound (1E) of the invention wherein $R^3$ is the group (6) and $Z^1$ is (a32) a hydrogen atom in the general formula (1) can be synthesized when the leaving group is cleaved from the compound (1D) of the invention wherein $R^3$ is the group (6) and $Z^1$ is the group of (a12) or (a28), that is, the compound has a group to be cleaved. To mention above in detail, the compound (1E) can be obtained, when the compound (1D) of the invention is reacted with an equimolecular to an excess molecular amount of base such as potassium carbonate, sodium bicarbonate, sodium acetate, sodium hydroxide, potassium hydroxide, sodium methoxide, and sodium ethoxide, or mineral acid such as hydrochloric acid and sulfuric acid, or organic acid such as acetic acid, trifluoroacetic acid and citric acid in an inert solvent such as water, DMF, DMSO, diethyl ether, THF, dioxane, acetone, MEK, methanol, ethanol, acetonitrile, methylene chloride, dichloroethane and chloroform or without solvent, and hydrolyzed. The hydrolytic reaction may be carried out at ice temperature, at room temperature or at enhanced temperature. In particular, it is preferable that the compound of the invention wherein $Z^{1a}$ is BOC group (t-butoxycarbonyl group) is stirred with an excess amount of trifluoroacetic acid at room temperature without solvent.

As shown in Scheme 11, the compound (1F) of the invention wherein $R^3$ is the group (6) and $Z^1$ is any one of the groups selected from (a1)-(a31) and (a33)-(a38) in the general formula (1) can be synthesized from the compound (1E) of the invention wherein $R^3$ is the group (6) and $Z^1$ is (a32) a hydrogen atom in the general formula according as the type of the $Z^1$ group thereof as follows.

That is, the compound (1E) can be reacted with an equimolecular to an excess molecular amount of an acylation agent such as alkylcarbonyl chloride, arylcarbonyl chloride and active ester in an inert solvent such as DMF, DMSO, diethyl ether, THF, dioxane, acetone, MEK, acetonitrile, methylene chloride, dichloroethane and chloroform in the presence of an equimolecular to an excess molecular amount of base such as potassium carbonate, sodium bicarbonate, sodium acetate, sodium hydroxide, potassium hydroxide, triethylamine and diisopropylethylamine at ice temperature, at room temperature or at enhanced temperature to provide the compound of the invention wherein $Z^1$ is the substituted carbonyl group of (a12)-(a28) or (a36)-(a38). It is preferable to react with an excess molecular amount of the substituted carbonyl chloride in acetonitrile in the presence of triethylamine.

The compound (1E) can be reacted with an equimolecular to an excess molecular amount of the carboxylic acid compound having a variety of substituents in an inert solvent such as DMSO, diethyl ether, THF, dioxane, acetone, MEK, acetonitrile, methylene chloride, dichloroethane and chloroform in the presence of an equimolecular to an excess molecular amount of a condensing agent such as DCC, WSC, BOP and DEPC, optionally in the presence of an equimolecular to an excess molecular amount of an activating agent such as HOSu, HOBt and HOOBt to give the compound of the invention wherein $Z^1$ is the substituted carbonyl group of (a12)-(a28) or (a36)-(a38). The reaction can be carried out at any temperature condition of ice temperature, room temperature and enhanced temperature. In particular, it is preferable that the reaction is carried out in the presence of WSC and HOBt at room temperature.

The compound (1E) can be reacted with an equimolecular to an excess molecular amount of a sulfonylating agent such as alkylsulfonyl chloride and arylsulfonyl chloride in the presence of an equimolecular to an excess molecular amount of base such as potassium carbonate, sodium bicarbonate, sodium acetate, sodium hydroxide, potassium hydroxide, triethylamine and diisopropylethylamine in an inert solvent such as DMF, DMSO, diethyl ether, THF, dioxane, acetone, MEK, acetonitrile, methylene chloride, dichloroethane and chloroform to provide the compound of the invention wherein $Z^1$ is any one of the groups selected from (a29)-(a31). The reaction can be carried out at any temperature condition of ice temperature, room temperature and enhanced temperature. In particular, it is preferable that the reaction is carried out in the presence of an excess molecular amount of diisopropyl-ethylamine in DMF at room temperature.

The compound (1E) can be reacted with an equimolecular to an excess molecular amount of alkylating agent including alkenylating agent such as alkyl halide (e.g. alkyl chloride) and alkylmethane sulfonate in the presence of an equimolecular to an excess molecular amount of base such as potassium carbonate, sodium bicarbonate, sodium acetate, sodium hydroxide, potassium hydroxide, triethylamine and diisopropylethylamine in an inert solvent such as DMF, DMSO, diethyl ether, THF, dioxane, acetone, MEK, acetonitrile, methylene chloride, dichloroethane and chloroform to provide the compound of the invention wherein $Z^1$ is any one of the groups selected from (a1)-(a11) and (a33)-(a35). The reaction can be carried out at any temperature condition of ice temperature, room temperature and enhanced temperature. In particular, it is preferable that the reaction is carried out with an excess molecular amount of an alkylating agent, preferably alkyl halide in the presence of an excess molecular amount of potassium carbonate in DMF at room temperature.

The compound (1E) can be reacted with an equimolecular to an excess molecular amount of the aldehyde compound having the corresponding substituent in an inert solvent such as DMF, DMSO, diethyl ether, THF, dioxane, acetonitrile, methylene chloride, dichloroethane, chloroform, methanol and ethanol, optionally in the presence of a catalytic amount to an excess molecular amount of catalyst such as acetic acid to give the isolated or unisolated imine compound. And the imine compound can be reacted with an equimolecular to an excess molecular amount of a reducing agent to one mole of the compound (1E), such as sodium borohydride, sodium cyanoborohydride and diborane to provide the compound of the invention wherein $Z^1$ is any one of the groups selected from (a1)-(a11) and (a33)-(a35) (reductive alkylation). The reaction can be carried out at any temperature condition of ice temperature, room temperature and enhanced temperature. It is preferable that the compound (1E) is reacted with an excess molecular amount of the aldehyde compound in the presence of 5 times of acetic acid and an excess molecular amount of sodium cyanoborohydride in DMF at room temperature.

The compound of the invention wherein $R^3$ is the group (7) and $Z^1$ is (a32) a hydrogen atom in the general formula (1) and the compound of the invention wherein $R^3$ is the group (8) and $Z^2$ is (b1) a hydrogen atom in the general formula (1) can be also synthesized from the compound of the invention wherein $R^3$ is the group (7) and $Z^1$ is any group of (a12) and (a28) in the general formula (1) and the compound of the invention wherein $R^3$ is the group (8) and $Z^2$ is the group of (b2) in the general formula (1) as the starting material as similar reaction to obtain the compound (1E) from the compound (1D) as shown in above Scheme 11.

In additions the compound of the invention wherein $R^3$ is the group (7) and $Z^1$ is any group of (a1)-(a31) or (a33)-(a38) in the general formula (1) and the compound of the invention wherein $R^3$ is the group (8) and $Z^2$ is any group of (b2)-(b8) in the general formula (1) can be prepared from the compound of the invention wherein $R^3$ is the group (7) and $Z^1$ is (a32) a hydrogen atom in the general formula (1) and the compound of the invention wherein $R^3$ is the group (8) and $Z^2$ is (b1) a hydrogen atom in the general formula (1) as the starting material as similar reaction to obtain the compound (1F) from the compound (1E) as shown in above Scheme 11.

Scheme 12

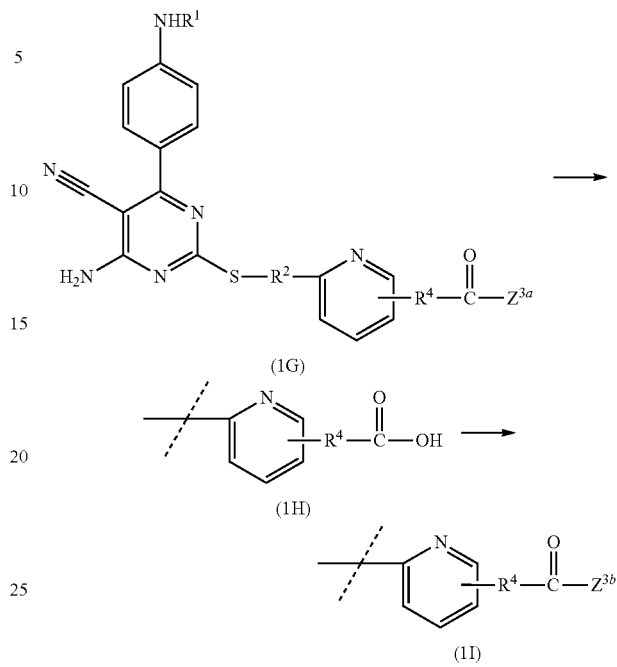

wherein $R^1$, $R^2$ and $R^4$ is defined the same as the above general formula (1). $Z^{3a}$ denotes (c2) a lower alkoxy group. $Z^{3b}$ is the $Z^3$ group of the general formula (1) except a hydroxy group and a lower alkoxy group, that is, any one of groups of (c3)-(c22) in the general formula (1).

As shown in Scheme 12, the compound of the invention (1H) wherein $R^3$ is the group (9) and $Z^3$ is (c1) a hydroxy group can be synthesized from the compound (1G) of the invention wherein $R^3$ is the group (9) and $Z^3$ is a lower alkoxy group. This reaction can be carried out, for example, when the compound (1G) of the invention is reacted with an equimolecular to an excess molecular amount of base such as potassium carbonate, sodium bicarbonate, sodium acetate, sodium hydroxide, potassium hydroxide, sodium methoxide and sodium ethoxide, mineral acid such as hydrochloric acid and sulfuric acid or organic acid such as acetic acid, trifluoroacetic acid and citric acid in an inert solvent such as water, DMF, DMSO, diethyl ether, THF, dioxane, acetone, MEK, methanol, ethanol, acetonitrile, methylene chloride, dichloroethane and chloroform or without solvent, and hydrolyzed. The hydrolytic reaction may proceed at ice temperature, at room temperature or at enhanced temperature. In particular, it is preferable that the compound of the invention wherein $Z^{3a}$ is tert-butoxy group is stirred with an excess amount of trifluoroacetic acid at room temperature without solvent.

In addition, as shown in Scheme 12, the compound (1I) of the invention wherein $R^3$ is the group (9) and $Z^3$ is the group selected from (c3)-(c22) in the general formula (1) can be synthesized from the compound (1H) of the invention wherein $R^3$ is the group (9) and $Z^3$ is (c1) a hydroxy group. To mention above in detail, this method can be carried out when the compound (1H) of the invention is reacted with an equimolecular to an excess molecular amount of the amine or aliphatic nitrogen-containing heterocyclic compound having the appropriate substituent corresponding to the desired $Z^3$ in an inert solvent such as DMF, DMSO, diethyl ether, THF, dioxane, acetone, MEK, acetonitrile, methylene chloride, dichloroethane and chloroform in the presence of an equimolecular to an excess molecular amount of a condensing agent such as DCC, WSC, BOP and DEPC, optionally in the presence of an equimolecular to an excess molecular amount of an activating agent such as HOSu, HOBt, HOOBt. In this way, the compound (1I) of the invention wherein $Z^3$ is the group selected from (c3)-(c20) can be provided. The reaction can be carried out at any temperature condition of ice temperature, room temperature and enhanced temperature. In particular, it is preferable to react in DMF or acetonitrile in the presence of BOP or WSC and HOBt at room temperature.

The compound of the invention wherein $R^3$ is the group (10) and $Z^3$ is (c1) a hydroxy group in the general formula (1) and the compound of the invention wherein $R^3$ is the group (11) and $Z^3$ is (c1) a hydroxy group in the general formula (1) can be also synthesized from the compound of the invention wherein $R^3$ is the group (12) and $Z^3$ is (c2) a lower alkoxy group in the general formula (1) and the compound of the invention wherein $R^3$ is the group (11) and $Z^3$ is (c2) a lower alkoxy group in the general formula (1) as a starting material as similar reaction to obtain the compound (1H) from the compound (1G) as shown in above Scheme 12.

In addition, the compound of the invention wherein $R^3$ is the group (10) and $Z^3$ is any group of (c3)-(c22) in the general formula (1) and the compound of the invention wherein $R^3$ is the group (11) and $Z^3$ is any group of (c3)-(c22) in the general formula (1) can be prepared from the compound of the invention wherein $R^3$ is the group (10) and $Z^3$ is (c1) a hydroxy group in the general formula (1) and the compound of the invention wherein $R^3$ is the group (11) and $Z^3$ is (c1) a hydroxy group in the general formula (1) as a starting material as similar reaction to obtain the compound (1I) from the compound (1H) as shown in above Scheme 12.

The desired compounds of each process shown in above each scheme and the compounds of the invention can be isolated or purified as a free form or a salt form thereof according to a conventional method. The means of such isolation and purification include some conventional chemical operations such as extraction, concentration, distillation, crystallization, filtration, re-crystallization and various types of chromatography.

When the compound of the invention is a mixture of isomers as mentioned above, each the isomer may be isolated by a conventional method using the different physical properties between the isomers. In more detail, the separation of a stereochemically pure isomer from racemic compounds can be carried out by a conventional racemic separation in which the racemic compounds are formed to diastereomeric salts with a usual optically active acid such as tartaric acid and then separated. The separation of each isomer from a diastereomeric mixture can be carried out, for example, by fractional crystallization and chromatography. In addition, the optically active compounds of the invention can be also prepared when using an optically active starting compound.

Pharmaceutical Composition of the Invention

The compounds of the invention and the salts thereof have an adenosine A2a receptor agonistic activity and thus they are useful as an adenosine A2a receptor agonist for mammals including human beings. Accordingly, the present inventions also provide pharmaceutical compositions as a medicament such as the adenosine A2a receptor agonist.

The present pharmaceutical composition can be prepared to a usual pharmaceutical formulation comprising an effective amount of one or more compounds selected from the group consisting of the compounds of the invention and the salts thereof, and some pharmaceutically acceptable carriers. The pharmaceutically acceptable carriers used in the pharmaceutical composition of the invention may be a solid such as excipient or a liquid such as diluent. The examples of these carriers include lactose, magnesium stearate, starch, talc, gelatine, agar, pectin, gum arabic, olive oil, sesame oil, cacao butter, ethylene glycol and the like.

In addition, the pharmaceutical composition can be prepared in formulation of dosage unit suitable for administration. The examples include a solid and liquid formulation suitable for oral administration such as tablet, pill, capsule, granule, powder and liquid as well as a formulation for parenteral administration such as injection (intravenous injection, intramuscular injection, etc.), eye drops, ophthalmic ointment, suppository, percutaneous absorption agent and the like. In particular, the preferable pharmaceutical formulation is an eye drops since it is considered that the pharmaceutical composition of the invention can be used as an intraocular pressure reducing agent, a medicine for the treatment of glaucoma and the like based on the adenosine A2a receptor agonistic activity thereof.

The eye drops can be prepared according to a conventional method, for example, optionally adding an isotonic agent such as sodium chloride, glycerin; a stabilizer such as sodium edetate; an antiseptic such as benzalkonium chloride and parabens; a pH adjuster such as disodium hydrogen phosphate, sodium dihydrogen phosphate, boric acid, sodium tetraborate (borax), hydrochloric acid and sodium hydroxide to the compound of the invention (including the salt thereof, the same hereinafter).

The solid medicament of the present invention for oral administration such as tablet, powder and granule can be prepared by mixing the compound of the invention with at least one inert carrier such as lactose, mannitol, glucose, hydroxypropyl cellulose, microcrystalline cellulose, starch, polyvinyl pyrrolidone, meta-silicic acid and magnesium aluminate, and forming the mixture according to a conventional method. The preparation may further incorporated by additional appropriate additives, for example, a lubricant such as magnesium stearate; a disintegrator such as carmellose calcium; a stabilizer such as lactose; a solubilizing agent such as glutamic acid and aspartic acid; and the like. It may further incorporated by a sweetener, a flavor, a perfume, an antiseptic agent and the like. The tablet and pill may be coated with a sugar-coating film such as sucrose, gelatin, hydroxypropyl cellulose and hydroxypropylmethyl cellulose phthalate or a film of intragastric- or enteric-coated material when necessary.

The liquid medicament for oral administration such as emulsion, solution, suspension, syrup and elixir can be prepared by solving or dispersing the compound of the invention in an inert diluent used in general such as purified water and ethanol. The liquid medicament may also contain an auxiliary agent such as wetting agent and suspending agent, a sweetener, a flavor, perfume, an antiseptic agent and the like.

The injection for parenteral administration includes aseptic aqueous or nonaqueous solution, suspension, emulsion and the like, and the aqueous solution and suspension can be prepared according to a conventional method, for example, using distilled water for injection and saline as a diluent. The nonaqueous solution and suspension can be prepared according to a conventional method, for example, using propylene glycol, polyethylene glycol or vegetable oil such as olive oil; alcohols such as ethanol; diluent or carrier such as polysorbate 80. The solution or suspension may further contain an auxiliary agent such as an antiseptic agent, a wetting agent, an emulsifying agent, a dispersing agent, a stabilizer (e.g., lactose) and a solubilizing agent (e.g., glutamic acid and aspartic acid). The injection is sterilized according to a conventional method, for example, by filtration with the filter for removal of bacteria, addition of antimicrobial or radiation such as gamma-ray. In addition, the injection can be also prepared as the extemporaneously preparing formulation, which the prepared aseptic solid medicament is dissolved with aseptic water or aseptic solvent for injection before use.

The dosage regimen for the pharmaceutical composition of the present invention in each the formulation will be determined in each case depending on the condition of the patients to which the pharmaceutical composition is administered (subject for administration), age, sex and so on. In general, the dosage of the eye drops which comprises the pharmaceutical composition of the present invention can be determined to be the amount so that the eye drops containing the active compound in a concentration of 0.0001-10% (w/v) is dropped or swabbed once to several times a day. The amount of the eye drops for one usage is generally about 0.001-1 mL for an adult.

In the case of the oral medicament or the injection of the pharmaceutical composition of the invention, the dosage can be determined so that the compound of the invention is administered in an amount of 0.001-1000 mg per day in adult. The daily dose may be administered once a day, but preferably be divided in several times. The above dosage is only guideline and hence it may be also increased or decreased. As mentioned above, it is hopeful to determine the dosage every time to be used depending on various conditions. Accordingly, depending on the conditions, the reduced dosage may still exhibit sufficient effects.

INDUSTRIAL APPLICABILITY

The compounds of the invention exhibit the action activating an adenosine A2a receptor (i.e. adenosine A2a receptor agonist activity) and are useful for the prevention and/or treatment of glaucoma and ocular hypertension by the intraocular pressure reducing action thereof.

BEST MODE FOR CARRYING OUT THE INVENTION

Hereinafter, the present invention is illustrated by Reference Examples for the preparing the starting compounds and by Example for the preparing the compounds of the invention, and also experiments of the pharmacological tests, but should not be construed to be limited thereto.

The nuclear magnetic resonance (NMR) spectra in the examples mentioned below were measured under the following conditions. The abbreviate symbols are defined as follows.
  Apparatus: JNM-AL300 (JEOL)
  Internal standard substance: TMS
  s: singlet, d: doublet, t: triplet, q: quartet, quint: quintet, sext: sextet
  The following abbreviations are employed in the examples.
  IPE: isopropyl ether
  WSC: 1-ethyl-3-(3-dimethylaminopropyl)carbodiimide hydrochloride
  LiAlH$_4$: lithium aluminum hydride
  THF: tetrahydrofuran
  TBAF: tetrabutyl ammonium fluoride
  TBAF/THF solution: a mixture of tetrabutyl ammonium fluoride and tetrahydrofuran
  DMF: N,N-dimethylformamide
  HOBt: 1-hydroxybenzotriazole
  m-CPBA: m-chloroperbenzoic acid
  EtOH: ethanol
  NBS: N-bromosuccinimide
  DDQ: 2,3-dichloro-5,6-dicyano-p-benzoquinone
  DMSO: dimethyl sulfoxide
  BOP and BOP reagent: benzotriazol-1-yloxytris(dimethyl-amino)phosphonium hexafluorophosphate
  TFA: trifluoroacetic acid Reference Example 1

Methyl (4-formylphenyl)carbamate (560 mg) and malononitrile (206 mg) were dissolved in 10 mL of ethanol, and one drop of piperidine was added to the resulting solution, and then the mixture was stirred at room temperature for 3 hours. IPE (10 mL) was added to the reaction mixture, and a precipitated crystal was filtrated to give 441 mg of methyl [4-(2,2-dicyanovinyl)phenyl]carbamate as a yellow powder.
$^1$H-NMR (CDCl$_3$) δ: 7.90 (2H, d, J=8.7 Hz), 7.65 (1H, s), 7.56 (2H, d, J=8.7 Hz), 6.92 (1H, br s), 3.83 (3H, s).

Reference Example 2

To 20 mL of absolute ethanol, 250 mg of metallic sodium was added in small portions. After dissolved completely, 760 mg of thiourea was added to the above solution, and the mixture was stirred at room temperature for 1 hour. To the reaction, 2.11 g of N-[4-(2,2-dicyanovinyl)phenyl]acetamide was added, and the mixture was heated to reflux for 3 hours. Then, the solvent was removed under reduced pressure from the reaction mixture, the residue was dissolved in 30 mL of water. In addition, the mixture was acidified by adding acetic acid in small portions, thereto 30 mL of ethyl acetate was added and then the solution was stirred overnight. Filtration of the precipitated material gave 1.2 g of N-[4-(6-amino-5-cyano-2-mercapto-2,3-dihydropyrimidin-4-yl)phenyl]acetamide as a white powder.
$^1$H-NMR (DMSO-d$_6$) δ: 9.98 (1H, s), 9.65 (1H, br s), 7.56 (2H, d, J=8.7 Hz), 7.14 (2H, d, J=8.7 Hz), 6.16 (2H, s), 4.92 (1H, s), 2.08 (3H, s).

Reference Example 3

2,6-Bis(bromomethyl)pyridine (265 mg) was suspended in 2 mL of ethanol, thereto 87 mg of morpholine was added at ice temperature, and the mixture was stirred at room temperature overnight. The reaction mixture was concentrated under reduced pressure, and the residue was purified by chromatography on silica gel (methylene chloride-ethanol-triethylamine=400:20:1 (v/v, the same hereinafter)) to give 90 mg of 4-(6-bromomethylpyridin-2-ylmethyl)morpholine as a white powder.
$^1$H-NMR (CDCl$_3$) δ: 10.0 (1H, s), 7.54-7.48 (2H, m), 7.42 (1H, s), 7.24 (1H, s), 4.08 (2H, t, J=6.0 Hz), 3.56 (2H, t, J=4.5 Hz), 2.49 (2H, t, J=7.2 Hz), 2.42-2.34 (4H, m), 1.89 (2H, quint., J=6.6 Hz).

Reference Example 4

(1) To a round-bottom flask was added 2.3 g of 6-bromopyridin-2-ylmethyl acetate, 1.18 g of trimethyl silylacetylene, 210 mg of bis(triphenylphosphine)-palladium(II) chloride, 114 mg of copper(I) iodide and 12 mL of triethylamine, and then the mixture was heated to reflux under argon atmosphere for 5 hours. After allowing to cool, the mixture was concentrated to dryness under reduced pressure, thereto water was added, and the mixture was extracted with ethyl acetate. The organic layer was concentrated under reduced pressure, 7 mL of methanol and 30 mL of 1N aqueous potassium hydroxide were added to the residue, and the mixture was stirred for 1 hour. The reaction mixture was acidified with 1N hydrochloric acid and concentrated under reduced pressure. The concentrated solution was basified with potassium carbonate, and extracted with ethyl acetate. The organic layer was washed with brine, dried over anhydrous magnesium sulfate, and then the solvent was removed off under reduced pressure. The product was purified by chromatography on silica gel (hexane-ethyl acetate=4:1) to give 212 mg of (6-ethynylpyridin-2-yl)methanol as a white powder.

$^1$H-NMR (CDCl$_3$) δ: 7.67 (1H, t, J=7.8 Hz), 7.40 (1H, d, J=7.8 Hz), 7.28 (1H, d, J=7.8 Hz), 4.76 (2H, d, J=5.1 Hz), 3.38 (1H, t, J=5.1 Hz), 3.18 (1H, s).

(2) (6-Ethynylpyridin-2-yl)methanol (320 mg) and morpholine (1 g) were dissolved in 3 mL of ethanol, and the solution was heated to reflux under argon atmosphere for 24 hours. After allowing the reaction to cool, the ethanol was removed under reduced pressure, and the residue was basified with aqueous sodium hydroxide, and extracted with chloroform. The organic layer was washed with brine, dried over anhydrous magnesium sulfate, and the solvent was removed. The residue was purified by chromatography on silica gel (chloroform-methanol-aqueous ammonia=200:10:1) to give 122 mg of [6-(2-morpholin-4-ylethyl)pyridin-2-yl]methanol as a yellow oil.

$^1$H-NMR (CDCl$_3$) δ: 7.60 (1H, t, J=7.8 Hz), 7.08 (1H, d, J=7.8 Hz), 7.03 (1H, d, J=7.8 Hz), 4.72 (2H, s), 3.73 (4H, t, J=4.5 Hz), 3.00 (2H, dd, J=10, 8.7 Hz), 2.77 (2H, dd, J=10, 8.7 Hz), 2.53 (4H, t, J=4.5 Hz).

(3) [6-(2-Morpholin-4-ylethyl)pyridin-2-yl]methanol (122 mg) and diisopropylethylamine (104 mg) were dissolved in 2.5 mL of dichloromethane, and 47 μL of methanesulfonyl chloride was added dropwise to the solution at ice temperature, and then the mixture was stirred at room temperature overnight. After removing the solvent from the reaction mixture under reduced pressure, the residue was purified by chromatography on silica gel (chloroform-methanol-aqueous ammonia=300:10:1) to give 80 mg of 4-[2-(6-chloromethylpyridin-2-yl)ethyl]morpholine as a yellow oil.

$^1$H-NMR (CDCl$_3$) δ: 7.62 (1H, t, J=7.8 Hz), 7.30 (1H, d, J=7.8 Hz), 7.12 (1H, d, J=7.8 Hz), 4.64 (2H, s), 3.72 (4H, t, J=4.8 Hz), 2.98 (2H, dd, J=10, 8.7 Hz), 2.74 (2H, dd, J=10, 8.7 Hz), 2.53 (4H, t, J=4.8 Hz).

Reference Example 5

(1) 6-(t-Butyldimethylsilanyloxymethyl)pyridine-2-carboxaldehyde (4.29 g) was dissolved in 50 mL of DMF, and 7.14 g of (carbethoxymethylene)triphenylphosphorane was added to the solution, and then the mixture was stirred at room temperature for 1 hour. The reaction mixture was poured into ice-water, and extracted with ethyl acetate. The organic layer was washed with water, dried over anhydrous magnesium sulfate, and concentrated to dryness under reduced pressure. To the residue, 100 mL of a mixture of hexane-ethyl acetate (5:1) was added, the insoluble material was filtrated off, and the filtrate was concentrated under reduced pressure. The residue was purified by chromatography on silica gel (hexane-ethyl acetate=10:1) to give 5.45 g of ethyl 3-[6-(t-butyldimethylsilanyloxymethyl)pyridin-2-yl]acrylate as a light yellow oil.

$^1$H-NMR (CDCl$_3$) δ: 7.72 (1H, t, J=7.5 Hz), 7.66 (1H, d, J=15.6 Hz), 7.49 (1H, d, J=7.5 Hz), 7.29 (1H, d, J=7.5 Hz), 6.88 (1H, d, J=15.6 Hz), 4.83 (2H, s), 4.27 (2H, q, J=7.2 Hz), 1.33 (3H, t, J=7.2 Hz), 0.97 (9H, s), 0.13 (6H, s).

(2) Ethyl 3-[6-(t-butyldimethylsilanyloxymethyl)pyridin-2-yl]acrylate (5.45 g) was dissolved in 100 mL of ethanol, and 200 mg of platinum dioxide was added to the solution, and then the mixture was stirred under atmospheric hydrogen pressure at room temperature for 5 hours. After the purge with nitrogen, the catalyst was filtrated off, and the solvent was removed to provide 5.07 g of ethyl 3-[6-(t-butyldimethylsilanyloxymethyl)pyridin-2-yl]propionate as a pale yellow oil.

$^1$H-NMR (CDCl$_3$) δ: 7.60 (1H, t, J=7.5 Hz), 7.33 (1H, d, J=7.5 Hz), 7.03 (1H, d, J=7.5 Hz), 4.79 (2H, s), 4.12 (2H, q, J=7.2 Hz), 3.07 (2H, t, J=7.5 Hz), 2.75 (2H, t, J=7.5 Hz), 1.23 (3H, t, J=7.2 Hz), 0.96 (9H, s), 0.11 (6H, s).

(3) Ethyl 3-[6-(t-butyldimethylsilanyloxymethyl)pyridin-2-yl]propionate (5.07 g) was dissolved in 100 mL of ethanol, and 23.5 mL of 1N aqueous sodium hydroxide was added to the solution, and then the mixture was stirred at room temperature for 2 hours. The reaction mixture was concentrated to approximate half volume thereof under reduced pressure, after adding ice-water, the solution was acidified with hydrochloric acid, and extracted with ethyl acetate. The organic layer was washed with brine, dried over anhydrous magnesium sulfate, and concentrated under reduced pressure. The residue was purified by chromatography on silica gel (chloroform-methanol=10:1) to give 2.77 g of 3-[6-(t-butyldimethylsilanyloxymethyl)pyridin-2-yl]propionic acid as a colorless powder.

$^1$H-NMR (CDCl$_3$) δ: 7.77 (1H, t, J=7.5 Hz), 7.47 (1H, d, J=7.5 Hz), 7.13 (1H, d, J=7.5 Hz), 4.84 (2H, s), 3.15 (2H, t, J=6.0 Hz), 2.82 (2H, t, J=6.0 Hz), 0.96 (9H, s), 0.14 (6H, s).

(4) 3-[6-(t-Butyldimethylsilanyloxymethyl)pyridin-2-yl]propionic acid (1.65 g) was dissolved in 20 mL of methylene chloride, and 584 μL of morpholine, 1.6 g of WSC and 1.56 mL of triethylamine were added to the solution, and then the mixture was stirred at room temperature overnight. The reaction mixture was diluted with chloroform, transferred into a separating funnel, and washed with water. The organic layer was dried over anhydrous magnesium sulfate, and concentrated under reduced pressure. The residue was purified by chromatography on silica gel (chloroform-methanol=30:1) to give 1.91 g of 3-[6-(t-butyldimethylsilanyloxymethyl)pyridin-2-yl]-1-morpholin-4-yl-propan-1-one as a yellow oil.

$^1$H-NMR (CDCl$_3$) δ: 7.60 (1H, t, J=7.5 Hz), 7.33 (1H, d, J=7.5 Hz), 7.08 (1H, d, J=7.5 Hz), 4.79 (2H, s), 3.62-3.43 (8H, m), 3.11 (2H, t, J=7.5 Hz), 2.77 (2H, t, J=7.5 Hz), 0.96 (9H, s), 0.12 (6H, s).

(5) To a suspension of 420 mg of LiAlH$_4$ in 20 mL of THF, the solution of 1.9 g of 3-[6-(t-butyldimethylsilanyl-oxymethyl)pyridin-2-yl]-1-morpholin-4-ylpropan-1-one in 30 mL of THF was added dropwise at ice temperature. After the reaction mixture was stirred at room temperature for 3 hours, the excess LiAlH$_4$ was quenched with water, and the solution was filtrated through Hyflo Super-Cel (Nacalai Tesque) and partitioned. The organic layer was washed with brine, and dried over anhydrous magnesium sulfate. After removing the solvent under reduced pressure, the residue was purified by chromatography on silica gel (methylene chloride-ethanol 40:1) to give 760 mg of 4-{3-[6-(t-butyldimethylsilanyloxymethyl)pyridin-2-yl]propyl}morpholine.

Then, to a solution of 760 mg of 4-{3-[6-(t-butyldimethylsilanyloxymethyl)pyridin-2-yl]propyl}morpholine in 4 mL of THF at ice temperature, 4.34 mL of a solution of TBAF/THF (1 mol/L) was added dropwise. After stirring the solution at room temperature for 2 hours, the solvent was removed, and the residue was purified by chromatography on silica gel (methylene chloride-ethanol=40:1) to give 495 mg of [6-(3-morpholin-4-ylpropyl)pyridin-2-yl]methanol.

Additionally, to the solution of 495 mg of the resulting [6-(3-morpholin-4-ylpropyl)pyridin-2-yl]methanol and 104 mg of diisopropylethylamine in 20 mL of methylene chloride at ice temperature, 0.18 mL of methanesulfonyl chloride was added dropwise and the mixture was stirred at room temperature overnight. After the solvent was removed, the residue was purified by chromatography on silica gel (methylene chloride-ethanol=40:1) to give 290 mg of 4-[3-(6-chloromethylpyridin-2-yl)propyl]morpholine as a yellow powder.

$^1$H-NMR (CDCl$_3$) δ: 7.57 (1H, t, J=7.8 Hz), 7.05 (1H, d, J=7.8 Hz), 7.02 (1H, d, J=7.8 Hz), 4.65 (2H, s), 3.72 (4H, t, J=4.8 Hz), 2.83 (2H, t, J=7.8 Hz), 2.47-2.23 (6H, m), 1.96 (2H, quint., J=7.8 Hz).

Reference Example 6

2,6-Bis(chloromethyl)pyridine (352 mg) was suspended in 4 mL of ethanol, and 372 mg of N-(t-butoxycarbonyl)piperazine was added into the suspension at ice temperature, and then the suspension was stirred at room temperature overnight. The reaction mixture was concentrated under reduced pressure, the residue was added to water and extracted with chloroform. The organic layer was washed with brine, dried over anhydrous magnesium sulfate, and the solvent was removed. The residue was purified by chromatography on silica gel (methylene chloride-ethanol=30:1) to give 250 mg of t-butyl 4-(6-chloromethylpyridin-2-ylmethyl)piperazine-1-carboxylate as a colorless oil.

$^1$H-NMR (CDCl$_3$) δ: 7.69 (1H, t, J=7.8 Hz), 7.37 (1H, dd, J=7.8, 2.1 Hz), 4.66 (2H, s), 3.67 (2H, s), 3.45 (4H, t, J=5.1 Hz), 2.45 (4H, t, J=5.1 Hz), 1.48 (9H, s).

Reference Example 7

(1) 6-Methylpicolinic acid (1.37 g) and morpholine (870 mg) was dissolved in 30 mL of DMF, and thereto 1.6 g of HOBt was added under stirring at ice temperature. After the mixture was stirred at same temperature for 15 minutes, additionally 2.3 g of WSC was added, and the solution was stirred at room temperature overnight. The reaction mixture was concentrated under reduced pressure, and water was added to the residue, and then the resulting mixture was extracted with ethyl acetate. The organic layer was washed with brine, dried over anhydrous magnesium sulfate, and then the solvent was removed. The resulting residue was purified by chromatography on silica gel (methylene chloride-methanol-triethylamine=900:30:1) to give 1.71 g of (6-methylpyridin-2-yl)morpholin-4-ylmethanone as a colorless oil.

$^1$H-NMR (CDCl$_3$) δ: 7.67 (1H, t, J=7.8 Hz), 7.41 (1H, d, J=7.8 Hz), 7.20 (1H, d, J=7.8 Hz), 3.80 (4H, br s), 3.67-3.58 (4H, m), 2.57 (3H, s).

(2) (6-Methylpyridin-2-yl)morpholin-4-ylmethanone (1.38 g) was dissolved in 10 mL of chloroform, and 1.77 g of m-CPBA in 23 mL of chloroform was added dropwise into the solution, and the mixture was stirred at room temperature for one day. To the reaction mixture, 15 mL of 10% aqueous sodium sulfite was added, and the mixture was partitioned. The organic layer was washed with saturated aqueous sodium bicarbonate and brine, dried over anhydrous magnesium sulfate, and the solvent was removed. The resulting residue was purified by chromatography on silica gel (methylene chloride-methanol-triethylamine=1000:25:1) to give 1.26 g of (6-methyl-1-oxypyridin-2-yl)morpholin-4-ylmethanone as a white powder.

$^1$H-NMR (CDCl$_3$) δ: 7.31-7.18 (3H, m), 3.94-3.64 (6H, m), 3.30-3.20 (1H, m), 3.18-3.12 (1H, m), 2.52 (3H, s).

(3) To 1.26 g of (6-methyl-1-oxypyridin-2-yl)morpholin-4-ylmethanone, 0.53 mL of acetic anhydride was added, and the mixture was stirred at 100° C. for 1 hour. To the reaction mixture, saturated aqueous sodium bicarbonate was added, and the resulting mixture was extracted with ethyl acetate. The organic layer was washed with brine, dried over anhydrous magnesium sulfate, and the solvent was removed. The residue was purified by chromatography on silica gel (methylene chloride-methanol-triethylamine=1000:25:1) to give 1.13 g of 6-(morpholin-4-carbonyl)pyridin-2-ylmethyl acetate as a yellow oil.

$^1$H-NMR (CDCl$_3$) δ: 7.82 (1H, t, J=7.8 Hz), 7.61 (1H, d, J=7.8 Hz), 7.42 (1H, d, J=7.8 Hz), 5.22 (2H, s), 3.82 (4H, br s), 3.67-3.65 (4H, m), 2.17 (3H, s).

(4) To 1.13 g of 6-(morpholin-4-carbonyl)pyridin-2-ylmethyl acetate, 233 mg of potassium hydroxide and 1.5 mL of ethanol were added, and the mixture was heated to reflux for 4 hours. The reaction mixture was concentrated under reduced pressure, water was added to the residue, and extracted with chloroform. The organic layer was washed with brine, dried over anhydrous magnesium sulfate, and then the solvent was removed off in vacuo. The residue was purified by chromatography on silica gel (chloroform-methanol-triethylamine=500:25:1) to give 530 mg of (6-hydroxymethyl-pyridin-2-yl)morpholin-4-ylmethanone as a white powder.

$^1$H-NMR (CDCl$_3$) δ: 7.81 (1H, t, J=7.8 Hz), 7.57 (1H, d, J=7.8 Hz), 7.33 (1H, d, J=7.8 Hz), 4.79 (2H, s), 3.82 (4H, br s), 3.6.8 (2H, t, J=4.8 Hz), 3.58 (2H, t, J=4.8 Hz).

(5) To a solution of 530 mg of (6-hydroxymethylpyridin-2-yl)morpholin-4-ylmethanone and 614 mg of diisopropylethyl-amine in 10 mL of methylene chloride at ice temperature, 0.28 mL of methanesulfonyl chloride was added dropwise, and the mixture was stirred at room temperature overnight. The reaction mixture was concentrated under reduced pressure, and the residue was purified by chromatography on silica gel (methylene chloride-ethanol=50:1) to give 570 mg of (6-chloromethylpyridin-2-yl)morpholin-4-ylmethanone as a yellow oil.

$^1$H-NMR (CDCl$_3$) δ: 7.84 (1H, t, J=7.8 Hz), 7.70 (1H, d, J=7.8 Hz), 7.52 (1H, d, J=7.8 Hz), 4.65 (2H, s), 3.82 (4H, br s), 3.69-3.65 (4H, m).

Reference Example 8

(1) t-Butyl 6-methylpyridine-2-carboxylate (3.03 g) was dissolved in 30 mL of chloroform, and the solution of 3.96 g of m-CPBA in 45 mL of chloroform was added dropwise into the above mixture, and the resulting mixture was stirred at room temperature overnight. The reaction mixture was transferred to a separating funnel, thereto 35 mL of 10% aqueous Na$_2$SO$_3$ was added and the resulting mixture was partitioned. The organic layer was washed with saturated aqueous sodium bicarbonate and brine, dried over anhydrous magnesium sulfate, and then the solvent was removed. The residue was purified by chromatography on silica gel (methylene chloride-ethanol=30:1) to give 3.28 g of t-butyl 6-methyl-1-oxypyridine-2-carboxylate as a colorless oil.

$^1$H-NMR (CDCl$_3$) δ: 7.29-7.13 (3H, m), 2.66 (3H, s), 1.63 (9H, s).

(2) To 3.28 g of t-butyl 6-methyl-1-oxypyridine-2-carboxylate, 1.5 mL of acetic anhydride was added, and the mixture was stirred at 100° C. for 1 hour. The reaction mixture was neutralized with saturated aqueous sodium bicarbonate, and extracted with chloroform. The organic layer was washed with brine, dried over anhydrous magnesium sulfate, and the solvent was removed. The residue was purified by chromatography on silica gel (methylene chloride-ethanol=30:1) to give t-butyl 6-acetoxymethylpyridine-2-carboxylate as a yellow oil.

¹H-NMR (CDCl₃) δ: 7.94 (1H, d, J=7.5 Hz), 7.80 (1H, t, J=7.5 Hz), 7.50 (1H, d, J=7.5 Hz), 5.32 (2H, s), 2.17 (3H, s), 1.58 (9H, s).

(3) To 3.0 g of t-butyl 6-acetoxymethylpyridine-2-carboxylate were added 330 mg of potassium carbonate, 20 mL of methanol and 20 mL of water, and the mixture was stirred at room temperature for 3 hours. The methanol was removed under reduced pressure, then the residue was extracted with chloroform. The organic layer was washed with brine, dried over anhydrous magnesium sulfate, and the solvent was removed. The residue was purified by chromatography on silica gel (chloroform-ethanol 50:1) to give t-butyl 6-hydroxymethylpyridine-2-carboxylate as a yellow powder.

¹H-NMR (CDCl₃) δ: 7.95 (1H, d, J=7.5 Hz), 7.80 (1H, t, J=7.5 Hz), 7.43 (1H, d, J=7.5 Hz), 4.83 (2H, d, J=5.1 Hz), 3.68 (1H, t, J=5.1 Hz), 1.59 (9H, s).

(4) t-Butyl 6-hydroxymethylpyridine-2-carboxylate (1.34 g) and diisopropylethylamine (1.24 g) were dissolved in 30 mL of methylene chloride, 0.54 mL of methanesulfonyl chloride was added dropwise thereto at ice temperature, and the mixture was stirred at room temperature overnight. The solvent was removed from the reaction mixture, and then the residue was purified by chromatography on silica gel (hexane-ethyl acetate=5:1) to give t-butyl 6-chloromethylpyridine-2-carboxylate as a yellow powder.

¹H-NMR (CDCl₃) δ: 7.96 (1H, d, J=7.5 Hz), 7.83 (1H, t, J=7.5 Hz), 7.67 (1H, d, J=7.5 Hz), 4.80 (2H, s), 1.59 (9H, s).

Reference Example 9

(1) 6-Methylpicolinic acid (2.15 g) and t-butyl piperazine-1-carboxylate (3.21 g) was dissolved in 45 mL of DMF, and 4.24 g of HOBt was added to the solution at ice temperature. After stirring for 15 minutes, additionally 3.0 g of WSC was added thereto and the mixture was stirred at room temperature overnight. After the solvent was removed under reduced pressure from the reaction mixture, then water was added to the residue and the mixture was extracted with ethyl acetate. The organic layer was washed with brine, dried over anhydrous magnesium sulfate, then the solvent was removed under reduced pressure. The residue was purified by chromatography on silica gel (methylene chloride-ethanol=30:1) to give 4.57 g of t-butyl 4-(6-methylpyridine-2-carbonyl)piperazine-1-carboxylate as a colorless oil.

¹H-NMR (CDCl₃) δ: 7.67 (1H, t, J=7.8 Hz), 7.35 (1H, d, J=7.8 Hz), 7.21 (1H, d, J=7.8 Hz), 3.77 (2H, t, J=4.8 Hz), 3.55 (4H, t, J=4.8 Hz), 3.46 (2H, t, J=4.8 Hz), 2.57 (3H, s), 1.47 (9H, s).

(2) t-Butyl 4-(6-methylpyridine-2-carbonyl)piperazine-1-carboxylate (4.57 g) was dissolved in 30 mL of chloroform, a solution of 3.9 g of m-CPBA in 40 mL of chloroform was slowly added dropwise into the resulting solution. After that, the mixture was stirred at room temperature for one day, then 10% aqueous sodium sulfite (35 mL) was added to the reaction mixture and the mixture was partitioned. The organic layer was washed with saturated aqueous sodium bicarbonate and brine, dried over anhydrous magnesium sulfate, and then the solvent was removed. The residue was purified by chromatography on silica gel (methylene chloride-ethanol=40:1) to give 4.2 g of t-butyl 4-(6-methyl-1-oxypyridine-2-carbonyl)piperazine-1-carboxylate as a white powder.

¹H-NMR (CDCl₃) δ: 7.31-7.17 (3H, m), 3.91 (1H, br s), 3.62-3.56 (4H, m), 3.45 (1H, br s), 3.26 (1H, br s), 3.13 (1H, br s), 2.51 (3H, s), 1.47 (9H, s).

(3) To t-butyl 4-(6-methyl-1-oxypyridine-2-carbonyl)-piperazine-1-carboxylate (4.2 g) was added 1.2 mL of acetic anhydride, and the mixture was stirred at 100° C. for 1 hour. After being cooled, the reaction solution was neutralized with saturated aqueous sodium bicarbonate, and extracted with chloroform. The organic layer was washed with brine, dried over anhydrous magnesium sulfate, and the solvent was removed under reduced pressure. The residue was purified by chromatography on silica gel (methylene chloride-ethanol 40:1) to give 3.7 g of t-butyl 4-(6-acetoxymethylpyridine-2-carbonyl)piperazine-1-carboxylate as a colorless oil.

¹H-NMR (CDCl₃) δ: 7.82 (1H, t, J=7.8 Hz), 7.60 (1H, d, J=7.8 Hz), 7.40 (1H, d, J=7.8 Hz), 5.22 (2H, s), 3.77 (2H, t, J=4.8 Hz), 3.59-3.56 (4H, br), 3.69 (2H, t, J=4.8 Hz), 2.17 (3H, s), 1.47 (9H, s).

(4) To a solution of 3.7 g of t-butyl 4-(6-acetoxy-methylpyridine-2-carbonyl)piperazine-1-carboxylate in 10 mL of methanol was added 840 mg of potassium hydroxide and the mixture was heated to reflux for 4 hours. After the solvent was removed, water was added to the solution and the mixture was extracted with chloroform. The organic layer was washed with brine, dried over anhydrous magnesium sulfate, then the solvent was removed under reduced pressure. The residue was purified by chromatography on silica gel (methylene chloride-ethanol=50:1) to give 1.26 g of t-butyl 4-(6-hydroxymethylpyridine-2-carbonyl)piperazine-1-carboxylate as a colorless oil.

¹H-NMR (CDCl₃) δ: 7.81 (1H, t, J=7.8 Hz), 7.55 (1H, d, J=7.8 Hz), 7.34 (1H, d, J=7.8 Hz), 4.79 (2H, s), 3.79 (2H, t, J=4.8 Hz), 3.58-3.45 (6H, br), 1.47 (9H, s).

(5) t-Butyl 4-(6-hydroxymethylpyridine-2-carbonyl)-piperazine-1-carboxylate (1.26 g) and diisopropylethylamine (1.0 g) were dissolved in 20 mL of methylene chloride, 0.1 mL of methanesulfonyl chloride was added dropwise into the above solution at ice temperature, and the mixture was stirred at room temperature overnight. After the solvent was removed under reduced pressure from the reaction mixture, the residue was purified by chromatography on silica gel (methylene chloride-ethanol=40:1) to give 1.07 g of t-butyl 4-(6-chloromethylpyridine-2-carbonyl)piperazine-1-carboxylate as a colorless oil.

¹H-NMR (CDCl₃) δ: 7.84 (1H, t, J=7.8 Hz), 7.60 (1H, d, J=7.8 Hz), 7.54 (1H, d, J=7.8 Hz), 4.66 (2H, s), 3.76 (2H, br), 3.57-3.48 (6H, br), 1.47 (9H, s).

Reference Example 10

(1) 6-Hydroxymethylpyridine-2-carbaldehyde (15.3 g) was dissolved in 250 mL of dry DMF, and 50 g of (t-butoxycarbonylmethylene)triphenylphosphorane was added to the above solution, and then the mixture was stirred at room temperature for 30 minutes. The reaction mixture was thrown into ice-water, and the mixture was extracted with ethyl acetate. The organic layer was washed with brine, dried over anhydrous magnesium sulfate, and concentrated under reduced pressure. To the residue was added 300 mL of a mixture of hexane-ethyl acetate (2:1), the insoluble portion was filtrated off. The filtrate was concentrated under reduced pressure, the residue was purified by chromatography on silica gel (hexane-ethyl acetate=2:1) to give 16.86 g of t-butyl 3-(6-hydroxymethylpyridin-2-yl)-trans-acrylate and 5.69 g of t-butyl 3-(6-hydroxymethylpyridin-2-yl)-cis-acrylate.

Trans form: a colorless oil

¹H-NMR (CDCl₃) δ: 7.70 (1H, t, J=7.5 Hz), 7.58 (1H, d, J=15.6 Hz), 7.31 (1H, d, J=7.5 Hz), 7.18 (1H, d, J=7.5 Hz), 6.88 (1H, d, J=15.6 Hz), 4.77 (2H, d, J=4.8 Hz), 3.88 (1H, t, J=4.8 Hz), 1.54 (9H, s).

Cis form: a colorless oil

¹H-NMR (CDCl₃) δ: 7.67 (1H, t, J=7.8 Hz), 7.51 (1H, d, J=7.8 Hz), 7.14 (1H, d, J=7.8 Hz), 6.86 (1H, d, J=12.6 Hz), 6.07 (1H, d, J=12.6 Hz), 4.74 (2H, d, J=4.8 Hz), 3.77 (1H, t, J=4.8 Hz), 1.46 (9H, s).

(2) t-Butyl 3-(6-hydroxymethylpyridin-2-yl)-trans-acrylate (trans form) (16.86 g) was dissolved in 200 mL of ethanol, and 0.5 g of platinum dioxide was added to the solution, and then the mixture was stirred under atmospheric hydrogen pressure at room temperature for 5 hours. After that, the catalyst was filtrated off, another platinum dioxide (0.5 g) was added, and then the mixture was stirred under atmospheric hydrogen pressure at room temperature for 6 hours. The catalyst was filtrated off from the reaction mixture, and the solvent was removed under reduced pressure to give 16.13 g of t-butyl 3-(6-hydroxymethylpyridin-2-yl)propionate as a light yellow oil.

¹H-NMR (CDCl₃) δ: 7.58 (1H, t, J=7.5 Hz), 7.08 (1H, d, J=7.5 Hz), 7.03 (1H, d, J=7.5 Hz), 4.70 (2H, s), 3.10 (2H, t, J=7.5 Hz), 2.72 (2H, t, J=7.5 Hz), 1.42 (9H, s).

(3) t-Butyl 3-(6-hydroxymethylpyridin-2-yl)propionate (16.13 g) was dissolved in 200 mL of dry methylene chloride, and 33.8 g of carbon tetrabromide was added to the above solution, additionally 21.5 g of triphenylphosphine was added thereto in small portions under stirring at ice temperature, and then the mixture was stirred at the same temperature for 30 minutes. The reaction mixture was transferred to a separating funnel, washed with saturated aqueous sodium bicarbonate, then brine, dried over anhydrous magnesium sulfate, and concentrated under reduced pressure. To the residue, 200 mL of a mixture of hexane-ethyl acetate (2:1) was added, the insoluble portion precipitated was filtrated off, and the filtrate was concentrated under reduced pressure. The residue was purified by chromatography on silica gel (hexane-ethyl acetate=5:1) to give 14.12 g of t-butyl 3-(6-bromomethylpyridin-2-yl)propionate as a light yellow oil.

¹H-NMR (CDCl₃) δ: 7.58 (1H, t, J=7.5 Hz), 7.26 (1H, d, J=7.5 Hz), 7.09 (1H, d, J=7.5 Hz), 4.51 (2H, s), 3.06 (2H, t, J=7.5 Hz), 2.70 (2H, t, J=7.5 Hz), 1.42 (9H, s).

Reference Example 11

(1) 2-Bromopyridine-6-methanol (2 g) was dissolved in 10 mL of dry DMF, and 1.73 mL of ethyl acrylate, 2.95 g of tetra(n-butyl)ammonium chloride, 1.78 g of sodium bicarbonate and 2 g of Molecular Sieves (Molecular Sieves 3A (1/16)) to the above solution, additionally under argon atmosphere 119 mg of palladium(II) acetate was added thereto, and then the mixture was stirred at 80° C. for 5 hours. After being cooled, the insoluble portion was filtrated off, and water was added thereto and then the mixture was extracted with ethyl acetate. The organic layer was washed with brine, dried over anhydrous magnesium sulfate, and concentrated under reduced pressure. The residue was purified by chromatography on silica gel (hexane-ethyl acetate=2:1) to give 1.39 g of ethyl 3-(6-hydroxymethylpyridin-2-yl)-trans-acrylate as a light yellow oil.

¹H-NMR (CDCl₃) δ: 7.71 (1H, t, J=7.5 Hz), 7.66 (1H, d, J=15.6 Hz), 7.32 (1H, d, J=7.5 Hz), 7.20 (1H, d, J=7.5 Hz), 6.96 (1H, d, J=15.6 Hz), 4.78 (2H, d, J=4.8 Hz), 4.29 (2H, q, J=7.2 Hz), 3.85 (1H, t, J=4.8 Hz), 1.35 (3H, t, J=7.2 Hz).

(2) According to the same procedure described in Reference Example 10-(2), ethyl 3-(6-hydroxymethylpyridin-2-yl)-trans-acrylate was reduced to give ethyl 3-(6-hydroxymethylpyridin-2-yl)propionate as a light yellow oil.

¹H-NMR (CDCl₃) δ: 7.58 (1H, t, J=7.5 Hz), 7.08 (1H, d, J=7.5 Hz), 7.02 (1H, d, J=7.5 Hz), 4.71 (2H, d, J=4.5 Hz), 4.14 (2H, q, J=7.2 Hz), 4.01 (1H, t, J=4.5 Hz), 3.15 (2H, t, J=7.5 Hz), 2.80 (2H, t, J=7.5 Hz), 1.24 (3H, t, J=7.2 Hz).

Reference Example 12

(1) According to the same procedure described in Reference Example 1, using methyl acrylate, methyl 3-(6-hydroxymethylpyridin-2-yl)-trans-acrylate was provided as a pale yellow powder.

¹H-NMR (CDCl₃) δ: 7.72 (1H, t, J=7.5 Hz), 7.68 (1H, d, J=15.6 Hz), 7.32 (1H, d, J=7.5 Hz), 7.21 (1H, d, J=7.5 Hz), 6.97 (1H, d, J=15.6 Hz), 4.78 (2H, d, J=4.2 Hz), 3.85 (1H, t, J=4.2 Hz), 3.83 (3H, s).

(2) According to the same procedure described in Reference Example 10-(2), methyl 3-(6-hydroxymethylpyridin-2-yl)-trans-acrylate was reduced to give methyl 3-(6-hydroxymethylpyridin-2-yl)propionate as a light brown oil.

¹H-NMR (CDCl₃) δ: 7.58 (1H, t, J=7.5 Hz), 7.09 (1H, d, J=7.5 Hz), 7.03 (1H, d, J=7.5 Hz), 4.71 (2H, s), 4.01 (1H, br s), 3.69 (3H, s), 3.15 (2H, t, J=7.2 Hz), 2.81 (2H, t, J=7.2 Hz).

The above compound was also prepared as follows: To a solution of 50.02 g of methyl 3-(6-hydroxymethylpyridin-2-yl)-trans-acrylate in IPA 502 mL, was added 2.51 g of 5% palladium-carbon (containing 50% water) under argon atmosphere, the reaction mixture was stirred under 1-4 atom hydrogen atmosphere at 50° C. for 2.5 hours. After cooling, the catalyst was filtrated off and the solvent was removed off under reduced pressure from the reaction mixture, which gave 50 g of methyl 3-(6-hydroxymethylpyridin-2-yl)propionate as a brown oil.

Reference Example 13

(1) 6-hydroxymethylpyridine-2-carbaldehyde (2.95 g) and triethyl 2-phosphonopropionate (5.12 g) were dissolved in 20 mL of dry DMF, and to the solution was added a solution of 1.30 g of sodium methoxide in 10 mL of methanol dropwise, and the mixture was stirred at room temperature for 20 minutes. The reaction mixture was thrown into ice-water, and extracted with ethyl acetate. The organic layer was washed with brine, dried over anhydrous magnesium sulfate, and concentrated under reduced pressure. The residue was purified by chromatography on silica gel (hexane-ethyl acetate=1:1) to give 2.42 g of ethyl (E)-3-(6-hydroxymethylpyridin-2-yl)-2-methylacrylate as a colorless oil.

¹H-NMR (CDCl₃) δ: 7.71 (1H, t, J=7.8 Hz), 7.63 (1H, q, J=1.5 Hz), 7.29 (1H, d, J=7.8 Hz), 7.14 (1H, d, J=7.8 Hz), 4.79 (2H, d, J=4.8 Hz), 4.29 (2H, q, J=7.2 Hz), 3.84 (1H, t, J=4.8 Hz), 2.35 (3H, d, J=1.5 Hz), 1.36 (3H, t, J=7.2 Hz).

(2) According to the same procedure described in Reference Example 10-(2), ethyl (E)-3-(6-hydroxymethyl-pyridin-2-yl)-2-methylacrylate was reduced to give ethyl 3-(6-hydroxymethylpyridin-2-yl)-2-methylpropionate as a colorless oil.

¹H-NMR (CDCl₃) δ: 7.57 (1H, t, J=7.5 Hz), 7.04 (1H, d, J=7.5 Hz), 7.02 (1H, d, J=7.5 Hz), 4.70 (2H, br s), 4.11 (2H, q, J=7.2 Hz), 3.22 (1H, dd, J=14.1, 7.8 Hz), 3.05 (1H, sextet, J=6.3 Hz), 2.88 (1H, dd, J=14.1, 6.3 Hz), 1.27-1.16 (6H, m).

Reference Example 14

To a solution prepared with t-butyl 3-(6-hydroxymethyl-pyridin-2-yl)-trans-acrylate (trans form, 2 g) described in Reference Example 10-(1) and carbon tetrabromide (4.23 g) in methylene chloride (20 mL) at ice temperature, triphenylphosphine (2.68 g) was added in small portions, and the mixture was stirred at the same temperature for 15 minutes.

The reaction solution was transferred to a separating funnel, diluted with chloroform, washed with saturated aqueous sodium bicarbonate and brine, dried over anhydrous magnesium sulfate, and then concentrated under reduced pressure. The residue was purified by chromatography on silica gel (hexane-ethyl acetate=10:1) to give 2.23 g of t-butyl 3-(6-bromomethylpyridin-2-yl)-trans-acrylate as a light yellow powder.

$^1$H-NMR (CDCl$_3$) δ: 7.70 (1H, t, J=7.8 Hz), 7.56 (1H, d, J=15.6 Hz), 7.41 (1H, d, J=7.8 Hz), 7.32 (1H, d, J=7.8 Hz), 6.87 (1H, d, J=15.6 Hz), 4.54 (2H, s), 1.53 (9H, s).

Reference Example 15

(1) 4-Pentynoic acid (1.03 g) and N-methylpiperazine (1.0 g) was dissolved in 30 mL of DMF, 1.6 g of HOBt was added to the solution at ice temperature under stirring. After the mixture was stirred at same temperature for 15 minutes, additionally 2.3 g of WSC was added, and the solution was stirred at room temperature overnight. The DMF was removed under reduced pressure from the reaction mixture, then water was added to the residue and the mixture was extracted with ethyl acetate. The organic layer was washed with brine, dried over anhydrous magnesium sulfate, and then the solvent was removed. The residue was purified by chromatography on silica gel (methylene chloride-methanol-triethylamine 600:20:1) to give 510 mg of 1-(4-methylpiperazin-1-yl)pent-4-yn-1-one as a colorless oil.

$^1$H-NMR (CDCl$_3$) δ: 3.64 (2H, t, J=5.1 Hz), 3.48 (2H, t, J=5.1 Hz), 2.59-2.52 (4H, m), 2.41-2.35 (4H, m), 2.30 (3H, s), 1.97 (1H, s).

(2) To a 50 mL round-bottom flask, 484 mg of 2-bromopyridine-6-methanol, 510 mg of 1-(4-methylpiperazin-1-yl)pent-4-yn-1-one, 20 mg of BHT, 162 mg of copper(I) iodide, 118 mg of tetrakis(triphenylphosphine)palladium (0), 375 mg of t-butylamine and 7.5 mL of DMF were added, and the mixture was stirred under argon atmosphere at 80° C. for 6 hours. The DMF was removed under reduced pressure, then saturated aqueous sodium bicarbonate was added thereto, and the mixture was extracted with chloroform. The organic layer was washed with brine, dried over anhydrous magnesium sulfate, and then the solvent was removed. The residue was purified by chromatography on silica gel (methylene chloride-methanol-triethylamine=600:20:1) to give 540 mg of 5-(6-hydroxymethylpyridin-2-yl)-1-(4-methylpiperazin-1-yl)pent-4-yn-1-one as a yellow oil.

$^1$H-NMR (CDCl$_3$) δ: 7.62 (1H, t, J=7.8 Hz), 7.27 (1H, d, J=7.8 Hz), 7.18 (1H, d, J=7.8 Hz), 4.73 (2H, s), 3.67 (2H, t, J=6.6 Hz), 3.53 (2H, t, J=6.6 Hz), 2.84-2.78 (2H, m), 2.72-2.67 (2H, m), 2.43-2.38 (4H, m), 2.30 (3H, s).

Reference Example 16

(1) To a 200 mL round-bottom flask, 3.49 g of 2-bromopyridine-6-methanol, 3.0 g of t-butyl 4-pentynoate, 190 mg of BHT, 1.17 g of copper(I) iodide, 877 mg of tetrakis(triphenylphosphine)palladium(0), 2.72 g of t-butylamine and 56 mL of DMF were added, and the mixture was stirred under argon atmosphere at 80° C. for 6 hours. After the DMF was removed under reduced pressure from the reaction mixture, saturated aqueous sodium bicarbonate was added thereto, and the mixture was extracted with ethyl acetate. The organic layer was washed with brine, dried over anhydrous magnesium sulfate, and then the solvent was removed. The residue was purified by chromatography on silica gel (n-hexane-ethyl acetate=2:1) to give 2.76 g of t-butyl 5-(6-hydroxymethylpyridin-2-yl)pent-4-ynoate as a yellow oil.

$^1$H-NMR (CDCl$_3$) δ: 7.61 (1H, t, J=7.8 Hz), 7.28 (1H, d, J=7.8 Hz), 7.17 (1H, d, J=7.8 Hz), 4.72 (2H, d, J=5.1 Hz), 3.32 (1H, t, J=5.1 Hz), 2.75 (2H, t, J=7.2 Hz), 2.57 (2H, t, J=7.2 Hz), 1.45 (12H, s).

(2) To a 200 mL round-bottom flask, 2.76 g of t-butyl 5-(6-hydroxymethylpyridin-2-yl)pent-4-ynoate, 50 mg of platinum dioxide and 25 mL of EtOH were added, the mixture was stirred under hydrogen atmosphere at room temperature for 8 hours. The insoluble material was removed off, and then the filtrate was concentrated to give 2.78 g of t-butyl 5-(6-hydroxymethylpyridin-2-yl)pentanoate as a yellow oil.

$^1$H-NMR (CDCl$_3$) δ: 7.57 (1H, t, J=7.8 Hz), 7.02 (2H, t, J=7.8 Hz), 4.71 (2H, s), 2.80 (2H, t, J=7.2 Hz), 2.56 (2H, t, J=7.2 Hz), 1.82-1.60 (4H, m), 1.42 (12H, s).

(3) To a 200 mL round-bottom flask, 50 mL of dichloromethane, 2.78 g of t-butyl 5-(6-hydroxymethylpyridin-2-yl)pentanoate and 2.0 g of diisopropylethylamine were added, and the mixture was stirred at ice temperature for 10 minutes. To the reaction mixture, 0.89 mL of methanesulfonyl chloride was added dropwise, and the mixture was stirred at room temperature for 3 hours. Water was added to the reaction mixture, and the mixture was partitioned. The organic layer was washed with saturated aqueous sodium bicarbonate and brine, dried over anhydrous magnesium sulfate, and then the solvent was removed. The residue was purified by chromatography on silica gel (n-hexane-ethyl acetate=3:1) to give 2.28 g of t-butyl 5-(6-methane-sulfonyloxymethylpyridin-2-yl)pentanoate as a yellow oil.

$^1$H-NMR (CDCl$_3$) δ: 7.65 (1H, t, J=7.8 Hz), 7.30 (1H, d, J=7.8 Hz), 7.13 (1H, d, J=7.8 Hz), 5.29 (2H, s), 3.08 (3H, s), 2.80 (2H, t, J=7.2 Hz), 2.25 (2H, t, J=7.2 Hz), 1.75-1.50 (4H, m), 1.44 (12H, s).

Reference Example 17

(1) According to the same procedure described in Reference Example 11, using ethylvinylketone instead of ethyl acrylate, (E)-1-(6-hydroxymethylpyridin-2-yl)pent-1-en-3-one was given as a colorless oil.

$^1$H-NMR (CDCl$_3$) δ: 7.72 (1H, t, J=7.5 Hz), 7.55 (1H, d, J=15.6 Hz), 7.36 (1H, d, J=7.5 Hz), 7.23 (1H, d, J=15.6 Hz), 7.22 (1H, d, J=7.5 Hz), 4.79 (2H, d, J=4.5 Hz), 3.84 (1H, br t, J=4.5 Hz), 2.74 (2H, q, J=7.2 Hz), 1.18 (3H, t, J=7.2 Hz).

(2) According to the same procedure described in Reference Example 10-(2), (E)-1-(6-hydroxymethylpyridin-2-yl)pent-1-en-3-one was reduced to give 1-(6-hydroxymethylpyridin-2-yl)pentan-3-one as a light brown oil.

$^1$H-NMR (CDCl$_3$) δ: 7.57 (1H, t, J=7.8 Hz), 7.09 (1H, d, J=7.8 Hz), 7.02 (1H, d, J=7.8 Hz), 4.70 (2H, s), 3.94 (1H, br s), 3.09 (2H, t, J=6.9 Hz), 2.92 (2H, t, J=6.9 Hz), 2.47 (2H, q, J=7.2 Hz), 1.06 (3H, t, J=7.2 Hz).

The structures of each compound obtained according to above Reference Examples 1-17-(2) are shown in the following summarized Table 1. The abbreviations in the tables are listed below. The abbreviations used in the other tables also means the same.

MeO and OMe: methoxy,
Me: methyl,
Et: ethyl,
AcO and OAc: acetyloxy,
TBDMS: tert-butyldimethylsilyl,
OEt and EtO: ethoxy,
OtBu and tBuO: tert-butyloxy,
Ac: acetyl,
tBu and t-Bu: tert-butyl,
n-Pr: n-propyl,
iPr and i-Pr: isopropyl, Ph: phenyl,
n-Bu: n-butyl,
i-Bu: 2-methylpropyl.
TABLE 1
| Reference Example No. | Structure |
|---|---|
| 1 | 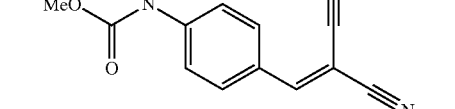 |
| 2 | 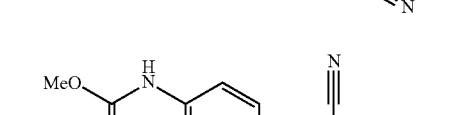 |
| 3 | 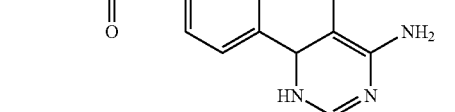 |
| 4-(1) | 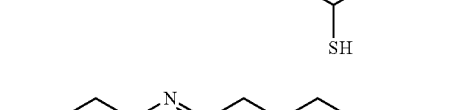 |
| 4-(2) | 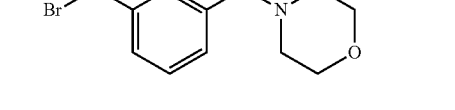 |
| 4-(3) | 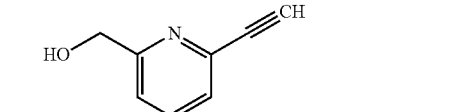 |
| 5-(1) | 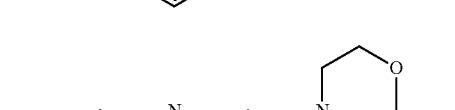 |
| 5-(2) | 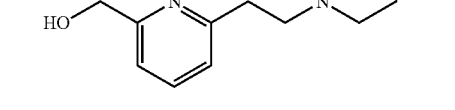 |
TABLE 1-continued
| Reference Example No. | Structure |
|---|---|
| 5-(3) | 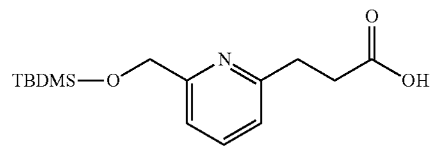 |
| 5-(4) | 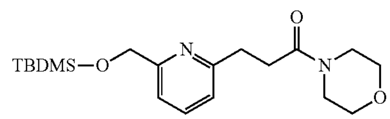 |
| 5-(5) | 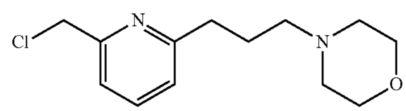 |
| 6 | 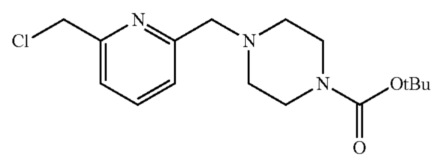 |
| 7-(1) | 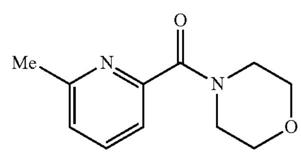 |
| 7-(2) | 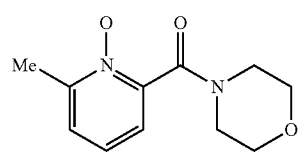 |
| 7-(3) | 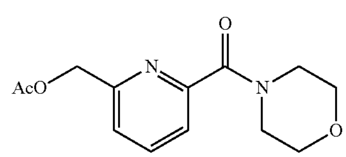 |
| 7-(4) | 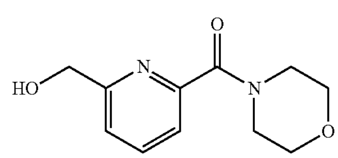 |
| 7-(5) | 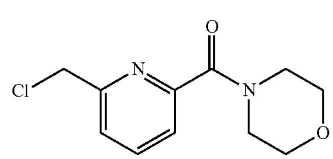 |
| 8-(1) | 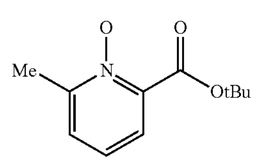 |

TABLE 1-continued
| Reference Example No. | Structure |
|---|---|
| 8-(2) | 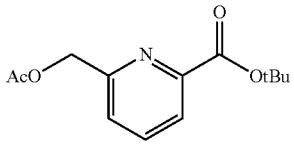 |
| 8-(3) | 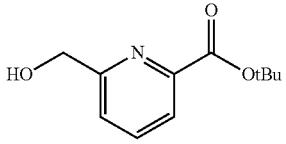 |
| 8-(4) | 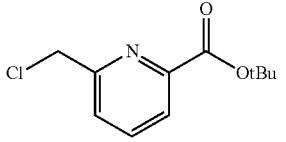 |
| 9-(1) | 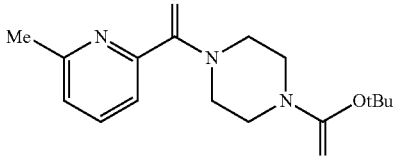 |
| 9-(2) | 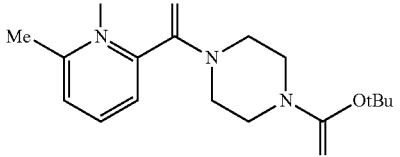 |
| 9-(3) | 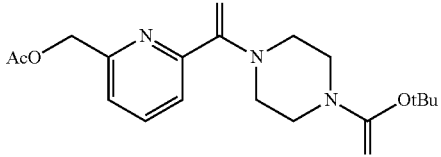 |
| 9-(4) | 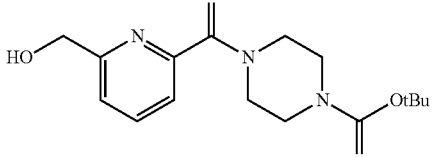 |
| 9-(5) | 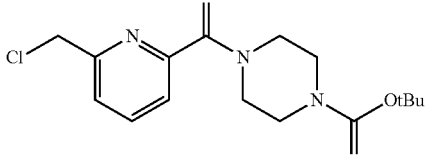 |
| 10-(1) | 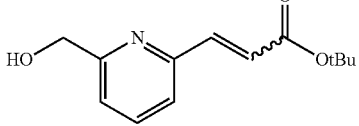 |
| 10-(2) | 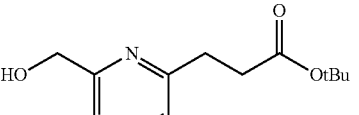 |
| 10-(3) | 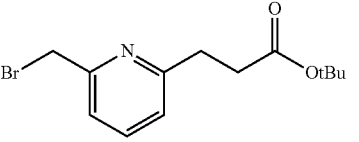 |
| 11-(1) | 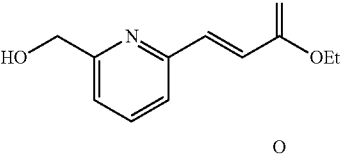 |
| 11-(2) | 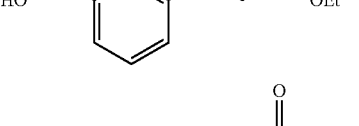 |
| 12-(1) | 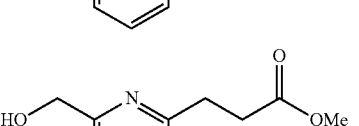 |
| 12-(2) | 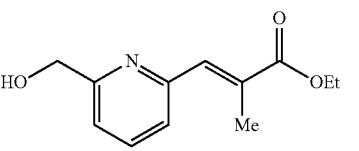 |
| 13-(1) | 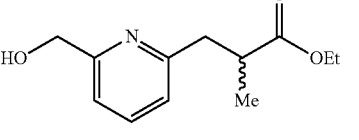 |
| 13-(2) | 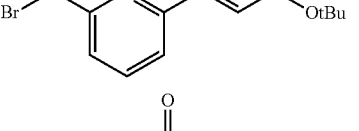 |
| 14 | 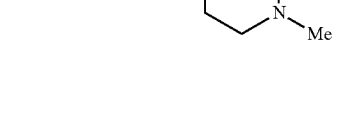 |
| 15-(1) | 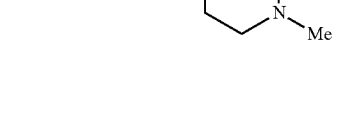 |

TABLE 1-continued

| Reference Example No. | Structure |
|---|---|
| 15-(2) | HO-pyridine-C≡C-CH2-C(O)-N(piperazine)N-Me |
| 16-(1) | HO-pyridine-C≡C-CH2CH2-C(O)-OtBu |
| 16-(2) | HO-pyridine-CH2CH2CH2-C(O)-OtBu |
| 16-(3) | Me-S(O)2-O-pyridine-CH2CH2CH2-C(O)-OtBu |
| 17-(1) | HO-pyridine-CH=CH-C(O)-Et |
| 17-(2) | HO-pyridine-CH2CH2-C(O)-Et |

Example 1

To DMF (3 mL) were added 285 mg of the compound of Reference Example 2, 172 mg of 2-(chloromethyl)pyridine hydrochloride, 184 mg of sodium bicarbonate and 157 mg of sodium iodide, and the mixture was stirred at room temperature overnight. Water was added to the reaction mixture, the mixture was extracted with ethyl acetate. The organic layer was washed with brine, dried over anhydrous magnesium sulfate, and the solvent was removed under reduced pressure. The residue was purified by chromatography on silica gel (methylene chloride-ethanol 40:1) to give 31 mg of N-{4-[6-amino-5-cyano-2-(pyridin-2-ylmethylsulfanyl)-pyrimidin-4-yl]phenyl}acetamide as a white powder.

$^1$H-NMR (DMSO-$d_6$) δ: 10.2 (1H, s), 8.51 (1H, d, J=4.8 Hz), 7.83 (2H, d, J=8.4 Hz), 7.75-7.70 (3H, m), 7.54 (1H, d, J=7.8 Hz), 7.26 (1H, dd, J=6.6, 4.8 Hz), 4.50 (2H, s), 2.08 (3H, s).

Example 2

6-Methyl-2-pyridinemethanol (5 g) was dissolved in 50 mL of methylene chloride, and 10.6 mL of diisopropylethylamine was added to the solution, and then 3.5 mL of methanesulfonyl chloride was added dropwise thereto under stirring at ice temperature. After stirring at ice temperature for 1 hour, water was added to the reaction solution, and the organic layer was washed with water (2×) and brine (1×). The organic layer was dried over magnesium sulfate, and then the solvent was removed to give 6.98 g of a brown oil.

The portion (4.56 g) was dissolved in 50 mL of ethanol, 1.72 g of thiourea was added to the solution, and the mixture was heated to reflux for 1 hour. Next, to the reaction solution added 20 mL of ethanol and the solution was cooled, and further 4.79 g of N-[4-(2,2-dicyanovinyl)phenyl]acetamide and 3 g of sodium bicarbonate were added thereto, and then the mixture was heated to reflux for 1.5 hours. After the reaction solution was allowed to cool, 2.02 g of NBS was added to the solution, and the mixture was heated to reflux for 30 minutes. After reaction solution was allowed to cool, furthermore diisopropyl ether was added thereto, and the inorganic material precipitated was filtrated off, then the filtrate was again concentrated and dissolved in ethanol. Saturated aqueous sodium bicarbonate was added to the solution and the resulting crystal was filtrated, washed with water and ethanol, and then dried under reduced pressure to give 3.2 g of N-{4-[6-amino-5-cyano-2-(6-methylpyridin-2-ylmethylsulfanyl)pyrimidin-4-yl]phenyl}acetamide as a white powder.

$^1$H-NMR (DMSO-$d_6$) δ: 10.2 (1H, s), 7.83 (2H, d, J=8.7 Hz), 7.72 (2H, d, J=8.7 Hz), 7.60 (1H, t, J=7.5 Hz), 7.33 (1H, d, J=7.5 Hz), 7.12 (1H, d, J=7.5 Hz), 4.44 (2H, s), 2.45 (3H, s), 2.09 (3H, s).

Example 3

According to the same procedure described in Example 2, using 5-methyl-2-pyridinemethanol instead of 6-methyl-2-pyridinemethanol, N-{4-[6-amino-5-cyano-2-(5-methylpyridin-2-ylmethylsulfanyl)pyrimidin-4-yl]phenyl}acetamide was given as a white powder.

$^1$H-NMR (DMSO-$d_6$) δ: 10.23 (1H, s), 8.34 (1H, s), 7.60-8.20 (2H, br s), 7.84 (2H, d, J=8.7 Hz), 7.72 (2H, d, J=8.7 Hz), 7.54 (1H, d, J=7.8 Hz), 7.43 (1H, d, J=7.8 Hz), 4.46 (2H, s), 2.26 (3H, s), 2.09 (3H, s).

Example 4

According to the same procedure described in Example 2, using 4-methyl-2-pyridinemethanol instead of 6-methyl-2-pyridinemethanol, N-{4-[6-amino-5-cyano-2-(4-methylpyridin-2-ylmethylsulfanyl)pyrimidin-4-yl]phenyl}acetamide was given as a light yellow powder.

$^1$H-NMR (DMSO-$d_6$) δ: 10.24 (1H, s), 8.62 (1H, s), 7.65-8.25 (2H, br s), 7.84 (2H, d, J=8.7 Hz), 7.73 (2H, d, J=8.7 Hz), 7.36 (1H, s), 7.00 (1H, d, J=7.8 Hz), 4.56 (2H, s), 2.26 (3H, s), 2.09 (3H, s).

Example 5

According to the same procedure described in Example 2, using 3-methyl-2-pyridinemethanol instead of 6-methyl-2-pyridinemethanol, N-{4-[6-amino-5-cyano-2-(3-methylpyridin-2-ylmethylsulfanyl)pyrimidin-4-yl]phenyl}acetamide was given as a white powder.

$^1$H-NMR (DMSO-$d_6$) δ: 10.24 (1H, s), 8.34 (1H, d, J=4.8 Hz), 7.70-8.25 (2H, br s), 7.87 (2H, d, J=8.7 Hz), 7.73 (2H, d, J=8.7 Hz), 7.60 (1H, d, J=7.5 Hz), 7.19-7.24 (1H, m), 4.61 (2H, s), 2.36 (3H, s), 2.09 (3H, s).

Example 6

According to the same procedure described in Example 2, using 1-(6-methylpyridin-2-yl)ethanol instead of 6-methyl- 2-pyridinemethanol, N-(4-{6-amino-5-cyano-2-[1-(6-methyl-pyridin-2-yl)ethylsulfanyl]pyrimidin-4-yl}phenyl)acetamide was given as a white powder.

¹H-NMR (CDCl₃) δ: 10.25 (1H, brs), 7.83 (2H, d, J=7 Hz), 7.73 (2H, d, J=6 Hz), 7.62 (1H, t, J=6 Hz), 7.32 (1H, d, J=6 Hz), 7.13 (1H, d, J=6 Hz), 5.10 (1H, q, J=6 Hz), 2.47 (3H, s), 2.09 (3H, s), 1.69 (3H, d, J=6 Hz).

Example 7

According to the same procedure described in Example 2, using 1-(6-methylpyridin-2-yl)pentan-1-ol instead of 6-methyl-2-pyridinemethanol, N-(4-{6-amino-5-cyano-2-[1-(6-methylpyridin-2-yl)pentylsulfanyl]pyrimidin-4-yl}phenyl)-acetamide was given as a white powder.

¹H-NMR (CDCl₃) δ: 8.40 (1H, brs), 7.94 (2H, d, J=6 Hz), 7.63 (2H, d, J=6 Hz), 7.52 (1H, t, J=6 Hz), 7.22 (1H, d, J=6 Hz), 7.00 (1H, d, J=6 Hz), 5.79 (1H, brs), 5.03 (1H, t, J=6 Hz), 2.55 (3H, s), 2.21 (3H, s), 2.00-2.15 (2H, m), 1.20-1.45 (4H, m), 0.86 (3H, t, J=6 Hz).

Example 8

The compound (5.5 g) of Example 2 was suspended in a mixture of 50 mL of ethanol and 50 mL of water, and to the suspension was added 50 mL of 5N hydrochloric acid, and the resulting mixture was heated at 80° C. for 5 hours under stirring. After cooling the reaction mixture, the ethanol was removed under reduced pressure, and the residue was neutralized with 5N aqueous sodium hydroxide at ice temperature. The resulting crystal was filtrated, and recrystallized with ethanol to give 2.3 g of 4-amino-6-(4-aminophenyl)-2-(6-methylpyridin-2-ylmethylsulfanyl)-pyrimidine-5-carbonitrile as a light yellow powder.

¹H-NMR (DMSO-d₆) δ: 7.48-7.98 (2H, br s), 7.74 (2H, d, J=8.7 Hz), 7.60 (1H, t, J=7.8 Hz), 7.32 (1H, d, J=7.8 Hz), 7.12 (1H, d, J=7.8 Hz), 6.61 (2H, d, J=8.7 Hz), 5.90 (2H, s), 4.44 (2H, s), 2.45 (3H, s).

Example 9

The compound of Example 8 (170 mg) and triethylamine (0.2 mL) were added to 10 mL of acetonitrile, 0.12 g of propionyl chloride was added dropwise to the solution, and then the mixture was stirred at room temperature overnight. The resulting crystal was filtrated, washed with diethyl ether, and then dried under reduced pressure to give 85 mg of N-{4-[6-amino-5-cyano-2-(6-methylpyridin-2-ylmethylsulfanyl)-pyrimidin-4-yl]phenyl}propionamide as a white powder.

¹H-NMR (DMSO-d₆) δ: 10.16 (1H, s), 7.84 (2H, d, J=8.7 Hz), 7.74 (2H, d, J=8.7 Hz), 7.61 (1H, t, J=7.8 Hz), 7.33 (1H, d, J=7.8 Hz), 7.12 (1H, d, J=7.8 Hz), 4.45 (2H, s), 2.45 (3H, s), 2.37 (2H, q, J=8.7 Hz), 1.10 (3H, t, J=7.5 Hz).

Example 10

According to the same procedure described in Example 9, using acryloyl chloride instead of propionyl chloride, N-{4-[6-amino-5-cyano-2-(6-methylpyridin-2-ylmethylsulfanyl)pyrimidin-4-yl]phenyl}acrylamide was given as a white powder.

¹H-NMR (DMSO-d₆) δ: 10.43 (1H, s), 7.79-7.89 (4H, m), 7.61 (1H, t, J=7.8 Hz), 7.33 (1H, d, J=7.8 Hz), 7.12 (1H, d, J=7.8 Hz), 6.42-6.52 (1H, m), 6.31 (1H, dd, J=16.8, 2.1 Hz), 5.81 (1H, dd, J=9.9, 2.1 Hz), 4.45 (2H, s), 2.45 (3H, s).

Example 11

According to the same procedure described in Example 9, using butyryl chloride instead of propionyl chloride, N-{4-[6-amino-5-cyano-2-(6-methylpyridin-2-ylmethylsulfanyl)pyrimidin-4-yl]phenyl}butylamide was given as a white powder.

¹H-NMR (DMSO-d₆) δ: 10.17 (1H, s), 7.65-8.20 (2H, br s), 7.83 (2H, d, J=8.7 Hz), 7.74 (2H, d, J=8.7 Hz), 7.61 (1H, t, J=7.8 Hz), 7.33 (1H, d, J=7.8 Hz), 7.12 (1H, d, J=7.8 Hz), 4.45 (2H, s), 2.45 (3H, s), 2.33 (2H, t, J=7.5 Hz), 1.63 (3H, sext, J=7.5 Hz), 0.93 (3H, t, J=7.5 Hz).

Example 12

According to the same procedure described in Example 9, using benzoyl chloride instead of propionyl chloride, N-{4-[6-amino-5-cyano-2-(6-methylpyridin-2-ylmethylsulfanyl)pyrimidin-4-yl]phenyl}benzamide was given as a white powder.

¹H-NMR (DMSO-d₆) δ: 10.53 (1H, s), 7.80-8.01 (6H, m), 7.51-7.70 (4H, m), 7.35 (1H, d, J=7.5 Hz), 7.13 (1H, d, J=7.5 Hz), 4.47 (2H, s), 2.46 (3H, s).

Example 13

According to the same procedure described in Example 2, using 6-methyl-2-pyridinemethanol, thiourea and the compound of Reference Example 1, methyl {4-[6-amino-5-cyano-2-(6-methylpyridin-2-ylmethylsulfanyl)pyrimidin-4-yl]phenyl}-carbamate was given as a yellow powder.

¹H-NMR (DMSO-d₆) δ: 10.01 (1H, s), 7.83 (2H, d, J=8.7 Hz), 7.61 (1H, t, J=7.5 Hz), 7.60 (2H, d, J=8.7 Hz), 7.33 (1H, d, J=7.5 Hz), 7.12 (1H, d, J=7.5 Hz), 4.45 (2H, s), 3.70 (3H, s), 2.45 (3H, s).

The structures of each compound obtained according to above Examples 1-13 are shown in the following Table 2.

TABLE 2

| Example No. | R¹ | |
|---|---|---|
| 1 | Ac | (2-pyridinyl)methyl (R² = CH₂, pyridine with N) |
| 2 | Ac | (6-methylpyridin-2-yl)methyl (R² = CH₂, 6-Me pyridine) |

TABLE 2-continued

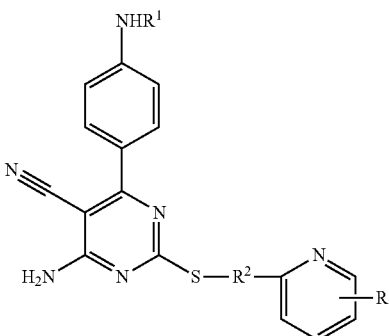

| Example No. | R¹ | —R²—pyridine—R³ |
|---|---|---|
| 3 | Ac | 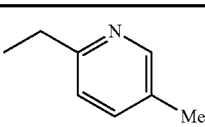 |
| 4 | Ac | 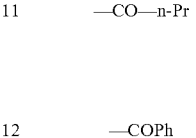 |
| 5 | Ac | 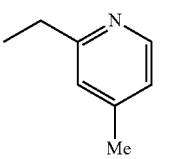 |
| 6 | Ac |  |
| 7 | Ac | 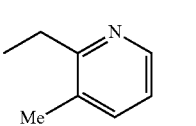 |
| 8 | H | 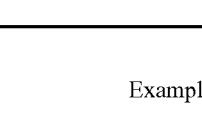 |
| 9 | —CO—Et | 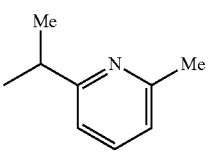 |
| 10 | —COCH=CH₂ | 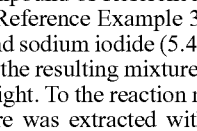 |

TABLE 2-continued

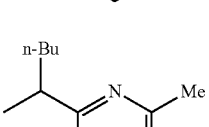

| Example No. | R¹ | —R²—pyridine—R³ |
|---|---|---|
| 11 | —CO—n-Pr | 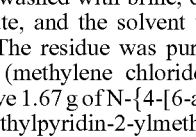 |
| 12 | —COPh | 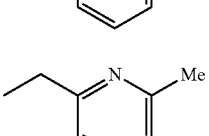 |
| 13 | —COOCH₃ | 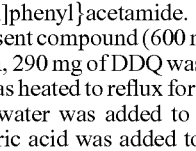 |

Example 14

The compound of Reference Example 2 (10 g), the compound of Reference Example 3 (9.8 g), sodium bicarbonate (3.52 g) and sodium iodide (5.40 g) were added to 100 mL of DMF, and the resulting mixture was stirred at room temperature overnight. To the reaction mixture was added water, and the mixture was extracted with ethyl acetate. The organic layer was washed with brine, dried over anhydrous magnesium sulfate, and the solvent was removed under reduced pressure. The residue was purified by chromatography on silica gel (methylene chloride-ethanol-triethylamine=800:40:1) to give 1.67 g of N-{4-[6-amino-5-cyano-2-(6-morpholin-4-ylmethylpyridin-2-ylmethylsulfanyl)-2,3-dihydropyrimidin-4-yl]phenyl}acetamide.

The present compound (600 mg) was dissolved in 12 mL of 1,4-dioxan, 290 mg of DDQ was added to the solution and the mixture was heated to reflux for 2 hours. After the solvent was removed, water was added to the residue, furthermore 1N hydrochloric acid was added to make the solution acidic. It was washed with ethyl acetate, the aqueous layer was basified with 1N aqueous sodium hydroxide, and extracted with ethyl acetate. The organic layer was washed with brine, dried over anhydrous magnesium sulfate, and then the solvent was removed under reduced pressure. The residue was recrystallized from ethanol to give 290 mg of N-{4-[6-amino-5-cyano-2-(6-morpholin-4-ylmethylpyridin-2-ylmethylsulfanyl)pyrimidin-4-yl]phenyl}acetamide.

The whole of the above product was dissolved in ethanol, thereto 1 mol/L of hydrochloric acid in ethanol (0.61 mL) was added, and the mixture was evaporated to dryness under reduced pressure to give the above compound as a hydrochloride form as a white powder.

$^1$H-NMR (DMSO-d$_6$) δ: 10.2 (1H, s), 7.82 (2H, d, J=8.7 Hz), 7.72-7.67 (3H, m), 7.40 (1H, d, J=7.8 Hz), 7.31 (1H, d, J=7.8 Hz), 4.47 (2H, s), 3.57 (4H, br t), 2.39 (4H, br t), 2.08 (3H, s).

Example 15

To a solution of the compound of Reference Example 2 (287 mg) in 3 mL of DMF, the compound of Reference Example 4 (260 mg), sodium bicarbonate (100 mg) and sodium iodide (150 mg) was added and the mixture was stirred at room temperature overnight. After water was added to the reaction mixture, the mixture was extracted with ethyl acetate, and the organic layer was washed with brine, dried over anhydrous magnesium sulfate, and then the solvent was removed under reduced pressure. To the residue, 1 mL of acetonitrile and 7.3 mg of NBS were added, and the mixture was heated to reflux for 30 minutes. After allowing to cool, water was added to the reaction mixture and the resulting mixture was extracted with ethyl acetate. The organic layer was washed with brine, dried over anhydrous magnesium sulfate, and then the solvent was removed under reduced pressure. The residue was recrystallized from ethanol to give 35 mg of N-(4-{6-amino-5-cyano-2-[6-(2-morpholin-4-yl-ethyl)pyridin-2-ylmethyl-sulfanyl]pyrimidin-4-yl}phenyl)acetamide. The whole of the resulting compound was dissolved in ethanol, 1 mol/L of hydrochloric acid in ethanol (0.14 mL) was added, and the mixture was evaporated to dryness under reduced pressure to give 40 mg of the desired compound as a hydrochloride salt form as a white powder.

$^1$H-NMR (DMSO-d$_6$) δ: 10.2 (1H, s), 7.83 (2H, d, J=8.7 Hz), 7.71 (2H, d, J=8.7 Hz), 7.66 (1H, t, J=7.2 Hz), 7.33 (1H, d, J=7.2 Hz), 7.15 (1H, d, J=7.2 Hz), 4.46 (2H, s), 3.55-3.52 (4H, m), 2.86 (2H, t, J=7.2 Hz), 2.60 (2H, t, J=7.2 Hz), 2.39 (4H, br t), 2.03 (3H, s).

Example 16

Thiourea (86 mg) and the compound of Reference Example 5 (290 mg) were suspended in 50 mL of ethanol, and the resulting suspension was stirred at 60° C. for 1 hour. After allowing to cool, 240 mg of N-[4-(2,2-dicyanovinyl)-phenyl]acetamide and 287 mg of sodium bicarbonate was added to the solution, and was heated to reflux for 5 hours. After allowing to cool, additionally 200 mg of NBS was added, and the mixture was heated to reflux for 1 hour. Water was added to the reaction solution, and the mixture was extracted with chloroform. The organic layer was washed with brine, dried over anhydrous magnesium sulfate, and then the solvent was removed. The residue was purified by chromatography on silica gel (chloroform-methanol-aqueous ammonia=300:10:1) to give 85 mg of N-(4-{6-amino-5-cyano-2-[6-(3-morpholin-4-ylpropyl)pyridin-2-ylmethylsulfanyl]pyrimidin-4-yl}phenyl)acetamide. The whole of the resulting compound was dissolved in ethanol, 1 mol/L of hydrochloric acid in ethanol (0.38 mL) was added to the solution, and then the solvent was removed off to give 110 mg of the desired compound as a hydrochloride salt as a yellow powder.

$^1$H-NMR (DMSO-d$_6$) δ: 10.2 (1H, s), 7.83 (2H, d, J=8.7 Hz), 7.71 (2H, d, J=8.7 Hz), 7.61 (1H, t, J=7.5 Hz), 7.32 (1H, d, J=7.5 Hz), 7.12 (1H, d, J=7.5 Hz), 4.40 (2H, s), 3.64-3.50 (4H, m), 2.70 (2H, t, J=7.5 Hz), 2.40-2.24 (6H, m), 2.08 (3H, s), 2.49-2.45 (2H, m).

Example 17

The compound of Reference Example 6 (15 g) and thiourea (3.8 g) was suspended in 200 mL of ethanol, the suspension was stirred at 60° C. for 1 hour. To the reaction mixture, 9.72 g of N-[4-(2,2-dicyanovinyl)phenyl]acetamide was added and the mixture was heated to reflux overnight. After the solvent was removed under reduced pressure, water was added to the residue, the mixture was extracted with chloroform. The organic layer was washed with brine, dried over anhydrous magnesium sulfate, and then concentrated to dryness under reduced pressure. The residue was purified by chromatography on silica gel (methylene chloride-methanol-aqueous ammonia=300:10:1) to give 10.3 g of t-butyl 4-{6-[4-(4-acetylaminophenyl)-6-amino-5-cyanopyrimidin-2-yl-sulfanyl-methyl]-pyridin-2-ylmethyl}piperazine-1-carboxylate as a white powder.

$^1$H-NMR (DMSO-d$_6$) δ: 10.2 (1H, s), 7.83 (2H, d, J=8.7 Hz), 7.72-7.70 (3H, m), 7.40 (1H, d, J=7.5 Hz), 7.32 (1H, d, J=7.5 Hz), 4.47 (2H, s), 3.57 (2H, s), 2.50-2.35 (8H, m), 2.20 (3H, s), 1.38 (9H, s).

Example 18

The compound of Example 17 (123 mg) was added into a round-bottom flask, thereto at ice temperature 0.35 mL of trifluoroacetic acid was added. The mixture was stirred at room temperature for 1 hour, and then the trifluoroacetic acid was removed off under reduced pressure. To the residue, 0.1 mol/L of hydrochloric acid in 6 mL of ethanol was added, and the solvent was evaporated to dryness. The residual solid was recrystallized from ethanol to give 80 mg of N-{4-[6-amino-5-cyano-2-(6-piperazin-1-ylmethylpyridin-2-ylmethyl-sulfanyl)pyrimidin-4-yl]phenyl}acetamide hydrochloride as a white powder.

$^1$H-NMR (DMSO-d$_6$) δ: 10.3 (1H, s), 9.42 (1H, br s), 7.89-7.81 (3H, m), 7.73 (2H, d, J=8.7 Hz), 7.63 (1H, d, J=7.5 Hz), 7.52 (1H, d, J=7.5 Hz), 4.55 (2H, s), 3.37-3.25 (10H, m), 2.03 (3H, s).

Example 19

The compound of Example 18 (292 mg), benzoic acid (61 mg) and triethylamine (0.2 mL) was dissolved in 3 mL of DMF, to the above solution, 80 mg of HOBt was added under stirring at ice temperature. After stirring the mixture at the same temperature for 15 minutes, thereto 115 mg of WSC was added, and the mixture was stirred at room temperature overnight. The reaction solution was evaporated to dryness under reduced pressure, and ice-water was added to the resulting residue, and the mixture was extracted with ethyl acetate. The organic layer was washed with brine, dried over anhydrous magnesium sulfate, and then concentrated to dryness under reduced pressure. The residue was purified by chromatography on silica gel (methylene chloride-methanol-triethylamine=300:10:1) to give 261 mg of N-(4-{6-amino-2-[6-(4-benzoylpiperazin-1-ylmethyl)pyridin-2-ylmethylsulfanyl]-5-cyanopyrimidin-4-yl}phenyl)acetamide as a white powder.

$^1$H-NMR (DMSO-d$_6$) δ: 10.2 (1H, s), 7.83 (2H, d, J=8.7 Hz), 7.72-7.70 (3H, m), 7.44-7.32 (7H, m), 4.48 (2H, s), 3.60 (2H, s), 2.08 (3H, s).

Example 20

The compound of Example 18 (146 mg), benzaldehyde (28 mg) and triethylamine (75 mg) were dissolved in a mixture of 1 mL of DMF and 2 mL of methanol, the resulting mixture was stirred at room temperature overnight. To the reaction mixture under ice temperature, 30 mg of sodium cyanoborohydride was added, and the mixture was stirred at the same temperature for 1 hour. The reaction solution was evaporated to dryness under reduced pressure, thereto ice-water was added and the mixture was extracted with ethyl acetate. The organic layer was washed with brine, dried over anhydrous magnesium sulfate, and then concentrated to dryness under reduced pressure. The residue was purified by chromatography on silica gel (methylene chloride-methanol-triethylamine=600:20:1) to give 60 mg of N-(4-{6-amino-2-[6-(4-benzylpiperazin-1-ylmethyl)pyridin-2-ylmethylsulfanyl]-5-cyanopyrimidin-4-yl}phenyl)acetamide as a white powder.

$^1$H-NMR (DMSO-$d_6$) δ: 7.98 (2H, d, J=8.7 Hz), 7.64 (2H, d, J=8.7 Hz), 7.58 (1H, t, J=7.5 Hz), 7.53-7.50 (2H, m), 7.42-7.29 (5H, m), 4.54 (2H, s), 3.75 (2H, s), 2.61-2.48 (10H, m), 2.20 (3H, s).

Example 21

According to the same procedure described in Example 19, using (4-methylpiperazin-1-yl)acetic acid instead of benzoic acid, N-{4-[6-amino-5-cyano-2-(6-{4-[2-(4-methylpiperazin-1-yl)acetyl]piperazin-1-ylmethyl}pyridin-2-ylmethylsulfanyl)pyrimidin-4-yl]phenyl}acetamide hydrochloride was given as a white powder.

$^1$H-NMR (DMSO-$d_6$) δ: 10.2 (1H, s), 7.83 (2H, d, J=8.7 Hz), 7.73-7.70 (3H, m), 7.40 (1H, d, J=7.5 Hz), 7.32 (1H, d, J=7.5 Hz), 4.48 (2H, s), 3.59 (2H, s), 3.43 (2H, br t), 3.36-3.33 (4H, m), 3.08 (2H, s), 2.49-2.27 (10H, m), 2.12 (3H, s), 2.08 (3H, s).

Example 22

According to the same procedure described in Example 19, using p-methoxybenzoic acid instead of benzoic acid, N-[4-(6-amino-5-cyano-2-{6-[4-(4-methoxybenzoyl)piperazin-1-ylmethyl]pyridin-2-ylmethylsulfanyl}pyrimidin-4-yl)phenyl]acetamide hydrochloride was given as a white powder.

$^1$H-NMR (DMSO-$d_6$) δ: 10.2 (1H, s), 7.97 (1H, d, J=8.4 Hz), 7.83 (2H, d, J=8.7 Hz), 7.73-7.68 (3H, m), 7.53 (1H, t, J=7.2 Hz), 7.43-7.32 (3H, m), 6.96 (1H, d, J=8.7 Hz), 4.47 (2H, s), 3.78 (3H, s), 3.62 (3H, s), 3.48-3.32 (2H, m), 2.49-2.45 (4H, m), 2.08 (3H, s).

Example 23

According to the same procedure described in Example 19, using N,N-dimethylglycine instead of benzoic acid, N-[4-(6-amino-5-cyano-2-{6-[4-(2-dimethylaminoacetyl)piperazin-1-ylmethyl]pyridin-2-ylmethylsulfanyl}pyrimidin-4-yl)phenyl]acetamide hydrochloride salt was given as a white powder.

$^1$H-NMR (DMSO-$d_6$) δ: 10.2 (1H, s), 7.83 (2H, d, J=9.0 Hz), 7.72-7.68 (3H, m), 7.42 (1H, d, J=7.5 Hz), 7.33 (1H, d, J=7.5 Hz), 4.48 (2H, s), 3.59 (2H, s), 3.49-3.41 (4H, m), 3.15 (2H, br s), 2.48-2.42 (4H, m), 2.21 (6H, s), 2.08 (3H, s).

Example 24

According to the same procedure described in Example 19, using piperidine-1-propionic acid instead of benzoic acid, N-[4-(6-amino-5-cyano-2-{6-[4-(3-piperidin-1-ylpropionyl)-1-piperazin-1-ylmethyl]pyridin-2-ylmethylsulfanyl}pyrimidin-4-yl)phenyl]acetamide hydrochloride salt as a white powder.

$^1$H-NMR (DMSO-$d_6$) δ: 10.2 (1H, s), 7.83 (2H, d, J=8.7 Hz), 7.74-7.68 (3H, m), 7.43 (1H, t, J=7.5 Hz), 7.33 (1H, d, J=7.5 Hz), 4.47 (2H, s), 3.60 (2H, s), 3.44-3.34 (4H, m), 2.51-2.50 (4H, m), 2.43-2.37 (4H, m), 2.09 (3H, s), 1.58 (4H, br s), 1.43 (2H, br t).

Example 25

According to the same procedure described in Example 19, using piperidin-1-ylacetic acid instead of benzoic acid, N-[4-(6-amino-5-cyano-2-{6-[4-(2-piperidin-1-ylacetyl)-piperazin-1-ylmethyl]pyridin-2-ylmethylsulfanyl}pyrimidin-4-yl)phenyl]acetamide hydrochloride as a white powder.

$^1$H-NMR (CD$_3$OD) δ: 7.90-7.81 (3H, m), 7.73 (2H, d, J=8.7 Hz), 7.69 (2H, d, J=7.8 Hz), 7.43 (1H, t, J=7.8 Hz), 4.64 (2H, s), 4.55 (2H, s), 4.42 (2H, s), 3.92 (1H, br s), 3.77-3.72 (3H, m), 3.58-3.51 (2H, m), 3.44-3.31 (2H, m), 3.29-3.14 (2H, m), 2.16 (3H, s), 2.10-2.06 (2H, m), 1.36-1.31 (2H, m).

The structures of each compound obtained according to Examples 14-25 are shown in the following Table 3.

TABLE 3

| Example No. | R$^3$ = |
|---|---|
| 14 | ethyl-morpholine |
| 15 | propyl-morpholine |
| 16 | butyl-morpholine |
| 17 | ethyl-piperazine-C(=O)-OtBu |
| 18 | ethyl-piperazine-NH |
| 19 | ethyl-piperazine-C(=O)-Ph |
| 20 | ethyl-piperazine-CH$_2$-Ph |

TABLE 3-continued

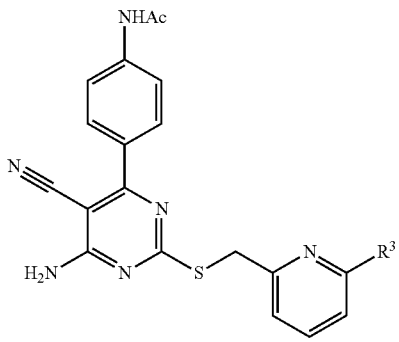

| Example No. | R³ = |
|---|---|
| 21 | 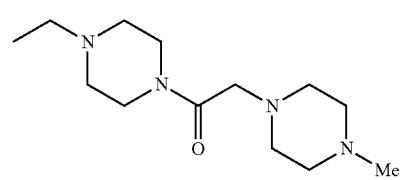 |
| 22 | 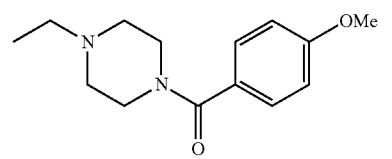 |
| 23 | 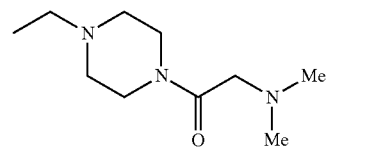 |
| 24 | 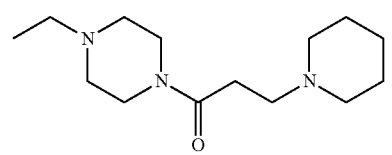 |
| 25 | 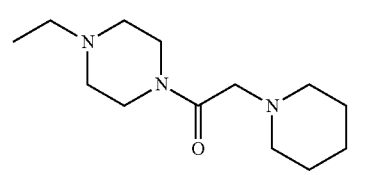 |

Example 26

The compound derived from Reference Example 7 (571 mg) and thiourea (180 mg) were dissolved in 20 mL of ethanol, and the solution was heated to reflux for 1 hour. After being cooled, 500 mg of N-[4-(2,2-dicyanovinyl)phenyl]acetamide and 600 mg of sodium bicarbonate were added to the reaction mixture, and the resulting mixture was heated to reflux for 4 hours. After being cooled, 356 mg of NBS was added to the reaction mixture and the resulting mixture was heated to reflux for 1 hour. After being cooled, 5 mL of saturated aqueous sodium bicarbonate and 10 mL of water were also added thereto, and the precipitate was filtrated, washed with water, and dried under reduced pressure to give 380 mg of N-(4-{6-amino-5-cyano-2-[6-(morpholin-4-carbonyl)pyridin-2-ylmethyl-sulfanyl]pyrimidin-4-yl}phenyl)acetamide hydrochloride salt as a white powder.

$^1$H-NMR (DMSO-$d_6$) δ: 10.2 (1H, s), 7.86 (1H, t, J=7.8 Hz), 7.79 (2H, d, J=9.0 Hz), 7.70 (2H, d, J=9.0 Hz), 7.62 (1H, d, J=7.8 Hz), 7.47 (1H, d, J=7.8 Hz), 4.53 (2H, s), 3.63 (4H, br t), 3.49-3.44 (2H, m), 2.08 (3H, s).

Example 27

According to the same procedure described in Example 26, using the compound of Reference Example 8 instead of the compound of Reference Example 7, t-butyl 6-[4-(4-acetylaminophenyl)-6-amino-5-cyanopyrimidin-2-ylsulfanyl-methyl]pyridine-2-carboxylate was given as a white powder.

$^1$H-NMR (DMSO-$d_6$) δ: 7.82-7.72 (7H, m), 4.55 (2H, s), 2.08 (3H, S), 1.54 (9H, s).

Example 28

According to the same procedure described in Example 26, using the compound of Reference Example 9 instead of the compound of Reference Example 7, t-butyl 4-{6-[4-(4-acetylaminophenyl)-6-amino-5-cyanopyrimidin-2-ylsulfanyl-methyl]pyridine-2-carbonyl}piperazine-1-carboxylate was given as a white powder.

$^1$H-NMR (DMSO-$d_6$) δ: 10.2 (1H, s), 7.89 (1H, t, J=7.8 Hz), 7.83 (2H, d, J=8.7 Hz), 7.75 (2H, d, J=8.7 Hz), 7.63 (1H, d, J=7.8 Hz), 7.47 (1H, d, J=7.8 Hz), 4.53 (2H, s), 3.60-3.56 (2H, br), 3.45-3.31 (6H, br), 2.09 (3H, s), 1.40 (12H, s).

Example 29

To the compound of Example 28 (600 mg) at ice temperature added 2 mL of TFA, and the mixture was stirred at room temperature for 1 hour. The residual TFA was removed under reduced pressure, and 20 mL of 0.1 mol/L hydrochloric acid in ethanol was added to the residue and the mixture was stirred. The resulting crystal was filtrated to give 80 mg of N-(4-{6-amino-5-cyano-2-[6-(piperazin-1-carbonyl)pyridin-2-ylmethylsulfanyl]pyrimidin-4-yl}phenyl)acetamide hydrochloride as a white powder.

$^1$H-NMR (DMSO-$d_6$) δ: 10.2 (1H, s), 9.16 (2H, br), 7.90 (1H, t, J=7.8 Hz), 7.80 (2H, d, J=8.7 Hz), 7.72 (2H, d, J=8.7 Hz), 7.69 (1H, d, J=7.8 Hz), 7.55 (1H, d, J=7.8 Hz), 4.54 (2H, s), 3.86 (2H, br), 3.70 (2H, br), 3.20-3.10 (4H, br), 2.09 (3H, s).

The structures of each compound obtained according to Examples 26-29 are shown in the following Table 4.

TABLE 4

| Example No. | R = |
|---|---|
| 26 | *N-morpholinyl* |
| 27 | OtBu |
| 28 | *4-methylpiperazine-1-carbonyl-OtBu* |
| 29 | *4-methylpiperazin-1-yl* (NH) |

Example 30 t-Butyl (6-hydroxymethylpyridin-2-ylmethyl)carbamate (1 g) and diisopropylethylamine (1.1 mL) were dissolved in 20 mL of dichloromethane, 0.33 mL of methanesulfonyl chloride was added dropwise to the solution at room temperature, and the mixture was stirred for 1 hour at same temperature. Water was added to the reaction solution, the organic layer was washed with water (twice) and brine (once), and dried over anhydrous magnesium sulfate. The solvent was removed under reduced pressure, the resulting oil was dissolved in 25 mL of ethanol together with 0.32 g of thiourea, and then was heated to reflux for 1 hour. To the reaction mixture added 0.4 g of NBS, and the mixture was heated to reflux for 5 minutes. After allowing to cool, the solvent was removed. The residue was dissolved in chloroform, washed with water (twice) and brine (once), and then dried over anhydrous magnesium sulfate. The solvent was removed under reduced pressure, and the residue was purified by chromatography on silica gel (methylene chloride-methanol-aqueous ammonia=90:10:1). The resulting crude crystal was purified by recrystallization from ethyl acetate-hexane to give 0.97 g of t-butyl {6-[4-(4-acetylaminophenyl)-6-amino-5-cyanopyrimidin-2-ylsulfanyl-methyl]pyridin-2-ylmethyl}carbamate as a white powder.

$^1$H-NMR (DMSO-$d_6$) δ: 10.25 (1H, s), 8.25-7.49 (2H, br s), 7.98 (1H, t, J=7.5 Hz), 7.83 (2H, d, J=8.7 Hz), 7.73 (2H, d, J=8.7 Hz), 7.64 (1H, d, J=7.5 Hz), 7.53 (1H, br s), 7.33 (1H, d, J=7.5 Hz), 4.54 (2H, s), 4.29 (2H, d, J=5.7 Hz), 2.09 (3H, s), 1.40 (9H, s).

Example 31

To 0.2 g of the compound of Example 30, 1 mL of trifluoroacetic acid was added, and the mixture was stirred for 30 minutes at room temperature, and then trifluoroacetic acid was removed. To the residue was added 2 mL of triethylamine, the mixture was stirred at room temperature, and then 0.19 g of WSC, 0.14 g of HOBt and 41 mg of N,N-dimethylglycine were added, and furthermore the mixture was stirred at room temperature overnight. Water was added to the reaction and the resulting crystal was filtrated, washed with ethanol, and then dried to give 76 mg of N-{6-[4-(4-acetylaminophenyl)-6-amino-5-cyanopyrimidin-2-ylsulfanyl-methyl]pyridin-2-ylmethyl}-2-dimethylaminoacetamide.

The whole product was dissolved in 2 mL of ethanol, to the solution was added 1 mL of 1 mol/L hydrochloric acid in ethanol, and then the ethanol was removed under reduced pressure to give the desired compound in a hydrochloride salt form as a white powder.

$^1$H-NMR (DMSO-$d_6$) δ: 10.24 (1H, s), 8.36 (1H, t, J=6.0 Hz), 8.25-7.65 (2H, br s), 7.85 (2H, d, J=8.7 Hz), 7.72-7.66 (3H, m), 7.41 (1H, d, J=7.5 Hz), 7.14 (1H, d, J=7.5 Hz), 4.48 (2H, s), 4.38 (2H, d, J=6.0 Hz), 2.94 (2H, s), 2.24 (6H, s), 2.09 (3H, s).

Example 32

To 0.3 g of the compound of Example 30 was added 2 mL of trifluoroacetic acid, and the mixture was stirred at room temperature for 1 hour. Then the trifluoroacetic acid was removed under reduced pressure from the reaction mixture, the residue was dissolved in 2 mL of acetonitrile. To resulting solution was added 4 mL of 28% aqueous ammonia, and the resulting crystal was filtrated to give 0.2 g of N-{4-[6-amino-2-(6-aminomethylpyridin-2-ylmethylsulfanyl)-5-cyano-pyrimidin-4-yl]phenyl}acetamide as a white powder.

$^1$H-NMR (DMSO-$d_6$) δ: 10.25 (1H, s), 8.25-7.65 (2H, br s), 7.84 (2H, d, J=8.7 Hz), 7.75-7.65 (3H, m), 7.29-7.40 (2H, m), 4.47 (2H, s), 3.78 (2H, s), 2.09 (3H, s).

Example 33

The compound of Example 32 (0.2 g) and triethylamine (0.5 mL) were dissolved in 2 mL of DMF. To the solution was added 0.1 g of 4-pyrrolidin-1-ylbutyric acid hydrochloride salt, 0.07 g of HOBt and 0.1 g of WSC, and the mixture was stirred at room temperature overnight. Water was added to the reaction, and the resulting crystal was filtrated. The crude crystal was recrystallized from ethanol to give 43 mg of N-{6-[4-(4-acetylaminophenyl)-6-amino-5-cyanopyrimidin-2-ylsulfanylmethyl]pyridin-2-ylmethyl}-4-pyrrolidin-1-ylbutyl-amide.

The whole product was dissolved in 2 mL of ethanol, to the solution was added 1 mL of 1 mol/L hydrochloric acid in ethanol, and then the ethanol was removed under reduced pressure to give the desired compound as a hydrochloride salt form as a white powder.

$^1$H-NMR (DMSO-$d_6$) δ: 10.24 (1H, s), 8.40 (1H, t, J=6.0 Hz), 8.25-7.65 (2H, br s), 7.85 (1H, d, J=8.7 Hz), 7.74-7.66 (3H, m), 7.41 (1H, d, J=7.5 Hz), 7.12 (1H, d, J=7.5 Hz), 4.47 (2H, s), 4.31 (2H, d, J=6.0 Hz), 2.32-2.38 (6H, m), 2.20 (2H, t, J=7.2 Hz), 2.09 (3H, s), 1.75-1.57 (6H, m).

Example 34 t-Butyl (6-hydroxymethylpyridin-2-ylmethyl)-methylcarbamate (0.76 g) and diisopropylethylamine (0.78 ml) were added in 10 ml of methylene chloride, thereto 0.23 ml of methanesulfonyl chloride was added at room temperature, and the mixture was stirred for 1 hour. Water was added to the reaction, the organic layer was washed with brine, dried over anhydrous magnesium sulfate, and then the solvent was removed under reduced pressure. The resulting oil was dissolved in 20 ml of ethanol, thereto 0.23 g of thiourea was added, and the mixture was heated to reflux for 1 hour. After allowing to cool the reaction mixture, the solvent was removed under reduced pressure, and the residue was washed with diethyl ether to give 0.9 g of a light brown oil. The whole product and 0.63 g of N-[4-(2,2-dicyanovinyl)phenyl]acetamide was dissolved in 20 mL of ethanol and the solution was heated to reflux for 2 hours. To the reaction mixture was added 0.32 g of NBS, and the mixture was heated to reflux for additional 5 minutes. After allowing to cool the mixture, the solvent was removed under reduced pressure. The residue was dissolved in chloroform, washed with water (twice) and brine (once), and then dried over anhydrous magnesium sulfate. The solvent was removed under reduced pressure, the resulting oil was purified by chromatography on silica gel (methylene chloride-methanol-aqueous ammonia=90:10:1). The given crude crystal was recrystallized from ethyl acetate-hexane to give 0.51 g of t-butyl {6-[4-(4-acetylaminophenyl)-6-amino-5-cyanopyrimidin-2-ylsulfanylmethyl]pyridin-2-yl-methyl}methylcarbamate as a white powder.

$^1$H-NMR (DMSO-$d_6$) δ: 10.24 (1H, s), 7.84 (2H, d, J=8.4 Hz), 7.75-7.69 (3H, m), 7.43 (1H, d, J=7.5 Hz), 7.05 (1H, d, J=7.5 Hz), 4.48 (3H, s), 4.43 (2H, s), 2.85 (3H, s) 2.09 (3H, s), 1.51-1.25 (9H, m).

Example 35

According to the same procedure described in Example 32, using the compound of Example 34 instead of the compound of Example 30 as a starting material, N-{4-[6-amino-5-cyano-2-(6-methylaminomethylpyridin-2-ylmethylsulfanyl)pyrimidin-4-yl]phenyl}acetamide was given as a white powder.

$^1$H-NMR (DMSO-$d_6$) δ: 10.24 (1H, s), 7.65-8.25 (2H, br s), 7.84 (2H, d, J=8.7 Hz), 7.72-7.66 (3H, m), 7.41 (1H, d, J=7.8 Hz), 7.30 (1H, d, J=7.8 Hz), 4.48 (2H, s), 3.74 (2H, s), 2.31 (3H, s), 2.09 (3H, s).

Example 36

According to the same procedure described in Example 33, using the compound of Example 35 instead of the compound of Example 32, N-{6-[4-(4-acetylaminophenyl)-6-amino-5-cyano-pyrimidin-2-ylsulfanylmethyl]pyridin-2-ylmethyl}-N-methyl-4-pyrrolidin-1-ylbutylamide hydrochloride salt was given as a white powder.

$^1$H-NMR (DMSO-$d_6$) δ: 10.23 (1H, s), 8.22-7.66 (2H, br s), 7.86-7.65 (5H, m), 7.47-7.39 (1H, m), 7.13-7.01 (1H, m), 4.71-4.42 (4H, m>, 3.05-2.78 (3H, m), 2.45-2.20 (8H, m), 2.09 (3H, s), 1.75-1.55 (6H, m).

Example 37

The compound of Example 32 (0.5 g) and triethylamine (0.3 mL) was dissolved in 5 mL of DMSO, to the solution at ice temperature added 0.17 g of 3-bromopropionyl chloride, and the mixture was stirred for 30 minutes. The reaction mixture was diluted with chloroform, washed with water (twice) and brine (once), and the organic layer was dried over anhydrous magnesium sulfate. The solvent was removed, and the resulting crude crystal was washed with diethyl ether to give 0.12 g of N-{6-[4-(4-acetylaminophenyl)-6-amino-5-cyanopyrimidin-2-ylsulfanylmethyl]pyridin-2-ylmethyl}acryl-amide as a white powder.

$^1$H-NMR (DMSO-$d_6$) δ: 10.29 (1H, s), 8.73-8.65 (1H, m), 8.25-7.65 (2H, br s), 7.84 (2H, d, J=9 Hz), 7.81-7.70 (3H, m), 7.50-7.45 (1H, m), 7.23-7.11 (1H, m), 6.20-5.79 (3H, m), 4.51-4.32 (4H, m), 2.10 (3H, s).

Example 38

The compound of Example 37 (0.11 g) and 4-piperidinopiperidine (0.1 g) was dissolved in 2 mL of DMSO, and the solution was stirred at room temperature overnight. To the reaction solution, chloroform and water were added, and the organic layer was washed with water (twice), then brine (once), and the organic layer was dried over magnesium sulfate. After removing the solvent, the residue was purified by chromatography on silica gel (methylene chloride-methanol-28% aqueous ammonia=90:10:1) to give 50 mg of N-{6-[4-(4-acetylaminophenyl)-6-amino-5-cyanopyrimidin-2-yl-sulfanylmethyl]pyridin-2-ylmethyl}-3-[1,4']bipiperidinyl-1'-ylpropionamide. This product was transformed to a hydrochloride salt form thereof (a light yellow oil) according to the procedure of Example 31.

$^1$H-NMR (DMSO-$d_6$) δ: 10.2 (1H, s), 7.83 (2H, d, J=8.7 Hz), 7.71 (2H, d, J=8.7 Hz), 7.66 (1H, t, J=7.2 Hz), 7.33 (1H, d, J=7.2 Hz), 7.15 (1H, d, J=7.2 Hz), 4.46 (2H, s), 3.55-3.52 (4H, m), 2.86 (2H, t, J=7.2 Hz), 2.60 (2H, t, J=7.2 Hz), 2.39 (4H, br t), 2.03 (3H, s).

Example 39

To 0.2 g of the compound of Example 30 was added 1 mL of trifluoroacetic acid, the mixture was stirred at room temperature for 30 minutes, and then the reaction mixture was concentrated to dryness under reduced pressure. The residue was dissolved in 5 mL of acetonitrile, and to the solution was added 2 mL of triethylamine and the mixture was stirred at room temperature. Then thereto 63 mg of 4-methylpiperazine-1-carbonylchloride hydrochloride salt was added and the mixture was stirred at room temperature overnight. To the reaction solution was added water, and the resulting crystal was filtrated, washed with ethanol, and then dried to give 35 mg of 4-methylpiperazine-1-carboxylic {6-[4-(4-acetylaminophenyl)-6-amino-5-cyanopyrimidin-2-yl-sulfanylmethyl]pyridin-2-ylmethyl}amide. This product was transformed to a hydrochloride salt form (a white powder) according to the procedure of Example 31.

$^1$H-NMR (DMSO-$d_6$) δ: 10.24 (1H, s), 8.25-7.65 (2H, br s), 7.86 (2H, d, J=8.7 Hz), 7.74-7.65 (3H, m), 7.38 (1H, d, J=7.5 Hz), 7.17-7.10 (2H, m), 4.47 (2H, s), 4.31 (2H, d, J=6.0 Hz), 3.35-3.30 (4H, m), 2.31-2.24 (4H, m), 2.37 (3H, s), 2.10 (3H, s).

Example 40

To a suspension of 0.1 g of the compound of Example 32 in 5 mL of DMSO, 0.25 mL of diisopropylethylamine was added, and 0.04 mL of 1-propanesulfonyl chloride was added dropwise under stirring. After 30 minutes, water was added to the reaction mixture, and the resulting crystal was filtrated, and dried under reduced pressure to give 80 mg of N-[4-(6-amino-5-cyano-2-{6-[(propane-1-sulfonylamino)methyl]pyridin-2-ylmethylsulfanyl}pyrimidin-4-yl)phenyl]acetamide as a white powder.

$^1$H-NMR (DMSO-$d_6$) δ: 10.23 (1H, s), 7.65-8.20 (5H, m), 7.46 (1H, d, J=7.8 Hz), 7.33 (1H, d, J=7.8 Hz), 4.48 (2H, s), 4.22 (2H, d, J=6.3 Hz), 2.94-3.01 (2H, m), 2.09 (3H, s), 1.55-1.70 (2H, m), 0.89 (3H, t, J=7.5 Hz).

Example 41

To a suspension of 0.1 g of the compound of Example 35 in 5 mL of acetonitrile, 0.25 mL of diisopropylethylamine was added, 0.04 mL of 1-propanesulfonyl chloride was added dropwise under stirring. After 1 hour, water was added to the reaction mixture, and the resulting crystal was filtrated, and dried under reduced pressure to give 80 mg of N-{4-[6-amino-5-cyano-2-(6-{[methyl(propan-1-sulfonyl)amino]methyl}-pyridin-2-ylmethylsulfanyl)pyrimidin-4-yl]phenyl}acetamide as a white powder.

$^1$H-NMR (DMSO-$d_6$) δ: 10.23 (1H, s), 7.65-8.20 (5H, m), 7.49 (1H, d, J=7.8 Hz), 7.27 (1H, d, J=7.8 Hz), 4.50 (2H, s), 4.40 (2H, s), 2.77-3.32 (2H, m), 2.79 (3H, s), 2.09 (3H, s), 1.61-1.76 (3H, m), 0.96 (3H, t, J=7.2 Hz).

The structures of each compound obtained according to Examples 30-41 are shown in the following Table 5.

TABLE 5

| Example No. | R³ = |
|---|---|
| 30 | ~N(H)-C(=O)-OtBu |
| 31 | ~N(H)-C(=O)-CH₂-N(Me)Me |
| 32 | ~NH₂ |
| 33 | ~N(H)-C(=O)-(CH₂)₃-pyrrolidinyl |
| 34 | ~N(Me)-C(=O)-OtBu |
| 35 | ~N(H)-Me |

TABLE 5-continued

| Example No. | R³ = |
|---|---|
| 36 | ~N(Me)-C(=O)-(CH₂)₃-pyrrolidinyl |
| 37 | ~N(H)-C(=O)-CH=CH₂ |
| 38 | ~N(H)-C(=O)-CH₂CH₂-(4-piperidinyl)-piperidinyl |
| 39 | ~N(H)-C(=O)-(4-methylpiperazin-1-yl) |
| 40 | ~N(H)-SO₂-n-Pr |
| 41 | ~N(Me)-SO₂-n-Pr |

Example 42

Thiourea (5.33 g) was dissolved in 70 mL of ethanol at 60° C., to the solution was added 19.21 g of the compound of Reference Example 10 in 50 mL of ethanol, and the mixture was stirred at same temperature for 2 hours. After being cooled, to the reaction mixture was added 14.7 g of sodium bicarbonate, and the mixture was stirred at room temperature for 10 minutes. Additionally, to the mixture were added 14.8 g of N-[4-(2,2-dicyanovinyl)phenyl]acetamide and 50 mL of ethanol, and the mixture was heated to reflux overnight. The reaction mixture was poured into ice-water, and extracted with ethyl acetate. The organic layer was washed with brine, dried over anhydrous magnesium sulfate, and concentrated to dryness under reduced pressure. The residue was dissolved in 200 mL of ethanol, and under reflux each 2 g of NBS was added every 1 hour and the total were 4 times. After being cooled, the reaction mixture was poured into saturated aqueous sodium bicarbonate, and extracted with ethyl acetate. The organic layer was washed with brine, dried over anhydrous magnesium sulfate, and concentrated to dryness under reduced pressure. The residue was purified by chromatography on silica gel (chloroform-methanol=10:1), and recrystallized from acetone-IPE to give 16.19 g of t-butyl 3-{6-[4-(4-acetylaminophenyl)-6-amino-5-cyanopyrimidin-2-ylsulfanyl-methyl]pyridin-2-yl}propionate as a light yellow powder.

$^1$H-NMR (DMSO-d$_6$) δ: 7.83 (2H, d, J=8.7 Hz), 7.72 (2H, d, J=8.7 Hz), 7.63 (1H, t, J=7.5 Hz), 7.35 (1H, d, J=7.5 Hz), 7.14 (1H, d, J=7.5 Hz), 4.45 (2H, s), 2.94 (2H, t, J=7.5 Hz), 2.61 (2H, t, J=7.5 Hz), 2.09 (3H, s), 1.34 (9H, s).

Example 43

The compound of Reference Example 11 (3 g) was dissolved in 50 mL of dichloromethane, thereto 4 mL of diisopropylethylamine was added, 1.3 mL of methanesulfonyl chloride was added dropwise under ice temperature, and the mixture was stirred for 1 hour. To the reaction mixture was added water, the organic layer was washed with water and brine, dried over anhydrous magnesium sulfate, and then the solvent was removed under reduced pressure. The resulting brown oil was dissolved in 50 mL of ethanol, thereto 1.0 g of thiourea was added and the mixture was heated to reflux for 1 hour. After allowing to cool the reaction solution, thereto 2.5 g of N-[4-(2,2-dicyanovinyl)phenyl]acetamide, 5 mL of diisopropylethylamine and one drop of DBU were added, and the mixture was stirred at room temperature overnight. After the reaction solvent was removed under reduced pressure, the residue was dissolved in 50 mL of ethyl acetate, thereto 1.8 g of NBS was added at ice temperature under stirring and the mixture was stirred for 30 minutes. To the reaction mixture was added water, the organic layer was washed with water and brine. The organic layer was dried over anhydrous magnesium sulfate, and then the solvent was removed under reduced pressure. The resulting white oil was crystallized from 2-propanol, additionally recrystallized from 2-propanol to give 2.3 g of ethyl 3-{6-[4-(4-acetylaminophenyl)-6-amino-5-cyano-pyrimidin-2-ylsulfanylmethyl]pyridin-2-yl}propionate as a white powder.

$^1$H-NMR (DMSO-d$_6$) δ: 10.23 (1H, s), 7.26-8.20 (2H, br s) 7.83 (2H, d, J=8.7 Hz), 7.72 (2H, d, J=8.7 Hz), 7.63 (1H, t, J=7.8 Hz), 7.35 (1H, d, J=7.8 Hz) 7.15 (1H, d, J=7.8 Hz) 4.45 (2H, s), 4.03 (2H, q, J=7.2 Hz), 2.98 (2H, t, J=7.2 Hz), 2.70 (2H, t, J=7.2 Hz), 2.09 (3H, s), 1.14 (3H, t, J=7.2 Hz).

Example 44

According to the procedure described in Example 43, using the compound of Reference Example 12 instead of the compound of Reference Example 11, thiourea and N-[4-(2,2-dicyanovinyl)phenyl]acetamide, methyl 3-{6-[4-(4-acetylamino-phenyl)-6-amino-5-cyanopyrimidin-2-ylsulfanylmethyl]pyridin-2-yl}propionate was given as a white powder.

$^1$H-NMR (DMSO-d$_6$) δ: 10.23 (1H, s), 8.20-7.60 (2H, br s), 7.83 (2H, d, J=8.7 Hz), 7.72 (2H, d, J=8.7 Hz), 7.63 (1H, t, J=7.8, 7.8 Hz), 7.35 (1H, d, J=7.8 Hz), 7.15 (1H, d, J=7.8 Hz), 4.45 (2H, s), 3.57 (3H, s), 2.96 (2H, t, J=7.2 Hz), 2.74 (2H, t, J=7.2 Hz), 2.09 (3H, s).

Example 45

The compound of Example 42 (8.21 g) was cooled to ice temperature, thereto 30 mL of TFA was added, and the mixture was stirred at room temperature for 1.5 hours. The TFA was removed off under reduced pressure, then 100 mL of chloroform was added to the residue and evaporated under reduced pressure again. The residue was dissolved in acetone, thereto 18 mL of 1N hydrochloric acid was added, and the mixture was concentrated to dryness under reduced pressure. The residue was disperse in acetone, and filtrated to give 6.82 g of 3-{6-[4-(4-acetylaminophenyl)-6-amino-5-cyano-pyrimidin-2-ylsulfanylmethyl]pyridin-2-yl}propionic acid hydrochloride as a light yellow powder.

$^1$H-NMR (CD$_3$OD) δ: 8.38 (1H, t, J=7.8 Hz), 8.05 (1H, d, J=7.8 Hz), 7.82 (2H, d, J=9.0 Hz), 7.81 (1H, d, J=7.8 Hz), 7.72 (2H, d, J=9.0 Hz), 4.69 (2H, s), 3.15 (2H, t, J=6.9 Hz), 2.84 (2H, t, J=6.9 Hz), 2.16 (3H, s).

Example 46

The compound of Example 45 (100 mg) was suspended in 2 mL of methylene chloride. To the suspension were added 34 μL of N-methylpiperazine, 79 mg of WSC and 72 μL of diisopropyl-ethylamine, and the mixture was stirred at room temperature overnight. To the reaction mixture was added brine, the mixture was extracted with ethyl acetate. The organic layer was washed with brine, dried over anhydrous magnesium sulfate, and concentrated under reduced pressure. The residue was purified by chromatography on silica gel (chloroform-methanol-28% aqueous ammonia=100:10:1) to give 95 mg of N-[4-(6-amino-5-cyano-2-{6-[3-(4-methylpiperazin-1-yl)-3-oxopropyl]pyridin-2-ylmethylsulfanyl}pyrimidin-4-yl)phenyl]-acetamide.

The compound (69 mg) was dissolved in methanol, and 0.29 mL of 1N hydrochloric acid was added and the mixture was concentrated to dryness under reduced pressure. The residue was recrystallized from methanol-IPE to give 67 mg of the hydrochloride of the above compound (a light yellow powder).

The characteristics of this hydrochloride salt are shown as follows:

$^1$H-NMR (CD$_3$OD) δ: 8.39 (1H, t, J=7.8 Hz), 8.04 (1H, d, J=7.8 Hz), 7.83 (1H, d, J=7.8 Hz), 7.82 (2H, d, J=8.7 Hz), 7.72 (2H, d, J=8.7 Hz), 4.72 (2H, s), 3.65-3.40 (4H, m), 3.26-2.99 (8H, m), 2.91 (3H, s), 2.16 (3H, s).

Example 47

According to the same procedure described in example 42, using the compound of Reference Example 14 instead of the compound of Reference Example 10, t-butyl 3-{6-[4-(4-acetyl-aminophenyl)-6-amino-5-cyanopyrimidin-2-ylsulfanylmethyl]-pyridin-2-yl}acrylate was given as a light brown powder.

$^1$H-NMR (DMSO-d$_6$) δ: 10.22 (1H, s), 7.82 (2H, d, J=8.7 Hz), 7.79° (1H, t, J=7.5 Hz), 7.70 (2H, d, J=8.7 Hz), 7.60 (1H, d, J=7.5 Hz), 7.55 (1H, d, J=7.5 Hz), 7.53 (1H, d, J=15.9 Hz), 6.78 (1H, d, J=15.9 Hz), 4.53 (2H, s), 2.08 (3H, s), 1.48 (9H, s).

Example 48

To a round-bottom flask, 251 mg of the compound of Example 47 was placed. After cooling the flask to ice temperature, 0.5 mL of TFA was also added and the mixture was stirred at room temperature for 1 hour. After the TFA was removed under reduced pressure, to the oily residue was added 5 mL of acetonitrile, additionally 5 mL of triethylamine was added dropwise under stirring. In addition, thereto 50 mg of N-methylpiperazine and 455 mg of BOP reagent were added and the mixture was stirred at room temperature overnight. The reaction mixture was concentrated under reduced pressure, purified by chromatography on silica gel (chloroform-methanol-aqueous ammonia=200:10:1) to give 40 mg of N-[4-(6-amino-5-cyano-2-{6-[3-(4-methylpiperazin-1-yl)-3-oxopropenyl]pyridin-2-ylmethylsulfanyl}pyrimidin-4-yl)-phenyl]acetamide. The whole product was dissolved in ethanol, 0.15 mL of 1 mol/L hydrochloric acid in ethanol was added to the above solution, and then the solvent was removed off to give 48 mg of above the compound as a hydrochloride salt form (a white powder).

The characteristics of this hydrochloride salt are shown as follows:

$^1$H-NMR (DMSO-d$_6$) δ: 10.2 (1H, s), 7.82 (2H, d, J=9.0 Hz), 7.76 (1H, d, J=7.8 Hz), 7.70 (2H, d, J=9.0 Hz), 7.61 (1H, d, J=7.8 Hz), 7.51 (1H, d, J=7.8 Hz), 7.46 (2H, s), 4.53 (2H, s), 3.57 (4H, br t), 2.31 (4H, br t), 2.19 (3H, s), 2.08 (3H, s).

Example 49

According to the same procedure described in Example 43, using the compound of Reference Example 13 instead of the compound of Reference Example 11, ethyl 3-{6-[4-(4-acetylaminophenyl)-6-amino-5-cyanopyrimidin-2-ylsulfanylmethyl]-pyridin-2-yl}-2-methylpropionate was given as a light yellow powder.

$^1$H-NMR (CDCl$_3$) δ: 7.99 (2H, d, J=9.0 Hz), 7.64 (2H, d, J=9.0 Hz), 7.50 (1H, t, J=7.5 Hz), 7.28 (1H, d, J=7.5 Hz), 6.99 (1H, d, J=7.5 Hz), 5.82 (2H, br s), 4.52 (1H, d, J=14.4 Hz), 4.44 (1H, d, J=14.4 Hz), 4.13 (2H, q, J=7.2 Hz), 3.17 (1H, dd, J=13.8, 7.8 Hz), 3.08-3.00 (1H, m), 2.87 (1H, dd, J=13.8, 6.0 Hz), 2.21 (3H, s), 1.26-1.12 (6H, m).

Example 50

The compound of Example 49 (1.13 g) was dissolved in 30 ml of ethanol, thereto 7.5 ml of 1N aqueous sodium hydroxide was added, and the mixture was stirred at room temperature overnight. The solvent was removed under reduced pressure, and the residue was neutralized with 2% aqueous citric acid and dispersed and then the insoluble substance was filtrated. The resultant crude product was purified by chromatography on silica gel (methylene chloride-methanol=10:1) to give 597 mg of 3-{6-[4-(4-acetylaminophenyl)-6-amino-5-cyano-pyrimidin-2-ylsulfanylmethyl]pyridin-2-yl}-2-methylpropionic acid as a colorless powder.

$^1$H-NMR (DMSO-d$_6$) δ: 10.23 (1H, s), 7.83 (2H, d, J=9.0 Hz), 7.71 (2H, d, J=9.0 Hz), 7.63 (1H, t, J=7.5 Hz), 7.36 (1H, d, J=7.5 Hz), 7.12 (1H, d, J=7.5 Hz), 4.47 (2H, s), 3.05 (1H, dd, J=13.8, 6.9 Hz), 2.86 (1H, sextet, J=6.9 Hz), 2.71 (1H, dd, J=13.8, 7.2 Hz), 2.09 (3H, s), 1.04 (3H, d, J=6.9 Hz).

Example 51

According to the same procedure described in Example 46, using the compound of Example 50 instead of the compound of Example 45, N-[4-(6-amino-5-cyano-2-{6-[2-methyl-3-(4-methyl-piperazin-1-yl)-3-oxopropyl]pyridin-2-ylmethylsulfanyl}pyrimidin-4-yl)phenyl]acetamide was given as a light yellow powder.

$^1$H-NMR (DMSO-d$_6$) δ: 10.24 (1H, s), 7.84 (2H, d, J=9.0 Hz), 7.72 (2H, d, J=9.0 Hz), 7.60 (1H, t, J=7.5 Hz), 7.35 (1H, d, J=7.5 Hz), 7.04 (1H, d, J=7.5 Hz), 4.49 (1H, d, J=13.8 Hz), 4.42 (1H, d, J=13.8 Hz), 3.35-3.25 (5H, m), 2.97 (1H, dd, J=17.1, 8.4 Hz), 2.69 (1H, dd, J=17.1, 6.0 Hz), 2.54-1.91 (4H, m), 2.09 (6H, s), 1.04 (3H, d, J=6.0 Hz).

Example 52

To 9 mL of dichloromethane was added the compound of Reference Example 15 (540 mg) and diisopropylethylamine (244 mg). After the mixture was stirred at ice temperature for 10 minutes, 0.16 mL of methanesulfonyl chloride was added dropwise to the mixture and then the mixture was stirred at room temperature for 1 hour. The resulting mesylate solution was added dropwise into the solution of 142 mg of thiourea in 2 mL of ethanol at 60° C., and the mixture was stirred at same temperature for 1 hour. After the solvent was removed from the reaction mixture, 9 mL of ethanol, 396 mg of N-[4-(2,2-dicyanovinyl)phenyl]acetamide and 473 mg of sodium bicarbonate were added to the residue, and the mixture was heated to reflux for 2 hours. After allowing to cool the reaction mixture, 270 mg of NBS was added thereto, and the mixture was heated to reflux for 30 minutes. After removed the solvent under reduced pressure, to the residue was added saturated aqueous sodium bicarbonate. The mixture was extracted with chloroform, the organic layer was washed with brine, dried over anhydrous magnesium sulfate, and then the solvent was removed under reduced pressure. The residue was purified by chromatography on silica gel (methylene chloride-methanol-triethylamine=600:20:1), then recrystallized from ethanol to give 190 mg of N-[4-(6-amino-5-cyano-2-{6-[5-(4-methylpiperazin-1-yl)-5-oxopent-1-ynyl]pyridin-2-ylmethylsulfanyl}pyrimidin-4-yl)phenyl]acetamide as a white powder.

$^1$H-NMR (DMSO-d$_6$) δ: 10.2 (1H, s), 7.83 (2H, d, J=8.7 Hz), 7.73-7.67 (3H, m), 7.49 (1H, d, J=7.5 Hz), 7.30 (1H, d, J=7.5 Hz), 4.45 (2H, s), 3.38-3.32 (4H, m), 2.62 (4H, s), 2.29-2.21 (4H, m), 2.14 (3H, s), 2.09 (3H, s).

Example 53

To 7 mL of ethanol was added the compound of Reference Example 16 (2.28 g) and thiourea (545 mg), and the mixture was stirred at 60° C. for 1.5 hours. After allowing to cool the mixture, 1.40 g of N-[4-(2,2-dicyanovinyl)phenyl]-acetamide and 1.46 g of triethylamine was added to the mixture and the mixture was stirred at 60° C. for 4 hours. The resulting reaction solution was cooled to ice temperature, thereto 827 mg of NBS was added and the mixture was stirred at same temperature for 30 minutes. From the reaction mixture, the solvent was removed under reduced pressure. Water was added to the residue and the mixture was extracted with ethyl acetate. The organic layer was washed with brine, dried over anhydrous magnesium sulfate, and then concentrated under reduced pressure. The residue was purified by chromatography on silica gel (methylene chloride-ethanol=30:1) to give 1.86 g of t-butyl 5-{6-[4-(4-acetyl-aminophenyl)-6-amino-5-cyanopyrimidin-2-ylsulfanylmethyl]-pyridin-2-yl}pentanoate as a white powder.

$^1$H-NMR (DMSO-d$_6$) δ: 10.2 (1H, s), 7.83 (2H, d, J=8.4 Hz), 7.70 (2H, d, J=8.4 Hz), 7.62 (1H, t, J=7.5 Hz), 7.34 (1H, d, J=7.5 Hz), 7.10 (1H, d, J=7.5 Hz), 4.45 (2H, s), 2.69 (2H, t, J=7.5 Hz), 2.19 (2H, t, J=7.5 Hz), 2.08 (3H, s), 1.66-1.47 (4H, m), 1.37 (9H, s).

Example 54

The compound of Example 53 (1.06 g) was cooled to ice temperature, thereto 2 mL of TFA was added dropwise, and the mixture was stirred at room temperature for 1.5 hours. The residual TFA was removed under reduced pressure, the residue was dissolved in 20 mL of DMF. The solution was neutralized with 3 mL of triethylamine at ice temperature and stirred for 15 minutes after adding further 1.8 g of HOBt. To the reaction mixture, 200 mg of N-methylpiperazine and 764 mg of WSC were added, and the mixture was stirred at room temperature overnight. The resulting reaction mixture was evaporated under reduced pressure, thereto saturated aqueous sodium bicarbonate was added, and the mixture was extracted with chloroform. The organic layer was washed with brine, dried over anhydrous magnesium sulfate, and then the solvent was removed. The residue was purified by chromatography on silica gel (methylene chloride-methanol-triethylamine=300:10:1) to give 1.0 g of N-[4-(6-amino-5-cyano-2-{6-[5-(4-methylpiperazin-1-yl)-5-oxopentyl]pyridin-2-ylmethyl-sulfanyl}pyrimidin-4-yl)phenyl]acetamide as a white powder.

$^1$H-NMR (CDCl$_3$) δ: 8.34 (1H, s), 7.90 (2H, d, J=8.4 Hz), 7.67 (2H, d, J=8.4 Hz), 7.52 (1H, t, J=7.5 Hz), 7.31 (1H, d, J=7.5 Hz), 7.01 (1H, d, J=7.5 Hz), 5.71 (2H, s), 4.50 (2H, s), 3.62 (2H, t, J=5.1 Hz), 3.50 (2H, t, J=5.1 Hz), 2.82 (2H, t, J=7.5 Hz), 2.44-2.34 (6H, m), 2.30 (3H, s), 2.20 (3H, s), 1.86-1.73 (4H, m).

Example 55

According to the same procedure described in Example 54, using 1-(2-diethylaminoethyl)piperazine instead of N-methylpiperazine, N-{4-[6-amino-5-cyano-2-(6-{5-[4-(2-diethylaminoethyl)piperazin-1-yl]-5-oxopentyl}pyridin-2-ylmethylsulfanyl)pyrimidin-4-yl]phenyl}acetamide hydrochloride was given as a white powder.

$^1$H-NMR (DMSO-d$_6$) δ: 10.2 (1H, s), 7.83 (2H, t, J=8.7 Hz), 7.72 (2H, d, J=8.7 Hz), 7.64 (1H, t, J=7.8 Hz), 7.34 (1H, d, J=7.8 Hz), 7.12 (1H, d, J=7.8 Hz), 4.46 (2H, s), 2.70 (2H, t, J=7.5 Hz), 2.31-2.26 (8H, m), 2.09 (3H, s), 1.65-1.63 (2H, m), 1.52-1.49 (2H, m), 0.97-0.90 (6H, m).

Example 56

The compound of Example 46 (1 g) was suspended in a mixed solvent of 10 mL of ethanol and 10 mL of water. To the suspension, 10 mL of 5N hydrochloric acid was added, and the mixture was stirred for 4 hours with heating at 60° C. After the ethanol was removed from the reaction mixture under reduced pressure, the mixture was neutralized with 5N aqueous sodium hydroxide at ice temperature. The resulting crystal was filtrated, washed with diethyl ether, and then dried under reduced pressure to give 0.85 g of 4-amino-6-(4-aminophenyl)-2-{6-[3-(4-methylpiperazin-1-yl)-3-oxopropyl]-pyridin-2-ylmethylsulfanyl}pyrimidin-5-carbonitrile as a white powder.

$^1$H-NMR (DMSO-d$_6$) δ: 7.73 (2H, d, J=8.7 Hz), 7.80-7.55 (2H, br s), 7.61 (1H, t, J=7.8 Hz), 7.33 (1H, d, J=7.8 Hz), 7.14 (1H, d, J=7.8 Hz), 6.61 (2H, d, J=8.7 Hz), 5.90 (2H, s), 4.45 (2H, s), 3.40-3.34 (4H, m), 2.94 (2H, t, J=7.2 Hz), 2.70 (2H, t, J=7.2 Hz), 2.25-2.19 (4H, m), 2.12 (3H, s).

Example 57

The compound of Example 56 (150 mg) and triethylamine (0.5 mL) were dissolved in 10 mL of acetonitrile, and 0.1 g of propionyl chloride was added dropwise to the mixture and the mixture was stirred at room temperature for 30 minutes. After removing the solvent, the residue was dissolved in chloroform. Thereto water was added, the organic layer was washed with water (twice), then brine (once), and dried over magnesium sulfate. After the solvent was removed under reduced pressure, the resulting oil was purified by chromatography on silica gel (methylene chloride-methanol-aqueous ammonia=90:10:1) to give 50 mg of N-[4-(6-amino-5-cyano-2-{6-[3-(4-methylpiperazin-1-yl)-3-oxopropyl]pyridin-2-ylmethylsulfanyl}pyrimidin-4-yl)phenyl]propionamide as a light yellow powder.

$^1$H-NMR (DMSO-d$_6$) δ: 10.16 (1H, s), 8.20-7.64 (2H, br s), 7.84 (2H, d, J=8.7 Hz), 7.74 (2H, d, J=8.7 Hz), 7.62 (1H, t, J=7.8 Hz), 7.34 (1H, d, J=7.8 Hz) 7.14 (1H, d, J=7.8 Hz), 4.46 (2H, s), 3.42-3.35 (4H, m), 2.94 (2H, t, J=7.2 Hz), 2.70 (2H, t, J=7.2 Hz), 2.37 (2H, q, J=7.5 Hz), 2.20-2.16 (4H, m), 2.12 (3H, s), 1.10 (3H, t, J=7.5 Hz).

Example 58

According to the same procedure described in Example 57, using butyryl chloride instead of propionyl chloride, N-[4-(6-amino-5-cyano-2-{6-[3-(4-methylpiperazin-1-yl)-3-oxopropyl]pyridin-2-ylmethylsulfanyl}pyrimidin-4-yl)phenyl]-butylamide was given as a white powder.

$^1$H-NMR (DMSO-d$_6$) δ: 10.24 (1H, s), 7.83 (2H, d, J=8.7 Hz), 7.73 (2H, d, J=8.7 Hz), 7.62 (1H, t, J=7.2 Hz), 7.34 (1H, d, J=7.2 Hz), 7.14 (1H, d, J=7.2 Hz), 4.46 (2H, s), 3.40-3.35 (4H, m), 2.94 (2H, t, J=7.5 Hz), 2.70 (2H, t, J=7.5 Hz), 2.20-2.16 (4H, m), 2.12 (3H, s), 1.63 (2H, sext, J=7.5 Hz), 0.93 (3H, t, J=7.5 Hz).

Example 59

According to the same procedure described in Example 46, using N-(tert-butoxycarbonyl)ethylene diamine instead of N-methylpiperazine, t-butyl [2-(3-{6-[4-(4-acetylaminophenyl)-6-amino-5-cyanopyrimidin-2-ylsulfanylmethyl]pyridin-2-yl}propionylamino)ethyl]carbamate as a colorless powder.

$^1$H-NMR (DMSO-d$_6$) δ: 10.24 (1H, s), 7.88 (1H, br t, J=7.5 Hz), 7.83 (2H, d, J=8.4 Hz), 7.72 (2H, d, J=8.4 Hz), 7.62 (1H, t, J=7.5 Hz), 7.35 (1H, d, J=7.5 Hz), 7.12 (1H, d, J=7.5 Hz), 6.77 (1H, br t, J=7.5 Hz), 4.46 (2H, s), 3.05 (2H, q, J=7.5 Hz), 2.98-2.90 (4H, m), 2.46 (2H, t, J=7.5 Hz), 2.09 (3H, s).

Example 60

To 100 mg of the compound of Example 59 at ice temperature, 1 mL of TFA was added, and the mixture was stirred for 30 minutes. The reaction solution was evaporated to dryness under reduced pressure and dissolved in 10 mL of ethanol. To the solution, 0.37 mL of 1N hydrochloric acid, and the mixture was concentrated to dryness under reduced pressure. The resulting solid was recrystallized from methanol-IPE to give 90 mg of 3-{6-[4-(4-acetylaminophenyl)-6-amino-5-cyanopyrimidin-2-ylsulfanylmethyl]pyridin-2-yl}-N-(2-aminoethyl)propionamide hydrochloride as a light yellow powder.

$^1$H-NMR (DMSO-d$_6$) δ: 10.23 (1H, s), 8.12 (1H, br t, J=7.5 Hz), 7.85 (2H, br s), 7.82 (2H, d, J=8.7 Hz), 7.72 (2H, d, J=8.7 Hz), 7.57 (1H, br d, J=7.5 Hz), 7.34 (1H, br d, J=7.5 Hz), 4.56 (2H, s), 3.29 (2H, q, J=6.0 Hz), 3.07 (2H, t, J=7.5 Hz), 2.85 (2H, q, J=6.0 Hz), 2.59 (2H, t, J=7.5 Hz), 2.09 (3H, s).

Example 61

The compound of Example 45 (200 mg) was dissolved in 3 mL of DMF. To the resulting solution, 54 mg of N,N-dimethylethylene diamine, 365 mg of BOP and 172 μL of triethylamine was added, and the mixture was stirred at room temperature overnight. From the reaction mixture, the solvent was removed under reduced pressure, the residue was purified by chromatography on silica gel (chloroform-methanol-aqueous ammonia=50:10:1).

The compound given at the above step as a free form (187 mg) was dissolved in methanol, thereto 0.721 mL of 1N hydrochloric acid was added and the mixture was evaporated to dryness under reduced pressure. The resulting solid was recrystallized from methanol-acetone-IPE to give 186 mg of 3-{6-[4-(4-acetylaminophenyl)-6-amino-5-cyanopyrimidin-2-ylsulfanylmethyl]pyridin-2-yl}-N-(2-dimethylaminoethyl)-propionamide hydrochloride as a light yellow powder.

The characteristics of this hydrochloride are shown as follows:

$^1$H-NMR (CD$_3$OD) δ: 8.38 (1H, t, J=7.8 Hz), 8.05 (1H, d, J=7.8 Hz), 7.83 (2H, d, J=9.0 Hz), 7.82 (1H, d, J=7.8 Hz), 7.72 (2H, d, J=9.0 Hz), 4.73 (2H, s), 3.53 (2H, t, J=6.0 Hz), 3.27-3.22 (4H, m), 2.90 (6H, s), 2.82 (2H, t, J=6.0 Hz), 2.16 (3H, s).

Example 62

According to the same procedure described in Example 61, using N,N,N'-trimethylethylene diamine instead of N,N-dimethylethylene diamine, 3-{6-[4-(4-acetylaminophenyl)-6-amino-5-cyanopyrimidin-2-ylsulfanylmethyl]pyridin-2-yl}-N-(2-dimethylaminoethyl)-N-methylpropionamide hydrochloride was given as a light yellow powder.

$^1$H-NMR (CD$_3$OD) δ: 8.37 (1H, t, J=8.1 Hz), 8.03 (1H, d, J=8.1 Hz), 7.84 (1H, d, J=8.1 Hz), 7.83 (2H, d, J=9.0 Hz), 7.72 (2H, d, J=9.0 Hz), 4.73 (2H, s), 3.72 (2H, t, J=5.4 Hz), 3.32-3.21 (4H, m), 3.07 (3H, s), 3.02 (2H, t, J=5.4 Hz), 2.92 (6H, s), 2.16 (3H, s).

Example 63

According to the same procedure described in Example 61, using 39 μL of 3-dimethylaminopropylamine instead of N,N-dimethylethylene diamine, 3-{6-[4-(4-acetylaminophenyl)-6-amino-5-cyanopyrimidin-2-ylsulfanylmethyl]pyridin-2-yl}-N-(2-dimethylaminopropyl)propionamide hydrochloride was given as a light yellow powder.

$^1$H-NMR (CD$_3$OD) δ: 8.38 (1H, t, J=7.8 Hz), 8.05 (1H, d, J=7.8 Hz), 7.83 (2H, d, J=9.0 Hz), 7.80 (1H, d, J=7.8 Hz), 7.72 (2H, d, J=9.0 Hz), 4.73 (2H, s), 3.23 (2H, t, J=6.9 Hz), 3.10 (2H, t, J=6.9 Hz), 2.87 (2H, t, J=6.9 Hz), 2.85 (6H, s), 2.79 (2H, t, J=6.9 Hz), 2.16 (3H, s), 1.89 (2H, quint, J=6.9 Hz).

Example 64

According to the same procedure described in Example 61, using N,N,N'-trimethyl-1,3-propane diamine instead of N,N-dimethylethylene diamine, 3-{6-[4-(4-acetylaminophenyl)-6-amino-5-cyanopyrimidin-2-ylsulfanylmethyl]pyridin-2-yl}-N-(2-dimethylaminopropyl)-N-methylpropionamide hydrochloride was given as a light yellow powder.

$^1$H-NMR (CD$_3$OD) δ: 8.36 (1H, t, J=7.8 Hz), 8.01 (1H, d, J=7.8 Hz), 7.84 (2H, d, J=9.0 Hz), 7.82 (1H, d, J=7.8 Hz), 7.72 (2H, d, J=9.0 Hz), 4.72 (2H, s), 3.40 (2H, t, J=6.9 Hz), 3.22 (2H, t, J=6.9 Hz), 3.06 (3H, s), 3.06-2.98 (4H, m), 2.82 (6H, s), 2.16 (3H, s).

Example 65

According to the same procedure described in Example 46, using 1-(2-aminoethyl)piperidine instead of N-methylpiperazine, 3-{6-[4-(4-acetylaminophenyl)-6-amino-5-cyanopyrimidin-2-ylsulfanylmethyl]pyridin-2-yl}-N-(2-methyl-piperidin-1-ylethyl)propionamide hydrochloride was given.

$^1$H-NMR (DMSO-d$_6$) δ: 10.24 (1H, s), 8.25-7.61 (3H, m), 7.83 (2H, d, J=8.7 Hz), 7.72 (2H, d, J=8.7 Hz), 7.62 (1H, t, J=7.8 Hz), 7.35 (1H, d, J=7.5 Hz), 7.12 (1H, d, J=7.5 Hz), 4.46 (2H, s) 3.17-3.12 (2H, m), 2.98-2.89 (2H, m), 2.49-2.45 (2H, m), 2.40-2.22 (6H, m), 2.09 (3H, s), 1.30-2.01 (6H, m).

Example 66

According to the same procedure described in Example 61, using N,N-diethylethylene diamine instead of N,N-dimethylethylene diamine, 3-{6-[4-(4-acetylaminophenyl)-6-amino-5-cyanopyrimidin-2-ylsulfanylmethyl]pyridin-2-yl}-N-(2-diethylaminoethyl)propionamide hydrochloride salt was given as a light yellow powder.

$^1$H-NMR (CD$_3$OD) δ: 8.39 (1H, t, J=8.1 Hz), 8.06 (1H, d, J=8.1 Hz), 7.83 (2H, d, J=9.0 Hz), 7.81 (1H, d, J=8.1 Hz), 7.72 (2H, d, J=9.0 Hz), 4.73 (2H, s), 3.51 (2H, t, J=6.3 Hz), 3.30-3.19 (8H, m), 2.82 (2H, t, J=6.3 Hz), 2.17 (3H, s), 1.29 (6H, t, J=9.0 Hz).

Example 67

According to the same procedure described in Example 61, using 1-methyl-4-(methylamino)piperidine instead of N,N-dimethylethylene diamine, 3-{6-[4-(4-acetylaminophenyl)-6-amino-5-cyanopyrimidin-2-ylsulfanylmethyl]pyridin-2-yl}-N-methyl-N-(1-methylpiperidin-4-yl)propionamide hydrochloride was given as a yellow powder.

$^1$H-NMR (CD$_3$OD) δ: 8.39 (1H, t, J=7.8 Hz), 8.03 (1H, d, J=7.8 Hz), 7.86 (2H, d, J=9.0 Hz), 7.83 (1H, d, J=7.8 Hz), 7.73 (2H, d, J=9.0 Hz), 4.80 (2H, s), 3.64-3.47 (2H, m), 3.24 (2H, t, J=6.3 Hz), 3.17-3.12 (1H, m), 2.99 (2H, t, J=6.3 Hz), 2.98-2.89 (2H, m), 2.91 (3H, s), 2.79 (3H, s), 2.16 (3H, s), 2.10-1.76 (4H, m).

Example 68

According to the same procedure described in Example 61, using 4-(diethylamino)piperidine instead of N,N-dimethylethylene diamine, N-[4-(6-amino-5-cyano-2-{6-[3-(4-diethylaminopiperidin-1-yl)-3-oxopropyl]pyridin-2-ylmethylsulfanyl}pyrimidin-4-yl)phenyl]acetamide hydrochloride salt was given as a colorless powder.

$^1$H-NMR (CD$_3$OD) δ: 8.39 (1H, t, J=7.2 Hz), 8.03 (1H, d, J=7.2 Hz), 7.84 (2H, d, J=8.7 Hz), 7.83 (1H, d, J=7.2 Hz), 7.72 (2H, d, J=8.7 Hz), 4.73 (2H, s), 4.58 (1H, br d, J=12.6 Hz), 4.06 (1H, br d, J=12.6 Hz), 3.64-3.53 (1H, m), 3.33-2.62 (8H, m), 2.16 (3H, s), 2.16-1.56 (4H, m), 1.35 (6H, t, J=7.2 Hz).

Example 69

According to the same procedure described in Example 46, using 4-piperidinopiperidine instead of N-methylpiperazine, N-(4-{6-amino-2-[6-(3-[1,4']bipiperidinyl-1'-yl-3-oxopropyl)pyridin-2-ylmethylsulfanyl]-5-cyanopyrimidin-4-yl}phenyl)acetamide hydrochloride was given as a light yellow powder.

$^1$H-NMR (DMSO-d$_6$) δ: 10.45 (1H, s), 8.27 (1H, t, J=7.5 Hz), 7.93 (1H, t, J=7.5 Hz), 7.81 (2H, d, J=9.0 Hz), 7.76 (2H, d, J=9.0 Hz), 7.74 (1H, d, J=7.5 Hz), 4.76 (2H, s), 4.46 (1H, br d, J=13.2 Hz), 4.00 (1H, br d, J=13.2 Hz), 3.35-3.17 (6H, m), 3.05-2.84 (4H, m), 2.56-2.48 (1H, m), 2.15-2.07 (2H, m), 2.10 (3H, s), 1.97-1.35 (8H, m).

Example 70

According to the same procedure described in Example 46, using 2-piperidine-methanol instead of N-methylpiperazine, N-[4-(6-amino-5-cyano-2-{6-[3-(2-hydroxymethylpiperidin-1-yl)-3-oxopropyl]pyridin-2-ylmethylsulfanyl}pyrimidin-4-yl)phenyl]acetamide hydrochloride was given as a white powder.

$^1$H-NMR (DMSO-$d_6$) δ: 10.24 (1H, s), 8.25-7.50 (2H, br s), 7.84 (2H, d, J=8.7 Hz), 7.72 (2H, d, J=8.7 Hz) 7.62 (1H, t, J=7.8 Hz), 7.34 (1H, d, J=7.8 Hz), 7.15 (1H, d, J=7.8 Hz), 4.47 (2H, s), 3.85-4.70 (5H, m), 3.70-3.35 (1H, m), 3.01-2.62 (4H, m), 2.09 (3H, s), 1.80-1.05 (6H, m).

Example 71

According to the same procedure described in Example 46, using 2-piperidin-1-ylmethylmorpholine instead of N-methyl-piperazine, N-[4-(6-amino-5-cyano-2-{6-[3-oxo-3-(2-piperidin-1-ylmethylmorpholin-4-yl)propyl]pyridin-2-ylmethylsulfanyl}-pyrimidin-4-yl)phenyl]acetamide hydrochloride was given as a white powder.

$^1$H-NMR (DMSO-$d_6$) δ: 10.2 (1H, s), 7.83 (2H, d, J=8.4 Hz), 7.71 (2H, d, J=8.4 Hz), 7.62 (1H, t, J=7.8 Hz), 7.34 (1H, d, J=7.8 Hz), 7.15 (1H, d, J=7.8 Hz), 4.45 (2H, s), 4.25-3.75 (3H, m), 2.94 (4H, m), 2.80-2.73 (2H, m), 2.48-2.20 (8H, m), 2.08 (3H, s), 1.42-1.32 (6H, m).

Example 72

According to the same procedure described in Example 46, using 2-(4-ethylpiperazin-1-ylmethyl)morpholine instead of N-methylpiperazine, N-{4-[6-amino-5-cyano-2-(6-{3-[2-(4-ethyl-piperazin-1-ylmethyl)morpholin-4-yl]-3-oxopropyl}pyridin-2-ylmethylsulfanyl)pyrimidin-4-yl]phenyl}acetamide hydrochloride was given as a white powder.

$^1$H-NMR (DMSO-$d_6$) δ: 10.2 (1H, s), 7.83 (2H, d, J=8.4 Hz), 7.71 (2H, d, J=8.4 Hz), 7.62 (1H, t, J=7.8 Hz), 7.34 (1H, d, J=7.8 Hz), 7.16 (1H, d, J=7.8 Hz), 4.46 (2H, s), 4.25-3.75 (3H, m), 2.94-2.73 (4H, m), 2.48-2.20 (13H, m), 2.08 (3H, s), 0.93 (3H, br t).

Example 73

According to the same procedure described in Example 61, using 1-tert-butoxycarbonylpiperazine instead of N,N-dimethylethylene diamine, t-butyl 4-(3-{6-[4-(4-acetylaminophenyl)-6-amino-5-cyanopyrimidin-2-ylsulfanylmethyl]pyridin-2-yl}propionyl)piperazine-1-carboxylate was given as a white powder.

$^1$H-NMR (DMSO-$d_6$) δ: 10.23 (1H, s), 7.83 (2H, d, J=8.7 Hz), 7.71 (2H, d, J=8.7 Hz), 7.62 (1H, t, J=7.8 Hz), 7.34 (1H, d, J=7.8 Hz), 7.16 (1H, d, J=7.8 Hz), 4.46 (2H, s), 3.41-3.38 (4H, m), 3.30-3.25 (4H, m), 2.95 (2H, t, J=7.5 Hz), 2.73 (2H, t, J=7.5 Hz), 2.09 (3H, s), 1.39 (9H, s).

Example 74

According to the same procedure described in Example 60, using the compound of Example 73, N-(4-{6-amino-5-cyano-2-[6-(3-oxo-3-piperazin-1-ylpropyl)pyridin-2-ylmethylsulfanyl]-pyrimidin-4-yl}phenyl)acetamide hydrochloride was given as a light yellow powder.

$^1$H-NMR (CD$_3$OD) δ: 8.34 (1H, t, J=7.8 Hz), 8.00 (1H, d, J=7.8 Hz), 7.83 (2H, d, J=8.7 Hz), 7.79 (1H, d, J=7.8 Hz), 7.71 (2H, d, J=8.7 Hz), 4.70 (2H, s), 3.77-3.74 (4H, m), 3.29-3.16 (6H, m), 3.04 (2H, t, J=6.6 Hz), 2.16 (3H, s).

Example 75

According to the same procedure described in Example 61, using 1-(2-diethylaminoethyl)piperazine instead of N,N-dimethylethylene diamine, N-{4-[6-amino-5-cyano-2-(6-{3-[4-(2-diethylaminoethyl)piperazin-1-yl]-3-oxopropyl}pyridin-2-ylmethylsulfanyl)pyrimidin-4-yl]phenyl}acetamide hydrochloride was given as a colorless powder.

$^1$H-NMR (CD$_3$OD) δ: 8.39 (1H, t, J=7.8 Hz), 8.05 (1H, d, J=7.8 Hz), 7.86 (1H, d, J=7.8 Hz), 7.83 (2H, d, J=9.0 Hz), 7.73 (2H, d, J=9.0 Hz), 4.73 (2H, s), 3.69-3.07 (20H, m), 2.17 (3H, s), 1.38 (6H, t, J=7.2 Hz).

Example 76

According to the same procedure described in Example 46, using 1-(2-diisopropylaminoethyl)piperazine instead of N-methylpiperazine, N-{4-[6-amino-5-cyano-2-(6-{3-[4-(2-diisopropylaminoethyl)piperazin-1-yl]-3-oxopropyl}pyridin-2-ylmethylsulfanyl)pyrimidin-4-yl]phenyl}acetamide hydrochloride was given as a colorless powder.

$^1$H-NMR (DMSO-$d_6$) δ: 10.23 (1H, s), 7.65-8.20 (2H, br s), 7.84 (2H, d, J=8.7 Hz), 7.72 (2H, d, J=8.7 Hz), 7.62 (1H, t, J=7.8 Hz), 7.34 (1H, d, J=7.8 Hz), 7.14 (1H, d, J=7.8 Hz), 4.47 (2H, s), 3.40-3.29 (4H, m), 2.97-2.71 (4H, m), 2.69-2.51 (2H, m), 2.49-2.42 (2H, m), 2.30-2.18 (6H, m) 2.09 (3H, s), 0.92 (12H, d, J=6.3 Hz).

Example 77

According to the same procedure described in Example 61, using 1-[2-(pyrrolidin-1-yl)ethyl]piperazine instead of N,N-dimethylethylene diamine, N-{4-[6-amino-5-cyano-2-(6-{3-oxo-3-[4-(2-pyrrolidin-1-ylethyl)piperazin-1-yl]propyl}pyridin-2-ylmethylsulfanyl)pyrimidin-4-yl]phenyl}acetamide hydrochloride was given as a light yellow powder.

$^1$H-NMR (DMSO-$d_6$+D$_2$O) δ: 8.09 (1H, t, J=7.8 Hz), 7.80 (2H, d, J=9.0 Hz), 7.77 (1H, d, J=7.8 Hz), 7.72 (2H, d, J=9.0 Hz), 7.57 (1H, d, J=7.8 Hz), 4.62 (2H, s), 3.58 (2H, t, J=7.2 Hz), 3.65-3.11 (16H, m), 2.91 (2H, t, J=7.2 Hz), 2.11 (3H, s), 1.99 (4H, br s).

Example 78

According to the same procedure described in Example 61, using 1-[2-(morpholin-4-yl)ethyl]piperazine instead of N,N-dimethylethylene diamine, N-{4-[6-amino-5-cyano-2-(6-{3-[4-(2-morpholin-4-ylethyl)piperazin-1-yl]-3-oxopropyl}pyridin-2-ylmethylsulfanyl)pyrimidin-4-yl]phenyl}acetamide hydrochloride was given as a light yellow powder.

$^1$H-NMR (CD$_3$OD) δ: 8.39 (1H, t, J=8.1 Hz), 8.05 (1H, d, J=8.1 Hz), 7.85 (1H, d, J=8.1 Hz), 7.83 (2H, d, J=8.7 Hz), 7.72 (2H, d, J=8.7 Hz), 4.73 (2H, s), 4.00 (4H, br s), 3.72 (4H, br s), 3.66-3.27 (14H, m), 3.09 (2H, br s), 2.17 (3H, s)

Example 79

According to the same procedure described in Example 61, using 1-(N-methylpiperidin-4-ylmethyl)piperazine instead of N,N-dimethylethylene diamine, N-{4-[6-amino-5-cyano-2-(6-{3-[4-(2-diethylaminoethyl)piperazin-1-yl]-3-oxopropyl}pyridin-2-ylmethylsulfanyl)pyrimidin-4-yl]phenyl}acetamide hydrochloride was given as a light yellow powder.

¹H-NMR (CD₃OD) δ: 8.39 (1H, t, J=8.1 Hz), 8.03 (1H, d, J=8.1 Hz), 7.84 (3H, br d, J=9.0 Hz), 7.72 (2H, d, J=9.0 Hz), 4.74 (2H, s), 3.58-2.92 (18H, m), 2.88 (3H, s), 2.28-1.57 (5H, m), 2.17 (3H, s).

Example 80

According to the same procedure described in Example 61, using 1-methylhomopiperazine instead of N,N-dimethylethylene diamine, N-[4-(6-amino-5-cyano-2-{6-[3-(4-methyl-[1,4]diazepan-1-yl)-3-oxopropyl]pyridin-2-ylmethylsulfanyl}pyrimidin-4-yl)phenyl]acetamide hydrochloride was given as a light yellow powder.

¹H-NMR (CD₃OD) δ: 8.38 (1H, t, J=7.8 Hz), 8.02 (1H, d, J=7.8 Hz), 7.84 (2H, d, J=9.0 Hz), 7.84 (1H, d, J=7.8 Hz), 7.72 (2H, d, J=9.0 Hz), 4.72 (2H, s), 4.03-3.05 (12H, m), 2.89 (3H, s), 2.23-2.06 (2H, m), 2.16 (3H, s).

Example 81

According to the same procedure described in Example 61, using 1-amino-4-methylpiperazine instead of N,N-dimethylethylene diamine, 3-{6-[4-(4-acetylaminophenyl)-6-amino-5-cyanopyrimidin-2-ylsulfanylmethyl]pyridin-2-yl}-N-(4-methyl-piperazin-1-yl)propionamide hydrochloride was given as a light yellow powder.

¹H-NMR (CD₃OD) δ: 8.40 (1H, t, J=8.1 Hz), 8.08 (1H, d, J=8.1 Hz), 7.83 (2H, d, J=8.7 Hz), 7.82 (1H, d, J=8.1 Hz), 7.72 (2H, d, J=8.7 Hz), 4.72 (2H, s), 3.48-2.70 (12H, m), 2.85 (3H, s), 2.16 (3H, s).

Example 82

According to the same procedure described in Example 43, using the compound of Reference Example 17 instead of the compound of Reference Example 11, N-(4-{6-amino-5-cyano-2-[6-(3-oxopentyl)pyridin-2-ylmethylsulfanyl]pyrimidin-4-yl}phenyl)acetamide was given as a colorless powder.

¹H-NMR (DMSO-d₆) δ: 10.23 (1H, s), 7.83 (2H, d, J=9.0 Hz), 7.72 (2H, d, J=9.0 Hz), 7.61 (1H, t, J=7.5 Hz), 7.33 (1H, d, J=7.5 Hz), 7.13 (1H, d, J=7.5 Hz), 4.45 (2H, s), 2.93 (2H, t, J=6.9 Hz), 2.81 (2H, t, J=6.9 Hz), 2.46 (2H, q, J=7.2 Hz), 2.09 (3H, s), 0.90 (3H, t, J=7.2 Hz).

The structures of each compound obtained according to Examples 42-82 are shown in the following Table 6.

TABLE 6

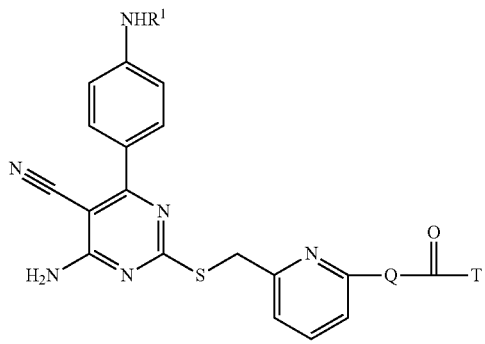

Q denotes R⁴, R⁶ or R⁷, and T denotes Z³ or R⁸.

| Example No. | R¹ | Q | T |
|---|---|---|---|
| 42 | Ac | —CH₂CH₂— | —O—tBu |
| 43 | Ac | —CH₂CH₂— | —OCH₂CH₃ |
| 44 | Ac | —CH₂CH₂— | —OCH₃ |
| 45 | Ac | —CH₂CH₂— | —OH |
| 46 | Ac | —CH₂CH₂— | —N(piperazine)N—Me |
| 47 | Ac | —CH=CH— | —O—tBu |
| 48 | Ac | —CH=CH— | —N(piperazine)N—Me |
| 49 | Ac | —CH₂CH(CH₃)— | —OCH₂CH₃ |
| 50 | Ac | —CH₂CH(CH₃)— | —OH |
| 51 | Ac | —CH₂CH(CH₃)— | —N(piperazine)N—Me |

TABLE 6-continued

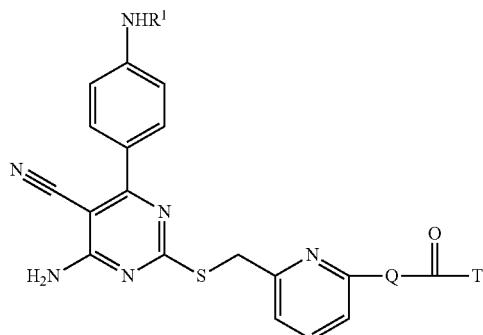

Q denotes R⁴, R⁶ or R⁷, and T denotes Z³ or R⁸.

| Example No. | R¹ | Q | T | |
|---|---|---|---|---|
| 52 | Ac | —C≡C—CH₂CH₂— | —N(piperazine)N—Me | |
| 53 | Ac | —(CH₂)₄— | —O—tBu | |
| 54 | Ac | —(CH₂)₄— | —N(piperazine)N—Me | |
| 55 | Ac | —(CH₂)₄— | —N(piperazine)N—CH₂CH₂—N(Et)(Et) | |
| 56 | H | —CH₂CH₂— | —N(piperazine)N—Me | |
| 57 | —CO—Et | —CH₂CH₂— | —N(piperazine)N—Me | |
| 58 | —CO—n-Pr | —CH₂CH₂— | —N(piperazine)N—Me | |
| 59 | Ac | —CH₂CH₂— | —NH—CH₂CH₂—NH—C(=O)—O-tBu | |
| 60 | Ac | —CH₂CH₂— | —NH—CH₂CH₂—NH₂ | |
| 61 | Ac | —CH₂CH₂— | —NH—CH₂CH₂—N(Me)(Me) | |
| 62 | Ac | —CH₂CH₂— | —N(Me)—CH₂CH₂—N(Me)(Me) | |
| 63 | Ac | —CH₂CH₂— | —NH—CH₂CH₂CH₂—N(Me)(Me) | |

TABLE 6-continued

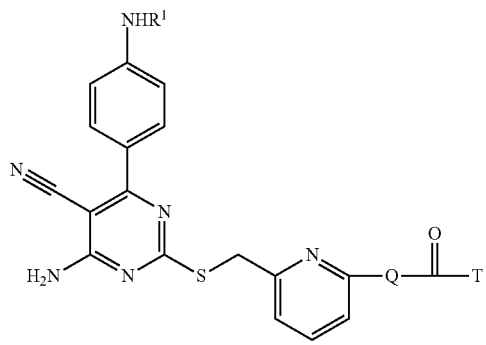

Q denotes R⁴, R⁶ or R⁷, and T denotes Z³ or R⁸.

| Example No. | R¹ | Q | T |
|---|---|---|---|
| 64 | Ac | —CH₂CH₂— | Me-N(CH₂)₃-N(Me)Me with N-Me |
| 65 | Ac | —CH₂CH₂— | NH-CH₂CH₂-piperidine |
| 66 | Ac | —CH₂CH₂— | NH-CH₂CH₂-N(Et)₂ |
| 67 | Ac | —CH₂CH₂— | N(Me)-(1-Me-piperidin-4-yl) |
| 68 | Ac | —CH₂CH₂— | 1-(piperidin-4-yl)-N(Et)₂ |
| 69 | Ac | —CH₂CH₂— | 4-(piperidin-1-yl)piperidine |
| 70 | Ac | —CH₂CH₂— | 1-Me-2-(hydroxymethyl)piperidine |
| 71 | Ac | —CH₂CH₂— | 4-Me-morpholin-2-yl-CH₂-piperidine |
| 72 | Ac | —CH₂CH₂— | 4-Me-morpholin-2-yl-CH₂-(4-Et-piperazine) |
| 73 | Ac | —CH₂CH₂— | 4-(Boc)piperazine |
| 74 | Ac | —CH₂CH₂— | piperazine |

TABLE 6-continued

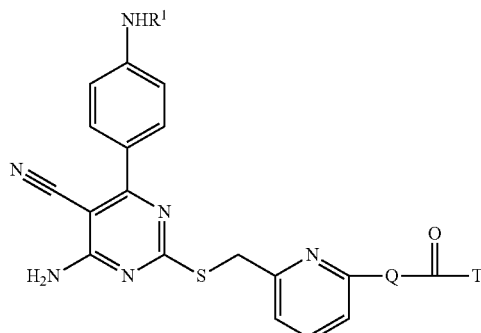

Q denotes R⁴, R⁶ or R⁷, and T denotes Z³ or R⁸.

| Example No. | R¹ | Q | T |
|---|---|---|---|
| 75 | Ac | —CH₂CH₂— | piperazine-CH₂CH₂-N(Et)₂ |
| 76 | Ac | —CH₂CH₂— | piperazine-CH₂CH₂-N(iPr)₂ |
| 77 | Ac | —CH₂CH₂— | piperazine-CH₂CH₂-pyrrolidine |
| 78 | Ac | —CH₂CH₂— | piperazine-CH₂CH₂-morpholine |
| 79 | Ac | —CH₂CH₂— | Me-piperazine-CH₂-(N-Me-piperidine) |
| 80 | Ac | —CH₂CH₂— | N-Me-homopiperazine |
| 81 | Ac | —CH₂CH₂— | —NH—piperazine-N—Me |
| 82 | Ac | —CH₂CH₂— | —CH₂CH₃ |

Example 83-193

The compound obtained in Example 18 (as a hydrochloride salt, 20 mg, 25 μM), an appropriate carboxylic acid compound (30 μM), MP-carbonate (25 μM, by Argonaut company, macroporous polystyrene anion-exchange resin) and HOBt-H₂O (4.5 mg, 29 μM) were added to methylene chloride-DMF (0.5 mL-0.1 mL), and the resulting suspension was shaken at room temperature for 1 hour. Then, to the reaction mixture, PS-carbodiimide (33 μM, by Argonaut company, N-cyclohexylcarbodiimide-N'-propyloxymethyl polystyrene) was added, and the mixture was shaken at room temperature overnight (about 18 hours). To the reaction solution, PS-isocyanate (75 μM, by Argonaut company, Polystyrene methylisocyanate) was added and the mixture was shaken at room temperature for 3 hours and then the unreacted starting compound was removed. Then MP-Carbonate was filtrated, and washed with 0.2 mL of methylene chloride and 0.2 mL of DMF. From the combination of the filtrate and the wash, the methylene chloride was evaporated with blowing nitrogen gas, and the residue was purified for separation by HPLC on the following condition to give the product. After the purification, the fraction solution was lyophilized and the lyophilized product was weighed and the structure was analyzed by LC/MS analysis on the following condition.

<HPLC Condition>
Column: CAPCELL PAK C18 (UG 120 S-5, 20 mm×50 mm) (for purification)
CAPCELL PAK C18 (UG 120 S-3, 3.0 mm×50 mm) (for analysis)

Eluent: mixture of 0.05% TFA-MeCN, 0.05% TFA-H₂O (optionally changing the ratio)
Flow Rate: 36 mL/min (for purification)
1.8 mL/min (for analysis)
<LC/MS Analytical Condition>
System: Waters Alliance 2795, Waters ZQ
MS Detector: ESI positive According to the above procedure, each the compound shown in the following Table 7 was synthesized. In each table, the calculated mass number and the observed LC/MS result ([M+H]) are described together.

TABLE 7

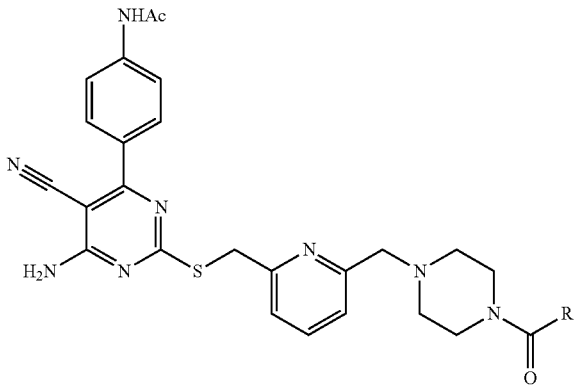

| Example No. | R | Calculated Mass Number | Observed Value [M + H] |
|---|---|---|---|
| 83 | 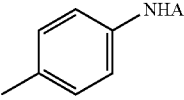 | 635 | 636 |
| 84 | 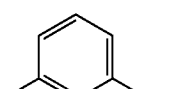 | 635 | 636 |
| 85 |  | 607 | 608 |
| 86 | 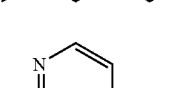 | 579 | 580 |
| 87 | 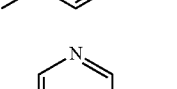 | 579 | 580 |
| 88 | 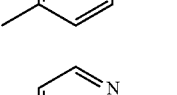 | 579 | 580 |
| 89 | 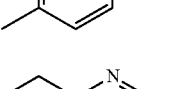 | 593 | 594 |

TABLE 7-continued
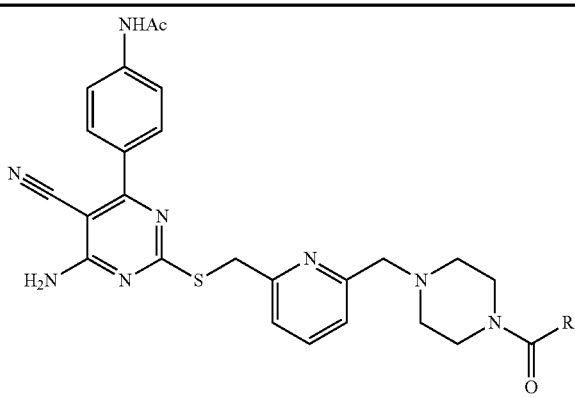
| Example No. | R | Calculated Mass Number | Observed Value [M + H] |
| --- | --- | --- | --- |
| 90 | 3-pyridyl-CH2CH2- | 593 | 594 |
| 91 | 4-pyridyl-CH2CH2- | 593 | 594 |
| 92 | 5-methyl-2-(1-pyrrolyl)pyridyl | 644 | 645 |
| 93 | PhOCH2CH2- | 608 | 609 |
| 94 | PhCH2CH2CH2- | 606 | 607 |
| 95 | PhCH=CHCH2- | 604 | 605 |
| 96 | PhOCH2CH2CH2- | 622 | 623 |
| 97 | 2-furyl-CH2- | 568 | 569 |
| 98 | 2-thienyl-CH2- | 584 | 585 |
| 99 | 4-methyl-3-furyl- | 568 | 569 |
| 100 | 3-thienyl-CH2- | 584 | 585 |
| 101 | 2-thienyl-CH2CH2- | 598 | 599 |
| 102 | 3-thienyl-CH2CH2- | 598 | 599 |

TABLE 7-continued
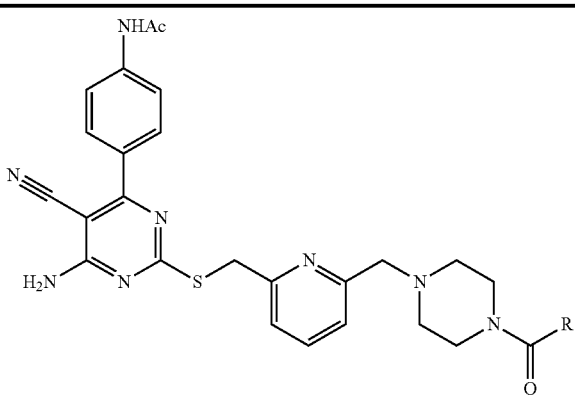
| Example No. | R | Calculated Mass Number | Observed Value [M + H] |
| --- | --- | --- | --- |
| 103 | ~~~Ph | 620 | 621 |
| 104 | ~~~~Ph | 634 | 635 |
| 105 | Me | 516 | 517 |
| 106 | Et | 530 | 531 |
| 107 | n-Pr | 544 | 545 |
| 108 | i-Pr | 544 | 545 |
| 109 | CH2-cyclopentyl | 570 | 571 |
| 110 | CH2-cyclohexyl | 584 | 585 |
| 111 | CH2CH2-cyclopentyl | 584 | 585 |
| 112 | CH2CH2-cyclohexyl | 598 | 599 |
| 113 | CH2-adamantyl | 650 | 651 |
| 114 | CH2-(1-acetylpiperidin-4-yl) | 627 | 628 |
| 115 | 2-methylchroman | 634 | 635 |
| 116 | CH2-(3-ethoxy-5-methoxyphenyl) | 622 | 623 |

TABLE 7-continued
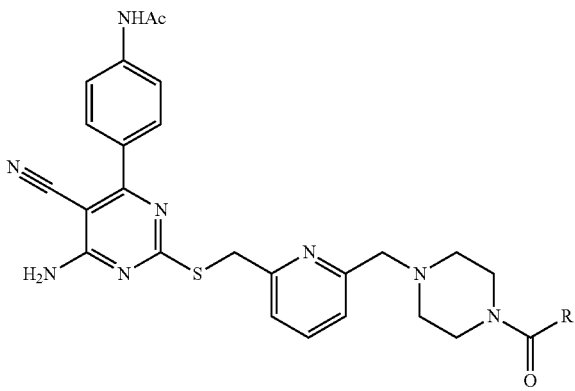
| Example No. | R | Calculated Mass Number | Observed Value [M + H] |
|---|---|---|---|
| 117 | ethoxy-methoxyphenyl | 638 | 639 |
| 118 | -CH2CH2-OMe | 546 | 547 |
| 119 | 2-NO2-phenyl | 623 | 624 |
| 120 | 2-NMe2-phenyl | 621 | 622 |
| 121 | 2-NHAc-phenyl | 635 | 636 |
| 122 | 3-OMe-phenyl | 608 | 609 |
| 123 | 3-Cl-phenyl | 612 | 613 |
| 124 | 3-Me-phenyl | 592 | 593 |
| 125 | 3-NO2-phenyl | 623 | 624 |

TABLE 7-continued
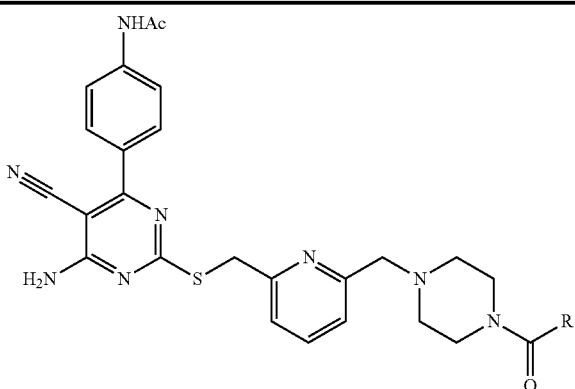
| Example No. | R | Calculated Mass Number | Observed Value [M + H] |
| --- | --- | --- | --- |
| 126 | 3-(NMe₂)-methylphenyl | 621 | 622 |
| 127 | 3-(OPh)-methylphenyl | 670 | 671 |
| 128 | 4-(NMe₂)-methylphenyl | 621 | 622 |
| 129 | methylenedioxyphenyl-methyl | 622 | 623 |
| 130 | 3-ethyl-2,4-dioxothiazolidinyl | 647 | 648 |
| 131 | 4-methyl-cyclohexyl-CH₂-NMe₂ | 641 | 642 |
| 132 | 4-methyl-2-nitrophenyl | 623 | 624 |
| 133 | 3-methyl-benzoate OMe | 636 | 637 |
| 134 | 3-methoxy-benzyl | 622 | 623 |

TABLE 7-continued
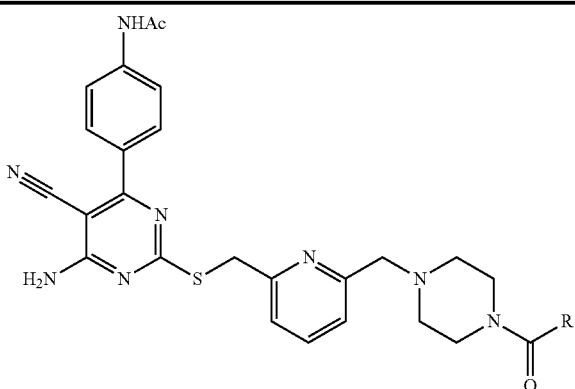
| Example No. | R | Calculated Mass Number | Observed Value [M + H] |
|---|---|---|---|
| 135 | | 636 | 637 |
| 136 | | 647 | 648 |
| 137 | | 605 | 606 |
| 138 | | 605 | 606 |
| 139 | | 625 | 626 |
| 140 | | 625 | 626 |
| 141 | | 617 | 618 |
| 142 | | 617 | 618 |
| 143 | | 567 | 568 |

TABLE 7-continued
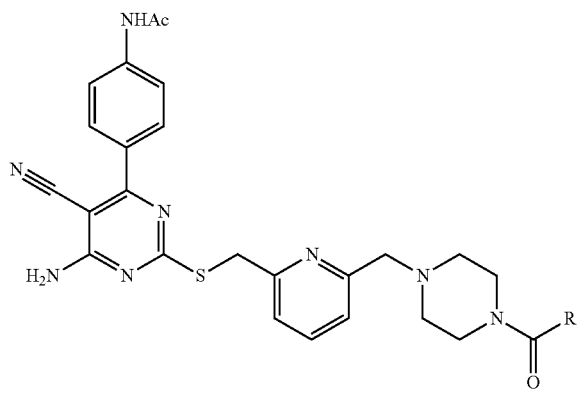
| Example No. | R | Calculated Mass Number | Observed Value [M + H] |
|---|---|---|---|
| 144 | | 619 | 620 |
| 145 | | 585 | 586 |
| 146 | | 618 | 619 |
| 147 | | 606 | 607 |
| 148 | | 627 | 628 |
| 149 | | 654 | 655 |
| 150 | | 645 | 646 |
| 151 | | 624 | 625 |
| 152 | | 634 | 635 |

TABLE 7-continued
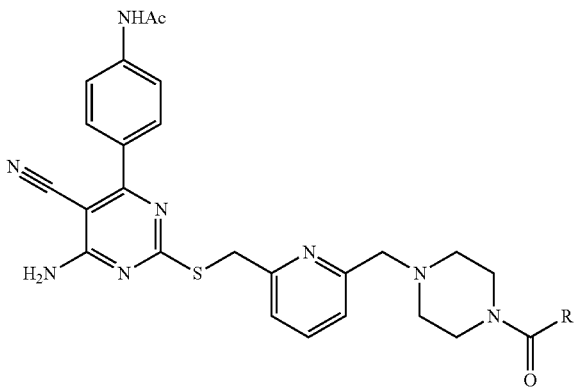
| Example No. | R | Calculated Mass Number | Observed Value [M + H] |
|---|---|---|---|
| 153 | 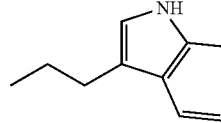 | 645 | 646 |
| 154 | 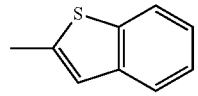 | 634 | 635 |
| 155 | 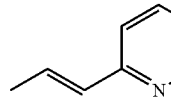 | 605 | 606 |
| 156 | 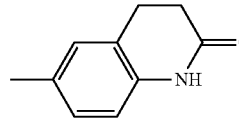 | 647 | 648 |
| 157 | 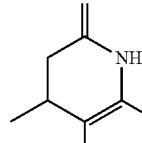 | 647 | 648 |
| 158 | 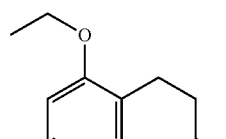 | 677 | 678 |

TABLE 7-continued
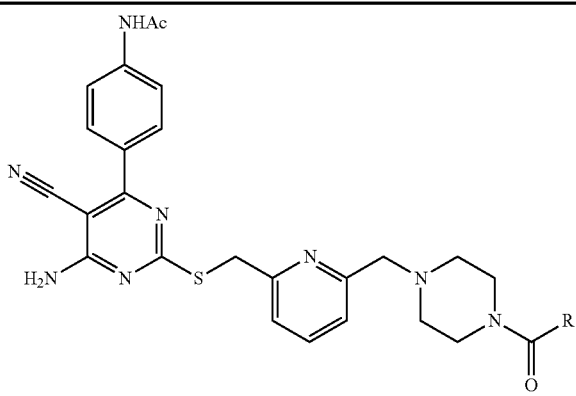
| Example No. | R | Calculated Mass Number | Observed Value [M + H] |
|---|---|---|---|
| 159 | | 705 | 706 |
| 160 | | 677 | 678 |
| 161 | | 661 | 662 |
| 162 | | 661 | 662 |
| 163 | | 643 | 644 |
| 164 | | 644 | 645 |
| 165 | | 645 | 646 |

TABLE 7-continued
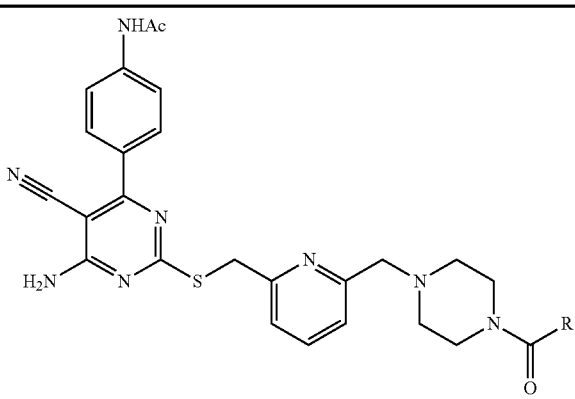
| Example No. | R | Calculated Mass Number | Observed Value [M + H] |
| --- | --- | --- | --- |
| 166 | | 644 | 645 |
| 167 | | 645 | 646 |
| 168 | | 679 | 680 |
| 169 | | 663 | 664 |
| 170 | | 686 | 687 |
| 171 | | 635 | 636 |
| 172 | | 674 | 675 |
| 173 | | 725 | 726 |
| 174 | | 587 | 588 |
| 175 | | 635 | 636 |

TABLE 7-continued
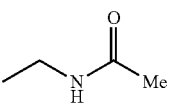
| Example No. | R | Calculated Mass Number | Observed Value [M + H] |
|---|---|---|---|
| 176 | 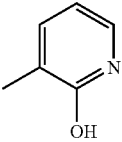 | 573 | 574 |
| 177 | 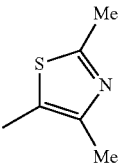 | 595 | 596 |
| 178 | 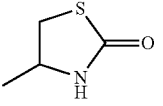 | 613 | 614 |
| 179 | 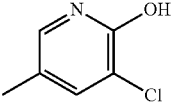 | 603 | 604 |
| 180 | 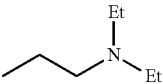 | 630 | 631 |
| 181 | 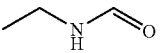 | 601 | 602 |
| 182 | 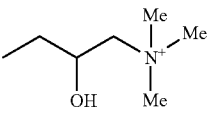 | 559 | 560 |
| 183 | 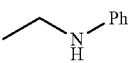 | 618 | 619 |
| 184 |  | 607 | 608 |

TABLE 7-continued
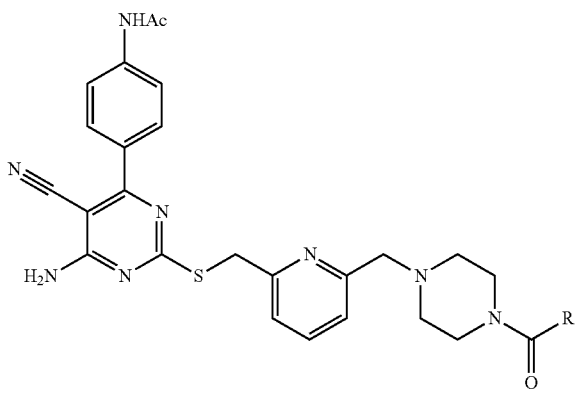
| Example No. | R | Calculated Mass Number | Observed Value [M + H] |
|---|---|---|---|
| 185 | ![Ac-N-pyrrolidinyl with methyl] | 613 | 614 |
| 186 | ![Me-N-pyrrole with methyl] | 581 | 582 |
| 187 | ![3,4-dimethyl-5-methylisoxazole] | 597 | 598 |
| 188 | ![propenyl imidazole] | 594 | 595 |
| 189 | ![methylpyrazine] | 580 | 581 |

TABLE 7-continued

| Example No. | R | Calculated Mass Number | Observed Value [M + H] |
|---|---|---|---|
| 190 | (pyrazine with Me, Me) | 594 | 595 |
| 191 | (6-methyluracil) | 612 | 613 |
| 192 | (ethyl-tetrazole) | 584 | 585 |
| 193 | (3-methyl-2-carbamoylpyrazine) | 623 | 624 |

Example 194-201

To a solution of 20 mg (25 µM) of the compound obtained in Example 18 (as a hydrochloride salt thereof) in 0.2 mL of DMF was added MP-Carbonate (125 µM) and the mixture was shaken at room temperature for 3 hours. Then, the reaction mixture was filtrated, the filtrate was added to a solution of an appropriate sulfonyl chloride compound in 0.1 mL of DMF (50 µM), then 8.7 µL of diisopropylethylamine (50 µM) was added to the mixture and the resulting mixture was shaken at room temperature overnight (approximately 18 hours).

The reaction solution was charged to HPLC as similar to the condition described in above-mentioned Examples 83-193 and purified to separate the product. After the purification, the fraction solution was lyophilized and the lyophilized product was weighed and the structure was analyzed by LC/MS analysis on the condition described in Examples 83-193. The structures and the calculated mass numbers and the observed LC/MS results of each obtained compound are shown in Table 8.

TABLE 8

| Example No. | R | Calculated Mass Number | Observed Value [M + H] |
|---|---|---|---|
| 194 | 4-OMe-C6H4 | 644 | 645 |
| 195 | Ph | 614 | 615 |

TABLE 8-continued

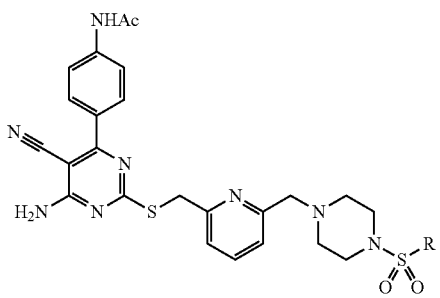

| Example No. | R | Calculated Mass Number | Observed Value [M + H] |
|---|---|---|---|
| 196 | (5-methyl-1-methyl-imidazol-2-yl) | 618 | 619 |
| 197 | (4-methylphenyl) | 628 | 629 |
| 198 | n-hexadecyl | 763 | 764 |
| 199 | Me | 552 | 553 |
| 200 | n-Bu | 594 | 595 |
| 201 | Et | 566 | 567 |

Example 202-243

The solution of 16 mg of the compound obtained in Example 18 (as a hydrochloride salt thereof, 20 μM), an appropriate alkyl halide (22 μM), saturated aqueous potassium carbonate (100 μM) in 0.2 mL of DMF was shaken at room temperature overnight (approximately 18 hours). To the reaction solution added 0.2 mL of DMF and thereby the solution was diluted, then the diluted solution was purified to separate the product by HPLC as similar to the condition described in above-mentioned Examples 83-193. In addition, after the purification, the fraction solution was lyophilized and the lyophilized product was weighed and the structure was analyzed by LC/MS analysis as mentioned above.

The structures and the calculated mass numbers and the observed LC/MS results of each obtained compound are shown in Table 9.

TABLE 9

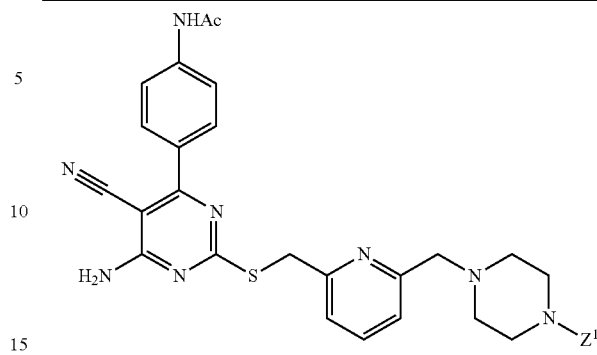

| Example No. | Z¹ | Calculated Mass Number | Observed Value [M + H] |
|---|---|---|---|
| 202 | (4-methoxybenzyl) | 594 | 595 |
| 203 | (3-methoxycarbonylbenzyl) | 622 | 623 |
| 204 | (2-methylthiazol-4-ylmethyl) | 585 | 586 |
| 205 | Et | 502 | 503 |
| 206 | (3-pyrrolidin-1-yl-propyl) | 571 | 572 |
| 207 | (pyridin-3-ylmethyl) | 565 | 566 |
| 208 | (4-carboxybenzyl) | 608 | 609 |
| 209 | (cinnamyl) | 590 | 591 |
| 210 | (5-carboxyfuran-2-ylmethyl) | 598 | 599 |
| 211 | (thiazol-2-ylmethyl) | 571 | 572 |
| 212 | (cyclohexylmethyl) | 570 | 571 |

TABLE 9-continued

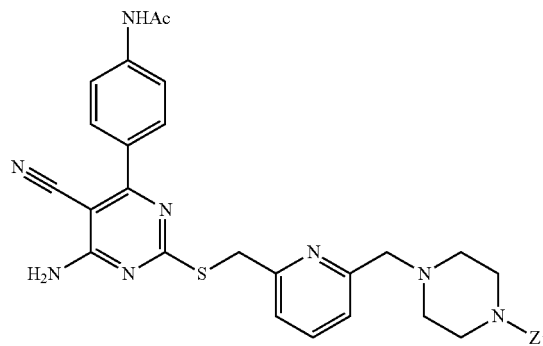

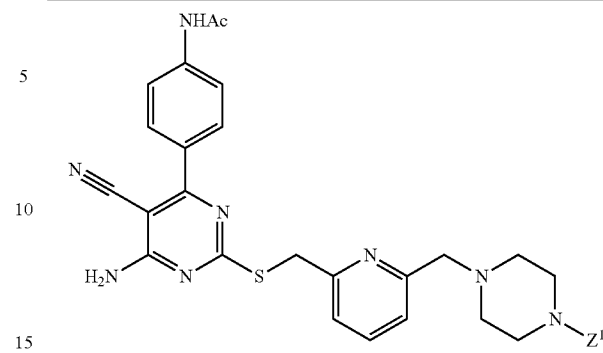

| Example No. | Z¹ | Calculated Mass Number | Observed Value [M + H] |
|---|---|---|---|
| 213 | ethyl-tetrazole-(CH₂)CH₅CH₃ | 640 | 641 |
| 214 | 3-ethyl-5-methyl-isoxazole | 569 | 570 |
| 215 | 3-methyl-4-ethyl-5-methyl-isoxazole | 583 | 584 |
| 216 | (CH₂)₃Ph | 592 | 593 |
| 217 | n-Bu | 530 | 531 |
| 218 | i-Bu | 530 | 531 |
| 219 | ethyl-4-pyridyl | 565 | 566 |
| 220 | ethyl-benzimidazole | 604 | 605 |
| 221 | ethyl-2-pyridyl | 565 | 566 |
| 222 | ethyl-2-phenyl-thiazole | 647 | 648 |
| 223 | CH₂CH₂C(O)NMe₂ | 559 | 560 |

| Example No. | Z¹ | Calculated Mass Number | Observed Value [M + H] |
|---|---|---|---|
| 224 | CH₂CH₂C(O)NH₂ | 531 | 532 |
| 225 | propyl-cyclohexyl | 584 | 585 |
| 226 | propyl-NMe₂ | 545 | 546 |
| 227 | propyl-piperidinyl | 585 | 586 |
| 228 | propyl-morpholinyl | 587 | 588 |
| 229 | (CH₂)₄OH | 532 | 533 |
| 230 | (CH₂)₅OH | 546 | 547 |
| 231 | propyl-NEt₂ | 573 | 574 |
| 232 | (CH₂)₃OPh | 608 | 609 |
| 233 | CH₂CH₂C(O)-piperidinyl | 599 | 600 |
| 234 | CH₂CH₂C(O)NH-cyclohexyl | 613 | 614 |

TABLE 9-continued

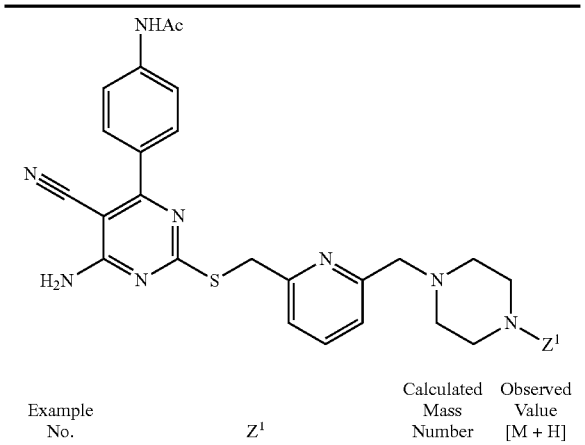

| Example No. | $Z^1$ | Calculated Mass Number | Observed Value [M + H] |
|---|---|---|---|
| 235 | (2-ethyl-imidazo[1,2-a]pyridine) | 604 | 605 |
| 236 | CH2CH2CH2-N(i-Pr)2 | 601 | 602 |
| 237 | CH2CH2-C(=NH)NH2 | 530 | 531 |
| 238 | CH2CH2-(azepan-1-yl) | 599 | 600 |
| 239 | (6-ethyl-uracil) | 598 | 599 |
| 240 | (8-ethyl-quinoline) | 615 | 616 |
| 241 | (6-ethyl-2-hydroxymethyl-pyridine) | 595 | 596 |
| 242 | CH2CH2-(1-methyl-piperidin-2-yl) | 599 | 600 |
| 243 | (4-ethyl-thiazole) | 571 | 572 |

Example 244-298

To a solution of 20 mg (25 μM) of the compound obtained in Example 18 (as a hydrochloride salt thereof) in 0.6 mL of a mixture of THF-DMF (3:1) was added an appropriate aldehyde compound (28 μM) in 28 μL of DMF and 7 μL (125 μM) of acetic acid. To the reaction mixture was added MP-cyanoborohydride (63 μM, Argonaut Company, Macroporous triethylammonium methylpolystyrene cyanoborohydride) and the mixture was shaken at room temperature for 2 days. MP-cyanoborohydride was filtrated off, the filtrate was charged to HPLC as similar to the condition described in above-mentioned Examples 83-193 and purified to separate the product. In addition, after the purification, the fraction solution was lyophilized and the lyophilized product was weighed and the structure was analyzed by LC/MS analysis as mentioned above.

The structures and the calculated mass numbers and the observed LC/MS results of each obtained compound are shown in Table 10.

TABLE 10

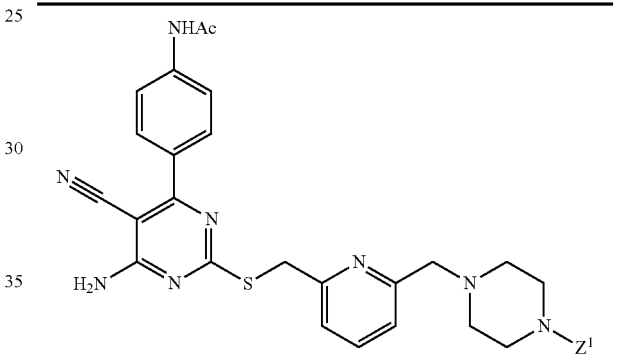

| Example No. | $Z^1$ | Calculated Mass Number | Observed Value [M + H] |
|---|---|---|---|
| 244 | (3-ethyl-furan) | 554 | 555 |
| 245 | (2-ethyl-1H-imidazole) | 554 | 555 |
| 246 | (5-methyl-2-ethyl-furan) | 568 | 569 |
| 247 | (2-ethyl-thiophene) | 570 | 571 |
| 248 | (3-methyl-2-ethyl-thiophene) | 584 | |

TABLE 10-continued

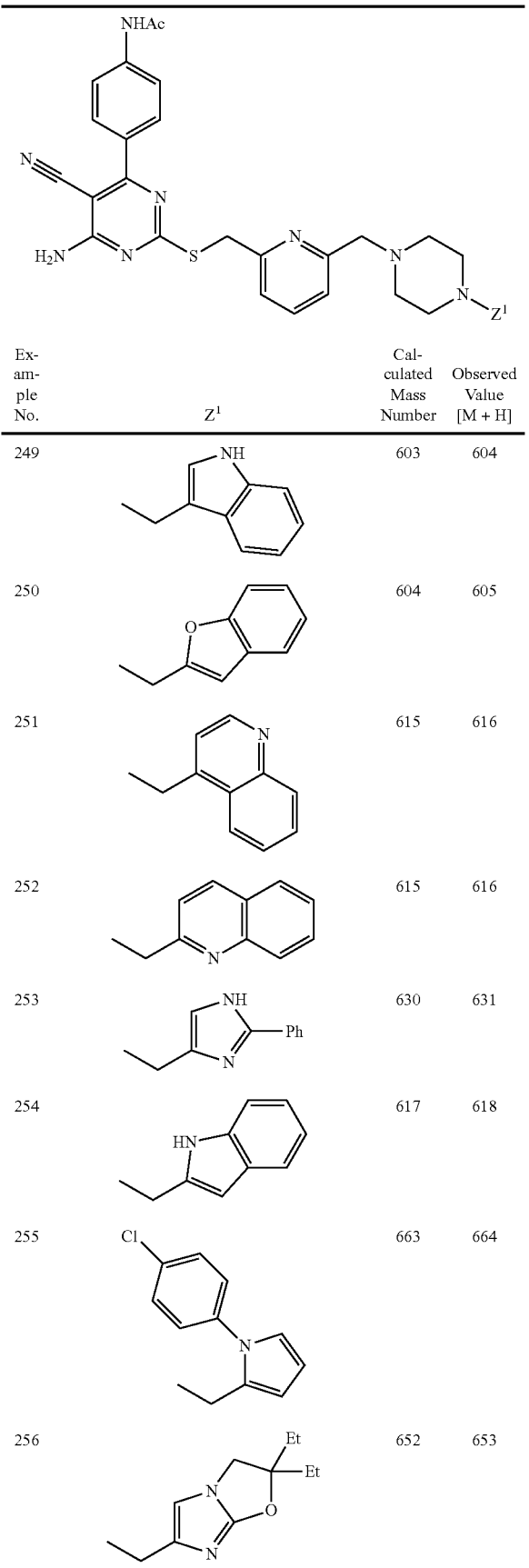
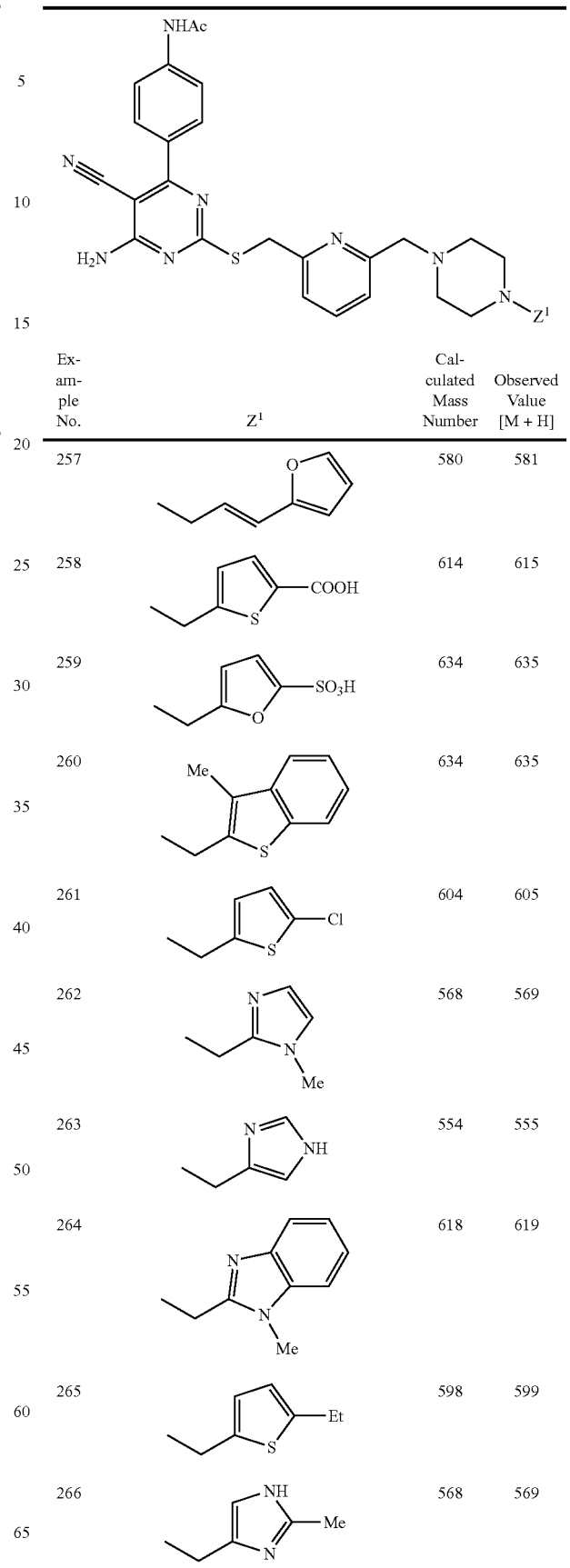

| Example No. | $Z^1$ | Calculated Mass Number | Observed Value [M + H] |
|---|---|---|---|
| 249 | (3-ethyl-1H-indole) | 603 | 604 |
| 250 | (2-ethyl-benzofuran) | 604 | 605 |
| 251 | (4-ethyl-quinoline) | 615 | 616 |
| 252 | (2-ethyl-quinoline) | 615 | 616 |
| 253 | (4-ethyl-2-phenyl-1H-imidazole) | 630 | 631 |
| 254 | (2-ethyl-1H-indole) | 617 | 618 |
| 255 | (1-(4-chlorophenyl)-2-ethyl-pyrrole) | 663 | 664 |
| 256 | (ethyl-diethyl-oxazoline imidazole) | 652 | 653 |
| 257 | (4-(furan-2-yl)-but-3-enyl) | 580 | 581 |
| 258 | (5-ethyl-thiophene-2-COOH) | 614 | 615 |
| 259 | (5-ethyl-furan-2-SO$_3$H) | 634 | 635 |
| 260 | (2-ethyl-3-methyl-benzothiophene) | 634 | 635 |
| 261 | (5-chloro-2-ethyl-thiophene) | 604 | 605 |
| 262 | (2-ethyl-1-methyl-imidazole) | 568 | 569 |
| 263 | (4-ethyl-1H-imidazole) | 554 | 555 |
| 264 | (2-ethyl-1-methyl-benzimidazole) | 618 | 619 |
| 265 | (2-ethyl-5-ethyl-thiophene) | 598 | 599 |
| 266 | (4-ethyl-2-methyl-1H-imidazole) | 568 | 569 |

TABLE 10-continued

[Common structure shown: 4-amino-6-(4-acetamidophenyl)-5-cyano-2-{[6-(piperazin-1-ylmethyl)pyridin-2-yl]methylthio}pyrimidine with Z¹ on distal piperazine N]

| Example No. | Z¹ | Calculated Mass Number | Observed Value [M + H] |
|---|---|---|---|
| 267 | 3-ethyl-methoxyphenyl (CH₂-C₆H₄-OMe) | 594 | 595 |
| 268 | 3,4,5-trimethoxybenzyl | 654 | 655 |
| 269 | (benzo[1,3]dioxol-5-yl)methyl | 608 | 609 |
| 270 | (2,3-dihydro-1,4-benzodioxin-6-yl)methyl | 622 | 623 |
| 271 | 4-hydroxybenzyl | 580 | 581 |
| 272 | 4-(diethylamino)benzyl | 635 | 636 |
| 273 | 4-[3-(dimethylamino)propoxy]benzyl | 665 | 666 |
| 274 | 3-phenoxybenzyl | 656 | 657 |
| 275 | 4-(n-butoxy)benzyl | 636 | 637 |
| 276 | 3-(trifluoromethoxy)benzyl | 648 | 649 |
| 277 | 3-acetoxybenzyl | 622 | 623 |
| 278 | 4-(dimethylamino)benzyl | 607 | 608 |
| 279 | furan-2-ylmethyl | 554 | 555 |
| 280 | (9-ethyl-9H-carbazol-3-yl)methyl | 681 | 682 |
| 281 | (benzo[1,3]dioxol-4-yl)methyl | 608 | 609 |
| 282 | 3-ethoxybenzyl | 608 | 609 |
| 283 | 3-(benzyloxy)benzyl | 670 | 671 |
| 284 | (1H-indol-7-yl)methyl | 603 | 604 |

TABLE 10-continued

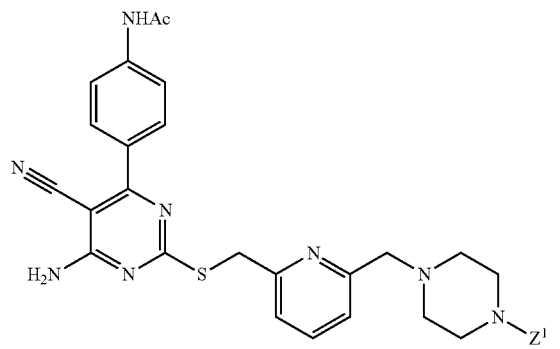

| Example No. | $Z^1$ | Calculated Mass Number | Observed Value [M + H] |
|---|---|---|---|
| 285 | *4-ethyl-2-fluorophenyl-N-methylpiperazine* | 680 | 681 |
| 286 | *4-ethylphenyl-1,2,4-triazole* | 631 | 632 |
| 287 | *2-ethylphenyl-NH-SO3Me* | 658 | 657 |
| 288 | *4-ethylphenoxy-acetyl-morpholine* | 707 | 708 |
| 289 | *4-ethylphenyl-N(nBu)2* | 691 | 692 |
| 290 | *5-ethyl-2,3-dihydrobenzofuran* | 606 | 607 |
| 291 | *4-ethylphenyl-imidazole* | 630 | 631 |

TABLE 10-continued

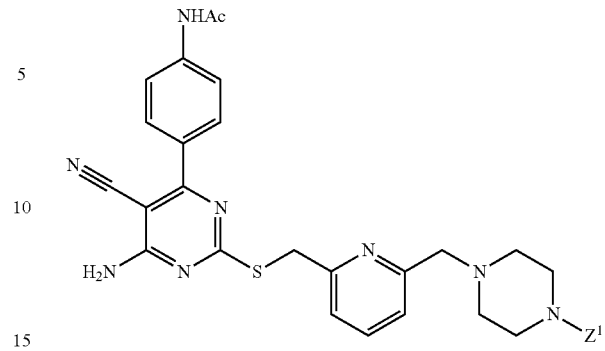

| Example No. | $Z^1$ | Calculated Mass Number | Observed Value [M + H] |
|---|---|---|---|
| 292 | *4-ethylphenyl-piperidine* | 647 | 648 |
| 293 | *3,4-diethoxyphenyl-4-ethyl-imidazole* | 718 | 719 |
| 294 | *2-ethyl-5-nBu-pyridine* | 621 | 622 |
| 295 | *2-ethyl-4,5-dichloroimidazole* | 622 | 623 |
| 296 | *2-ethyl-6-CF3-benzofuran* | 672 | 673 |
| 297 | *5-ethyl-2,2-difluorobenzodioxole* | 644 | 645 |
| 298 | *4-ethyl-2,2-difluorobenzodioxole* | 644 | 645 |

Example 299-416

The suspension of 24 mg (50 μM) of the compound obtained in Example 45, an appropriate primary or secondary alkylamine compound (100 μM) and 8.9 mg of HOBt-H₂O (58 μM) in a mixture of ethylene chloride-DMF (0.5 mL-0.2 mL) was shaken at room temperature for 10 minutes. When a salt of an amine compound was used as a starting material, an equimolecular amount of MP-Carbonate (Argonaut Company) was added to the reaction medium. Then, to the reaction mixture was added PS-Carbodiimide (Argonaut Company, 67 μM) and the mixture was shaken at room temperature overnight (approximately 18 hours).

The reaction mixture was then filtrated and washed with DMF (0.15 mL) to remove the resin, PS-Carbodiimide and MP-Carbonate when it was used. The filtrate and the washing solution were combined, the ethylene chloride was evaporated with the flow of nitrogen gas, the residue was diluted with 0.15 mL of DMF, and the diluted solution was purified to separate the product by HPLC as similar to the condition described in above-mentioned Examples 83-193. In addition, after the purification, the fraction solution was lyophilized and the lyophilized product was weighed and the structure was analyzed by LC/MS analysis as mentioned above.

The structures and the calculated mass numbers and the observed LC/MS results of each obtained compound are shown in Table 11.

TABLE 11

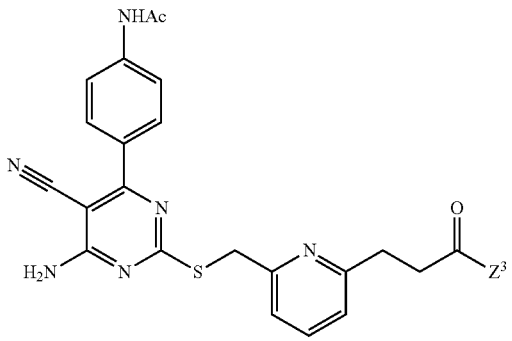

| Example No. | Z³ | Calculated Mass Number | Observed Value [M + H] |
|---|---|---|---|
| 299 | 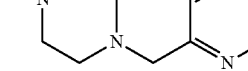 | 607 | 608 |
| 300 | 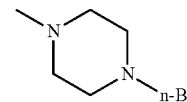 | 572 | 573 |
| 301 | 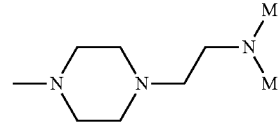 | 587 | 588 |
| 302 | 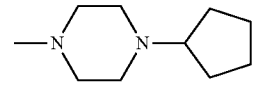 | 584 | 585 |
| 303 | 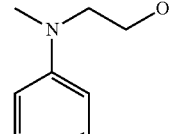 | 567 | 568 |
| 304 | 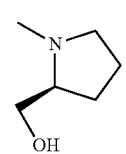 | 531 | 532 |

TABLE 11-continued
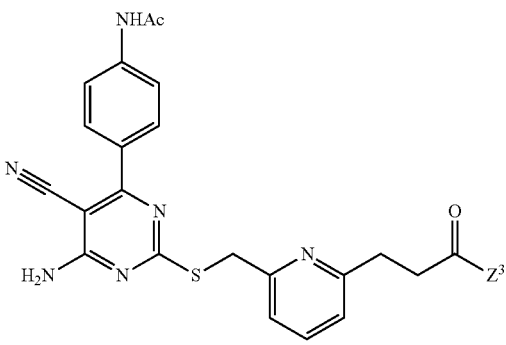
| Example No. | Z³ | Calculated Mass Number | Observed Value [M + H] |
|---|---|---|---|
| 305 | 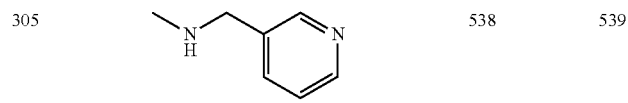 | 538 | 539 |
| 306 | 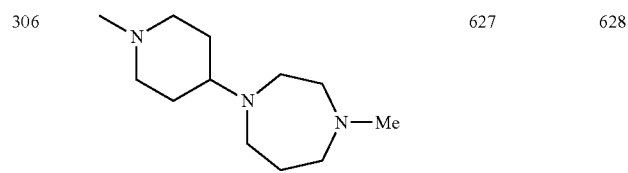 | 627 | 628 |
| 307 | 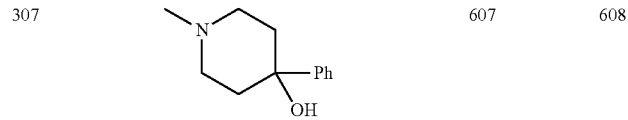 | 607 | 608 |
| 308 | 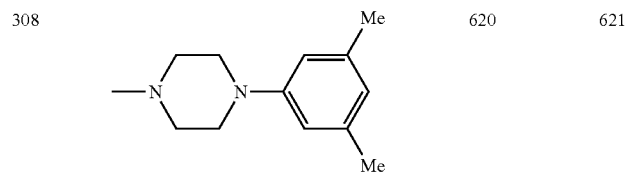 | 620 | 621 |
| 309 | 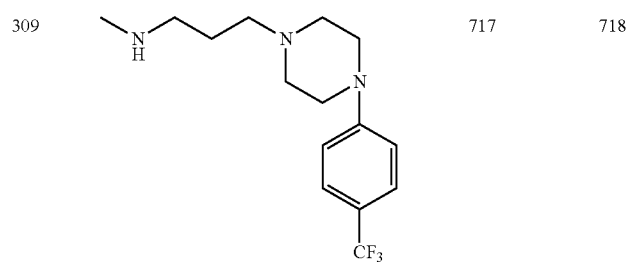 | 717 | 718 |
| 310 | 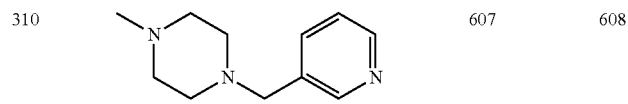 | 607 | 608 |

TABLE 11-continued
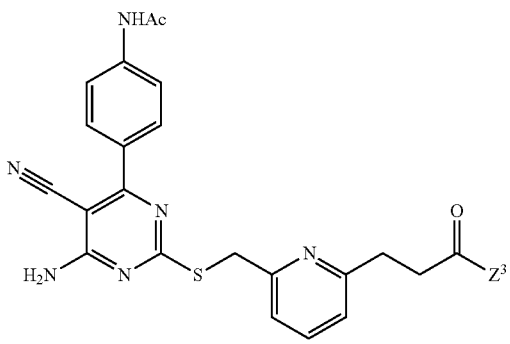
| Example No. | $Z^3$ | Calculated Mass Number | Observed Value [M + H] |
|---|---|---|---|
| 311 | | 639 | 640 |
| 312 | | 574 | 575 |
| 313 | | 750 | 751 |
| 314 | | 593 | 594 |
| 315 | | 538 | 539 |
| 316 | | 649 | 650 |

TABLE 11-continued
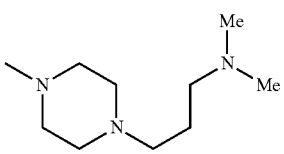
| Example No. | Z³ | Calculated Mass Number | Observed Value [M + H] |
|---|---|---|---|
| 317 | 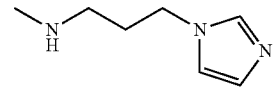 | 601 | 602 |
| 318 | 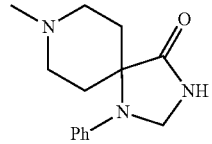 | 555 | 556 |
| 319 | 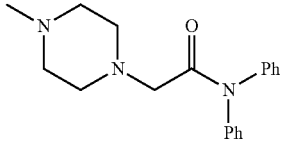 | 661 | 662 |
| 320 | 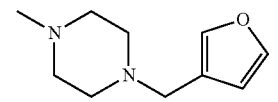 | 663 | 664 |
| 321 | 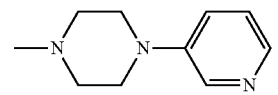 | 596 | 597 |
| 322 | 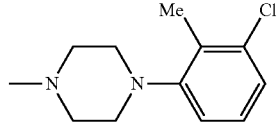 | 593 | 594 |
| 323 | 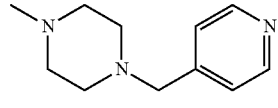 | 640 | 641 |
| 324 | 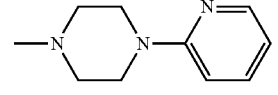 | 607 | 608 |
| 325 | | 593 | 594 |

TABLE 11-continued

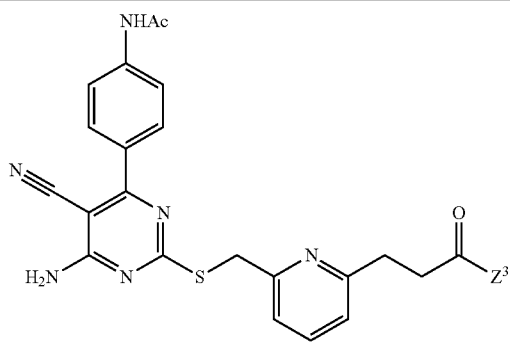

| Example No. | Z³ | Calculated Mass Number | Observed Value [M + H] |
|---|---|---|---|
| 326 | (4-methylpiperazin-1-yl)-(1-methylpiperidin-4-yl) | 613 | 614 |
| 327 | 4-methylpiperazin-1-yl ethyl piperidine | 627 | 628 |
| 328 | N-methyl-bis(2-hydroxyethyl)amine | 535 | 536 |
| 329 | N-methyl-N-[3-(dimethylamino)propyl]-N'-(dimethylamino)propylamine | 617 | 618 |
| 330 | N,N,N',N'-tetraethyl-propane-1,3-diamine | 574 | 575 |
| 331 | N,N,N',N'-tetraethyl-ethane-1,2-diamine | 574 | 575 |
| 332 | 4-methyl-1-(pyrazin-2-yl)piperazine | 594 | 595 |
| 333 | 1-benzyl-4-methylpiperazine | 606 | 607 |

TABLE 11-continued
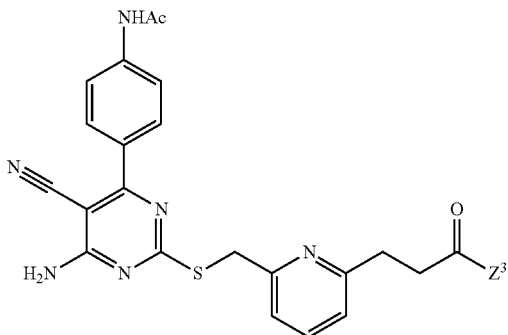
| Example No. | Z³ | Calculated Mass Number | Observed Value [M + H] |
|---|---|---|---|
| 334 | (N-methylaminomethyl-2-pyridine) | 538 | 539 |
| 335 | (4-methylpiperazine-N-N(Me)-CH2-cyclohexyl) | 640 | 641 |
| 336 | (4-methylpiperazine-N-N(Me)-CH2-cyclopropyl) | 598 | 599 |
| 337 | (1-methyl-piperidinyl-piperazine-diMe) | 627 | 628 |
| 338 | (4-methylpiperazine-N-N(Me)-CH(OH)-tetrahydrofuran) | 658 | 659 |
| 339 | (4-methylpiperazine-N-N(Me)-CH2CH2-N(Me)Ph) | 677 | 678 |
| 340 | (4-methylpiperazine-N-N-(2-Ph-morpholine)) | 676 | 677 |

TABLE 11-continued
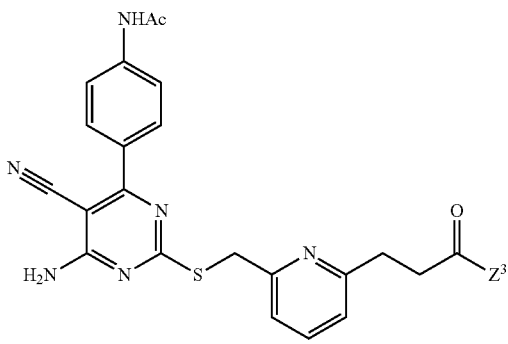
| Example No. | Z³ | Calculated Mass Number | Observed Value [M + H] |
|---|---|---|---|
| 341 | | 643 | 644 |
| 342 | | 633 | 634 |
| 343 | | 683 | 684 |
| 344 | | 649 | 650 |
| 345 | | 617 | 618 |
| 346 | | 622 | 623 |
| 347 | | 649 | 650 |

TABLE 11-continued
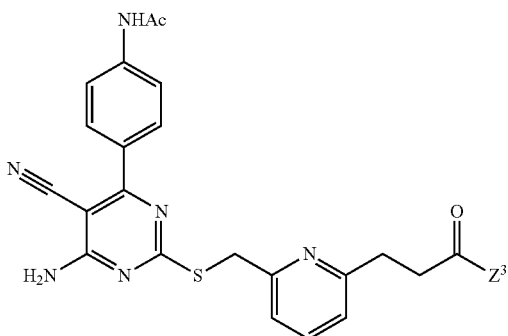
| Example No. | Z³ | Calculated Mass Number | Observed Value [M + H] |
|---|---|---|---|
| 348 | —N(Me)CH₂CH₂N(Me)CH₂Ph (Me,Me,Ph) | 608 | 609 |
| 349 | 4-phenylpiperazin-1-yl | 592 | 593 |
| 350 | 4-(n-propyl)piperazin-1-yl | 558 | 559 |
| 351 | 4-[4-(dimethylamino)piperidin-1-yl]benzonitrile | 645 | 646 |
| 352 | 4-(2-methoxyethyl)piperazin-1-yl | 574 | 575 |
| 353 | 4-methyl-1-[(1-methylpiperidin-3-yl)methyl]piperazine | 627 | 628 |
| 354 | N-methyl-4-[4-(diphenylmethyl)piperazin-1-yl]butylamine | 753 | 754 |

TABLE 11-continued

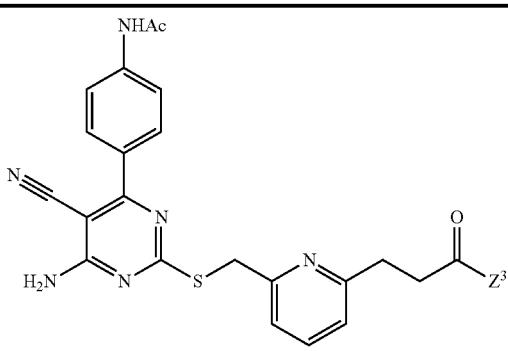

| Example No. | Z³ | Calculated Mass Number | Observed Value [M + H] |
|---|---|---|---|
| 355 | 4-Me, 2-Et-imidazol-1-yl-C₆H₄-4-NMe₂ | 645 | 646 |
| 356 | 4-methylpiperazin-1-yl, 3-CN-pyridin-2-yl | 618 | 619 |
| 357 | 4-methylpiperazin-1-yl, morpholin-4-yl (piperidine linker) | 600 | 601 |
| 358 | 4-methylpiperazin-1-yl-CH₂CH₂-imidazol-1-yl | 610 | 611 |
| 359 | 4-methylpiperazin-1-yl, 3-Me-pyridin-2-yl | 607 | 608 |
| 360 | 4-methylpiperazin-1-yl, 4-Me-pyridin-2-yl | 607 | 608 |
| 361 | 4-methylpiperazin-1-yl, 3-CF₃-pyridin-2-yl | 661 | 662 |
| 362 | 4-methylpiperazin-1-yl-CH₂C(O)NH-CH₂CH₂-Ph | 677 | 678 |

TABLE 11-continued
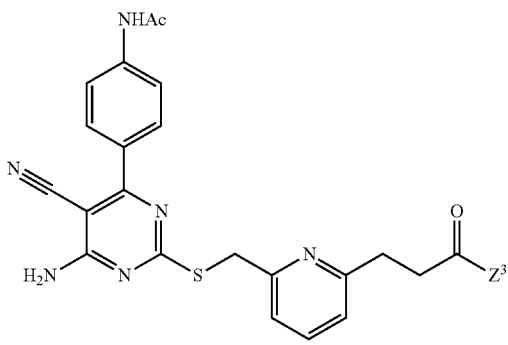
| Example No. | Z³ | Calculated Mass Number | Observed Value [M + H] |
|---|---|---|---|
| 363 | | 613 | 614 |
| 364 | | 650 | 651 |
| 365 | | 607 | 608 |
| 366 | | 621 | 622 |
| 367 | | 663 | 664 |
| 368 | | 621 | 622 |

TABLE 11-continued
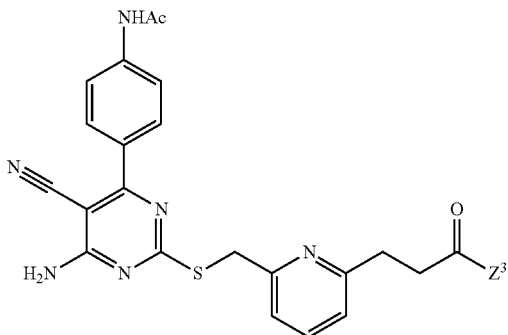
| Example No. | Z³ | Calculated Mass Number | Observed Value [M + H] |
|---|---|---|---|
| 369 | 4-methyl-1,4-diazepanyl-propyl-N(n-Pr)(n-Pr) | 671 | 672 |
| 370 | 4-methyl-1,4-diazepanyl-propyl-morpholine | 657 | 658 |
| 371 | 4-methyl-piperazinyl-Et | 544 | 545 |
| 372 | 4-methyl-piperazinyl-ethanol | 560 | 561 |
| 373 | 4-methyl-piperazinyl-C(O)-pyrrolidine | 627 | 628 |
| 374 | MeNH-propyl-(4-Me-piperazinyl) | 587 | 588 |
| 375 | 4-methyl-piperazinyl-(4-OH-phenyl) | 608 | 609 |

TABLE 11-continued

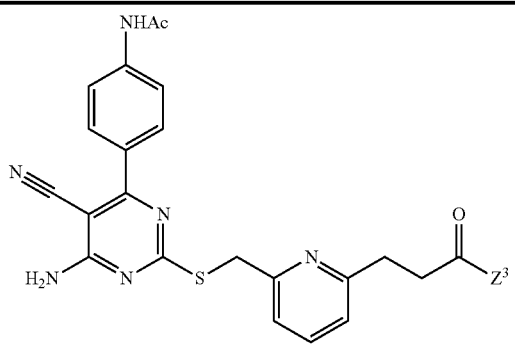

| Example No. | Z³ | Calculated Mass Number | Observed Value [M + H] |
|---|---|---|---|
| 376 | 1-methyl-3-hydroxypiperidine | 531 | 532 |
| 377 | 1-methyl-2-(hydroxymethyl)piperidine | 545 | 546 |
| 378 | 1-methyl-4-(hydroxymethyl)piperidine | 545 | 546 |
| 379 | 1-methyl-4-benzyl-4-hydroxypiperidine | 621 | 622 |
| 380 | N-methyl-(1-ethylpyrrolidin-2-yl)methylamine | 558 | 559 |
| 381 | N-methyl-2-(pyrrolidin-1-yl)ethylamine | 544 | 545 |
| 382 | N-methyl-3-(pyrrolidin-1-yl)propylamine | 558 | 559 |
| 383 | N-methyl-2-(morpholin-4-yl)ethylamine | 560 | 561 |
| 384 | N-methyl-3-(morpholin-4-yl)propylamine | 574 | 575 |
| 385 | 1-methyl-4-[N-(4-trifluoromethylphenyl)amino]piperazine | 675 | 676 |

TABLE 11-continued
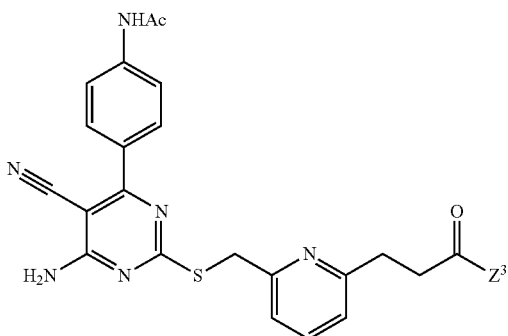
| Example No. | Z³ | Calculated Mass Number | Observed Value [M + H] |
|---|---|---|---|
| 386 | | 657 | 658 |
| 387 | | 643 | 644 |
| 388 | | 586 | 587 |
| 389 | | 558 | 559 |
| 390 | | 612 | 613 |
| 391 | | 620 | 621 |
| 392 | | 662 | 663 |

TABLE 11-continued

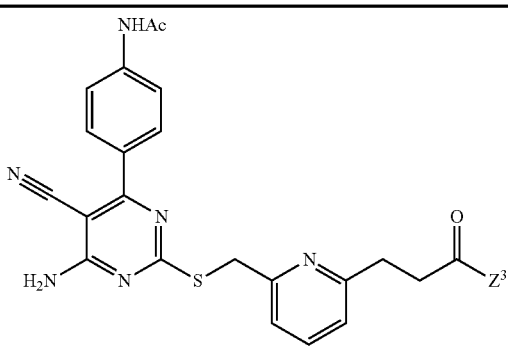

| Example No. | Z³ | Calculated Mass Number | Observed Value [M + H] |
|---|---|---|---|
| 393 | 1-methylpiperidin-4-yl-CH₂CH₂-N(Me)(Ph) | 648 | 649 |
| 394 | 1-methylpiperidin-4-yl-N(Me)-CH₂CH₂-cyclohexyl | 654 | 655 |
| 395 | 1-methylpiperidin-4-yl-N(Me)-CH₂-Ph | 634 | 635 |
| 396 | 3-benzyl-1,4-dimethylpiperazinyl | 620 | 621 |
| 397 | 4-methyl-1-phenylpiperazin-2-one | 606 | 607 |
| 398 | 1-acetyl-4-(N-methylamino)piperidinyl | 586 | 587 |
| 399 | N-methyl-N-(2-phenylethyl)-N',N'-diethylethylenediamine | 650 | 651 |
| 400 | 4-methyl-1-(3,4-dimethoxybenzyl)-6-methylpiperazin-2-one | 680 | 681 |

TABLE 11-continued

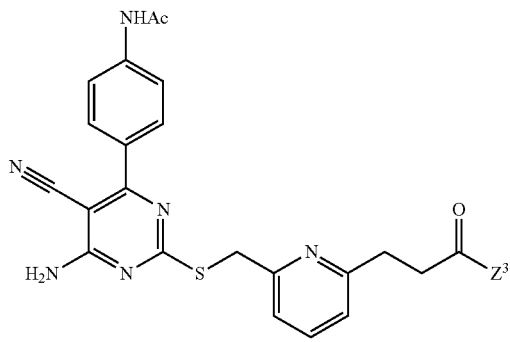

| Example No. | Z³ | Calculated Mass Number | Observed Value [M + H] |
|---|---|---|---|
| 401 | N-methyl piperidinone with N(Me)-(3,4-dimethoxyphenyl) | 680 | 681 |
| 402 | NHMe-benzyl-4-(3-(thiomorpholin-4-yl)propoxy) | 696 | 697 |
| 403 | N(Me)(Et)-1-benzylpiperidin-4-yl | 648 | 649 |
| 404 | N(Me)(Et)-CH₂-(4-benzylmorpholin-2-yl) | 664 | 665 |
| 405 | 4-methyl-1-(2-phenylethyl)-1,4-diazepane | 634 | 635 |
| 406 | 1-methyl-4-(3-methoxypropyl)piperazine | 588 | 589 |
| 407 | 1-methyl-4-((1,3-dioxolan-2-yl)methyl)piperazine | 602 | 603 |
| 408 | 1-methyl-4-((tetrahydrofuran-2-yl)methyl)piperazine | 600 | 601 |

TABLE 11-continued
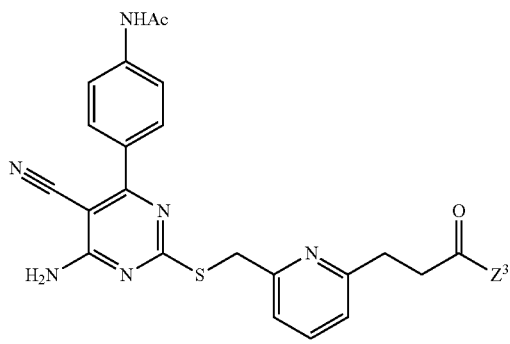
| Example No. | Z³ | Calculated Mass Number | Observed Value [M + H] |
|---|---|---|---|
| 409 | | 566 | 567 |
| 410 | | 712 | 713 |
| 411 | | 616 | 617 |
| 412 | | 668 | 669 |
| 413 | | 600 | 601 |
| 414 | | 640 | 641 |
| 415 | | 588 | 589 |

TABLE 11-continued

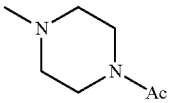

| Example No. | $Z^3$ | Calculated Mass Number | Observed Value [M + H] |
|---|---|---|---|
| 416 | (N-methyl-N'-acetyl-piperazinyl) | 558 | 559 |

Hereinafter, the examples of the pharmacological tests using the compounds of the invention are described.

(1) c-AMP Generating Action in Cell Expressing Adenosine A2a Receptor

The test was carried out as mentioned below with reference to the method disclosed in the reference (Klotz k. N. et al., Naunyn-Schmiedeberg's Arch. Pharmacol., (1998) 357, 1-9; Shryock J. C. et al., Molecular Pharmacology, (1998) 53, 886-893).

As to the cell, HEK293 cell expressing adenosine A2a receptor (Human) (PerkinElmer Life Sciences, Code No. RBHA2AC) was used.

As to the culture medium, Dulbecco's modified Eagles medium (DMEM) including 10% FBS (Fetal bovine serum) and 1 mM of sodium pyruvate was used.

The cell was placed on 96 well plate ($1 \times 10^5$/well), and cultured overnight. After removing off the supernatant, to each well, 0.1 ml of DMEM (without FBS) containing 20 mM HEPES, 0.1 mM of IBMX (3-isobutyl-1-methylxanthine) and 2 unit/mL adenosine deaminase was added, and they were incubated at 37° C. for 30 minutes. To each well, 0.1 ml of the culture medium including the DMSO solution of the test compound in an appropriate concentration was added and they were incubated for additional 30 minutes. After removing off the supernatant, the cytolytic solution was added to quench the reaction. The amount of c-AMP in each well was measured by using the c-AMP enzyme immunoassay (EIA) system (Amersham Biosciences, Code No. RPN225).

The same assay was repeated using CGS-21680 (2-p-carboxyethyl)phenethylamino-5'-N-ethylcarboxamidoadenosine hydrochloride, (Sigma, code C141) as reference compound. The amount of resultant c-AMP in the medium, caused by 1 μM of reference compound, was defined to be 100%. A concentration of assayed compound in the medium, producing 50% c-AMP amounts, was calculated to be $EC_{50}$ value.

The above test results obtained using the following compounds of the invention prepared in the above-mentioned examples are shown in the following Table 12. In addition, in the Table, the results of the same test using the compound described in Example 6 of WO 03/053441 A1 (referred to the Comparative Compound A) and the compound described in Example 1 of WO 03/008384 A1 (referred to the Comparative Compound B) having the following structures are also shown together.

<Comparative Compound A>

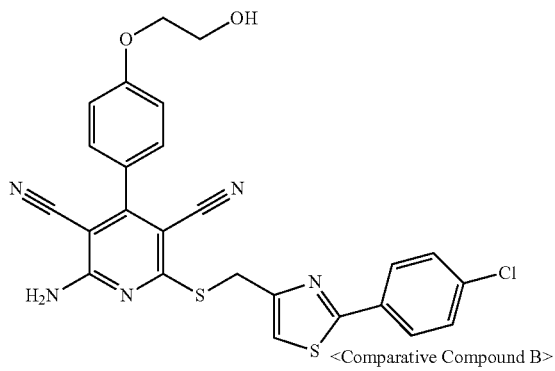

<Comparative Compound B>

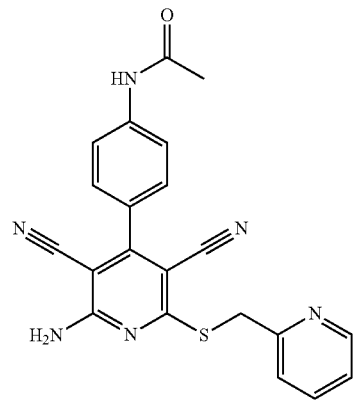

TABLE 12

| Test Compound (Example No.) | A2a Agonistic Action ($EC_{50}$, nM) |
|---|---|
| 1 | 39.6 |
| 2 | 11.9 |
| 3 | 65.7 |
| 4 | 879 |
| 8 | 34.8 |
| 9 | 9.0 |
| 10 | 19.1 |
| 11 | 395 |

TABLE 12-continued

| Test Compound (Example No.) | A2a Agonistic Action (EC$_{50}$, nM) |
|---|---|
| 13 | 13.5 |
| 14 | 39.6 |
| 17 | 6.8 |
| 19 | 7.4 |
| 21 | 10.6 |
| 26 | 30.7 |
| 28 | 8.2 |
| 33 | 48.0 |
| 41 | 23.0 |
| 42 | 10.0 |
| 46 | 7.4 |
| 48 | 29.1 |
| 52 | 7.0 |
| 54 | 5.3 |
| 55 | 5.5 |
| 56 | 5.1 |
| 57 | 3.4 |
| 58 | 38.0 |
| 60 | 2.8 |
| 61 | 3.4 |
| 62 | 5.1 |
| 64 | 4.3 |
| 66 | 5.2 |
| 67 | 6.8 |
| 68 | 7.5 |
| 69 | 7.0 |
| 70 | 8.8 |
| 72 | 13.6 |
| 74 | 2.5 |
| 75 | 3.0 |
| 76 | 7.6 |
| 77 | 9.5 |
| 78 | 6.0 |
| 79 | 8.4 |
| 80 | 2.4 |
| 82 | 8.2 |
| Comparative Compound A | >1000 |
| Comparative Compound B | 14.3 |

From the results shown in Table 12, it is obvious that all of the compounds of the invention have a potent A2a receptor stimulating activity.

(2) Adenosine A1 Agonistic Action

The test was carried out as mentioned below with reference to the method disclosed in the literature (Shryock J. C. et al., Molecular Pharmacology, (1998) 53, 886-893; Ito H. et al., European Journal of Pharmacology, (1999) 365, 309-315). That is, cerebral cortex of male Wistar rats (Charles River Japan, Inc) was extirpated, thereto Tris buffer (50 mM Tris-HCl: pH 7.4) was added, it was homogenized, and then centrifuged (1000×g, 10 min). The supernatant was taken, and centrifuged (20,000×g, 20 min). After removing off the supernatant, the precipitate was suspended in Tris buffer, and recentrifuged (20,000×g, 20 min). After removing off the supernatant, the precipitate was suspended in Tris buffer including 2 units/mL ADA (adenosine deaminase) and reserved at −80° C. until used as a liquid preparation of cell membrane for the following tests.

The above liquid preparation of cell membrane in an amount corresponding to 10 μg of cell membrane was added to Tris-buffer comprising 5 mM of MgCl$_2$, 1 mM of EDTA, 1 mM of dithiothreitol, 100 mM of NaCl, 0.01 mM of GDP (guanosine diphosphate), 5 mg/mL of BSA and 2 units/mL of ADA and the mixture was incubated at 25° C. for 30 minutes. Additionally, [$^{35}$S]GTPγS (Guanosine 5'-[γ-thio]triphosphate) (the final concentration: 0.4 nM) and the test compound of the given concentration (which was calculated based on the final concentration of the test compound) were added to the mixture and the resulting mixture was incubated at 25° C. for 45 minutes. The reaction mixture was filtrated through a glass fiber filter (unifilter-96 GF/B, Perkin Elmer Life Sciences) to quench reaction. The filter was washed 5 times with ice-cooled Tris-buffer including 5 mM MgCl$_2$. The radioactivity of the filter was measured with Top count NXT(Perkin Elmer Life Sciences). The nonspecific binding was shown as the binding activity of [$^{35}$S]GTPγS in the presence of 0.01 mM GTPγS.

The activity (%, A1 agonistic action) of each test compound was calculated on the basis of the test result ([$^{35}$S] GTPγS binding activity) derived with 1 μM of CPA (N$^6$-Cyclopentyladenosine, Sigma, code C-8031) in control which was counted as 100%.

The following Table 13 shows the results in 1 μM, 100 nM and 10 nM of the test compounds of the invention (including the salts thereof) of above-mentioned examples. Also, Table 13 shows the results of Control Compounds A and B which are the same as used in the pharmacological test (1).

TABLE 13

| | A1 Agonistic Action (%) (calculated as a percentage to 100% of the test with CPA 1 μM) | | |
|---|---|---|---|
| Test Compound | 1 μM | 100 nM | 10 nM |
| Comparative Compound A | 79 | 55 | 14 |
| Comparative Compound B | 77 | 63 | 20 |
| Compound of Invention (Example No.) | | | |
| 46 | 45 | 26 | 4 |
| 62 | 39 | 30 | 8 |
| 75 | 50 | 22 | 3 |
| 76 | 46 | 14 | 0 |
| 77 | 40 | 18 | 2 |
| 79 | 45 | 12 | 0 |

As is seen from the result shown in Table 13, the A1 receptor activating action (A1 agonistic action) of the compounds of the invention is still lower than those of the control compounds. This finding indicates that the compounds of the invention may selectively act on the adenosine A2a receptor.

On testing the compounds of the invention of all other examples than the compounds used in above Table 13, it was observed that all of the compounds exhibited almost the same A1 agonistic action as the compounds of the invention shown in Table 13.

(3) Measuring Test for Intraocular Pressure in Rabbit

The test compounds were dissolved in 10 mM of phosphate buffer (pH 7.5) (hereinafter, referred to as "vehicle of ophthalmic preparation"), and they were instilled in a given concentration. In addition, the compounds insoluble in that concentration was used as a suspension. Female New Zealand white rabbits (KITAYAMA LABES Co., Ltd.) whose weights were 2.0-4.0 kg were used.

The measurement of the intraocular pressure was carried out using Pneumatonometer (Model 30 Classic, Mentor company) without anesthesia. In addition, before the measurement of the intraocular pressure, the surface anesthesia with 0.4% oxybuprocaine hydrochloride ("Benoxil" 0.4% ophthalmic solution, Santen Pharmaceutical Co., Ltd.) was carried out.

The animals whose intraocular pressure was stable before instillation were selected, and these animals were divided to every 4 animal in each one group, 50 μL of eye drops including each the test compound was administered to one-sided eye and vehicle was administered to contralateral eye as the control eye. The measurement of intraocular pressure was carried out before instillation and after 0.5, 1, 2, 3, 4 and 6 hours from instillation. The effect on the intraocular pressure was shown as the difference from pre-instillation (ΔIOP, mmHg, mean±standard error). The following Tables 14 and 15 show the results of Control Compounds A and B used as 1% suspensions which are the same as in the pharmacological test (1).

TABLE 14

Control Compound A, 1% Suspended Ophthalmic Preparation (n = 4)

| | ΔIOP (mmHg) Time (hr) | | | | | |
|---|---|---|---|---|---|---|
| | 0.5 | 1 | 2 | 3 | 4 | 6 |
| Test Eye | −1.5 ± 0.8 | −1.4 ± 1.3 | −2.3 ± 1.4 | −2.2 ± 1.2 | −1.9 ± 1.9 | 0.9 ± 1.4 |
| Control Eye | 0.4 ± 0.7 | 0.5 ± 0.7 | −0.2 ± 0.6 | −0.4 ± 0.4 | −0.4 ± 1.2 | 1.1 ± 1.2 |

TABLE 15

Control Compound B, 1% Suspended Ophthalmic Preparation (n = 4)

| | ΔIOP (mmHg) Time (hr) | | | | | |
|---|---|---|---|---|---|---|
| | 0.5 | 1 | 2 | 3 | 4 | 6 |
| Test Eye | 0.7 ± 0.2 | 0.6 ± 0.2 | −0.9 ± 0.3 | 0.6 ± 0.2 | 0.3 ± 1.0 | 0.2 ± 0.2 |
| Control Eye | 1.0 ± 0.7 | 1.1 ± 0.5 | −0.4 ± 0.7 | 0.4 ± 0.5 | 0.4 ± 0.9 | 0.4 ± 0.2 |

The animals were pretreated as mentioned above, and among them animals whose intraocular pressure was stable before instillation were selected, and these animals were divided to every 5 to 8 animal in each one group. Every two group was used for each of the test compounds. The test compound was administered unilaterally to the eye of the test group rabbit and the intraocular pressure was measured. The vehicle was administered unilaterally to the eye of the control group rabbit and the intraocular pressure was measured. As mentioned above, the measurement of intraocular pressure was carried out before instillation and after 0.5, 1, 2, 3, 4 and 6 hours from instillation, and the effect on the intraocular pressure was shown as the difference from pre-instillation (ΔIOP, mmHg, mean±standard error).

The following Tables 16 to 32 show the results of the control compound CGS-21680 and the compounds of the invention (the compound obtained from the examples) wherein each of the test compounds is summarized in the individual table.

TABLE 16

CGS-21680(Control Compound), 0.3% Suspended Ophthalmic Preparation (n = 6)

| | ΔIOP (mmHg) Time (hr) | | | | | |
|---|---|---|---|---|---|---|
| | 0.5 | 1 | 2 | 3 | 4 | 6 |
| Test Group | −2.5 ± 0.4 | −6.3 ± 0.6 | −4.2 ± 0.4 | −3.5 ± 0.4 | −1.5 ± 0.7 | 0.3 ± 0.4 |
| Control Group | −1.1 ± 0.7 | −1.8 ± 0.2 | −0.9 ± 0.5 | −1.3 ± 0.5 | −0.3 ± 0.9 | 1.0 ± 0.8 |

TABLE 17

Compound of Example 2, 1% Suspended Ophthalmic Preparation (n = 8)

| | ΔIOP (mmHg) Time (hr) | | | | | |
|---|---|---|---|---|---|---|
| | 0.5 | 1 | 2 | 3 | 4 | 6 |
| Test Group | 1.1 ± 0.6 | −3.1 ± 0.6 | −4.2 ± 0.7 | −4.0 ± 0.9 | −2.0 ± 0.4 | 0.4 ± 0.9 |
| Control Group | 0.6 ± 0.4 | −0.5 ± 0.6 | −0.6 ± 0.8 | −0.6 ± 0.7 | 1.4 ± 0.3 | 2.7 ± 0.8 |

TABLE 18

Compound of Example 14, 0.3% Suspended Ophthalmic Preparation (n = 6)

| | ΔIOP (mmHg) Time (hr) | | | | | |
|---|---|---|---|---|---|---|
| | 0.5 | 1 | 2 | 3 | 4 | 6 |
| Test Group | −0.3 ± 1.2 | −3.9 ± 1.3 | −4.4 ± 1.0 | −4.8 ± 1.4 | −4.3 ± 1.0 | −1.0 ± 1.0 |
| Control Group | −0.7 ± 0.5 | −0.6 ± 1.0 | −0.4 ± 1.1 | −0.2 ± 1.0 | 0.3 ± 1.2 | 1.2 ± 1.4 |

TABLE 19

Compound of Example 46, 0.01% Ophthalmic, Solution (n = 6)

| | ΔIOP (mmHg) Time (hr) | | | | | |
|---|---|---|---|---|---|---|
| | 0.5 | 1 | 2 | 3 | 4 | 6 |
| Test Group | −0.6 ± 0.6 | −4.4 ± 0.8 | −4.9 ± 0.6 | −3.8 ± 0.7 | −2.9 ± 0.5 | −0.5 ± 0.6 |
| Control Group | 0.0 ± 0.8 | 0.0 ± 0.6 | 0.3 ± 0.7 | −0.1 ± 0.9 | 0.7 ± 0.6 | 3.5 ± 0.5 |

TABLE 20

Compound of Example 69, 0.01% Ophthalmic Solution (n = 6)

| | ΔIOP (mmHg) Time (hr) | | | | | |
|---|---|---|---|---|---|---|
| | 0.5 | 1 | 2 | 3 | 4 | 6 |
| Test Group | −1.5 ± 1.0 | −4.9 ± 0.7 | −3.6 ± 0.4 | −3.8 ± 0.7 | −2.6 ± 1.0 | 0.5 ± 0.9 |
| Control Group | 0.5 ± 0.5 | −0.5 ± 0.4 | −0.1 ± 0.5 | 0.5 ± 0.6 | 0.6 ± 0.5 | 2.6 ± 0.8 |

TABLE 21

Compound of Example 75, 0.01% Ophthalmic Solution (n = 5)

| | ΔIOP (mmHg) Time (hr) | | | | | |
|---|---|---|---|---|---|---|
| | 0.5 | 1 | 2 | 3 | 4 | 6 |
| Test Group | −0.8 ± 0.4 | −5.1 ± 0.5 | −5.3 ± 0.9 | −4.0 ± 0.9 | −4.3 ± 0.9 | −1.3 ± 0.4 |
| Control Group | −0.1 ± 0.3 | −0.4 ± 0.6 | −1.3 ± 0.6 | −0.5 ± 0.4 | −0.2 ± 0.6 | 0.6 ± 0.7 |

TABLE 22

Compound of Example 76, 0.01% Ophthalmic Solution (n = 5)

| | ΔIOP (mmHg) Time (hr) | | | | | |
|---|---|---|---|---|---|---|
| | 0.5 | 1 | 2 | 3 | 4 | 6 |
| Test Group | −3.7 ± 0.5 | −6.0 ± 0.8 | −5.7 ± 0.1 | −6.1 ± 0.3 | −5.2 ± 0.4 | −3.6 ± 0.7 |
| Control Group | −0.4 ± 0.3 | −0.3 ± 0.4 | −0.3 ± 0.7 | −0.4 ± 0.4 | −0.6 ± 0.4 | 0.2 ± 0.7 |

TABLE 23

Compound of Example 61, 0.03% Ophthalmic Solution
(n = 6)

ΔIOP (mmHg)
Time (hr)

| | 0.5 | 1 | 2 | 3 | 4 | 6 |
|---|---|---|---|---|---|---|
| Test Group | −0.5 ± 0.4 | −4.2 ± 0.6 | −4.5 ± 0.7 | −4.8 ± 0.7 | −4.4 ± 0.7 | −1.2 ± 0.8 |
| Control Group | −0.4 ± 0.3 | −0.9 ± 0.6 | −1.1 ± 0.8 | −1.4 ± 0.6 | −0.2 ± 0.8 | 1.3 ± 1.0 |

TABLE 24

Compound of Example 62, 0.03% Ophthalmic Solution
(n = 5)

ΔIOP (mmHg)
Time (hr)

| | 0.5 | 1 | 2 | 3 | 4 | 6 |
|---|---|---|---|---|---|---|
| Test Group | −1.2 ± 0.7 | −4.7 ± 0.5 | −5.1 ± 0.3 | −4.9 ± 0.3 | −3.6 ± 0.3 | −1.0 ± 0.6 |
| Control Group | −0.5 ± 0.6 | −0.6 ± 0.4 | −1.0 ± 0.4 | −1.1 ± 0.5 | −0.8 ± 0.2 | 1.4 ± 0.9 |

TABLE 25

Compound of Example 64, 0.03% Ophthalmic Solution
(n = 6)

ΔIOP (mmHg)
Time (hr)

| | 0.5 | 1 | 2 | 3 | 4 | 6 |
|---|---|---|---|---|---|---|
| Test Group | −2.7 ± 0.7 | −4.9 ± 0.5 | −3.8 ± 0.8 | −3.2 ± 0.9 | −4.0 ± 0.7 | −1.8 ± 0.4 |
| Control Group | −0.3 ± 0.7 | −1.2 ± 0.5 | −0.7 ± 0.5 | −0.3 ± 0.4 | −0.6 ± 0.6 | 2.3 ± 1.0 |

TABLE 26

Compound of Example 66, 0.03% Ophthalmic Solution
(n = 6)

ΔIOP (mmHg)
Time (hr)

| | 0.5 | 1 | 2 | 3 | 4 | 6 |
|---|---|---|---|---|---|---|
| Test Group | −1.3 ± 0.9 | −4.0 ± 0.6 | −5.5 ± 0.7 | −5.0 ± 0.5 | −3.7 ± 0.5 | −1.8 ± 0.5 |
| Control Group | −0.3 ± 0.2 | −0.5 ± 0.3 | −0.8 ± 0.5 | 0.0 ± 0.4 | 0.3 ± 0.5 | 1.6 ± 0.4 |

TABLE 27

Compound of Example 67, 0.03% Ophthalmic Solution
(n = 6)

ΔIOP (mmHg)
Time (hr)

| | 0.5 | 1 | 2 | 3 | 4 | 6 |
|---|---|---|---|---|---|---|
| Test Group | −1.1 ± 1.0 | −5.3 ± 0.7 | −4.6 ± 0.7 | −4.6 ± 0.9 | −4.2 ± 0.7 | −2.0 ± 0.7 |
| Control Group | −1.3 ± 0.4 | −1.3 ± 0.3 | −0.9 ± 0.8 | −1.0 ± 0.4 | −0.4 ± 0.6 | 1.9 ± 0.5 |

TABLE 28

Compound of Example 72, 0.03% Ophthalmic Solution
(n = 6)

ΔIOP (mmHg)
Time (hr)

| | 0.5 | 1 | 2 | 3 | 4 | 6 |
|---|---|---|---|---|---|---|
| Test Group | −1.9 ± 0.6 | −5.3 ± 0.6 | −4.7 ± 0.6 | −5.0 ± 0.7 | −4.0 ± 1.0 | −1.9 ± 0.9 |
| Control Group | −0.6 ± 0.2 | −0.7 ± 0.3 | −0.8 ± 0.7 | −0.2 ± 0.7 | 0.0 ± 0.3 | 1.5 ± 0.5 |

TABLE 29

Compound of Example 77, 0.03% Ophthalmic Solution
(n = 6)

ΔIOP (mmHg)
Time (hr)

| | 0.5 | 1 | 2 | 3 | 4 | 6 |
|---|---|---|---|---|---|---|
| Test Group | −0.8 ± 0.5 | −5.0 ± 0.6 | −5.1 ± 0.4 | −4.4 ± 0.6 | −4.9 ± 0.7 | −3.1 ± 0.7 |
| Control Group | −1.4 ± 0.8 | −1.3 ± 0.4 | −1.8 ± 0.4 | −1.2 ± 0.6 | −1.0 ± 0.7 | 0.5 ± 0.6 |

TABLE 30

Compound of Example 78, 0.03% Ophthalmic Solution
(n = 6)

ΔIOP (mmHg)
Time (hr)

| | 0.5 | 1 | 2 | 3 | 4 | 6 |
|---|---|---|---|---|---|---|
| Test Group | 0.6 ± 0.5 | −3.3 ± 0.4 | −4.4 ± 0.6 | −4.3 ± 0.9 | −5.4 ± 0.7 | −3.2 ± 0.9 |
| Control Group | −0.1 ± 0.3 | −0.9 ± 0.4 | −0.9 ± 0.5 | −0.1 ± 0.3 | −0.8 ± 0.6 | 0.0 ± 0.3 |

TABLE 31

Compound of Example 79, 0.03% Ophthalmic Solution
(n = 6)

ΔIOP (mmHg)
Time (hr)

| | 0.5 | 1 | 2 | 3 | 4 | 6 |
|---|---|---|---|---|---|---|
| Test Group | 0.3 ± 0.9 | −3.9 ± 0.5 | −5.4 ± 0.7 | −5.8 ± 0.8 | −4.8 ± 0.7 | −2.8 ± 1.0 |
| Control Group | 0.0 ± 0.2 | 0.5 ± 0.5 | −0.5 ± 0.4 | −0.1 ± 0.2 | 0.5 ± 0.4 | 1.0 ± 0.5 |

TABLE 32

Compound of Example 80, 0.03% Ophthalmic Solution
(n = 6)

ΔIOP (mmHg)
Time (hr)

| | 0.5 | 1 | 2 | 3 | 4 | 6 |
|---|---|---|---|---|---|---|
| Test Group | −0.9 ± 1.3 | −5.0 ± 1.0 | −5.9 ± 0.7 | −4.9 ± 0.5 | −5.0 ± 0.8 | −1.8 ± 0.8 |
| Control Group | −0.5 ± 0.7 | −1.1 ± 0.6 | −1.6 ± 0.8 | −0.9 ± 1.1 | −0.6 ± 1.0 | 1.3 ± 0.9 |

On testing the compounds of the invention derived from each of the above Examples 1-84 except the compounds of the invention described in above Tables 16-32 in the same way mentioned above, it was observed that all of the compounds exhibited almost the same result shown in Tables 16-32.

From the result shown in Tables 14-32, the following is obvious. That is, as shown in Tables 14 and 15, Control Compounds A and B did not exhibit any significant intraocular pressure lowering action even in 1% suspension which was a relatively high concentration.

As shown in Tables 17-32, all of the tested compounds of the invention exhibited the intraocular pressure lowering action. In particular, the compounds of the invention shown in Tables 19-32 in a lower concentration than that of CGS-21680 exhibited the same level of the intraocular pressure lowering action of CGS-21680 which was already reported to have an intraocular hypotensive action (see Table 16). In addition, the compounds of the invention shown in Tables 20 to 32 were soluble in a high concentration (0.3%-1%) beyond the concentrations used in said measuring test (0.01%-0.03%) without a solubilizing agent, hence it appeared that they were useful as ophthalmic solution.

The invention claimed is:

1. A 4-amino-5-cyanopyrimidine compound of the formula (1):

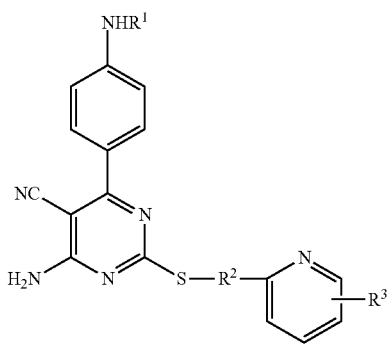

or a pharmaceutically acceptable salt thereof,
wherein
$R^1$ is a hydrogen atom, a lower alkylcarbonyl group, a lower alkenylcarbonyl group, a phenylcarbonyl group or a lower alkoxycarbonyl group;
$R^2$ is a lower alkylene group;
$R^3$ is

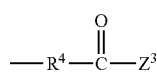

Group (9)

wherein
$R^4$ is a lower alkylene group, and
$Z^3$ is (c3) an amino group, (c4) an amino-lower alkylamino group, (c5) a piperazino group, (c6) an amino-lower alkylpiperazino group, (c8) a 1,4-diazepan-1-yl group, (c10) a piperidino group, (c11) an aminopiperidino group, (c18) a lower alkylpiperazino group having a saturated heterocycle, (c21) a piperidino group having a saturated heterocycle, or (c22) a lower alkylmorpholino group having a saturated heterocycle;
the amino group of the above (c3) and the amino moiety included as a part of the groups in the above (c4), (c6), and (c11) may be optionally substituted with 1 or 2 substituents selected from the group consisting of a lower alkyl group, a hydroxy-lower alkyl group, a phenyl group, and a lower alkoxycarbonyl group;
the amino moiety included as a part of the groups in the above (c11) may be optionally substituted with an aryl-lower alkylcarbonyl group;
the piperazino group of the above (c5) and 1,4-diazepan-1-yl group of the above (c8) may be substituted with any one of the substituents selected from the group consisting of a lower alkyl group, a hydroxy-lower alkyl group, a lower alkoxy-lower alkyl group, a phenyl group, a lower alkylphenyl group, a hydroxyphenyl group, a cyanophenyl group, a halogenophenyl group, a phenyl-lower alkyl group, a lower alkoxyphenyl-lower alkyl group, a halogenophenoxy-lower alkyl group, a pyridyl group, a lower alkylpyridyl group, a halogeno-lower alkylpyridyl group, a cyanopyridyl group, a pyridyl-lower alkyl group, a lower alkoxycarbonyl group and a lower alkylcarbonyl group on 4-position of the ring system; further
the saturated heterocycle moiety included as a part of the groups in the above (c18), (c21) and (c22) may be a monovalent saturated heterocycle group selected from the group consisting of pyrrolidinyl, pyrrolidino, piperidyl, piperidino, piperazinyl, piperazino, 1,4-diazepan-1-yl, tetrahydrofuryl, 1,3-dioxolanyl, tetrahydrothienyl, morpholinyl, morpholino and tetrahydroimidazolyl, optionally having any one of the substituents selected from the group consisting of a lower alkyl group, a phenyl group, a cyanophenyl group, a lower alkylcarbonyl group, a halogeno-lower alkylphenyl group and a phenyl-lower alkyl group on the nitrogen atom of the ring system; and furthermore
the piperazino group of the above (c5), the piperidino group of the above (c10) and the saturated heterocycle moiety included as a part of the groups in the above (c18), a lower alkylpiperazino group having a saturated heterocycle and (c22) a lower alkylmorpholino group having a saturated heterocycle may be substituted with any one of the substituents selected from the group consisting of a hydroxy group, an oxo group, a lower alkyl group, a hydroxy-lower alkyl group, a phenyl group, a phenyl-lower alkyl group, an aminocarbonyl group and a lower alkylamino group on the carbon atom of the ring system.

2. The 4-amino-5-cyanopyrimidine compound according to claim 1 or a pharmaceutically acceptable salt thereof, wherein
$R^3$ is

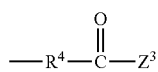

Group (9)

wherein
$R^4$ is a lower alkylene group, and
$Z^3$ is
(c3) an amino group which may be optionally substituted with 1 or 2 lower alkyl groups,
(c4) an amino-lower alkylamino group wherein the amino moiety included as a part of the groups may be optionally substituted with 1 or 2 substituents selected from the group consisting of a lower alkyl group and a lower alkoxycarbonyl group, (c5) a piperazino group which may be optionally substituted with any one of substituents selected from the group consisting of a lower alkyl group and a lower alkoxycarbonyl group,
(c6) an amino-lower alkylpiperazino group wherein the amino moiety included as a part of the groups may be optionally substituted with 1 or 2 lower alkyl groups,
(c8) a 1,4-diazepan-1-yl group which may be optionally substituted with 1 lower alkyl group,
(c10) a 2-hydroxymethylpiperidino group,
(c11) an aminopiperidino group wherein the amino moiety included as a part of the groups may be optionally substituted with 1 or 2 lower alkyl groups,
(c18) a lower alkylpiperazino group having a saturated heterocycle selected from the group consisting of pyrrolidinyl, pyrrolidino, piperidyl, piperidino, morpholinyl, and morpholino, optionally having a lower alkyl group on the nitrogen atom of the saturated heterocycle ring system,
(c21) a 4-(1-piperidyl)piperidino group or
(c22) a lower alkylmorpholino group having a saturated heterocycle selected from the group consisting of piperidyl, piperidino, piperazinyl and piperazino, optionally having a lower alkyl group on the nitrogen atom of the saturated heterocycle ring system.

3. The 4-amino-5-cyanopyrimidine compound according to claim 2 or a pharmaceutically acceptable salt thereof, wherein
$R^1$ is a hydrogen atom or a lower alkylcarbonyl group;
$R^2$ is a methylene group;
$R^3$ is

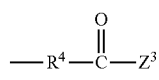

Group (9)

wherein
$R^4$ is a lower alkylene group, and
$Z^3$ is
(c3) an amino group which may be optionally substituted with 1 or 2 lower alkyl groups,
(c4) an amino-lower alkylamino group wherein the amino moiety included as a part of the groups may be optionally substituted with 1 or 2 substituents selected from the group consisting of a lower alkyl group and a lower alkoxycarbonyl group,
(c5) a piperazino group which may be optionally substituted with any one of substituents selected from the group consisting of a lower alkyl group and a lower alkoxycarbonyl group,
(c6) an amino-lower alkylpiperazino group wherein the amino moiety included as a part of the groups may be optionally substituted with 1 or 2 lower alkyl groups,
(c8) a 1,4-diazepan-1-yl group which may be optionally substituted with 1 lower alkyl group,
(c10) a 2-hydroxymethylpiperidino group,
(c11) an aminopiperidino group wherein the amino moiety included as a part of the groups may be optionally substituted with 1 or 2 lower alkyl groups,
(c18) a pyrrolidino-lower alkylpiperazino group, piperidyl-lower alkylpiperazino, optionally having a lower alkyl group on the nitrogen atom of the piperidine ring system, or a morpholino-lower alkylpiperazino group,
(c21) a 4-(1-piperidyl)piperidino group or
(c22) a piperidino-lower alkylmorpholino or piperazino-lower alkylmorpholino, optionally having a lower alkyl group on the nitrogen atom of the morpholino ring system.

4. A 4-amino-5-cyanopyrimidine compound or a pharmaceutically acceptable salt thereof, wherein the compound is selected from the group consisting of the following 1)-3):
 1) 3-{6-[4-(4-acetylaminophenyl)-6-amino-5-cyanopyrimidin-2-ylsulfanylmethyl]pyridin-2-yl}-N-(piperidin-1-ylethyl)propionamide,
 2) 3-{6-[4-(4-acetylaminophenyl)-6-amino-5-cyanopyrimidin-2-ylsulfanylmethyl]pyridin-2-yl}-N-methyl-N-(1-methylpiperidin-4-yl)propionamide, and
 3) 3-{6-[4-(4-acetylaminophenyl)-6-amino-5-cyanopyrimidin-2-ylsulfanylmethyl]pyridin-2-yl}-N-(4-methylpiperazin-1-yl) propionamide.

5. A medicine for the treatment of ocular hypertension or glaucoma comprising a 4-amino-5-cyanopyrimidine compound as set forth in claim 1 or a pharmaceutically acceptable salt thereof as an active ingredient.

* * * * *